US011987824B2

(12) United States Patent
Yang et al.

(10) Patent No.: US 11,987,824 B2
(45) Date of Patent: May 21, 2024

(54) ADDITIONAL ENDOGLUCANASE VARIANTS AND METHODS

(71) Applicant: Fornia BioSolutions, Inc., Hayward, CA (US)

(72) Inventors: Jie Yang, Foster City, CA (US); Xiyun Zhang, San Ramon, CA (US); William Buchanan Porterfield, Oakland, CA (US); Wenhua Lu, Dublin, CA (US); Khin Oo, Daly City, CA (US); Goutami Banerjee, Daly City, CA (US); Tatsuya Fukushima, Fremont, CA (US); Eric Lin Hu, Millbrae, CA (US)

(73) Assignee: FORNIA BIOSOLUTIONS, INC., Hayward, CA (US)

( * ) Notice: Subject to any disclaimer, the term of this patent is extended or adjusted under 35 U.S.C. 154(b) by 0 days.

(21) Appl. No.: 17/556,504

(22) Filed: Dec. 20, 2021

(65) Prior Publication Data

US 2022/0204956 A1 Jun. 30, 2022

Related U.S. Application Data

(60) Provisional application No. 63/129,143, filed on Dec. 22, 2020.

(51) Int. Cl.

| | |
|---|---|
| ***C12N 9/42*** | (2006.01) |
| ***C12N 15/63*** | (2006.01) |
| *D21H 17/00* | (2006.01) |

(52) U.S. Cl.

CPC ........... *C12N 9/2437* (2013.01); *C12N 15/63* (2013.01); *C12Y 302/01004* (2013.01); *D21H 17/005* (2013.01)

(58) Field of Classification Search

CPC ..................................................... C12N 9/1264

See application file for complete search history.

(56) References Cited

U.S. PATENT DOCUMENTS

2019/0367894 A1* 12/2019 Bott ........................ D21C 5/005

OTHER PUBLICATIONS

B5BNY1_9ASCO. UniProtKB/TrEMBL Database. Dec. 11, 2019.*

* cited by examiner

*Primary Examiner* — Yong D Pak

(74) *Attorney, Agent, or Firm* — Morgan, Lewis & Bockius LLP

(57) ABSTRACT

The invention is directed to novel variant endoglucanases and their use thereof.

19 Claims, 38 Drawing Sheets

Specification includes a Sequence Listing.

Figure 2

| Name | PF w.r.t. G1P | Mutation w.r.t. G1P (numbering based on Mature protein) |
|---|---|---|
| G1V1 | ++ | D215* |
| G1V2 (G2P) | + | I38L/Y39S/G42N/A43V/K44Q/E48N |
| G1V3 | ++ | D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292- |
| G1V4 | + | T-18S/F-5L/T-4A/V-3A/A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F |
| G2V1 | + | I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292- |

Figure 3

| Name | Bio stoning performace | Mutation w.r.t. G1P (numbering based on Mature protein) |
|---|---|---|
| G1P | ++ | |
| G1V1 | + | D215* |
| G1V2 (G2P) | +++ | I38L/Y39S/G42N/A43V/K44Q/E48N |
| G1V3 | ++ | D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292- |
| G1V4 | ++ | T-18S/F-5L/T-4A/V-3A/A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F |
| G2V1 | ++ | I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292- |

Figure 4A

| Colony Tracking Number | PF w.r.t. G2P | Active Mutations w.r.t. to G1P |
|---|---|---|
| CL00138437 | + | A23D/I38L/Y39S/G42N/A43V/K44Q/E48N |
| CL00138465 | + | I38L/Y39S/G42N/A43V/K44Q/E48N/S54T |
| CL00138527 | + | I38L/Y39S/G42N/A43V/K44Q/E48N/A77Q |
| CL00138708 | + | S25N/I38L/Y39S/G42N/A43V/K44Q/E48N |
| CL00138875 | + | I38L/Y39S/G42N/A43S/K44Q/E48N |
| CL00138934 | + | I38L/Y39S/G42N/A43V/K44E/E48N |
| CL00138960 | + | I38L/Y39S/G42N/A43L/K44Q/E48N |
| CL00139156 | + | I38L/Y39S/G42N/A43V/K44Q/E48N/A77E |
| CL00139269 | + | I38L/Y39S/G42N/K44Q/E48N |
| CL00139338 | + | I38L/Y39S/G42N/A43T/K44Q/E48N |
| CL00139402 | + | I38L/Y39S/G42N/A43V/K44Q/E48N/A194T |
| CL00139415 | + | I38L/Y39S/G42N/A43E/K44Q/E48N |
| CL00139453 | + | S17G/I38L/Y39S/G42N/A43V/K44Q/E48N |
| CL00139670 | + | I38L/Y39S/G42N/A43V/K44Q/E48N/V102Q |
| CL00139950 | + | I38L/Y39S/G42N/A43V/K44Q/E48N/P164S |
| CL00140074 | + | I38L/Y39S/G42N/A43V/K44Q/E48N/N116D |
| CL00140143 | + | I38L/Y39S/G42N/A43V/K44Q/E48N/N116S |
| CL00140696 | + | I38L/Y39S/G42N/A43V/K44Q/E48N/N122A |
| CL00140962 | + | I38L/Y39S/G42N/A43V/K44Q/E48N/A161P |
| CL00141018 | + | I38L/Y39S/G42N/A43V/K44Q/E48N/G268N |
| CL00141118 | + | I38L/Y39S/G42N/A43V/K44Q/E48N/V273G/C278L/T279H/K280Q/L281A/N282E/D283* |
| CL00141119 | + | I38L/Y39S/G42N/A43V/K44Q/E48N/L281K |
| CL00141133 | + | I38L/Y39S/G42N/A43V/K44Q/E48N/C269R |
| CL00141188 | + | I38L/Y39S/G42N/A43V/K44Q/E48N/G275* |
| CL00141271 | + | I38L/Y39S/G42N/A43V/K44Q/E48N/W284R |
| CL00141276 | + | I38L/Y39S/G42N/A43V/K44Q/E48N/V273* |
| CL00141309 | + | I38L/Y39S/G42N/A43V/K44Q/E48N/W258R |
| CL00141368 | + | I38L/Y39S/G42N/A43V/K44Q/E48N/T277E |
| CL00141446 | + | I38L/Y39S/G42N/A43V/K44Q/E48N/W258* |
| CL00141474 | ++ | I38L/Y39S/G42N/A43V/K44Q/E48N/C269S/W284* |
| CL00141551 | + | I38L/Y39S/G42N/A43V/K44Q/E48N/T276H/C278* |
| CL00141595 | ++ | I38L/Y39S/G42N/A43V/K44Q/E48N/T276R/K280Q/L281A/N282E/D283* |
| CL00141620 | + | I38L/Y39S/G42N/A43V/K44Q/E48N/L281G |
| CL00141633 | + | I38L/Y39S/G42N/A43V/K44Q/E48N/T277D |
| CL00141636 | + | I38L/Y39S/G42N/A43V/K44Q/E48N/W284M |
| CL00141658 | + | I38L/Y39S/G42N/A43V/K44Q/E48N/I291S |
| CL00141679 | + | I38L/Y39S/G42N/A43V/K44Q/E48N/I291Q |

Figure 4B

| Colony Tracking Number | PF w.r.t. G2P | Active Mutations w.r.t. to G1P |
|---|---|---|
| CL00141691 | + | I38L/Y39S/G42N/A43V/K44Q/E48N/L281E |
| CL00141721 | + | I38L/Y39S/G42N/A43V/K44Q/E48N/W284G |
| CL00141792 | + | I38L/Y39S/G42N/A43V/K44Q/E48N/S286A |
| CL00141857 | + | I38L/Y39S/G42N/A43V/K44Q/E48N/D283* |
| CL00141878 | + | I38L/Y39S/G42N/A43V/K44Q/E48N/N282S |
| CL00141895 | ++ | I38L/Y39S/G42N/A43V/K44Q/E48N/G275T |
| CL00141938 | + | I38L/Y39S/G42N/A43V/K44Q/E48N/A259D |
| CL00141947 | + | I38L/Y39S/G42N/A43V/K44Q/E48N/A259* |
| CL00142034 | + | I38L/Y39S/G42N/A43V/K44Q/E48N/V273D/S274R/G275A/T276P/T277L/C278A/T279P/K280S/L281* |
| CL00142121 | + | I38L/Y39S/G42N/A43V/K44Q/E48N/G275N |
| CL00142161 | ++ | I38L/Y39S/G42N/A43V/K44Q/E48N/W284T |
| CL00142306 | + | I38L/Y39S/G42N/A43V/K44Q/E48N/L293T |
| CL00142324 | + | I38L/Y39S/G42N/A43V/K44Q/E48N/T276G/K280S/L281* |
| CL00142362 | + | I38L/Y39S/G42N/A43V/K44Q/E48N/L293N |
| CL00142429 | + | I38L/Y39S/G42N/A43V/K44Q/E48N/L281S/Q287H |
| CL00142450 | + | I38L/Y39S/G42N/A43V/K44Q/E48N/T270* |
| CL00142466 | + | I38L/Y39S/G42N/A43V/K44Q/E48N/W258S |
| CL00142468 | + | I38L/Y39S/G42N/A43V/K44Q/E48N/S286G |
| CL00142490 | + | I38L/Y39S/G42N/A43V/K44Q/E48N/L293V |
| CL00145164 | ++ | D2N/A23D/I38L/Y39S/G42N/A43V/K44Q/E48N/S54T/V102Q/A161P/W258S/T277D/W284M/I291A |
| CL00145180 | + | A23D/I38L/Y39S/G42N/A43V/K44Q/E48N/S54T/I291A |
| CL00145218 | + | A23D/I38L/Y39S/G42N/A43V/K44Q/E48N/V102Q/W258S/I291Q |
| CL00145220 | ++ | A23N/I38L/Y39S/G42N/A43V/K44Q/E48N/S54T/N116D/A161P/G275T/L281E |
| CL00145330 | + | I38L/Y39S/G42N/A43V/K44E/E48N/S286A/I291A |
| CL00145352 | + | I38L/Y39S/G42N/A43V/K44Q/E48N/V102Q/N116D |
| CL00145392 | + | A23D/I38L/Y39S/G42N/A43V/K44E/E48N/A77E/N116D/G275T/L281E |
| CL00145406 | + | A23N/I38L/Y39S/G42N/A43V/K44Q/E48N/V102Q/G275T/W284M |
| CL00145419 | + | A23D/I38L/Y39S/G42N/A43V/K44Q/E48N/W258S/I291A |
| CL00145424 | + | I38L/Y39S/G42N/A43V/K44Q/E48N/V102Q/T277D/L281G |
| CL00145450 | + | I38L/Y39S/G42N/A43V/K44Q/E48N/A77E/V102Q/W258S/G275T/T277E/W284M/S286A/I291A |

Figure 4C

| Colony Tracking Number | PF w.r.t. G2P | Active Mutations w.r.t. to G1P |
|---|---|---|
| CL00145465 | ++ | A23D/I38L/Y39S/G42N/A43V/K44Q/E48N/S54T/N116D/W284M/I291Q |
| CL00145493 | + | A23D/I38L/Y39S/G42N/A43T/K44E/E48N/V102Q/N116D/L281G/N282S |
| CL00145509 | + | A23D/I38L/Y39S/G42N/A43V/K44Q/E48N/S54T/V102Q/W258S/W284M/S286A |
| CL00145517 | + | A23D/I38L/Y39S/G42N/A43V/K44Q/E48N/S54T/V102Q/W258S/G275T/T277D/N282S |
| CL00145518 | + | A23N/I38L/Y39S/G42N/A43V/K44Q/E48N/S54T/V102Q/W258S/G275T/N282S |
| CL00145534 | + | A23N/I38L/Y39S/G42N/A43E/K44Q/E48N/S54T/V102Q/N116D/W258S/G275T/L281E/N282S/I291A |
| CL00145559 | ++ | A23D/I38L/Y39S/G42N/A43V/K44Q/E48N/S54T/W258S |
| CL00145591 | + | A23D/I38L/Y39S/G42N/A43V/K44Q/E48N/S54T/L281E |
| CL00145601 | + | A23D/I38L/Y39S/G42N/K44Q/E48N/A77E/N116D/L281E/I291A |
| CL00145610 | + | S17G/I38L/Y39S/G42N/A43V/K44Q/E48N/S54T/A77E/V102Q/G275T |
| CL00145622 | + | A23D/I38L/Y39S/G42N/A43S/K44Q/E48N/S54T/N116D/W258S/G275T/L281E/I291Q |
| CL00145624 | + | I38L/Y39S/G42N/A43V/K44Q/E48N/S54T/G275T/T277D/L281G/N282S/I291A |
| CL00145626 | ++ | A23D/I38L/Y39S/G42N/A43V/K44Q/E48N/S54T/V102Q/N116D/W258S/L281G/I291A |
| CL00145648 | + | A23D/I38L/Y39S/G42N/A43V/K44Q/E48N/N116D/G275T/L281E/N282S/I291A |
| CL00145685 | + | A23D/I38L/Y39S/G42N/A43V/K44Q/E48N/S54T/N116D/A161P/L281E/N282S |
| CL00145701 | + | S17G/I38L/Y39S/G42N/A43T/K44Q/E48N/S54T/V102Q/N116D/A161P/L281E/N282S |
| CL00145710 | ++ | A23D/I38L/Y39S/G42N/A43V/K44Q/E48N/S54T/N116D/A161P/W258S/W284M/I291A |
| CL00145714 | + | A23D/I38L/Y39S/G42N/A43V/K44Q/E48N/V102Q/A161P/W258S |
| CL00145721 | + | A23N/I38L/Y39S/G42N/A43S/K44Q/E48N/S54T/N116D/S286A/I291A |
| CL00145722 | + | A23D/I38L/Y39S/G42N/A43V/K44Q/E48N/S54T/A77E/V102Q/G275T/T277D/W284M/I291Q |
| CL00145728 | + | S17G/A23N/I38L/Y39S/G42N/A43V/K44Q/E48N/S54T/V102Q/W258S/W284M/I291Q |

Figure 4D

| Colony Tracking Number | PF w.r.t. G2P | Active Mutations w.r.t. to G1P |
|---|---|---|
| CL00145731 | ++ | S17G/I38L/Y39S/G42N/A43S/K44Q/E48N/S54T/V102Q/N116D/A161P/W258S/N282S/W284M/I291A |
| CL00145732 | + | A23D/I38L/Y39S/G42N/A43V/K44Q/E48N/A77E/N116D/W258S/L281E |
| CL00145735 | + | A23D/I38L/Y39S/G42N/A43V/K44Q/E48N/S54T/V102Q/N116D/W258S/G275T/T277E |
| CL00145736 | + | A23N/I38L/Y39S/G42N/A43V/K44Q/E48N/S54T/A77E/V102Q/A161P/W258S/W284M |
| CL00145737 | + | A23N/I38L/Y39S/G42N/A43V/K44Q/E48N/A161P/G275T/L281E/N282S/I291A |
| CL00145738 | + | S17G/A23D/I38L/Y39S/G42N/A43V/K44Q/E48N/S54T/A77E/V102Q/N116D/A161P/L281G |
| CL00145739 | + | A23D/I38L/Y39S/G42N/A43V/K44Q/E48N/S54T/A77E/T277E/L281E/S286A |
| CL00145747 | + | I38L/Y39S/G42N/K44E/E48N/S54T/N116D/W258S/G275T/W284M/I291Q |
| CL00145750 | + | S17G/A23N/I38L/Y39S/G42N/A43E/K44E/E48N/N116D/W258S/G275T/W284M/S286A |
| CL00145754 | + | A23N/I38L/Y39S/G42N/A43S/K44Q/E48N/S54T/A77E/I291Q |
| CL00145761 | + | A23D/I38L/Y39S/G42N/A43V/K44Q/E48N/S54T/V102Q/N116D/A161P/T277D/W284M/I291Q |
| CL00145762 | ++ | S17G/A23N/I38L/Y39S/G42N/A43V/K44Q/E48N/S54T/W258S/G275T/T277E |
| CL00145765 | + | A23N/I38L/Y39S/G42N/A43V/K44Q/E48N/S54T/V102Q/W258S/T277D/L281E |
| CL00145773 | + | A23D/I38L/Y39S/G42N/A43T/K44Q/E48N/A77E/V102Q/N116D/W258S/G275T/L281E/I291A |
| CL00145795 | + | S17G/A23D/I38L/Y39S/G42N/A43V/K44Q/E48N/S54T/V102Q/W258S/L281E |
| CL00145797 | + | A23N/I38L/Y39S/G42N/A43V/K44Q/E48N/A77E/N116D/R195S/W258S/T277E/N282S/I291A |
| CL00145804 | + | A23N/I38L/Y39S/G42N/A43V/K44Q/E48N/A77E/V102Q/W284M/S286A/I291A |
| CL00145822 | + | S17G/A23N/I38L/Y39S/G42N/A43V/K44Q/E48N/V102Q/N116D/A161P/W258S |
| CL00145830 | + | S17G/A23D/I38L/Y39S/G42N/A43V/K44Q/E48N/V102Q/A161P/T277D/W284M |
| CL00145841 | + | A23D/I38L/Y39S/G42N/A43V/K44Q/E48N/S54T/A77E/A161P/W258S/W284M/I291Q |
| CL00145843 | + | A23N/I38L/Y39S/G42N/A43E/K44Q/E48N/S54T/A77E/N116D/W284M/S286A/I291Q |

Figure 4E

| Colony Tracking Number | PF w.r.t. G2P | Active Mutations w.r.t. to G1P |
|---|---|---|
| CL00145846 | + | A23N/I38L/Y39S/G42N/A43E/K44Q/E48N/S54T/A77E/A161P/G275T/N282S/I291Q |
| CL00145847 | + | S17G/A23D/I38L/Y39S/G42N/A43T/K44E/E48N/A77E/V102Q/A161P/G275T/N282S/I291A |
| CL00145852 | + | I38L/Y39S/G42N/A43V/K44Q/E48N/S54T/A77E/S286A/I291A |
| CL00145853 | + | S17G/A23D/I38L/Y39S/G42N/A43V/K44Q/E48N/A77E/V102Q/A161P/W258S/L281E/I291Q |
| CL00145859 | ++ | A23D/I38L/Y39S/G42N/A43V/K44Q/E48N/S54T/N116D/A161P/W258S/G275T/L281E/I291A |
| CL00145860 | + | S17G/I38L/Y39S/G42N/A43V/K44Q/E48N/S54T/V102Q/N116D/A161P/W258S/W284M/I291A |
| CL00145863 | + | A23N/I38L/Y39S/G42N/A43V/K44Q/E48N/S54T/V102Q/W258S/N282S/I291A |
| CL00145864 | + | A23N/I38L/Y39S/G42N/A43V/K44Q/E48N/S54T/A161P/G275T/L281G/I291Q |
| CL00145873 | + | A23D/I38L/Y39S/G42N/A43V/K44Q/E48N/S54T/N116D/W258S/G275T/N282S/I291A |
| CL00145911 | + | I38L/Y39S/G42N/A43V/K44Q/E48N/W284M/I291Q |
| CL00145926 | + | S17G/A23N/I38L/Y39S/G42N/A43V/K44Q/E48N/A77E/V102Q/A161P/W284M/I291Q |
| CL00145934 | ++ | A23D/I38L/Y39S/G42N/A43V/K44Q/E48N/S54T/A77E/W258S/T277D/W284M/I291A |
| CL00145969 | + | A23N/I38L/Y39S/G42N/A43E/K44E/E48N/S54T/A77E/V102Q/N116D/W258S/W284M/I291Q |
| CL00145973 | + | S17G/A23N/I38L/Y39S/G42N/A43S/K44E/E48N/A77E/V102Q/G275T |
| CL00146011 | + | A23N/I38L/Y39S/G42N/A43V/K44Q/E48N/T277E/W284M |
| CL00146014 | + | A23D/I38L/Y39S/G42N/A43V/K44Q/E48N/S54T/V102Q/N116D/W258S/G275T/T277E/L281G |
| CL00146031 | + | A23D/I38L/Y39S/G42N/A43V/K44Q/E48N/N116D/W258S/L281G |
| CL00146035 | + | S17G/A23D/I38L/Y39S/G42N/A43V/K44Q/E48N/S54T/A77E/V102Q/S286A/I291Q |
| CL00146040 | + | A23D/I38L/Y39S/G42N/A43S/K44Q/E48N/V102Q/W258S/L281E/N282S/I291A |
| CL00146043 | + | I38L/Y39S/G42N/A43V/K44Q/E48N/G275T/T277E/L281E/N282S/I291A |
| CL00146047 | + | S17G/A23D/I38L/Y39S/G42N/A43V/K44Q/E48N/S54T/W258S/L281G/N282S/I291A |

Figure 4F

| Colony Tracking Number | PF w.r.t. G2P | Active Mutations w.r.t. to G1P |
|---|---|---|
| CL00146131 | + | A23D/I38L/Y39S/G42N/A43V/K44Q/E48N/S54T/V102Q/N116D/W258S/G275T/I291Q |
| CL00146181 | + | D2E/I38L/Y39S/G42N/A43V/K44Q/E48N |
| CL00146209 | + | I38L/Y39S/G42N/A43V/K44Q/E48N/P51E |
| CL00146300 | + | I38L/Y39S/G42N/A43V/K44Q/E48N/E184N |
| CL00146309 | + | I38L/Y39S/G42N/A43V/K44Q/E48N/P51T |
| CL00146349 | + | D2T/I38L/Y39S/G42N/A43V/K44Q/E48N |
| CL00146385 | + | I38L/Y39S/G42N/A43V/K44Q/E48N/T271E |
| CL00146407 | + | I38L/Y39S/G42N/A43V/K44Q/E48N/E184A |
| CL00146472 | + | D2S/I38L/Y39S/G42N/A43V/K44Q/E48N |
| CL00146594 | + | I38L/Y39S/G42N/A43V/K44Q/E48N/E184R |
| CL00146599 | + | I38L/Y39S/G42N/A43V/K44Q/E48N/P51N |
| CL00146686 | + | I38L/Y39S/G42N/A43V/K44Q/E48N/E184K |
| CL00146715 | + | I38L/Y39S/G42N/A43V/K44Q/E48N/E184T |
| CL00146852 | + | D2F/I38L/Y39S/G42N/A43V/K44Q/E48N |
| CL00146863 | + | D2Q/I38L/Y39S/G42N/A43V/K44Q/E48N |
| CL00146985 | + | I38L/Y39S/G42N/A43V/K44Q/E48N/E184S |
| CL00147584 | + | I38L/Y39S/G42N/K44Q/E48N/S54T/N116D/L141S |
| CL00147590 | + | I38L/Y39S/G42N/A43V/K44E/E48N/S54T/N116S/L141S |
| CL00147606 | + | S17G/I38L/Y39S/G42N/A43S/K44Q/E48N/S54T/N116D/L141S |
| CL00147609 | + | S17G/I38L/Y39S/G42N/A43V/K44Q/E48N/S54T/N116E/L141S |
| CL00147616 | + | I38L/Y39S/G42N/A43E/K44Q/E48N/S54T/N116E/L141S |
| CL00147619 | + | S17G/I38L/Y39S/G42N/A43V/K44Q/E48N/S54T/N116D |
| CL00147735 | + | I38L/Y39S/G42N/A43V/K44Q/E48N/S54T/N116D |
| CL00147784 | + | I38L/Y39S/G42N/K44E/E48N/S54T/N116E/N122S/L141S |
| CL00147787 | + | I38L/Y39S/G42N/K44E/E48N/S54T/N116S/N122A |
| CL00147788 | + | S17G/I38L/Y39S/G42N/A43V/K44Q/E48N/S54T |
| CL00147803 | + | S17G/I38L/Y39S/G42N/A43S/K44Q/E48N/S54T/L141S |
| CL00147839 | + | S17G/I38L/Y39S/G42N/K44Q/E48N/N122S/L141S |
| CL00147850 | + | S17G/I38L/Y39S/G42N/A43E/K44Q/E48N/S54T/N122S |
| CL00147859 | + | S17G/I38L/Y39S/G42N/A43V/K44E/E48N/S54T/N116S/N122S |
| CL00147885 | + | I38L/Y39S/G42N/A43V/K44Q/E48N/S54T/N122A |
| CL00147886 | + | I38L/Y39S/G42N/K44E/E48N/N116D/L141S |
| CL00147898 | + | S17G/I38L/Y39S/G42N/A43E/K44Q/E48N/L141S |
| CL00147931 | + | I38L/Y39S/G42N/A43L/K44E/E48N |
| CL00147957 | + | I38L/Y39S/G42N/A43V/K44Q/E48N/S54T/L141S |
| CL00147967 | + | S17G/I38L/Y39S/G42N/A43V/K44Q/E48N/S54T/N116E |
| CL00147972 | + | S17G/I38L/Y39S/G42N/A43V/K44Q/E48N/N122S |

Figure 4G

| Colony Tracking Number | PF w.r.t. G2P | Active Mutations w.r.t. to G1P |
|---|---|---|
| CL00148041 | + | S17G/I38L/Y39S/G42N/K44Q/E48N/S54T/N116E/N122S/L141S |
| CL00148055 | + | I38L/Y39S/G42N/A43V/K44Q/E48N/S54T/N116S/N122S/L141S |
| CL00148069 | + | A23D/S25N/I38L/Y39S/G42N/A43V/K44Q/E48N/F67Y/N180T |
| CL00148070 | + | I38L/Y39S/G42N/A43V/K44Q/E48N/N180T |
| CL00148072 | + | A23N/S25N/I38L/Y39S/G42N/A43V/K44Q/E48N/N180T/A194T |
| CL00148074 | ++ | A23N/I38L/Y39S/G42N/A43V/K44Q/E48N/N180T |
| CL00148084 **(G2V3)** | ++ | A23D/S25N/I38L/Y39S/G42N/A43V/K44Q/E48N/A77E |
| CL00148088 | + | A23N/S25N/I38L/Y39S/G42N/A43V/K44Q/E48N/A77E/N180T |
| CL00148090 | + | S25N/I38L/Y39S/G42N/A43V/K44Q/E48N/F67Y/A161K |
| CL00148092 | +++ | A23D/I38L/Y39S/G42N/A43V/K44Q/E48N/A77Q/N180T |
| CL00148096 | ++ | A23N/I38L/Y39S/G42N/A43V/K44Q/E48N |
| CL00148126 | ++ | A23D/S25N/I38L/Y39S/G42N/A43V/K44Q/E48N/A161K/N180T |
| CL00148153 | + | I38L/Y39S/G42N/A43V/K44Q/E48N/A77Q/N180T |
| CL00148164 | + | A23D/I38L/Y39S/G42N/A43V/K44Q/E48N/A77E/A161K/P164T/N180T |
| CL00148167 | ++ | A23D/S25N/I38L/Y39S/G42N/A43V/K44Q/E48N/A77E/N180T |
| CL00148177 | +++ | A23D/S25N/I38L/Y39S/G42N/A43V/K44Q/E48N/Q66T/F67Y/A77Q/N180T |
| CL00148181 | ++ | A23N/I38L/Y39S/G42N/A43V/K44Q/E48N/V102R/N180T |
| CL00148187 | + | S25N/I38L/Y39S/G42N/A43V/K44Q/E48N/A77E |
| CL00148189 | ++ | A23N/I38L/Y39S/G42N/A43V/K44Q/E48N/A77E/N180T |
| CL00148205 | ++ | A23N/I38L/Y39S/G42N/A43V/K44Q/E48N/A161P/N180T |
| CL00148221 | ++ | A23D/S25N/I38L/Y39S/G42N/A43V/K44Q/E48N/A77E/V102Q/N180T |
| CL00148257 | ++ | S25N/I38L/Y39S/G42N/A43V/K44Q/E48N/N180T/A194T |
| CL00148281 | + | S25N/I38L/Y39S/G42N/A43V/K44Q/E48N/A161P/N180T/A194T |
| CL00148317 | ++ | A23D/S25N/I38L/Y39S/G42N/A43V/K44Q/E48N/A77Q/V102Q/N180T/A194T |

Figure 4H

| Colony Tracking Number | PF w.r.t. G2P | Active Mutations w.r.t. to G1P |
|---|---|---|
| CL00148345 | ++ | A23D/S25N/I38L/Y39S/G42N/A43V/K44Q/E48N/A161P |
| CL00148355 | + | A23D/I38L/Y39S/G42N/A43V/K44Q/E48N/F67Y/N180T |
| CL00148356 | ++ | A23D/I38L/Y39S/G42N/A43V/K44Q/E48N/N180T |
| CL00148357 | + | A23D/I38L/Y39S/G42N/A43V/K44Q/E48N/V102R/N180T |
| CL00148367 | + | A23D/I38L/Y39S/G42N/A43V/K44Q/E48N/A161K/P164T/N180T |
| CL00148375 | ++ | A23N/I38L/Y39S/G42N/A43V/K44Q/E48N/A77E/N180T/A194T |
| CL00148421 | + | A23D/S25N/I38L/Y39S/G42N/A43V/K44Q/E48N/N180T |
| CL00148469 | + | A23D/S25N/I38L/Y39S/G42N/A43V/K44Q/E48N/F67Y/A77E/A161P/P164T/N180T |
| CL00148510 | +++ | S17G/I38L/Y39S/G42N/A43V/K44Q/E48N/N116S/N180T/T277E/W284R/L293T |
| CL00148530 | +++ | A23D/S25N/I38L/Y39S/G42N/A43V/K44Q/E48N/L281E/N282S/N292S/L293G |
| CL00148571 | ++++ | A23D/I38L/Y39S/G42N/A43S/K44E/E48N/A77E/N116S/N122A/N180T/W258S/A259D/G275E/T277D/I291S/L293T |
| CL00148616 | ++ | S17G/A23N/S25N/I38L/Y39S/G42N/A43V/K44Q/E48N/Q66T/F67Y/N116E/L141S/N180T/A194T/G275E/W284G/I291S/N292S |
| CL00148619 | ++++ | A23D/S25N/I38L/Y39S/G42N/A43V/K44Q/E48N/A77Q/W258S/G275T/T277D/W284M/I291S/L293T |
| CL00148657 | ++++ | S17G/A23D/S25N/I38L/Y39S/G42N/A43V/K44Q/E48N/S54T/Q66T/F67Y/A77Q/N116E/L141S/N180T/A194T/W258S/A259D/G275E/L281G/N282S/I291S/N292S/L293T |
| CL00148662 | ++++ | I38L/Y39S/G42N/A43S/K44Q/E48N/S54T/A77Q/L141S/W258S/W284G/I291Q/N292S/L293T |
| CL00148666 | + | I38L/Y39S/G42N/A43V/K44Q/E48N/F67Y/N116D/N122S |
| CL00148741 | + | I38L/Y39S/G42N/A43V/K44Q/E48N/L141S/N180T/A259D/L281G/N282S/L293N |
| CL00148742 | ++ | A23D/I38L/Y39S/G42N/A43E/K44E/E48N/S54T/A77Q/N116D/N122S/L141S/L281G |
| CL00148800 | +++ | S25N/I38L/Y39S/G42N/A43V/K44Q/E48N/S54T/A77Q/N116S/N180T/A194T/A259D/T277D/W284G/I291Q |
| CL00148823 | +++ | S25N/I38L/Y39S/G42N/A43S/K44E/E48N/S54T/A77Q/V102Q/N116D/L141S/A194T/W258S/W284M |

Figure 4I

| Colony Tracking Number | PF w.r.t. G2P | Active Mutations w.r.t. to G1P |
|---|---|---|
| CL00148847 | +++ | A23D/I38L/Y39S/G42N/A43V/K44Q/E48N/F67Y/A77Q/N116S/N180T/W258S/A259D/G275T/T277E/L281K/N282S/I291S/L293N |
| CL00148998 | + | S17G/I38L/Y39S/G42N/K44Q/E48N/Q66T/F67Y/T277D/L281G |
| CL00149009 | +++ | A23N/S25N/I38L/Y39S/G42N/A43S/K44Q/E48N/S54T/F67Y/A77E/N122S/N180T/A259D/W284R |
| CL00149017 | ++ | A23N/I38L/Y39S/G42N/A43V/K44E/E48N/A77Q/N122S/L141S/N180T/W284M/S286A |
| CL00149024 | +++ | S17G/A23D/I38L/Y39S/G42N/A43V/K44Q/E48N/F67Y/G275T/W284M/I291S |
| CL00149028 | ++++ | I38L/Y39S/G42N/A43S/K44Q/E48N/S54T/A77E/N116E/N180T/A259D/W284G/I291Q/L293G |
| CL00149029 | ++++ | S25N/I38L/Y39S/G42N/A43V/K44Q/E48N/S54T/L141S/N180T/G275T/W284M/I291S/L293T |
| CL00149032 | +++ | A23D/I38L/Y39S/G42N/A43T/K44Q/E48N/A77Q/N180T/W258S/G275E/I291Q |
| CL00149054 | +++ | A23N/I38L/Y39S/G42N/A43S/K44Q/E48N/S54T/Q66T/F67Y/N116D/L141S |
| CL00149062 | ++++ | A23N/I38L/Y39S/G42N/A43V/K44Q/E48N/S54T/W258R/A259D/I291S/L293T |
| CL00149066 | ++ | A23N/S25N/I38L/Y39S/G42N/A43E/K44Q/E48N/S54T/Q66T/N116E/N122S/A161P/A259D/L281G |
| CL00149067 | +++ | A23D/S25N/I38L/Y39S/G42N/A43S/K44Q/E48N/S54T/Q66T/L141S/N180T/W258S/A259D/T277D/W284G/Y285* |
| CL00149072 | ++++ | A23D/I38L/Y39S/G42N/A43E/K44Q/E48N/S54T/N116E/W258S/A259D/G275E/T277D |
| CL00149077 | ++ | A23D/I38L/Y39S/G42N/A43V/K44E/E48N/N122A/N180T/T277D/L281E/N282S |
| CL00149092 | ++++ | S25N/I38L/Y39S/G42N/A43V/K44Q/E48N/S54T/A77Q/N116D/W258S/A259D/L281G |
| CL00149095 | + | A23N/I38L/Y39S/G42N/A43L/K44Q/E48N/Q66T/F67Y/A77E/V102Q/N116D/L141S/N180T/W258R/I291S |
| CL00149110 | +++ | S25N/I38L/Y39S/G42N/A43E/K44Q/E48N/S54T/N180T/W258S/G275E |
| CL00149133 | ++ | S17G/I38L/Y39S/G42N/A43S/K44E/E48N/S54T/N180T/W258S/A259D |
| CL00149135 | ++++ | A23N/I38L/Y39S/G42N/A43V/K44Q/E48N/S54T/Q66T/N116S/A259D/W284G/I291S/L293T |
| CL00149146 | +++ | A23N/I38L/Y39S/G42N/A43V/K44Q/E48N/S54T/N116D/A161P/P164T/G275E/L281E |

Figure 4J

| Colony Tracking Number | PF w.r.t. G2P | Active Mutations w.r.t. to G1P |
|---|---|---|
| CL00149153 | ++ | A23D/I38L/Y39S/G42N/A43V/K44Q/E48N/N180T/A259D/G275T/N282S |
| CL00149173 | +++ | A23N/I38L/Y39S/G42N/A43V/K44Q/E48N/S54T/Q66T/F67Y/A161P/W284M/I291Q |
| CL00149174 | +++ | A23D/I38L/Y39S/G42N/A43S/K44Q/E48N/A77Q/N116E/L141S/G275E/T277D/W284R |
| CL00149223 | + | A23D/I38L/Y39S/G42N/A43V/K44Q/E48N/A77Q/N116S/N180T/G275E/T277E |
| CL00149268 | + | S25N/I38L/Y39S/G42N/A43T/K44E/E48N/A77E/N116S/L141S |
| CL00149281 | + | A23N/S25N/I38L/Y39S/G42N/A43V/K44Q/E48N/S54T/F67Y/N122S/L141S/A161P/P164T/A194T/G275T |
| CL00149283 | +++ | S17G/A23D/S25N/I38L/Y39S/G42N/A43S/K44E/E48N/V102Q/N116D/L141S/N180T/L281G/I291Q/N292S/L293N |
| CL00149288 | +++ | S17G/A23N/I38L/Y39S/G42N/A43S/K44Q/E48N/S54T/V102Q/N116E |
| CL00149297 | +++ | A23N/I38L/Y39S/G42N/A43V/K44Q/E48N/F67Y/A77Q/N116D/N180T/G275E/T277D/W284R/I291S/L293N |
| CL00149340 | + | A23D/I38L/Y39S/G42N/A43V/K44Q/E48N/F67Y/A77Q/N122S/L141S/N180T/A194T/W258R/L281K |
| CL00149350 | ++ | A23D/S25N/I38L/Y39S/G42N/A43V/K44Q/E48N/Q66T/N122S/L141S/W284R/C288* |
| CL00149361 | +++ | S25N/I38L/Y39S/G42N/A43S/K44E/E48N/S54T/Q66T/A77E/N116E/N180T/A259D/G275T/T277D/S286A/I291Q/N292S/L293T |
| CL00149384 | +++ | A23D/S25N/I38L/Y39S/G42N/A43V/K44Q/E48N/N116D/A194T/W258S/A259D/G275T/W284G/S286G/L293T |
| CL00149392 | +++ | S17G/A23N/S25N/I38L/Y39S/G42N/A43T/K44Q/E48N/S54T/Q66T/N116E/A259D/W284G |
| CL00149395 | +++ | A23D/S25N/I38L/Y39S/G42N/A43V/K44Q/E48N/N116E/N122S/A194T/T277L/C278A/T279P/K280S/L281* |
| CL00149474 | +++ | S25N/I38L/Y39S/G42N/A43S/K44E/E48N/S54T/N116D/N122S/L141S/N180T/W258R/G275T/T277E/W284M/I291Q/N292S/L293T |
| CL00149488 | +++ | A23D/S25N/I38L/Y39S/G42N/A43V/K44Q/E48N/S54T/Q66T/F67Y/A77Q/N122S/L141S/W258R/N282S |
| CL00149500 | +++ | A23D/I38L/Y39S/G42N/A43V/K44Q/E48N/S54T/N116D/L141S/A161K/N180T/W258R/A259D/G275E/T277D/W284R/I291Q/N292S/L293G |
| CL00149505 | + | I38L/Y39S/G42N/A43V/K44Q/E48N/N116D/L141S/N180T/A259D/N282S |

Figure 4K

| Colony Tracking Number | PF w.r.t. G2P | Active Mutations w.r.t. to G1P |
|---|---|---|
| CL00149547 | +++ | A23D/I38L/Y39S/G42N/A43V/K44Q/E48N/S54T/N116E/L141S/N180T/L281G/N282S |
| CL00149573 | +++ | A23D/I38L/Y39S/G42N/A43S/K44E/E48N/S54T/A77E/N122S/P164T/N180T/A259D/S286A/L293T |
| CL00149594 | +++ | A23D/S25N/I38L/Y39S/G42N/A43V/K44Q/E48N/S54T/L281E/N282S/C288A/T289Q/M290* |
| CL00149602 | + | I38L/Y39S/G42N/A43V/K44Q/E48N/F67Y/N122A/L141S |
| CL00149606 | ++ | A23D/I38L/Y39S/G42N/A43V/K44Q/E48N/L141S |
| CL00149629 | ++ | A23N/S25N/I38L/Y39S/G42N/A43V/K44Q/E48N/F67Y/A77E/N180T/A194T/G275T/L281G |
| CL00149659 | ++++ | I38L/Y39S/G42N/A43V/K44Q/E48N/S54T/P164T/N180T/W258R/A259D/L281G/N282S/I291S/N292S/L293N |
| CL00149684 | + | I38L/Y39S/G42N/A43E/K44Q/E48N/G275E/L281G/N282S/S286A |
| CL00149687 | + | I38L/Y39S/G42N/K44E/E48N/Q66T/F67Y/A77Q/N122A/A161K/S286G/T289K/M290* |
| CL00149714 | ++ | I38L/Y39S/G42N/A43S/K44E/E48N/S54T/F67Y/A77Q/V102R/N116D/N122S/W258R/L281K/I291S/N292S/L293G |
| CL00149730 | + | I38L/Y39S/G42N/A43V/K44Q/E48N/F67Y/G275E/T277E/W284M/Q287S/C288A/T289Q/M290* |
| CL00149740 | ++ | I38L/Y39S/G42N/A43V/K44Q/E48N/Q66T/F67Y/A77Q/N116E/N122A/A161K/N180T/W258S/L293G |
| CL00149763 | ++++ | A23D/S25N/I38L/Y39S/G42N/A43V/K44Q/E48N/S54T/N116D/A161P/N180T/W258R/G275E/T277E/I291S/L293G |
| CL00149768 | + | I38L/Y39S/G42N/A43L/K44Q/E48N/A161P/A194T |
| CL00149779 | + | S17G/I38L/Y39S/G42N/A43V/K44Q/E48N/Q66T/A77E/N116S/G275T/W284M |
| CL00149784 | ++ | S25N/I38L/Y39S/G42N/A43S/K44Q/E48N/Q66T/N116E/L141S/N180T/W258S |
| CL00149797 | + | I38L/Y39S/G42N/A43V/K44Q/E48N/N116S/L141S/P164T/W258S/L281G/N282S/S286A |
| CL00149808 | + | I38L/Y39S/G42N/A43V/K44E/E48N/S54T/Q66T/V102Q/N116S/L141S/N180T/W258R |
| CL00149816 | + | S25N/I38L/Y39S/G42N/A43V/K44Q/E48N/L141S/N180T/A194T/W258S/A259D/L281K/N282S |
| CL00149817 | + | I38L/Y39S/G42N/A43T/K44E/E48N/Q66T/N116E/A161P/P164T/A194T/G275T/L281K/N282S |
| CL00149826 | + | S17G/A23N/I38L/Y39S/G42N/A43V/K44Q/E48N/N116S/N122S/G275T/L281E |

Figure 4L

| Colony Tracking Number | PF w.r.t. G2P | Active Mutations w.r.t. to G1P |
|---|---|---|
| CL00149827 | ++ | A23D/I38L/Y39S/G42N/A43V/K44Q/E48N/N116D/L281K/N282S/I291S/N292S/L293N |
| CL00149845 | +++ | A23D/S25N/I38L/Y39S/G42N/K44Q/E48N/S54T/A77E/V102R/N122S/L141S/A259D/W284G/I291S/L293T |
| CL00149855 | ++ | S17G/I38L/Y39S/G42N/A43V/K44Q/E48N/S54T/A77E/N116D/L141S/L281E |
| CL00149884 | ++ | S17G/I38L/Y39S/G42N/A43V/K44Q/E48N/S54T/A77Q/N116S/L141S/A194T/W258R/L281G |
| CL00149900 | + | I38L/Y39S/G42N/A43S/K44Q/E48N/F67Y |
| CL00149915 | + | S17G/I38L/Y39S/G42N/A43V/K44Q/E48N/I291S/N292S/L293N |
| CL00149920 | ++ | A23D/I38L/Y39S/G42N/A43V/K44Q/E48N/Q66T/A77Q/N122A/L141S/G275T/W284G/S286A |
| CL00149936 | ++ | I38L/Y39S/G42N/A43S/K44E/E48N/S54T/Q66T/N116E/L141S/N180T/W258R/A259D |
| CL00149966 | +++ | A23D/S25N/I38L/Y39S/G42N/A43V/K44Q/E48N/S54T/N180T/L281E/N282S/C288A/T289Q/M290* |
| CL00149975 | ++ | S25N/I38L/Y39S/G42N/A43V/K44Q/E48N/S54T/A77Q/L141S/N180T/G275E/W284G/I291Q/N292S/L293G |
| CL00149977 | ++ | S25N/I38L/Y39S/G42N/A43V/K44Q/E48N/Q66T/A77Q/N116D/A161K/P164T/W284G/N292S/L293G |
| CL00149990 | +++ | A23D/I38L/Y39S/G42N/A43V/K44Q/E48N/S54T/Q66T/F67Y/N122S/N180T/L281G/I291S/N292S/L293G |
| CL00150004 | +++ | A23N/I38L/Y39S/G42N/A43V/K44Q/E48N/S54T/W258S/A259D/L281K/N282S |
| CL00150022 | + | S17G/A23D/S25N/I38L/Y39S/G42N/A43V/K44Q/E48N/Q66T/A77E/A194T |
| CL00150029 | ++ | A23D/S25N/I38L/Y39S/G42N/K44E/E48N/A161P/A194T/G275E/T277D |
| CL00150039 | ++ | S17G/A23N/S25N/I38L/Y39S/G42N/A43S/K44Q/E48N/Q66T/V102Q/N122S/A161P/P164T/L281K/N282S |
| CL00150054 | ++ | S25N/I38L/Y39S/G42N/A43V/K44Q/E48N/S54T/L141S/N180T/W258R/A259D |
| CL00150082 | + | I38L/Y39S/G42N/A43V/K44Q/E48N/L141S/W258R |
| CL00150112 | ++ | A23D/I38L/Y39S/G42N/A43T/K44E/E48N/P164T/N180T/A194T/W258S/A259D/G275T/L281G |
| CL00150132 | ++ | S25N/I38L/Y39S/G42N/A43V/K44Q/E48N/A77Q/N116D/L141S/N180T/W258R/G275E/T277E |
| CL00150152 | +++ | A23D/I38L/Y39S/G42N/A43V/K44Q/E48N/S54T/N116S/G275E/Y285* |

Figure 4M

| Colony Tracking Number | PF w.r.t. G2P | Active Mutations w.r.t. to G1P |
|---|---|---|
| CL00150154 | +++ | A23D/S25N/I38L/Y39S/G42N/A43V/K44Q/E48N/A77E/N180T/A259D/L281K/L293T |
| CL00150157 | +++ | S17G/A23N/I38L/Y39S/G42N/A43V/K44Q/E48N/S54T/N116D/L141S/N180T/G275T/T277E/W284G |
| CL00150190 | + | I38L/Y39S/G42N/A43V/K44Q/E48N/F67Y/A77Q/N116D/A161P |
| CL00150202 | + | A23D/S25N/I38L/Y39S/G42N/A43E/K44E/E48N/V102R/N116S/N122A/L141S/A161K/P164T/A194T/W258R/A259D/L281E |
| CL00150219 | + | I38L/Y39S/G42N/A43T/K44E/E48N/F67Y/N116S/W284R/N292S |
| CL00150244 | +++ | A23D/S25N/I38L/Y39S/G42N/A43V/K44Q/E48N/A77Q/N180T/A194T/W258S/W284G/S286G |
| CL00150251 | ++++ | A23D/I38L/Y39S/G42N/A43V/K44Q/E48N/S54T/N116D/L141S/N180T/G275T/W284R/I291Q/L293N |
| CL00150256 | ++ | S17G/I38L/Y39S/G42N/A43S/K44E/E48N/Q66T/A77Q/V102Q/N116S/N122S/L141S/W258R/A259D/W284R |
| CL00150272 | ++ | A23N/I38L/Y39S/G42N/K44E/E48N/S54T/N180T/A194T/G275T/I291S/N292S/L293N |
| CL00150296 | + | S17G/A23N/I38L/Y39S/G42N/A43L/K44E/E48N/N116S/A161K/A194T |
| CL00150333 | + | S17G/I38L/Y39S/G42N/A43S/K44E/E48N/S54T/A77Q/N116E/N122A/L141S/A161K/P164T/N180T/A194T/T277E/W284G |
| CL00150360 | ++ | S17G/A23D/I38L/Y39S/G42N/A43V/K44Q/E48N/F67Y/V102Q/N116S/N122A/L141S/N180T/A194T/W284R/N292S/L293T |
| CL00150364 | + | A23N/S25N/I38L/Y39S/G42N/A43V/K44Q/E48N |
| CL00150374 | +++ | A23D/S25N/I38L/Y39S/G42N/A43V/K44Q/E48N/S54T/A77Q/N116D/L141S/W258S/A259D/G275T/L281E/N292S/L293T |
| CL00150402 | ++ | A23N/I38L/Y39S/G42N/A43S/K44E/E48N/S54T/A77E/L141S/W258S/G275T |
| CL00150403 | + | A23D/S25N/I38L/Y39S/G42N/A43E/K44Q/E48N/Q66T/F67Y/L141S/N180T |
| CL00150429 | ++ | S17G/I38L/Y39S/G42N/A43V/K44Q/E48N/N122A/A194T/A259D/G275T/T277D/L281K/L293N |
| CL00150432 | +++ | A23N/S25N/I38L/Y39S/G42N/A43V/K44Q/E48N/S54T/N116D/L141S/A161K/N180T/A194T/W258S/A259D/W284R/I291Q/N292S |

Figure 4N

| Colony Tracking Number | PF w.r.t. G2P | Active Mutations w.r.t. to G1P |
|---|---|---|
| CL00150436 | + | S17G/I38L/Y39S/G42N/A43S/K44Q/E48N/Q66T/N116D/N122S/N180T |
| CL00150463 | +++ | A23N/I38L/Y39S/G42N/A43S/K44Q/E48N/S54T/A77E/N116E/N180T/W258S/W284R/S286G |
| CL00150464 | +++ | S17G/I38L/Y39S/G42N/A43V/K44Q/E48N/S54T/A77Q/N116E/L141S/N180T/A194T/W258S/A259D/W284G/S286G/I291Q/L293G |
| CL00150495 | ++ | A23D/I38L/Y39S/G42N/A43S/K44Q/E48N/V102R/W258R/A259D/L281E/N282S |

Figure 5A

| Position | Residue in Ct.EG G1P | Particular variants |
|---|---|---|
| -18 | T | S |
| -5 | F | L |
| -4 | T | A |
| -3 | V | A |
| 2 | D | E, F, N, Q, S, T |
| 17 | S | G |
| 23 | A | D, N, S |
| 25 | S | N |
| 29 | F | Y |
| 33 | R | A |
| 36 | N | Q |
| 38 | I | L |
| 39 | Y | S |
| 42 | G | N |
| 43 | A | E, L, S, T, V |
| 44 | K | E, Q |
| 48 | E | N |
| 51 | P | E, N, S, T |
| 54 | S | T |
| 66 | Q | N, T |
| 67 | F | L, Y |
| 68 | S | A |
| 75 | N | S |
| 77 | A | E, Q |
| 80 | N | S |
| 82 | A | S |
| 90 | K | A |
| 102 | V | Q, R, T |
| 116 | N | D, E, S |
| 121 | L | I |
| 122 | N | A, S |
| 123 | I | M |
| 132 | D | N |
| 135 | T | S |
| 136 | P | S |
| 141 | L | S |
| 144 | E | A |
| 145 | R | Q |
| 153 | S | D |
| 160 | D | A |

Figure 5B

| Position | Residue in Ct.EG G1P | Particular variants |
|---|---|---|
| 161 | A | K, P |
| 164 | P | S, T |
| 167 | Y | Q |
| 174 | L | Q |
| 180 | N | T |
| 184 | E | A, K, N, Q, R, S, T |
| 185 | R | Q |
| 190 | S | A |
| 192 | L | I |
| 194 | A | T |
| 195 | R | S |
| 196 | T | S |
| 204 | G | S |
| 205 | N | S |
| 206 | Y | F |
| 215 | D | *, G |
| 216 | S | N |
| 217 | P | G |
| 218 | S | G |
| 219 | S | T |
| 220 | S | G |
| 221 | S | - |
| 222 | A | - |
| 223 | A | T |
| 228 | S | A |
| 229 | T | P |
| 230 | S | G |
| 231 | Q | S |
| 232 | Q | G |
| 233 | P | Q |
| 234 | Q | T |
| 235 | Q | S |
| 237 | T | G |
| 238 | S | G |
| 239 | S | G |
| 241 | S | - |
| 242 | Q | - |
| 243 | A | - |
| 244 | S | - |
| 245 | V | - |

Figure 5C

| Position | Residue in Ct.EG G1P | Particular variants |
|---|---|---|
| 246 | P | - |
| 247 | T | - |
| 248 | S | - |
| 249 | N | - |
| 250 | P | - |
| 251 | G | - |
| 258 | W | *, R, S |
| 259 | A | *, D |
| 267 | T | S |
| 268 | G | N |
| 269 | C | R, S |
| 270 | T | * |
| 271 | T | E |
| 273 | V | *, D, G |
| 274 | S | R |
| 275 | G | *, A, E, N, T |
| 276 | T | G, H, P, R |
| 277 | T | D, E, L |
| 278 | C | *, A, L |
| 279 | T | H, P, Q |
| 280 | K | Q, S |
| 281 | L | *, A, E, G, K, S |
| 282 | N | E, S |
| 283 | D | * |
| 284 | W | *, G, M, R, T, Y |
| 285 | Y | * |
| 286 | S | A, G |
| 287 | Q | H, S |
| 288 | C | *, A |
| 289 | T | -, K, Q |
| 290 | M | -, * |
| 291 | I | -, A, Q, S |
| 292 | N | -, S |
| 293 | L | G, N, T, V |

Figure 6

| Name | Biostoning performance | Mutation w.r.t. G1P |
|---|---|---|
| G2P | +++ | I38L/Y39S/G42N/A43V/K44Q/E48N |
| G2V1 | ++ | I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292- |
| G2V2 | ++ | A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292- |
| G2V3 (CL00148084) | +++ | A23D/S25N/I38L/Y39S/G42N/A43V/K44Q/E48N/A77E |

Figure 7

| Name | Alkaline depilling performance (high dose) | Alkaline depilling performance (Low dose) |
|---|---|---|
| G2P | + | + |
| G2V1 | ++ | + |
| G2V2 | ++ | + |
| G2V3 | + | + |

Figure 8

| Name | Alkaline decontimination performance | | |
|---|---|---|---|
| | Protein | Sebum | Carbon black |
| G2P | ++ | + | ++ |
| G2V1 | + | + | ++ |
| G2V2 | + | - | ++ |
| G2V3 | ++ | - | + |

Figure 9A

```
                     1                                                50
(SEQ ID NO:11)G1P   MRSTPVLRTA LAAALPFTVL AADGKSTRYW DCCKPSCSWP GKAAVSQPVF
(SEQ ID NO:13)G1V1  MRSTPVLRTA LAAALPFTVL AADGKSTRYW DCCKPSCSWP GKAAVSQPVF
(SEQ ID NO:15)G1V2  MRSTPVLRTA LAAALPFTVL AADGKSTRYW DCCKPSCSWP GKAAVSQPVF
(SEQ ID NO:17)G1V3  MRSTPVLRTA LAAALPFTVL AADGKSTRYW DCCKPSCSWP GKAAVSQPVF
(SEQ ID NO:19)G1V4  MRSSPVLRTA LAAALPLAAL AADGKSTRYW DCCKPSCSWP GKASVNQPVY
(SEQ ID NO:29)G2V1  MRSTPVLRTA LAAALPFTVL AADGKSTRYW DCCKPSCSWP GKAAVSQPVF
(SEQ ID NO:31)G2V2  MRSTPVLRTA LAAALPFTVL AADGKSTRYW DCCKPSCSWP GKADVSQPVF
(SEQ ID NO:33)G2V3  MRSTPVLRTA LAAALPFTVL AADGKSTRYW DCCKPSCSWP GKADVNQPVF

                    51                                               100
(SEQ ID NO:11)G1P   ACDRNFNRIY DFGAKSGCEG GPAYSCADQT PWAVNDQFSY GFAATNIAGG
(SEQ ID NO:13)G1V1  ACDRNFNRIY DFGAKSGCEG GPAYSCADQT PWAVNDQFSY GFAATNIAGG
(SEQ ID NO:15)G1V2  ACDRNFNRLS DFNVQSGCNG GPAYSCADQT PWAVNDQFSY GFAATNIAGG
(SEQ ID NO:17)G1V3  ACDRNFNRIY DFGAKSGCEG GPAYSCADQT PWAVNDQFSY GFAATNIAGG
(SEQ ID NO:19)G1V4  ACDANFQRLS DFNVQSGCNG GSAYSCADQT PWAVNDNLAY GFAATSIAGG
(SEQ ID NO:29)G2V1  ACDRNFNRLS DFNVQSGCNG GPAYSCADQT PWAVNDQFSY GFAATNIAGG
(SEQ ID NO:31)G2V2  ACDRNFNRLS DFNVQSGCNG GPAYTCADQT PWAVNDQFSY GFAATNIAGG
(SEQ ID NO:33)G2V3  ACDRNFNRLS DFNVQSGCNG GPAYSCADQT PWAVNDQFSY GFAATNIEGG

                    101                                              150
(SEQ ID NO:11)G1P   NEASWCCACY KLTFTSGPVA GKVMVVQSTS TGGDLGNNHF DLNIPGGGVG
(SEQ ID NO:13)G1V1  NEASWCCACY KLTFTSGPVA GKVMVVQSTS TGGDLGNNHF DLNIPGGGVG
(SEQ ID NO:15)G1V2  NEASWCCACY KLTFTSGPVA GKVMVVQSTS TGGDLGNNHF DLNIPGGGVG
(SEQ ID NO:17)G1V3  NEASWCCACY KLTFTSGPVA GKVMVVQSTS TGGDLGNNHF DLNIPGGGVG
(SEQ ID NO:19)G1V4  SESSWCCACY ALTFTSGPVA GKTMVVQSTS TGGDLGSNHF DIAMPGGGVG
(SEQ ID NO:29)G2V1  NEASWCCACY KLTFTSGPVA GKVMVVQSTS TGGDLGNNHF DLNIPGGGVG
(SEQ ID NO:31)G2V2  NEASWCCACY KLTFTSGPVA GKVMVVQSTS TGGDLGDNHF DLNIPGGGVG
(SEQ ID NO:33)G2V3  NEASWCCACY KLTFTSGPVA GKVMVVQSTS TGGDLGNNHF DLNIPGGGVG

                    151                                              200
(SEQ ID NO:11)G1P   IFDGCTPQFG GLPGERYGGI SSRSQCDSFP DALKPGCYWR FDWFLNADNP
(SEQ ID NO:13)G1V1  IFDGCTPQFG GLPGERYGGI SSRSQCDSFP DALKPGCYWR FDWFLNADNP
(SEQ ID NO:15)G1V2  IFDGCTPQFG GLPGERYGGI SSRSQCDSFP DALKPGCYWR FDWFLNADNP
(SEQ ID NO:17)G1V3  IFDGCTPQFG GLPGERYGGI SSRSQCDSFP DALKPGCYWR FDWFLNADNP
(SEQ ID NO:19)G1V4  IFNGCSSQFG GLPGAQYGGI SSRDQCDSFP APLKPGCQWR FDWFQNADNP
(SEQ ID NO:29)G2V1  IFDGCTPQFG GLPGERYGGI SSRSQCDSFP DALKPGCYWR FDWFLNADNP
(SEQ ID NO:31)G2V2  IFDGCTPQFG GLPGERYGGI SSRSQCDSFP DALKPGCYWR FDWFLNADNP
(SEQ ID NO:33)G2V3  IFDGCTPQFG GLPGERYGGI SSRSQCDSFP DALKPGCYWR FDWFLNADNP
```

Figure 9B

```
                    201                                                  250
(SEQ ID NO:11)G1P   NFTFERVQCP SELVARTGCK RNDDGNYPVF TPPSGDSPSS SSAAPTSTST
(SEQ ID NO:13)G1V1  NFTFERVQCP SELVARTGCK RNDDGNYPVF TPPSG----- ----------
(SEQ ID NO:15)G1V2  NFTFERVQCP SELVARTGCK RNDDGNYPVF TPPSGDSPSS SSAAPTSTST
(SEQ ID NO:17)G1V3  NFTFERVQCP SELVARTGCK RNDDGNYPVF TPPSGGNGGT G--TPTSTAP
(SEQ ID NO:19)G1V4  TFTFQQVQCP AEIVARSGCK RNDDSSFPVF TPPSGDSPSS SSAAPTSTST
(SEQ ID NO:29)G2V1  NFTFERVQCP SELVARTGCK RNDDGNYPVF TPPSGGNGGT G--TPTSTAP
(SEQ ID NO:31)G2V2  NFTFERVQCP SELVARTGCK RNDDGNYPVF TPPSGGNGGT G--TPTSTAP
(SEQ ID NO:33)G2V3  NFTFERVQCP SELVARTGCK RNDDGNYPVF TPPSGDSPSS SSAAPTSTST

                    251                                                  300
(SEQ ID NO:11)G1P   SQQPQQPTSS SSQASVPTSN PGGCTSQKWA QCGGIGFTGC TTCVSGTTCT
(SEQ ID NO:13)G1V1  ---------- ---------- ---------- ---------- ----------
(SEQ ID NO:15)G1V2  SQQPQQPTSS SSQASVPTSN PGGCTSQKWA QCGGIGFTGC TTCVSGTTCT
(SEQ ID NO:17)G1V3  GSGQTSPGGG S--------- --GCTSQKWA QCGGIGFSGC TTCVSGTTCQ
(SEQ ID NO:19)G1V4  SQQPQQPTSS SSQASVPTSN PGGCTSQKWA QCGGIGFTGC TTCVSGTTCT
(SEQ ID NO:29)G2V1  GSGQTSPGGG S--------- --GCTSQKWA QCGGIGFSGC TTCVSGTTCQ
(SEQ ID NO:31)G2V2  GSGQTSPGGG S--------- --GCTSQKWA QCGGIGFSGC TTCVSGTTCQ
(SEQ ID NO:33)G2V3  SQQPQQPTSS SSQASVPTSN PGGCTSQKWA QCGGIGFTGC TTCVSGTTCT

                    301         314
(SEQ ID NO:11)G1P   KLNDWYSQCT MINL
(SEQ ID NO:13)G1V1  ---------- ----
(SEQ ID NO:15)G1V2  KLNDWYSQCT MINL
(SEQ ID NO:17)G1V3  KLNDYYSQC- ---L
(SEQ ID NO:19)G1V4  KLNDWYSQCT MINL
(SEQ ID NO:29)G2V1  KLNDYYSQC- ---L
(SEQ ID NO:31)G2V2  KLNDYYSQC- ---L
(SEQ ID NO:33)G2V3  KLNDWYSQCT MINL
```

Figure 10A

Ct.EG G1P (wild-type) protein: Mature (SEQ ID NO:1)
ADGKSTRYWDCCKPSCSWPGKAAVSQPVFACDRNFNRIYDFGAKSGCEGGPAYSCADQT
PWAVNDQFSYGFAATNIAGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSGDSPSSSSAAPTSTSTSQQPQQPTSSSS
QASVPTSNPGGCTSQKWAQCGGIGFTGCTTCVSGTTCTKLNDWYSQCTMINL N.A. encoding Ct.EG G1P (wild-type) protein: Mature (SEQ ID NO:2)
GCCGACGGCAAGTCCACTAGGTACTGGGACTGCTGCAAGCCTTCTTGCTCGTGGCCCG
GCAAGGCTGCTGTGAGCCAACCCGTCTTCGCCTGTGACCGCAACTTCAACCGCATCTAT
GACTTCGGTGCCAAGTCTGGCTGCGAGGGCGGTCCGGCCTATTCTTGCGCCGACCAGA
CCCCGTGGGCTGTCAACGACCAATTCTCGTACGGCTTCGCTGCCACCAACATTGCCGGC
GGTAACGAGGCTTCATGGTGCTGCGCTTGCTACAAGCTCACCTTCACCTCGGGACCCGT
GGCCGGCAAGGTCATGGTTGTCCAGTCGACCAGCACGGGCGGTGACCTTGGCAACAAC
CATTTCGACCTGAACATCCCAGGTGGAGGCGTTGGTATCTTCGATGGTTGCACGCCCCA
GTTCGGCGGTCTGCCCGGCGAGCGGTACGGCGGGATCTCGTCGCGCAGCCAGTGCGAC
AGCTTCCCGGATGCCCTCAAGCCTGGCTGCTACTGGCGCTTCGACTGGTTCCTGAACGC
TGACAACCCGAACTTCACCTTCGAGCGCGTCCAGTGTCCTTCCGAGCTTGTTGCCCGCA
CCGGCTGCAAGCGCAATGACGACGGCAACTACCCCGTCTTCACTCCTCCTTCGGGAGA
CAGCCCCAGCAGCAGCAGCGCTGCTCCTACCTCCACCTCGACTTCGCAGCAGCCGCAG
CAGCCGACCTCCAGCAGCTCGCAGGCTTCTGTGCCGACTAGCAACCCTGGTGGCTGCA
CCTCTCAAAAGTGGGCTCAGTGCGGCGGCATTGGCTTCACTGGCTGCACTACCTGCGTC
TCGGGCACCACTTGCACCAAGCTGAATGACTGGTACTCGCAGTGCACAATGATCAACC
TGTAA Ct.EG G1V1 variant protein: Mature (SEQ ID NO:3)
ADGKSTRYWDCCKPSCSWPGKAAVSQPVFACDRNFNRIYDFGAKSGCEGGPAYSCADQT
PWAVNDQFSYGFAATNIAGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSG N.A. encoding Ct.EG G1V1 variant protein: Mature (SEQ ID NO:4)
GCCGACGGCAAGTCCACTAGGTACTGGGACTGCTGCAAGCCTTCTTGCTCGTGGCCCG
GCAAGGCTGCTGTGAGCCAACCCGTCTTCGCCTGTGACCGCAACTTCAACCGCATCTAT
GACTTCGGTGCCAAGTCTGGCTGCGAGGGCGGTCCGGCCTATTCTTGCGCCGACCAGA
CCCCGTGGGCTGTCAACGACCAATTCTCGTACGGCTTCGCTGCCACCAACATTGCCGGC
GGTAACGAGGCTTCATGGTGCTGCGCTTGCTACAAGCTCACCTTCACCTCGGGACCCGT
GGCCGGCAAGGTCATGGTTGTCCAGTCGACCAGCACGGGCGGTGACCTTGGCAACAAC
CATTTCGACCTGAACATCCCAGGTGGAGGCGTTGGTATCTTCGATGGTTGCACGCCCCA
GTTCGGCGGTCTGCCCGGCGAGCGGTACGGCGGGATCTCGTCGCGCAGCCAGTGCGAC
AGCTTCCCGGATGCCCTCAAGCCTGGCTGCTACTGGCGCTTCGACTGGTTCCTGAACGC
TGACAACCCGAACTTCACCTTCGAGCGCGTCCAGTGTCCTTCCGAGCTTGTTGCCCGCA
CCGGCTGCAAGCGCAATGACGACGGCAACTACCCCGTCTTCACTCCTCCTTCGGGATA
A

Figure 10B

Ct.EG G1V2 variant protein: Mature (SEQ ID NO:5)
ADGKSTRYWDCCKPSCSWPGKAAVSQPVFACDRNFNRLSDFNVQSGCNGGPAYSCADQT
PWAVNDQFSYGFAATNIAGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSGDSPSSSSAAPTSTSTSQQPQQPTSSSS
QASVPTSNPGGCTSQKWAQCGGIGFTGCTTCVSGTTCTKLNDWYSQCTMINL N.A. encoding Ct.EG G1V2 variant protein: Mature (SEQ ID NO:6)
GCCGACGGCAAGTCCACTAGGTACTGGGACTGCTGCAAGCCTTCTTGCTCGTGGCCCG
GCAAGGCTGCTGTGAGCCAACCCGTCTTCGCCTGTGACCGCAACTTCAACCGCCTGTCC
GACTTCAATGTCCAGTCTGGCTGCAACGGCGGTCCGGCCTATTCTTGCGCCGACCAGA
CCCCGTGGGCTGTCAACGACCAATTCTCGTACGGCTTCGCTGCCACCAACATTGCCGGC
GGTAACGAGGCTTCATGGTGCTGCGCTTGCTACAAGCTCACCTTCACCTCGGGACCCGT
GGCCGGCAAGGTCATGGTTGTCCAGTCGACCAGCACGGGCGGTGACCTTGGCAACAAC
CATTTCGACCTGAACATCCCAGGTGGAGGCGTTGGTATCTTCGATGGTTGCACGCCCCA
GTTCGGCGGTCTGCCCGGCGAGCGGTACGGCGGGATCTCGTCGCGCAGCCAGTGCGAC
AGCTTCCCGGATGCCCTCAAGCCTGGCTGCTACTGGCGCTTCGACTGGTTCCTGAACGC
TGACAACCCGAACTTCACCTTCGAGCGCGTCCAGTGTCCTTCCGAGCTTGTTGCCCGCA
CCGGCTGCAAGCGCAATGACGACGGCAACTACCCCGTCTTCACTCCTCCTTCGGGAGA
CAGCCCCAGCAGCAGCAGCGCTGCTCCTACCTCCACCTCGACTTCGCAGCAGCCGCAG
CAGCCGACCTCCAGCAGCTCGCAGGCTTCTGTGCCGACTAGCAACCCTGGTGGCTGCA
CCTCTCAAAAGTGGGCTCAGTGCGGCGGCATTGGCTTCACTGGCTGCACTACCTGCGTC
TCGGGCACCACTTGCACCAAGCTGAATGACTGGTACTCGCAGTGCACAATGATCAACC
TGTAA Ct.EG G1V3 variant protein: Mature (SEQ ID NO:7)
ADGKSTRYWDCCKPSCSWPGKAAVSQPVFACDRNFNRIYDFGAKSGCEGGPAYSCADQT
PWAVNDQFSYGFAATNIAGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSGGNGGTGTPTSTAPGSGQTSPGGGSG
CTSQKWAQCGGIGFSGCTTCVSGTTCQKLNDYYSQCL

Figure 10C

N.A. encoding Ct.EG G1V3 variant protein: Mature (SEQ ID NO:8)
GCCGACGGCAAGTCCACTAGGTACTGGGACTGCTGCAAGCCTTCTTGCTCGTGGCCCG
GCAAGGCTGCTGTGAGCCAACCCGTCTTCGCCTGTGACCGCAACTTCAACCGCATCTAT
GACTTCGGTGCCAAGTCTGGCTGCGAGGGCGGTCCGGCCTATTCTTGCGCCGACCAGA
CCCCGTGGGCTGTCAACGACCAATTCTCGTACGGCTTCGCTGCCACCAACATTGCCGGC
GGTAACGAGGCTTCATGGTGCTGCGCTTGCTACAAGCTCACCTTCACCTCGGGACCCGT
GGCCGGCAAGGTCATGGTTGTCCAGTCGACCAGCACGGGCGGTGACCTTGGCAACAAC
CATTTCGACCTGAACATCCCAGGTGGAGGCGTTGGTATCTTCGATGGTTGCACGCCCCA
GTTCGGCGGTCTGCCCGGCGAGCGGTACGGCGGGATCTCGTCGCGCAGCCAGTGCGAC
AGCTTCCCGGATGCCCTCAAGCCTGGCTGCTACTGGCGCTTCGACTGGTTCCTGAACGC
TGACAACCCGAACTTCACCTTCGAGCGCGTCCAGTGTCCTTCCGAGCTTGTTGCCCGCA
CCGGCTGCAAGCGCAATGACGACGGCAACTACCCCGTCTTCACTCCTCCTTCGGGAGG
CAACGGTGGCACCGGCACCCCTACCTCCACTGCCCCCGGCTCCGGTCAGACCTCCCCC
GGCGGTGGTTCCGGTTGCACCTCCCAGAAGTGGGCCCAGTGCGGTGGCATCGGTTTCT
CCGGCTGCACCACTTGCGTCTCCGGCACCACTTGCCAGAAGCTGAACGACTACTACTC
CCAGTGTCTGTAA Ct.EG G1V4 variant protein: Mature (SEQ ID NO:9)
ADGKSTRYWDCCKPSCSWPGKASVNQPVYACDANFQRLSDFNVQSGCNGGSAYSCADQ
TPWAVNDNLAYGFAATSIAGGSESSWCCACYALTFTSGPVAGKTMVVQSTSTGGDLGSN
HFDIAMPGGGVGIFNGCSSQFGGLPGAQYGGISSRDQCDSFPAPLKPGCQWRFDWFQNAD
NPTFTFQQVQCPAEIVARSGCKRNDDSSFPVFTPPSGDSPSSSSAAPTSTSTSQQPQQPTSSSS
QASVPTSNPGGCTSQKWAQCGGIGFTGCTTCVSGTTCTKLNDWYSQCTMINL N.A. encoding Ct.EG G1V4 variant protein: Mature (SEQ ID NO:10)
GCCGATGGCAAGTCGACCCGCTACTGGGACTGTTGCAAGCCGTCGTGCTCGTGGCCCG
GCAAGGCCTCGGTGAACCAGCCCGTCTACGCGTGCGATGCCAACTTCCAGCGCCTGTC
CGACTTCAATGTCCAGTCGGGCTGCAACGGCGGCTCGGCCTACTCCTGCGCCGACCAG
ACTCCCTGGGCGGTGAACGACAATCTCGCCTACGGCTTCGCCGCGACGAGCATCGCCG
GCGGGTCCGAATCCTCGTGGTGCTGCGCCTGCTACGCGCTCACCTTCACTTCCGGTCCC
GTCGCCGGCAAGACAATGGTGGTGCAGTCAACGAGCACTGGCGGCGACCTGGGAAGT
AACCATTTCGATATCGCCATGCCCGGCGGCGGCGTGGGCATCTTCAACGGCTGCAGCT
CGCAGTTCGGCGGCCTCCCCGGCGCTCAATACGGCGGCATTTCGTCGCGCGACCAGTG
CGATTCCTTCCCCGCGCCGCTCAAGCCCGGCTGCCAGTGGCGGTTTGACTGGTTCCAGA
ACGCCGACAACCCGACGTTCACGTTCCAGCAGGTGCAGTGCCCCGCCGAGATCGTTGC
CCGCTCCGGCTGCAAGCGCAACGACGACTCCAGCTTCCCCGTCTTCACCCCCCCAAGC
GGTGACAGCCCCAGCAGCAGCAGCGCTGCTCCTACCTCCACCTCGACTTCGCAGCAGC
CGCAGCAGCCGACCTCCAGCAGCTCGCAGGCTTCTGTGCCGACTAGCAACCCTGGTGG
CTGCACCTCTCAAAAGTGGGCTCAGTGCGGCGGCATTGGCTTCACTGGCTGCACTACCT
GCGTCTCGGGCACCACTTGCACCAAGCTGAATGACTGGTACTCGCAGTGCACAATGAT
CAACCTGTAA

Figure 10D

Ct.EG G1P (wild-type) protein: SP + Mature (SEQ ID NO:11)
MRSTPVLRTALAAALPFTVLAADGKSTRYWDCCKPSCSWPGKAAVSQPVFACDRNFNRIY
DFGAKSGCEGGPAYSCADQTPWAVNDQFSYGFAATNIAGGNEASWCCACYKLTFTSGPV
AGKVMVVQSTSTGGDLGNNHFDLNIPGGGVGIFDGCTPQFGGLPGERYGGISSRSQCDSFP
DALKPGCYWRFDWFLNADNPNFTFERVQCPSELVARTGCKRNDDGNYPVFTPPSGDSPSS
SSAAPTSTSTSQQPQQPTSSSSQASVPTSNPGGCTSQKWAQCGGIGFTGCTTCVSGTTCTKL
NDWYSQCTMINL N.A. encoding Ct.EG G1P (wild-type) protein: SP + Mature (SEQ ID NO:12)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGCTGTGAGCCAACCCGTCTTCGCCTGTGACCGCAACTTCAACCGCAT
CTATGACTTCGGTGCCAAGTCTGGCTGCGAGGGCGGTCCGGCCTATTCTTGCGCCGACC
AGACCCCGTGGGCTGTCAACGACCAATTCTCGTACGGCTTCGCTGCCACCAACATTGC
CGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCA
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGAGACAGCCCCAGCAGCAGCAGCGCTGCTCCTACCTCCACCTCGACTTCGCAGCAG
CCGCAGCAGCCGACCTCCAGCAGCTCGCAGGCTTCTGTGCCGACTAGCAACCCTGGTG
GCTGCACCTCTCAAAAGTGGGCTCAGTGCGGCGGCATTGGCTTCACTGGCTGCACTAC
CTGCGTCTCGGGCACCACTTGCACCAAGCTGAATGACTGGTACTCGCAGTGCACAATG
ATCAACCTGTAA Ct.EG G1V1 variant protein: SP + Mature (SEQ ID NO:13)
MRSTPVLRTALAAALPFTVLAADGKSTRYWDCCKPSCSWPGKAAVSQPVFACDRNFNRIY
DFGAKSGCEGGPAYSCADQTPWAVNDQFSYGFAATNIAGGNEASWCCACYKLTFTSGPV
AGKVMVVQSTSTGGDLGNNHFDLNIPGGGVGIFDGCTPQFGGLPGERYGGISSRSQCDSFP
DALKPGCYWRFDWFLNADNPNFTFERVQCPSELVARTGCKRNDDGNYPVFTPPSG

Figure 10E

N.A. encoding Ct.EG G1V1 variant protein: SP + Mature (SEQ ID NO:14)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGCTGTGAGCCAACCCGTCTTCGCCTGTGACCGCAACTTCAACCGCAT
CTATGACTTCGGTGCCAAGTCTGGCTGCGAGGGCGGTCCGGCCTATTCTTGCGCCGACC
AGACCCCGTGGGCTGTCAACGACCAATTCTCGTACGGCTTCGCTGCCACCAACATTGC
CGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCA
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGATAA Ct.EG G1V2 variant protein: SP + Mature (SEQ ID NO:15)
MRSTPVLRTALAAALPFTVLAADGKSTRYWDCCKPSCSWPGKAAVSQPVFACDRNFNRL
SDFNVQSGCNGGPAYSCADQTPWAVNDQFSYGFAATNIAGGNEASWCCACYKLTFTSGP
VAGKVMVVQSTSTGGDLGNNHFDLNIPGGGVGIFDGCTPQFGGLPGERYGGISSRSQCDSF
PDALKPGCYWRFDWFLNADNPNFTFERVQCPSELVARTGCKRNDDGNYPVFTPPSGDSPS
SSSAAPTSTSTSQQPQQPTSSSSQASVPTSNPGGCTSQKWAQCGGIGFTGCTTCVSGTTCTK
LNDWYSQCTMINL

Figure 10F

N.A. encoding Ct.EG G1V2 variant protein: SP + Mature (SEQ ID NO:16)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGCTGTGAGCCAACCCGTCTTCGCCTGTGACCGCAACTTCAACCGCCT
GTCCGACTTCAATGTCCAGTCTGGCTGCAACGGCGGTCCGGCCTATTCTTGCGCCGACC
AGACCCCGTGGGCTGTCAACGACCAATTCTCGTACGGCTTCGCTGCCACCAACATTGC
CGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCA
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGAGACAGCCCCAGCAGCAGCAGCGCTGCTCCTACCTCCACCTCGACTTCGCAGCAG
CCGCAGCAGCCGACCTCCAGCAGCTCGCAGGCTTCTGTGCCGACTAGCAACCCTGGTG
GCTGCACCTCTCAAAAGTGGGCTCAGTGCGGCGGCATTGGCTTCACTGGCTGCACTAC
CTGCGTCTCGGGCACCACTTGCACCAAGCTGAATGACTGGTACTCGCAGTGCACAATG
ATCAACCTGTAA Ct.EG G1V3 variant protein: SP + Mature (SEQ ID NO:17)
MRSTPVLRTALAAALPFTVLAADGKSTRYWDCCKPSCSWPGKAAVSQPVFACDRNFNRIY
DFGAKSGCEGGPAYSCADQTPWAVNDQFSYGFAATNIAGGNEASWCCACYKLTFTSGPV
AGKVMVVQSTSTGGDLGNNHFDLNIPGGGVGIFDGCTPQFGGLPGERYGGISSRSQCDSFP
DALKPGCYWRFDWFLNADNPNFTFERVQCPSELVARTGCKRNDDGNYPVFTPPSGGNGG
TGTPTSTAPGSGQTSPGGGSGCTSQKWAQCGGIGFSGCTTCVSGTTCQKLNDYYSQCL

Figure 10G

N.A. encoding Ct.EG G1V3 variant protein: SP + Mature (SEQ ID NO:18)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGCTGTGAGCCAACCCGTCTTCGCCTGTGACCGCAACTTCAACCGCAT
CTATGACTTCGGTGCCAAGTCTGGCTGCGAGGGCGGTCCGGCCTATTCTTGCGCCGACC
AGACCCCGTGGGCTGTCAACGACCAATTCTCGTACGGCTTCGCTGCCACCAACATTGC
CGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCA
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGAGGCAACGGTGGCACCGGCACCCCTACCTCCACTGCCCCCGGCTCCGGTCAGACC
TCCCCCGGCGGTGGTTCCGGTTGCACCTCCCAGAAGTGGGCCCAGTGCGGTGGCATCG
GTTTCTCCGGCTGCACCACTTGCGTCTCCGGCACCACTTGCCAGAAGCTGAACGACTAC
TACTCCCAGTGTCTGTAA Ct.EG G1V4 variant protein: SP + Mature (SEQ ID NO:19)
MRSSPVLRTALAAALPLAALAADGKSTRYWDCCKPSCSWPGKASVNQPVYACDANFQRL
SDFNVQSGCNGGSAYSCADQTPWAVNDNLAYGFAATSIAGGSESSWCCACYALTFTSGPV
AGKTMVVQSTSTGGDLGSNHFDIAMPGGGVGIFNGCSSQFGGLPGAQYGGISSRDQCDSFP
APLKPGCQWRFDWFQNADNPTFTFQQVQCPAEIVARSGCKRNDDSSFPVFTPPSGDSPSSS
SAAPTSTSTSQQPQQPTSSSSQASVPTSNPGGCTSQKWAQCGGIGFTGCTTCVSGTTCTKLN
DWYSQCTMINL

Figure 10H

N.A. encoding Ct.EG G1V4 variant protein: SP + Mature (SEQ ID NO:20)
ATGCGTTCCTCCCCCGTCCTCCGCACGGCCCTGGCCGCTGCCCTCCCCCTGGCCGCCCT
CGCTGCCGATGGCAAGTCGACCCGCTACTGGGACTGTTGCAAGCCGTCGTGCTCGTGG
CCCGGCAAGGCCTCGGTGAACCAGCCCGTCTACGCGTGCGATGCCAACTTCCAGCGCC
TGTCCGACTTCAATGTCCAGTCGGGCTGCAACGGCGGCTCGGCCTACTCCTGCGCCGA
CCAGACTCCCTGGGCGGTGAACGACAATCTCGCCTACGGCTTCGCCGCGACGAGCATC
GCCGGCGGGTCCGAATCCTCGTGGTGCTGCGCCTGCTACGCGCTCACCTTCACTTCCGG
TCCCGTCGCCGGCAAGACAATGGTGGTGCAGTCAACGAGCACTGGCGGCGACCTGGG
AAGTAACCATTTCGATATCGCCATGCCCGGCGGCGGCGTGGGCATCTTCAACGGCTGC
AGCTCGCAGTTCGGCGGCCTCCCCGGCGCTCAATACGGCGGCATTTCGTCGCGCGACC
AGTGCGATTCCTTCCCCGCGCCGCTCAAGCCCGGCTGCCAGTGGCGGTTTGACTGGTTC
CAGAACGCCGACAACCCGACGTTCACGTTCCAGCAGGTGCAGTGCCCCGCCGAGATCG
TTGCCCGCTCCGGCTGCAAGCGCAACGACGACTCCAGCTTCCCCGTCTTCACCCCCCCA
AGCGGTGACAGCCCCAGCAGCAGCAGCGCTGCTCCTACCTCCACCTCGACTTCGCAGC
AGCCGCAGCAGCCGACCTCCAGCAGCTCGCAGGCTTCTGTGCCGACTAGCAACCCTGG
TGGCTGCACCTCTCAAAAGTGGGCTCAGTGCGGCGGCATTGGCTTCACTGGCTGCACT
ACCTGCGTCTCGGGCACCACTTGCACCAAGCTGAATGACTGGTACTCGCAGTGCACAA
TGATCAACCTGTAA Signal peptide (wild-type) (SEQ ID NO:21)
MRSTPVLRTALAAALPFTVLA Variant signal peptide (SEQ ID NO:22)
MRSSPVLRTALAAALPLAALA

Figure 10I

Ct.EG G2V1 protein: Mature (SEQ ID NO:23)
ADGKSTRYWDCCKPSCSWPGKAAVSQPVFACDRNFNRLSDFNVQSGCNGGPAYSCADQT
PWAVNDQFSYGFAATNIAGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSGGNGGTGTPTSTAPGSGQTSPGGGSG
CTSQKWAQCGGIGFSGCTTCVSGTTCQKLNDYYSQCL N.A. encoding Ct.EG G2V1 protein: Mature (SEQ ID NO:24)
GCCGACGGCAAGTCCACTAGGTACTGGGACTGCTGCAAGCCTTCTTGCTCGTGGCCCG
GCAAGGCTGCTGTGAGCCAACCCGTCTTCGCCTGTGACCGCAACTTCAACCGCCTGTCC
GACTTCAATGTCCAGTCTGGCTGCAACGGCGGTCCGGCCTATTCTTGCGCCGACCAGA
CCCCGTGGGCTGTCAACGACCAATTCTCGTACGGCTTCGCTGCCACCAACATTGCCGGC
GGTAACGAGGCTTCATGGTGCTGCGCTTGCTACAAGCTCACCTTCACCTCGGGACCCGT
GGCCGGCAAGGTCATGGTTGTCCAGTCGACCAGCACGGGCGGTGACCTTGGCAACAAC
CATTTCGACCTGAACATCCCAGGTGGAGGCGTTGGTATCTTCGATGGTTGCACGCCCCA
GTTCGGCGGTCTGCCCGGCGAGCGGTACGGCGGGATCTCGTCGCGCAGCCAGTGCGAC
AGCTTCCCGGATGCCCTCAAGCCTGGCTGCTACTGGCGCTTCGACTGGTTCCTGAACGC
TGACAACCCGAACTTCACCTTCGAGCGCGTCCAGTGTCCTTCCGAGCTTGTTGCCCGCA
CCGGCTGCAAGCGCAATGACGACGGCAACTACCCCGTCTTCACTCCTCCTTCGGGAGG
CAACGGTGGCACCGGGACGCCCACGTCGACTGCGCCTGGGTCGGGCCAGACGTCTCCC
GGCGGCGGCAGTGGCTGCACCTCTCAAAAGTGGGCTCAGTGCGGCGGCATTGGCTTCA
GCGGCTGCACTACCTGCGTCTCGGGCACCACTTGCCAGAAGCTGAATGACTACTACTC
GCAGTGCCTGTAA Ct.EG G2V2 variant protein: Mature (SEQ ID NO:25)
ADGKSTRYWDCCKPSCSWPGKAAVSQPVFACDRNFNRLSDFNVQSGCNGGPAYSCADQT
PWAVNDQFSYGFAATNIAGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSGGNGGTGTPTSTAPGSGQTSPGGGSG
CTSQKWAQCGGIGFSGCTTCVSGTTCQKLNDYYSQCL N.A. encoding Ct.EG G2V2 protein: Mature (SEQ ID NO:26)
GCCGACGGCAAGTCCACTAGGTACTGGGACTGCTGCAAGCCTTCTTGCTCGTGGCCCG
GCAAGGCTGATGTGAGCCAACCCGTCTTCGCCTGTGACCGCAACTTCAACCGCCTGTC
CGACTTCAATGTCCAGTCTGGCTGCAACGGCGGTCCGGCCTATACTTGCGCCGACCAG
ACCCCGTGGGCTGTCAACGACCAATTCTCGTACGGCTTCGCTGCCACCAACATTGCCG
GCGGTAACGAGGCTTCATGGTGCTGCGCTTGCTACAAGCTCACCTTCACCTCGGGACC
CGTGGCCGGCAAGGTCATGGTTGTCCAGTCGACCAGCACGGGCGGTGACCTTGGCGAC
AACCATTTCGACCTGAACATCCCAGGTGGAGGCGTTGGTATCTTCGATGGTTGCACGC
CCCAGTTCGGCGGTCTGCCCGGCGAGCGGTACGGCGGGATCTCGTCGCGCAGCCAGTG
CGACAGCTTCCCGGATGCCCTCAAGCCTGGCTGCTACTGGCGCTTCGACTGGTTCCTGA
ACGCTGACAACCCGAACTTCACCTTCGAGCGCGTCCAGTGTCCTTCCGAGCTTGTTGCC
CGCACCGGCTGCAAGCGCAATGACGACGGCAACTACCCCGTCTTCACTCCTCCTTCGG
GAGGCAACGGTGGCACCGGGACGCCCACGTCGACTGCGCCTGGGTCGGGCCAGACGT
CTCCCGGCGGCGGCAGTGGCTGCACCTCTCAAAAGTGGGCTCAGTGCGGCGGCATTGG
CTTCAGCGGCTGCACTACCTGCGTCTCGGGCACCACTTGCCAGAAGCTGAATGACTAC
TACTCGCAGTGCCTGTAA

Figure 10J

Ct.EG G2V3 protein: Mature (SEQ ID NO:27)
ADGKSTRYWDCCKPSCSWPGKADVNQPVFACDRNFNRLSDFNVQSGCNGGPAYSCADQ
TPWAVNDQFSYGFAATNIEGGNEASWCCACYKLTFTSGPVAGKVMVVQSTSTGGDLGNN
HFDLNIPGGGVGIFDGCTPQFGGLPGERYGGISSRSQCDSFPDALKPGCYWRFDWFLNADN
PNFTFERVQCPSELVARTGCKRNDDGNYPVFTPPSGDSPSSSSAAPTSTSTSQQPQQPTSSSS
QASVPTSNPGGCTSQKWAQCGGIGFTGCTTCVSGTTCTKLNDWYSQCTMINL N.A. encoding Ct.EG G2V3 protein: Mature (SEQ ID NO:28)
GCCGACGGCAAGTCCACTAGGTACTGGGACTGCTGCAAGCCTTCTTGCTCGTGGCCCG
GCAAGGCTGATGTGAACCAACCCGTCTTCGCCTGTGACCGCAACTTCAACCGCCTGTC
CGACTTCAATGTCCAGTCTGGCTGCAACGGCGGTCCGGCCTATTCTTGCGCCGACCAG
ACCCCGTGGGCTGTCAACGACCAATTCTCGTACGGCTTCGCTGCCACCAACATTGAAG
GCGGTAACGAGGCTTCATGGTGCTGCGCTTGCTACAAGCTCACCTTCACCTCGGGACC
CGTGGCCGGCAAGGTCATGGTTGTCCAGTCGACCAGCACGGGCGGTGACCTTGGCAAC
AACCATTTCGACCTGAACATCCCAGGTGGAGGCGTTGGTATCTTCGATGGTTGCACGC
CCCAGTTCGGCGGTCTGCCCGGCGAGCGGTACGGCGGGATCTCGTCGCGCAGCCAGTG
CGACAGCTTCCCGGATGCCCTCAAGCCTGGCTGCTACTGGCGCTTCGACTGGTTCCTGA
ACGCTGACAACCCGAACTTCACCTTCGAGCGCGTCCAGTGTCCTTCCGAGCTTGTTGCC
CGCACCGGCTGCAAGCGCAATGACGACGGCAACTACCCCGTCTTCACTCCTCCTTCGG
GAGACAGCCCCAGCAGCAGCAGCGCTGCTCCTACCTCCACCTCGACTTCGCAGCAGCC
GCAGCAGCCGACCTCCAGCAGCTCGCAGGCTTCTGTGCCGACTAGCAACCCTGGTGGC
TGCACCTCTCAAAAGTGGGCTCAGTGCGGCGGCATTGGCTTCACTGGCTGCACTACCT
GCGTCTCGGGCACCACTTGCACCAAGCTGAATGACTGGTACTCGCAGTGCACAATGAT
CAACCTGTAA

Figure 10K

Ct.EG G2V1 protein: SP + Mature (SEQ ID NO:29)
MRSTPVLRTALAAALPFTVLAADGKSTRYWDCCKPSCSWPGKAAVSQPVFACDRNFNRL
SDFNVQSGCNGGPAYSCADQTPWAVNDQFSYGFAATNIAGGNEASWCCACYKLTFTSGP
VAGKVMVVQSTSTGGDLGNNHFDLNIPGGGVGIFDGCTPQFGGLPGERYGGISSRSQCDSF
PDALKPGCYWRFDWFLNADNPNFTFERVQCPSELVARTGCKRNDDGNYPVFTPPSGGNG
GTGTPTSTAPGSGQTSPGGGSGCTSQKWAQCGGIGFSGCTTCVSGTTCQKLNDYYSQCL N.A. encoding Ct.EG G2V1 protein: SP + Mature (SEQ ID NO:30)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGCTGTGAGCCAACCCGTCTTCGCCTGTGACCGCAACTTCAACCGCCT
GTCCGACTTCAATGTCCAGTCTGGCTGCAACGGCGGTCCGGCCTATTCTTGCGCCGACC
AGACCCCGTGGGCTGTCAACGACCAATTCTCGTACGGCTTCGCTGCCACCAACATTGC
CGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCA
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGAGGCAACGGTGGCACCGGGACGCCCACGTCGACTGCGCCTGGGTCGGGCCAGAC
GTCTCCCGGCGGCGGCAGTGGCTGCACCTCTCAAAAGTGGGCTCAGTGCGGCGGCATT
GGCTTCAGCGGCTGCACTACCTGCGTCTCGGGCACCACTTGCCAGAAGCTGAATGACT
ACTACTCGCAGTGCCTGTAA

Figure 10L

Ct.EG G2V2 variant protein: SP + Mature (SEQ ID NO:31)
MRSTPVLRTALAAALPFTVLAADGKSTRYWDCCKPSCSWPGKAAVSQPVFACDRNFNRL
SDFNVQSGCNGGPAYSCADQTPWAVNDQFSYGFAATNIAGGNEASWCCACYKLTFTSGP
VAGKVMVVQSTSTGGDLGNNHFDLNIPGGGVGIFDGCTPQFGGLPGERYGGISSRSQCDSF
PDALKPGCYWRFDWFLNADNPNFTFERVQCPSELVARTGCKRNDDGNYPVFTPPSGGNG
GTGTPTSTAPGSGQTSPGGGSGCTSQKWAQCGGIGFSGCTTCVSGTTCQKLNDYYSQCL N.A. encoding Ct.EG G2V2 protein: SP + Mature (SEQ ID NO:32)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGATGTGAGCCAACCCGTCTTCGCCTGTGACCGCAACTTCAACCGCCT
GTCCGACTTCAATGTCCAGTCTGGCTGCAACGGCGGTCCGGCCTATACTTGCGCCGACC
AGACCCCGTGGGCTGTCAACGACCAATTCTCGTACGGCTTCGCTGCCACCAACATTGC
CGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCG
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGAGGCAACGGTGGCACCGGGACGCCCACGTCGACTGCGCCTGGGTCGGGCCAGAC
GTCTCCCGGCGGCGGCAGTGGCTGCACCTCTCAAAAGTGGGCTCAGTGCGGCGGCATT
GGCTTCAGCGGCTGCACTACCTGCGTCTCGGGCACCACTTGCCAGAAGCTGAATGACT
ACTACTCGCAGTGCCTGTAA

Figure 10M

Ct.EG G2V3 protein: SP + Mature (SEQ ID NO:33)
MRSTPVLRTALAAALPFTVLAADGKSTRYWDCCKPSCSWPGKADVNQPVFACDRNFNRL
SDFNVQSGCNGGPAYSCADQTPWAVNDQFSYGFAATNIEGGNEASWCCACYKLTFTSGP
VAGKVMVVQSTSTGGDLGNNHFDLNIPGGGVGIFDGCTPQFGGLPGERYGGISSRSQCDSF
PDALKPGCYWRFDWFLNADNPNFTFERVQCPSELVARTGCKRNDDGNYPVFTPPSGDSPS
SSSAAPTSTSTSQQPQQPTSSSSQASVPTSNPGGCTSQKWAQCGGIGFTGCTTCVSGTTCTK
LNDWYSQCTMINL N.A. encoding Ct.EG G2V3 protein: SP + Mature (SEQ ID NO:34)
ATGCGGTCGACTCCTGTTCTCCGTACCGCCCTTGCGGCTGCTCTCCCCTTCACTGTCCTG
GCTGCCGACGGCAAGTCCACTAGGTACTGGGACTGCTGCAAGCCTTCTTGCTCGTGGC
CCGGCAAGGCTGATGTGAACCAACCCGTCTTCGCCTGTGACCGCAACTTCAACCGCCT
GTCCGACTTCAATGTCCAGTCTGGCTGCAACGGCGGTCCGGCCTATTCTTGCGCCGACC
AGACCCCGTGGGCTGTCAACGACCAATTCTCGTACGGCTTCGCTGCCACCAACATTGA
AGGCGGTAACGAGGCTTCATGGTGCTGCGCTTGCTACAAGCTCACCTTCACCTCGGGA
CCCGTGGCCGGCAAGGTCATGGTTGTCCAGTCGACCAGCACGGGCGGTGACCTTGGCA
ACAACCATTTCGACCTGAACATCCCAGGTGGAGGCGTTGGTATCTTCGATGGTTGCAC
GCCCCAGTTCGGCGGTCTGCCCGGCGAGCGGTACGGCGGGATCTCGTCGCGCAGCCAG
TGCGACAGCTTCCCGGATGCCCTCAAGCCTGGCTGCTACTGGCGCTTCGACTGGTTCCT
GAACGCTGACAACCCGAACTTCACCTTCGAGCGCGTCCAGTGTCCTTCCGAGCTTGTTG
CCCGCACCGGCTGCAAGCGCAATGACGACGGCAACTACCCCGTCTTCACTCCTCCTTC
GGGAGACAGCCCCAGCAGCAGCAGCGCTGCTCCTACCTCCACCTCGACTTCGCAGCAG
CCGCAGCAGCCGACCTCCAGCAGCTCGCAGGCTTCTGTGCCGACTAGCAACCCTGGTG
GCTGCACCTCTCAAAAGTGGGCTCAGTGCGGCGGCATTGGCTTCACTGGCTGCACTAC
CTGCGTCTCGGGCACCACTTGCACCAAGCTGAATGACTGGTACTCGCAGTGCACAATG
ATCAACCTGTAA

SEQUENCE LISTING

<160> NUMBER OF SEQ ID NOS: 34

<210> SEQ ID NO 1
<211> LENGTH: 293
<212> TYPE: PRT
<213> ORGANISM: Artificial Sequence
<220> FEATURE:
<223> OTHER INFORMATION: Synthetic Sequence_Ct.EG G1P (wild-type) protein: Mature

<400> SEQUENCE: 1

Ala Asp Gly Lys Ser Thr Arg Tyr Trp Asp Cys Cys Lys Pro Ser Cys
1 5 10 15

Ser Trp Pro Gly Lys Ala Ala Val Ser Gln Pro Val Phe Ala Cys Asp
20 25 30

Arg Asn Phe Asn Arg Ile Tyr Asp Phe Gly Ala Lys Ser Gly Cys Glu
35 40 45

Gly Gly Pro Ala Tyr Ser Cys Ala Asp Gln Thr Pro Trp Ala Val Asn
50 55 60

Asp Gln Phe Ser Tyr Gly Phe Ala Ala Thr Asn Ile Ala Gly Gly Asn
65 70 75 80

Glu Ala Ser Trp Cys Cys Ala Cys Tyr Lys Leu Thr Phe Thr Ser Gly
85 90 95

Pro Val Ala Gly Lys Val Met Val Val Gln Ser Thr Ser Thr Gly Gly
100 105 110

Asp Leu Gly Asn Asn His Phe Asp Leu Asn Ile Pro Gly Gly Gly Val
115 120 125

Gly Ile Phe Asp Gly Cys Thr Pro Gln Phe Gly Gly Leu Pro Gly Glu
130 135 140

Arg Tyr Gly Gly Ile Ser Ser Arg Ser Gln Cys Asp Ser Phe Pro Asp
145 150 155 160

Ala Leu Lys Pro Gly Cys Tyr Trp Arg Phe Asp Trp Phe Leu Asn Ala
165 170 175

Asp Asn Pro Asn Phe Thr Phe Glu Arg Val Gln Cys Pro Ser Glu Leu
180 185 190

Val Ala Arg Thr Gly Cys Lys Arg Asn Asp Asp Gly Asn Tyr Pro Val
195 200 205

Phe Thr Pro Pro Ser Gly Asp Ser Pro Ser Ser Ser Ser Ala Ala Pro
210 215 220

Thr Ser Thr Ser Thr Ser Gln Gln Pro Gln Gln Pro Thr Ser Ser Ser
225 230 235 240

Ser Gln Ala Ser Val Pro Thr Ser Asn Pro Gly Gly Cys Thr Ser Gln
245 250 255

Lys Trp Ala Gln Cys Gly Gly Ile Gly Phe Thr Gly Cys Thr Thr Cys
260 265 270

Val Ser Gly Thr Thr Cys Thr Lys Leu Asn Asp Trp Tyr Ser Gln Cys
275 280 285

Thr Met Ile Asn Leu
290

<210> SEQ ID NO 2
<211> LENGTH: 882
<212> TYPE: DNA
<213> ORGANISM: Artificial Sequence
<220> FEATURE:
<223> OTHER INFORMATION: Synthetic Sequence_N.A. encoding Ct.EG G1P (wild-type) protein: Mature

<400> SEQUENCE: 2

```
gccgacggca agtccactag gtactgggac tgctgcaagc cttcttgctc gtggcccggc     60
aaggctgctg tgagccaacc cgtcttcgcc tgtgaccgca acttcaaccg catctatgac    120
ttcggtgcca agtctggctg cgagggcggt ccggcctatt cttgcgccga ccagaccccg    180
tgggctgtca acgaccaatt ctcgtacggc ttcgctgcca ccaacattgc cggcggtaac    240
gaggcttcat ggtgctgcgc ttgctacaag ctcaccttca cctcgggacc cgtggccggc    300
aaggtcatgg ttgtccagtc gaccagcacg ggcggtgacc ttggcaacaa ccatttcgac    360
ctgaacatcc caggtggagg cgttggtatc ttcgatggtt gcacgcccca gttcggcggt    420
ctgcccggcg agcggtacgg cgggatctcg tcgcgcagcc agtgcgacag cttcccggat    480
gccctcaagc ctggctgcta ctggcgcttc gactggttcc tgaacgctga caacccgaac    540
ttcaccttcg agcgcgtcca gtgtccttcc gagcttgttg cccgcaccgg ctgcaagcgc    600
aatgacgacg gcaactaccc cgtcttcact cctccttcgg gagacagccc cagcagcagc    660
agcgctgctc ctacctccac ctcgacttcg cagcagccgc agcagccgac ctccagcagc    720
tcgcaggctt ctgtgccgac tagcaaccct ggtggctgca cctctcaaaa gtgggctcag    780
tgcggcggca ttggcttcac tggctgcact acctgcgtct cgggcaccac ttgcaccaag    840
ctgaatgact ggtactcgca gtgcacaatg atcaacctgt aa                       882
```

<210> SEQ ID NO 3
<211> LENGTH: 214
<212> TYPE: PRT
<213> ORGANISM: Artificial Sequence
<220> FEATURE:
<223> OTHER INFORMATION: Synthetic Sequence_Ct.EG G1V1 variant protein: Mature

<400> SEQUENCE: 3

```
Ala Asp Gly Lys Ser Thr Arg Tyr Trp Asp Cys Cys Lys Pro Ser Cys
1               5                   10                  15

Ser Trp Pro Gly Lys Ala Ala Val Ser Gln Pro Val Phe Ala Cys Asp
            20                  25                  30

Arg Asn Phe Asn Arg Ile Tyr Asp Phe Gly Ala Lys Ser Gly Cys Glu
        35                  40                  45

Gly Gly Pro Ala Tyr Ser Cys Ala Asp Gln Thr Pro Trp Ala Val Asn
    50                  55                  60

Asp Gln Phe Ser Tyr Gly Phe Ala Ala Thr Asn Ile Ala Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
            100                 105                 110

Asp Leu Gly Asn Asn His Phe Asp Leu Asn Ile Pro Gly Gly Gly Val
        115                 120                 125

Gly Ile Phe Asp Gly Cys Thr Pro Gln Phe Gly Gly Leu Pro Gly Glu
    130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
            180                 185                 190
```

-continued

```
Val Ala Arg Thr Gly Cys Lys Arg Asn Asp Asp Gly Asn Tyr Pro Val
        195                 200                 205

Phe Thr Pro Pro Ser Gly
    210
```

<210> SEQ ID NO 4
<211> LENGTH: 645
<212> TYPE: DNA
<213> ORGANISM: Artificial Sequence
<220> FEATURE:
<223> OTHER INFORMATION: Synthetic Sequence_N.A. encoding Ct.EG G1V1 variant protein: Mature

<400> SEQUENCE: 4

```
gccgacggca agtccactag gtactgggac tgctgcaagc cttcttgctc gtggcccggc      60

aaggctgctg tgagccaacc cgtcttcgcc tgtgaccgca acttcaaccg catctatgac     120

ttcggtgcca agtctggctg cgagggcggt ccggcctatt cttgcgccga ccagaccccg     180

tgggctgtca acgaccaatt ctcgtacggc ttcgctgcca ccaacattgc cggcggtaac     240

gaggcttcat ggtgctgcgc ttgctacaag ctcaccttca cctcgggacc cgtggccggc     300

aaggtcatgg ttgtccagtc gaccagcacg ggcggtgacc ttggcaacaa ccatttcgac     360

ctgaacatcc caggtggagg cgttggtatc ttcgatggtt gcacgcccca gttcggcggt     420

ctgcccggcg agcggtacgg cgggatctcg tcgcgcagcc agtgcgacag cttcccggat     480

gccctcaagc ctggctgcta ctggcgcttc gactggttcc tgaacgctga caacccgaac     540

ttcaccttcg agcgcgtcca gtgtccttcc gagcttgttg cccgcaccgg ctgcaagcgc     600

aatgacgacg gcaactaccc cgtcttcact cctccttcgg gataa                     645
```

<210> SEQ ID NO 5
<211> LENGTH: 293
<212> TYPE: PRT
<213> ORGANISM: Artificial Sequence
<220> FEATURE:
<223> OTHER INFORMATION: Synthetic Sequence_Ct.EG G1V2 variant protein: Mature

<400> SEQUENCE: 5

```
Ala Asp Gly Lys Ser Thr Arg Tyr Trp Asp Cys Cys Lys Pro Ser Cys
1               5                   10                  15

Ser Trp Pro Gly Lys Ala Ala Val Ser Gln Pro Val Phe Ala Cys Asp
            20                  25                  30

Arg Asn Phe Asn Arg Leu Ser Asp Phe Asn Val Gln Ser Gly Cys Asn
        35                  40                  45

Gly Gly Pro Ala Tyr Ser Cys Ala Asp Gln Thr Pro Trp Ala Val Asn
    50                  55                  60

Asp Gln Phe Ser Tyr Gly Phe Ala Ala Thr Asn Ile Ala Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
            100                 105                 110

Asp Leu Gly Asn Asn His Phe Asp Leu Asn Ile Pro Gly Gly Gly Val
        115                 120                 125

Gly Ile Phe Asp Gly Cys Thr Pro Gln Phe Gly Gly Leu Pro Gly Glu
    130                 135                 140

Arg Tyr Gly Gly Ile Ser Ser Arg Ser Gln Cys Asp Ser Phe Pro Asp
145                 150                 155                 160
```

-continued

```
Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
            180                 185                 190

Val Ala Arg Thr Gly Cys Lys Arg Asn Asp Asp Gly Asn Tyr Pro Val
        195                 200                 205

Phe Thr Pro Pro Ser Gly Asp Ser Pro Ser Ser Ser Ser Ala Ala Pro
    210                 215                 220

Thr Ser Thr Ser Thr Ser Gln Gln Pro Gln Gln Pro Thr Ser Ser Ser
225                 230                 235                 240

Ser Gln Ala Ser Val Pro Thr Ser Asn Pro Gly Gly Cys Thr Ser Gln
                245                 250                 255

Lys Trp Ala Gln Cys Gly Gly Ile Gly Phe Thr Gly Cys Thr Thr Cys
            260                 265                 270

Val Ser Gly Thr Thr Cys Thr Lys Leu Asn Asp Trp Tyr Ser Gln Cys
        275                 280                 285

Thr Met Ile Asn Leu
    290
```

<210> SEQ ID NO 6
<211> LENGTH: 882
<212> TYPE: DNA
<213> ORGANISM: Artificial Sequence
<220> FEATURE:
<223> OTHER INFORMATION: Synthetic Sequence_N.A. encoding Ct.EG G1V2 variant protein: Mature

<400> SEQUENCE: 6

```
gccgacggca agtccactag gtactgggac tgctgcaagc cttcttgctc gtggcccggc     60

aaggctgctg tgagccaacc cgtcttcgcc tgtgaccgca acttcaaccg cctgtccgac    120

ttcaatgtcc agtctggctg caacggcggt ccggcctatt cttgcgccga ccagaccccg    180

tgggctgtca acgaccaatt ctcgtacggc ttcgctgcca ccaacattgc cggcggtaac    240

gaggcttcat ggtgctgcgc ttgctacaag ctcaccttca cctcgggacc cgtggccggc    300

aaggtcatgg ttgtccagtc gaccagcacg ggcggtgacc ttggcaacaa ccatttcgac    360

ctgaacatcc caggtggagg cgttggtatc ttcgatggtt gcacgcccca gttcggcggt    420

ctgcccggcg agcggtacgg cgggatctcg tcgcgcagcc agtgcgacag cttcccggat    480

gccctcaagc ctggctgcta ctggcgcttc gactggttcc tgaacgctga caacccgaac    540

ttcaccttcg agcgcgtcca gtgtccttcc gagcttgttg cccgcaccgg ctgcaagcgc    600

aatgacgacg gcaactaccc cgtcttcact cctccttcgg gagacagccc cagcagcagc    660

agcgctgctc ctacctccac ctcgacttcg cagcagccgc agcagccgac ctccagcagc    720

tcgcaggctt ctgtgccgac tagcaaccct ggtggctgca cctctcaaaa gtgggctcag    780

tgcggcggca ttggcttcac tggctgcact acctgcgtct cgggcaccac ttgcaccaag    840

ctgaatgact ggtactcgca gtgcacaatg atcaacctgt aa                       882
```

<210> SEQ ID NO 7
<211> LENGTH: 276
<212> TYPE: PRT
<213> ORGANISM: Artificial Sequence
<220> FEATURE:
<223> OTHER INFORMATION: Synthetic Sequence_Ct.EG G1V3 variant protein: Mature

<400> SEQUENCE: 7

```
Ala Asp Gly Lys Ser Thr Arg Tyr Trp Asp Cys Cys Lys Pro Ser Cys
1               5                   10                  15

Ser Trp Pro Gly Lys Ala Ala Val Ser Gln Pro Val Phe Ala Cys Asp
            20                  25                  30

Arg Asn Phe Asn Arg Ile Tyr Asp Phe Gly Ala Lys Ser Gly Cys Glu
        35                  40                  45

Gly Gly Pro Ala Tyr Ser Cys Ala Asp Gln Thr Pro Trp Ala Val Asn
    50                  55                  60

Asp Gln Phe Ser Tyr Gly Phe Ala Ala Thr Asn Ile Ala Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
            100                 105                 110

Asp Leu Gly Asn Asn His Phe Asp Leu Asn Ile Pro Gly Gly Gly Val
        115                 120                 125

Gly Ile Phe Asp Gly Cys Thr Pro Gln Phe Gly Gly Leu Pro Gly Glu
    130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
            180                 185                 190

Val Ala Arg Thr Gly Cys Lys Arg Asn Asp Asp Gly Asn Tyr Pro Val
        195                 200                 205

Phe Thr Pro Pro Ser Gly Gly Asn Gly Gly Thr Gly Thr Pro Thr Ser
    210                 215                 220

Thr Ala Pro Gly Ser Gly Gln Thr Ser Pro Gly Gly Gly Ser Gly Cys
225                 230                 235                 240

Thr Ser Gln Lys Trp Ala Gln Cys Gly Gly Ile Gly Phe Ser Gly Cys
                245                 250                 255

Thr Thr Cys Val Ser Gly Thr Thr Cys Gln Lys Leu Asn Asp Tyr Tyr
            260                 265                 270

Ser Gln Cys Leu
        275
```

<210> SEQ ID NO 8
<211> LENGTH: 831
<212> TYPE: DNA
<213> ORGANISM: Artificial Sequence
<220> FEATURE:
<223> OTHER INFORMATION: Synthetic Sequence_N.A. encoding Ct.EG G1V3 variant protein: Mature

<400> SEQUENCE: 8

```
gccgacggca agtccactag gtactgggac tgctgcaagc cttcttgctc gtggcccggc     60

aaggctgctg tgagccaacc cgtcttcgcc tgtgaccgca acttcaaccg catctatgac    120

ttcggtgcca agtctggctg cgagggcggt ccggcctatt cttgcgccga ccagaccccg    180

tgggctgtca acgaccaatt ctcgtacggc ttcgctgcca ccaacattgc cggcggtaac    240

gaggcttcat ggtgctgcgc ttgctacaag ctcaccttca cctcgggacc cgtggccggc    300

aaggtcatgg ttgtccagtc gaccagcacg ggcggtgacc ttggcaacaa ccatttcgac    360

ctgaacatcc caggtggagg cgttggtatc ttcgatggtt gcacgcccca gttcggcggt    420
```

```
ctgcccggcg agcggtacgg cgggatctcg tcgcgcagcc agtgcgacag cttcccggat    480

gccctcaagc ctggctgcta ctggcgcttc gactggttcc tgaacgctga caacccgaac    540

ttcaccttcg agcgcgtcca gtgtccttcc gagcttgttg cccgcaccgg ctgcaagcgc    600

aatgacgacg gcaactaccc cgtcttcact cctccttcgg gaggcaacgg tggcaccggc    660

acccctacct ccactgcccc cggctccggt cagacctccc ccggcggtgg ttccggttgc    720

acctcccaga agtgggccca gtgcggtggc atcggtttct ccggctgcac cacttgcgtc    780

tccggcacca cttgccagaa gctgaacgac tactactccc agtgtctgta a             831
```

<210> SEQ ID NO 9
<211> LENGTH: 293
<212> TYPE: PRT
<213> ORGANISM: Artificial Sequence
<220> FEATURE:
<223> OTHER INFORMATION: Synthetic Sequence_Ct.EG G1V4 variant protein: Mature

<400> SEQUENCE: 9

```
Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Tyr Ala Cys Asp
            20                  25                  30

Ala Asn Phe Gln Arg Leu Ser Asp Phe Asn Val Gln Ser Gly Cys Asn
        35                  40                  45

Gly Gly Ser Ala Tyr Ser Cys Ala Asp Gln Thr Pro Trp Ala Val Asn
    50                  55                  60

Asp Asn Leu Ala Tyr Gly Phe Ala Ala Thr Ser Ile Ala Gly Gly Ser
65                  70                  75                  80

Glu Ser Ser Trp Cys Cys Ala Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Ser Asn His Phe Asp Ile Ala Met Pro Gly Gly Gly Val
        115                 120                 125

Gly Ile Phe Asn Gly Cys Ser Ser Gln Phe Gly Gly Leu Pro Gly Ala
    130                 135                 140

Gln Tyr Gly Gly Ile Ser Ser Arg Asp Gln Cys Asp Ser Phe Pro Ala
145                 150                 155                 160

Pro Leu Lys Pro Gly Cys Gln Trp Arg Phe Asp Trp Phe Gln Asn Ala
                165                 170                 175

Asp Asn Pro Thr Phe Thr Phe Gln Gln Val Gln Cys Pro Ala Glu Ile
            180                 185                 190

Val Ala Arg Ser Gly Cys Lys Arg Asn Asp Asp Ser Ser Phe Pro Val
        195                 200                 205

Phe Thr Pro Pro Ser Gly Asp Ser Pro Ser Ser Ser Ser Ala Ala Pro
    210                 215                 220

Thr Ser Thr Ser Thr Ser Gln Gln Pro Gln Gln Pro Thr Ser Ser Ser
225                 230                 235                 240

Ser Gln Ala Ser Val Pro Thr Ser Asn Pro Gly Gly Cys Thr Ser Gln
                245                 250                 255

Lys Trp Ala Gln Cys Gly Gly Ile Gly Phe Thr Gly Cys Thr Thr Cys
            260                 265                 270

Val Ser Gly Thr Thr Cys Thr Lys Leu Asn Asp Trp Tyr Ser Gln Cys
        275                 280                 285
```

Thr Met Ile Asn Leu
    290

<210> SEQ ID NO 10
<211> LENGTH: 882
<212> TYPE: DNA
<213> ORGANISM: Artificial Sequence
<220> FEATURE:
<223> OTHER INFORMATION: Synthetic Sequence_N.A. encoding Ct.EG G1V4
      variant protein: Mature

<400> SEQUENCE: 10
gccgatggca agtcgacccg ctactgggac tgttgcaagc cgtcgtgctc gtggcccggc 60
aaggcctcgg tgaaccagcc cgtctacgcg tgcgatgcca acttccagcg cctgtccgac 120
ttcaatgtcc agtcgggctg caacggcggc tcggcctact cctgcgccga ccagactccc 180
tgggcggtga acgacaatct cgcctacggc ttcgccgcga cgagcatcgc cggcgggtcc 240
gaatcctcgt ggtgctgcgc ctgctacgcg ctcaccttca cttccggtcc cgtcgccggc 300
aagacaatgg tggtgcagtc aacgagcact ggcggcgacc tgggaagtaa ccatttcgat 360
atcgccatgc ccggcggcgg cgtgggcatc ttcaacggct gcagctcgca gttcggcggc 420
ctccccggcg ctcaatacgg cggcatttcg tcgcgcgacc agtgcgattc cttccccgcg 480
ccgctcaagc ccggctgcca gtggcggttt gactggttcc agaacgccga caacccgacg 540
ttcacgttcc agcaggtgca gtgccccgcc gagatcgttg cccgctccgg ctgcaagcgc 600
aacgacgact ccagcttccc cgtcttcacc cccccaagcg gtgacagccc cagcagcagc 660
agcgctgctc ctacctccac ctcgacttcg cagcagccgc agcagccgac ctccagcagc 720
tcgcaggctt ctgtgccgac tagcaaccct ggtggctgca cctctcaaaa gtgggctcag 780
tgcggcggca ttggcttcac tggctgcact acctgcgtct cgggcaccac ttgcaccaag 840
ctgaatgact ggtactcgca gtgcacaatg atcaacctgt aa 882

<210> SEQ ID NO 11
<211> LENGTH: 314
<212> TYPE: PRT
<213> ORGANISM: Artificial Sequence
<220> FEATURE:
<223> OTHER INFORMATION: Synthetic Sequence_Ct.EG G1P (wild-type)
      protein: SP + Mature

<400> SEQUENCE: 11

Met Arg Ser Thr Pro Val Leu Arg Thr Ala Leu Ala Ala Ala Leu Pro
1               5                   10                  15

Phe Thr Val Leu Ala Ala Asp Gly Lys Ser Thr Arg Tyr Trp Asp Cys
            20                  25                  30

Cys Lys Pro Ser Cys Ser Trp Pro Gly Lys Ala Ala Val Ser Gln Pro
        35                  40                  45

Val Phe Ala Cys Asp Arg Asn Phe Asn Arg Ile Tyr Asp Phe Gly Ala
    50                  55                  60

Lys Ser Gly Cys Glu Gly Gly Pro Ala Tyr Ser Cys Ala Asp Gln Thr
65                  70                  75                  80

Pro Trp Ala Val Asn Asp Gln Phe Ser Tyr Gly Phe Ala Ala Thr Asn
                85                  90                  95

Ile Ala Gly Gly Asn Glu Ala Ser Trp Cys Cys Ala Cys Tyr Lys Leu
            100                 105                 110

Thr Phe Thr Ser Gly Pro Val Ala Gly Lys Val Met Val Val Gln Ser
        115                 120                 125

-continued

```
Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly Asp Ser Pro Ser Ser
225                 230                 235                 240

Ser Ser Ala Ala Pro Thr Ser Thr Ser Thr Ser Gln Gln Pro Gln Gln
                245                 250                 255

Pro Thr Ser Ser Ser Ser Gln Ala Ser Val Pro Thr Ser Asn Pro Gly
            260                 265                 270

Gly Cys Thr Ser Gln Lys Trp Ala Gln Cys Gly Gly Ile Gly Phe Thr
        275                 280                 285

Gly Cys Thr Thr Cys Val Ser Gly Thr Thr Cys Thr Lys Leu Asn Asp
    290                 295                 300

Trp Tyr Ser Gln Cys Thr Met Ile Asn Leu
305                 310


<210> SEQ ID NO 12
<211> LENGTH: 945
<212> TYPE: DNA
<213> ORGANISM: Artificial Sequence
<220> FEATURE:
<223> OTHER INFORMATION: Synthetic Sequence_N.A. encoding Ct.EG G1P
      (wild-type) protein: SP + Mature

<400> SEQUENCE: 12

atgcggtcga ctcctgttct ccgtaccgcc cttgcggctg ctctcccctt cactgtcctg      60

gctgccgacg gcaagtccac taggtactgg gactgctgca agccttcttg ctcgtggccc     120

ggcaaggctg ctgtgagcca acccgtcttc gcctgtgacc gcaacttcaa ccgcatctat     180

gacttcggtg ccaagtctgg ctgcgagggc ggtccggcct attcttgcgc cgaccagacc     240

ccgtgggctg tcaacgacca attctcgtac ggcttcgctg ccaccaacat tgccggcggt     300

aacgaggctt catggtgctg cgcttgctac aagctcacct tcacctcggg acccgtggcc     360

ggcaaggtca tggttgtcca gtcgaccagc acgggcggtg accttggcaa caaccatttc     420

gacctgaaca tcccaggtgg aggcgttggt atcttcgatg gttgcacgcc ccagttcggc     480

ggtctgcccg gcgagcggta cggcgggatc tcgtcgcgca gccagtgcga cagcttcccg     540

gatgccctca agcctggctg ctactggcgc ttcgactggt tcctgaacgc tgacaacccg     600

aacttcacct tcgagcgcgt ccagtgtcct tccgagcttg ttgcccgcac cggctgcaag     660

cgcaatgacg acggcaacta ccccgtcttc actcctcctt cgggagacag ccccagcagc     720

agcagcgctg ctcctacctc cacctcgact tcgcagcagc cgcagcagcc gacctccagc     780

agctcgcagg cttctgtgcc gactagcaac cctggtggct gcacctctca aaagtgggct     840

cagtgcggcg gcattggctt cactggctgc actacctgcg tctcgggcac cacttgcacc     900

aagctgaatg actggtactc gcagtgcaca atgatcaacc tgtaa                     945
```

<210> SEQ ID NO 13
<211> LENGTH: 235
<212> TYPE: PRT
<213> ORGANISM: Artificial Sequence
<220> FEATURE:
<223> OTHER INFORMATION: Synthetic Sequence_Ct.EG G1V1 variant protein: SP + Mature

<400> SEQUENCE: 13

```
Met Arg Ser Thr Pro Val Leu Arg Thr Ala Leu Ala Ala Ala Leu Pro
1               5                   10                  15

Phe Thr Val Leu Ala Ala Asp Gly Lys Ser Thr Arg Tyr Trp Asp Cys
            20                  25                  30

Cys Lys Pro Ser Cys Ser Trp Pro Gly Lys Ala Ala Val Ser Gln Pro
        35                  40                  45

Val Phe Ala Cys Asp Arg Asn Phe Asn Arg Ile Tyr Asp Phe Gly Ala
    50                  55                  60

Lys Ser Gly Cys Glu Gly Gly Pro Ala Tyr Ser Cys Ala Asp Gln Thr
65                  70                  75                  80

Pro Trp Ala Val Asn Asp Gln Phe Ser Tyr Gly Phe Ala Ala Thr Asn
                85                  90                  95

Ile Ala Gly Gly Asn Glu Ala Ser Trp Cys Cys Ala Cys Tyr Lys Leu
            100                 105                 110

Thr Phe Thr Ser Gly Pro Val Ala Gly Lys Val Met Val Val Gln Ser
        115                 120                 125

Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly
225                 230                 235
```

<210> SEQ ID NO 14
<211> LENGTH: 708
<212> TYPE: DNA
<213> ORGANISM: Artificial Sequence
<220> FEATURE:
<223> OTHER INFORMATION: Synthetic Sequence_N.A. encoding Ct.EG G1V1 variant protein: SP + Mature

<400> SEQUENCE: 14

```
atgcggtcga ctcctgttct ccgtaccgcc cttgcggctg ctctcccctt cactgtcctg      60

gctgccgacg gcaagtccac taggtactgg gactgctgca agccttcttg ctcgtggccc     120

ggcaaggctg ctgtgagcca acccgtcttc gcctgtgacc gcaacttcaa ccgcatctat     180

gacttcggtg ccaagtctgg ctgcgagggc ggtccggcct attcttgcgc cgaccagacc     240

ccgtgggctg tcaacgacca attctcgtac ggcttcgctg ccaccaacat tgccggcggt     300

aacgaggctt catggtgctg cgcttgctac aagctcacct tcacctcggg acccgtggcc     360
```

```
ggcaaggtca tggttgtcca gtcgaccagc acgggcggtg accttggcaa caaccatttc    420

gacctgaaca tcccaggtgg aggcgttggt atcttcgatg gttgcacgcc ccagttcggc    480

ggtctgcccg gcgagcggta cggcgggatc tcgtcgcgca gccagtgcga cagcttcccg    540

gatgccctca agcctggctg ctactggcgc ttcgactggt tcctgaacgc tgacaacccg    600

aacttcacct tcgagcgcgt ccagtgtcct tccgagcttg ttgcccgcac cggctgcaag    660

cgcaatgacg acggcaacta ccccgtcttc actcctcctt cgggataa                708


<210> SEQ ID NO 15
<211> LENGTH: 314
<212> TYPE: PRT
<213> ORGANISM: Artificial Sequence
<220> FEATURE:
<223> OTHER INFORMATION: Synthetic Sequence_Ct.EG G1V2 variant protein:
      SP + Mature

<400> SEQUENCE: 15

Met Arg Ser Thr Pro Val Leu Arg Thr Ala Leu Ala Ala Ala Leu Pro
1               5                   10                  15

Phe Thr Val Leu Ala Ala Asp Gly Lys Ser Thr Arg Tyr Trp Asp Cys
            20                  25                  30

Cys Lys Pro Ser Cys Ser Trp Pro Gly Lys Ala Ala Val Ser Gln Pro
        35                  40                  45

Val Phe Ala Cys Asp Arg Asn Phe Asn Arg Leu Ser Asp Phe Asn Val
    50                  55                  60

Gln Ser Gly Cys Asn Gly Gly Pro Ala Tyr Ser Cys Ala Asp Gln Thr
65                  70                  75                  80

Pro Trp Ala Val Asn Asp Gln Phe Ser Tyr Gly Phe Ala Ala Thr Asn
                85                  90                  95

Ile Ala Gly Gly Asn Glu Ala Ser Trp Cys Cys Ala Cys Tyr Lys Leu
            100                 105                 110

Thr Phe Thr Ser Gly Pro Val Ala Gly Lys Val Met Val Val Gln Ser
        115                 120                 125

Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly Asp Ser Pro Ser Ser
225                 230                 235                 240

Ser Ser Ala Ala Pro Thr Ser Thr Ser Thr Ser Gln Gln Pro Gln Gln
                245                 250                 255

Pro Thr Ser Ser Ser Ser Gln Ala Ser Val Pro Thr Ser Asn Pro Gly
            260                 265                 270

Gly Cys Thr Ser Gln Lys Trp Ala Gln Cys Gly Gly Ile Gly Phe Thr
        275                 280                 285

Gly Cys Thr Thr Cys Val Ser Gly Thr Thr Cys Thr Lys Leu Asn Asp
```

290 295 300

Trp Tyr Ser Gln Cys Thr Met Ile Asn Leu
305 310

<210> SEQ ID NO 16
<211> LENGTH: 945
<212> TYPE: DNA
<213> ORGANISM: Artificial Sequence
<220> FEATURE:
<223> OTHER INFORMATION: Synthetic Sequence_N.A. encoding Ct.EG G1V2
variant protein: SP + Mature

<400> SEQUENCE: 16
atgcggtcga ctcctgttct ccgtaccgcc cttgcggctg ctctcccctt cactgtcctg 60
gctgccgacg gcaagtccac taggtactgg gactgctgca agccttcttg ctcgtggccc 120
ggcaaggctg ctgtgagcca acccgtcttc gcctgtgacc gcaacttcaa ccgcctgtcc 180
gacttcaatg tccagtctgg ctgcaacggc ggtccggcct attcttgcgc cgaccagacc 240
ccgtgggctg tcaacgacca attctcgtac ggcttcgctg ccaccaacat tgccggcggt 300
aacgaggctt catggtgctg cgcttgctac aagctcacct tcacctcggg acccgtggcc 360
ggcaaggtca tggttgtcca gtcgaccagc acgggcggtg accttggcaa caaccatttc 420
gacctgaaca tcccaggtgg aggcgttggt atcttcgatg gttgcacgcc ccagttcggc 480
ggtctgcccg gcgagcggta cggcgggatc tcgtcgcgca gccagtgcga cagcttcccg 540
gatgccctca agcctggctg ctactggcgc ttcgactggt tcctgaacgc tgacaacccg 600
aacttcacct tcgagcgcgt ccagtgtcct tccgagcttg ttgcccgcac cggctgcaag 660
cgcaatgacg acggcaacta ccccgtcttc actcctcctt cgggagacag ccccagcagc 720
agcagcgctg ctcctacctc cacctcgact tcgcagcagc cgcagcagcc gacctccagc 780
agctcgcagg cttctgtgcc gactagcaac cctggtggct gcacctctca aaagtgggct 840
cagtgcggcg gcattggctt cactggctgc actacctgcg tctcgggcac cacttgcacc 900
aagctgaatg actggtactc gcagtgcaca atgatcaacc tgtaa 945

<210> SEQ ID NO 17
<211> LENGTH: 297
<212> TYPE: PRT
<213> ORGANISM: Artificial Sequence
<220> FEATURE:
<223> OTHER INFORMATION: Synthetic Sequence_Ct.EG G1V3 variant protein:
SP + Mature

<400> SEQUENCE: 17

Met Arg Ser Thr Pro Val Leu Arg Thr Ala Leu Ala Ala Ala Leu Pro
1 5 10 15

Phe Thr Val Leu Ala Ala Asp Gly Lys Ser Thr Arg Tyr Trp Asp Cys
20 25 30

Cys Lys Pro Ser Cys Ser Trp Pro Gly Lys Ala Ala Val Ser Gln Pro
35 40 45

Val Phe Ala Cys Asp Arg Asn Phe Asn Arg Ile Tyr Asp Phe Gly Ala
50 55 60

Lys Ser Gly Cys Glu Gly Gly Pro Ala Tyr Ser Cys Ala Asp Gln Thr
65 70 75 80

Pro Trp Ala Val Asn Asp Gln Phe Ser Tyr Gly Phe Ala Ala Thr Asn
85 90 95

Ile Ala Gly Gly Asn Glu Ala Ser Trp Cys Cys Ala Cys Tyr Lys Leu
100 105 110

-continued

```
Thr Phe Thr Ser Gly Pro Val Ala Gly Lys Val Met Val Val Gln Ser
        115                 120                 125

Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly Gly Asn Gly Gly Thr
225                 230                 235                 240

Gly Thr Pro Thr Ser Thr Ala Pro Gly Ser Gly Gln Thr Ser Pro Gly
                245                 250                 255

Gly Gly Ser Gly Cys Thr Ser Gln Lys Trp Ala Gln Cys Gly Gly Ile
            260                 265                 270

Gly Phe Ser Gly Cys Thr Thr Cys Val Ser Gly Thr Thr Cys Gln Lys
        275                 280                 285

Leu Asn Asp Tyr Tyr Ser Gln Cys Leu
    290                 295
```

<210> SEQ ID NO 18
<211> LENGTH: 894
<212> TYPE: DNA
<213> ORGANISM: Artificial Sequence
<220> FEATURE:
<223> OTHER INFORMATION: Synthetic Sequence_N.A. encoding Ct.EG G1V3
      variant protein: SP + Mature

<400> SEQUENCE: 18

```
atgcggtcga ctcctgttct ccgtaccgcc cttgcggctg ctctcccctt cactgtcctg      60

gctgccgacg gcaagtccac taggtactgg gactgctgca agccttcttg ctcgtggccc     120

ggcaaggctg ctgtgagcca acccgtcttc gcctgtgacc gcaacttcaa ccgcatctat     180

gacttcggtg ccaagtctgg ctgcgagggc ggtccggcct attcttgcgc cgaccagacc     240

ccgtgggctg tcaacgacca attctcgtac ggcttcgctg ccaccaacat tgccggcggt     300

aacgaggctt catggtgctg cgcttgctac aagctcacct tcacctcggg acccgtggcc     360

ggcaaggtca tggttgtcca gtcgaccagc acgggcggtg accttggcaa caaccatttc     420

gacctgaaca tcccaggtgg aggcgttggt atcttcgatg gttgcacgcc ccagttcggc     480

ggtctgcccg gcgagcggta cggcgggatc tcgtcgcgca gccagtgcga cagcttcccg     540

gatgccctca agcctggctg ctactggcgc ttcgactggt tcctgaacgc tgacaacccg     600

aacttcacct tcgagcgcgt ccagtgtcct tccgagcttg ttgcccgcac cggctgcaag     660

cgcaatgacg acggcaacta ccccgtcttc actcctcctt cgggaggcaa cggtggcacc     720

ggcaccccta cctccactgc ccccggctcc ggtcagacct cccccggcgg tggttccggt     780

tgcacctccc agaagtgggc ccagtgcggt ggcatcggtt tctccggctg caccacttgc     840

gtctccggca ccacttgcca gaagctgaac gactactact cccagtgtct gtaa           894
```

-continued

<210> SEQ ID NO 19
<211> LENGTH: 314
<212> TYPE: PRT
<213> ORGANISM: Artificial Sequence
<220> FEATURE:
<223> OTHER INFORMATION: Synthetic Sequence_Ct.EG G1V4 variant protein: SP + Mature

<400> SEQUENCE: 19

```
Met Arg Ser Ser Pro Val Leu Arg Thr Ala Leu Ala Ala Ala Leu Pro
1               5                   10                  15

Leu Ala Ala Leu Ala Ala Asp Gly Lys Ser Thr Arg Tyr Trp Asp Cys
            20                  25                  30

Cys Lys Pro Ser Cys Ser Trp Pro Gly Lys Ala Ser Val Asn Gln Pro
        35                  40                  45

Val Tyr Ala Cys Asp Ala Asn Phe Gln Arg Leu Ser Asp Phe Asn Val
    50                  55                  60

Gln Ser Gly Cys Asn Gly Gly Ser Ala Tyr Ser Cys Ala Asp Gln Thr
65                  70                  75                  80

Pro Trp Ala Val Asn Asp Asn Leu Ala Tyr Gly Phe Ala Ala Thr Ser
                85                  90                  95

Ile Ala Gly Gly Ser Glu Ser Ser Trp Cys Cys Ala Cys Tyr Ala Leu
            100                 105                 110

Thr Phe Thr Ser Gly Pro Val Ala Gly Lys Thr Met Val Val Gln Ser
        115                 120                 125

Thr Ser Thr Gly Gly Asp Leu Gly Ser Asn His Phe Asp Ile Ala Met
    130                 135                 140

Pro Gly Gly Gly Val Gly Ile Phe Asn Gly Cys Ser Ser Gln Phe Gly
145                 150                 155                 160

Gly Leu Pro Gly Ala Gln Tyr Gly Gly Ile Ser Ser Arg Asp Gln Cys
                165                 170                 175

Asp Ser Phe Pro Ala Pro Leu Lys Pro Gly Cys Gln Trp Arg Phe Asp
            180                 185                 190

Trp Phe Gln Asn Ala Asp Asn Pro Thr Phe Thr Phe Gln Gln Val Gln
        195                 200                 205

Cys Pro Ala Glu Ile Val Ala Arg Ser Gly Cys Lys Arg Asn Asp Asp
    210                 215                 220

Ser Ser Phe Pro Val Phe Thr Pro Pro Ser Gly Asp Ser Pro Ser Ser
225                 230                 235                 240

Ser Ser Ala Ala Pro Thr Ser Thr Ser Thr Ser Gln Gln Pro Gln Gln
                245                 250                 255

Pro Thr Ser Ser Ser Ser Gln Ala Ser Val Pro Thr Ser Asn Pro Gly
            260                 265                 270

Gly Cys Thr Ser Gln Lys Trp Ala Gln Cys Gly Gly Ile Gly Phe Thr
        275                 280                 285

Gly Cys Thr Thr Cys Val Ser Gly Thr Thr Cys Thr Lys Leu Asn Asp
    290                 295                 300

Trp Tyr Ser Gln Cys Thr Met Ile Asn Leu
305                 310
```

<210> SEQ ID NO 20
<211> LENGTH: 945
<212> TYPE: DNA
<213> ORGANISM: Artificial Sequence
<220> FEATURE:
<223> OTHER INFORMATION: Synthetic Sequence_N.A. encoding Ct.EG G1V4 variant protein: SP + Mature

<400> SEQUENCE: 20
atgcgttcct cccccgtcct ccgcacggcc ctggccgctg ccctccccct ggccgccctc 60
gctgccgatg gcaagtcgac ccgctactgg gactgttgca agccgtcgtg ctcgtggccc 120
ggcaaggcct cggtgaacca gcccgtctac gcgtgcgatg ccaacttcca gcgcctgtcc 180
gacttcaatg tccagtcggg ctgcaacggc ggctcggcct actcctgcgc cgaccagact 240
ccctgggcgg tgaacgacaa tctcgcctac ggcttcgccg cgacgagcat cgccggcggg 300
tccgaatcct cgtggtgctg cgcctgctac gcgctcacct tcacttccgg tcccgtcgcc 360
ggcaagacaa tggtggtgca gtcaacgagc actggcggcg acctgggaag taaccatttc 420
gatatcgcca tgcccggcgg cggcgtgggc atcttcaacg gctgcagctc gcagttcggc 480
ggcctccccg gcgctcaata cggcggcatt tcgtcgcgcg accagtgcga ttccttcccc 540
gcgccgctca agcccggctg ccagtggcgg tttgactggt tccagaacgc cgacaacccg 600
acgttcacgt tccagcaggt gcagtgcccc gccgagatcg ttgcccgctc cggctgcaag 660
cgcaacgacg actccagctt ccccgtcttc accccccaa gcggtgacag ccccagcagc 720
agcagcgctg ctcctacctc cacctcgact tcgcagcagc cgcagcagcc gacctccagc 780
agctcgcagg cttctgtgcc gactagcaac cctggtggct gcacctctca aaagtgggct 840
cagtgcggcg gcattggctt cactggctgc actacctgcg tctcgggcac cacttgcacc 900
aagctgaatg actggtactc gcagtgcaca atgatcaacc tgtaa 945

<210> SEQ ID NO 21
<211> LENGTH: 21
<212> TYPE: PRT
<213> ORGANISM: Artificial Sequence
<220> FEATURE:
<223> OTHER INFORMATION: Synthetic Sequence_Signal peptide (wild-type)

<400> SEQUENCE: 21

Met Arg Ser Thr Pro Val Leu Arg Thr Ala Leu Ala Ala Ala Leu Pro
1 5 10 15

Phe Thr Val Leu Ala
20

<210> SEQ ID NO 22
<211> LENGTH: 21
<212> TYPE: PRT
<213> ORGANISM: Artificial Sequence
<220> FEATURE:
<223> OTHER INFORMATION: Synthetic Sequence_Variant signal peptide

<400> SEQUENCE: 22

Met Arg Ser Ser Pro Val Leu Arg Thr Ala Leu Ala Ala Ala Leu Pro
1 5 10 15

Leu Ala Ala Leu Ala
20

<210> SEQ ID NO 23
<211> LENGTH: 276
<212> TYPE: PRT
<213> ORGANISM: Artificial Sequence
<220> FEATURE:
<223> OTHER INFORMATION: Synthetic Sequence_Ct.EG G2V1 protein: Mature

<400> SEQUENCE: 23

Ala Asp Gly Lys Ser Thr Arg Tyr Trp Asp Cys Cys Lys Pro Ser Cys
1 5 10 15

-continued

```
Ser Trp Pro Gly Lys Ala Ala Val Ser Gln Pro Val Phe Ala Cys Asp
            20                  25                  30

Arg Asn Phe Asn Arg Leu Ser Asp Phe Asn Val Gln Ser Gly Cys Asn
        35                  40                  45

Gly Gly Pro Ala Tyr Ser Cys Ala Asp Gln Thr Pro Trp Ala Val Asn
    50                  55                  60

Asp Gln Phe Ser Tyr Gly Phe Ala Ala Thr Asn Ile Ala Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
            100                 105                 110

Asp Leu Gly Asn Asn His Phe Asp Leu Asn Ile Pro Gly Gly Gly Val
        115                 120                 125

Gly Ile Phe Asp Gly Cys Thr Pro Gln Phe Gly Gly Leu Pro Gly Glu
    130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
            180                 185                 190

Val Ala Arg Thr Gly Cys Lys Arg Asn Asp Asp Gly Asn Tyr Pro Val
        195                 200                 205

Phe Thr Pro Pro Ser Gly Gly Asn Gly Gly Thr Gly Thr Pro Thr Ser
    210                 215                 220

Thr Ala Pro Gly Ser Gly Gln Thr Ser Pro Gly Gly Gly Ser Gly Cys
225                 230                 235                 240

Thr Ser Gln Lys Trp Ala Gln Cys Gly Gly Ile Gly Phe Ser Gly Cys
                245                 250                 255

Thr Thr Cys Val Ser Gly Thr Thr Cys Gln Lys Leu Asn Asp Tyr Tyr
            260                 265                 270

Ser Gln Cys Leu
        275
```

<210> SEQ ID NO 24
<211> LENGTH: 831
<212> TYPE: DNA
<213> ORGANISM: Artificial Sequence
<220> FEATURE:
<223> OTHER INFORMATION: Synthetic Sequence_N.A. encoding Ct.EG G2V1 protein: Mature

<400> SEQUENCE: 24

```
gccgacggca agtccactag gtactgggac tgctgcaagc cttcttgctc gtggcccggc      60

aaggctgctg tgagccaacc cgtcttcgcc tgtgaccgca acttcaaccg cctgtccgac     120

ttcaatgtcc agtctggctg caacggcggt ccggcctatt cttgcgccga ccagaccccg     180

tgggctgtca acgaccaatt ctcgtacggc ttcgctgcca ccaacattgc cggcggtaac     240

gaggcttcat ggtgctgcgc ttgctacaag ctcaccttca cctcgggacc cgtggccggc     300

aaggtcatgg ttgtccagtc gaccagcacg ggcggtgacc ttggcaacaa ccatttcgac     360

ctgaacatcc caggtggagg cgttggtatc ttcgatggtt gcacgcccca gttcggcggt     420

ctgcccggcg agcggtacgg cgggatctcg tcgcgcagcc agtgcgacag cttcccggat     480

gccctcaagc ctggctgcta ctggcgcttc gactggttcc tgaacgctga caacccgaac     540
```

```
ttcaccttcg agcgcgtcca gtgtccttcc gagcttgttg cccgcaccgg ctgcaagcgc    600

aatgacgacg gcaactaccc cgtcttcact cctccttcgg gaggcaacgg tggcaccggg    660

acgcccacgt cgactgcgcc tgggtcgggc cagacgtctc ccggcggcgg cagtggctgc    720

acctctcaaa agtgggctca gtgcggcggc attggcttca gcggctgcac tacctgcgtc    780

tcgggcacca cttgccagaa gctgaatgac tactactcgc agtgcctgta a             831
```

<210> SEQ ID NO 25
<211> LENGTH: 276
<212> TYPE: PRT
<213> ORGANISM: Artificial Sequence
<220> FEATURE:
<223> OTHER INFORMATION: Synthetic Sequence_Ct.EG G2V2 variant protein: Mature

<400> SEQUENCE: 25

```
Ala Asp Gly Lys Ser Thr Arg Tyr Trp Asp Cys Cys Lys Pro Ser Cys
1               5                   10                  15

Ser Trp Pro Gly Lys Ala Ala Val Ser Gln Pro Val Phe Ala Cys Asp
            20                  25                  30

Arg Asn Phe Asn Arg Leu Ser Asp Phe Asn Val Gln Ser Gly Cys Asn
        35                  40                  45

Gly Gly Pro Ala Tyr Ser Cys Ala Asp Gln Thr Pro Trp Ala Val Asn
    50                  55                  60

Asp Gln Phe Ser Tyr Gly Phe Ala Ala Thr Asn Ile Ala Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
            100                 105                 110

Asp Leu Gly Asn Asn His Phe Asp Leu Asn Ile Pro Gly Gly Gly Val
        115                 120                 125

Gly Ile Phe Asp Gly Cys Thr Pro Gln Phe Gly Gly Leu Pro Gly Glu
    130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
            180                 185                 190

Val Ala Arg Thr Gly Cys Lys Arg Asn Asp Asp Gly Asn Tyr Pro Val
        195                 200                 205

Phe Thr Pro Pro Ser Gly Gly Asn Gly Gly Thr Gly Thr Pro Thr Ser
    210                 215                 220

Thr Ala Pro Gly Ser Gly Gln Thr Ser Pro Gly Gly Gly Ser Gly Cys
225                 230                 235                 240

Thr Ser Gln Lys Trp Ala Gln Cys Gly Gly Ile Gly Phe Ser Gly Cys
                245                 250                 255

Thr Thr Cys Val Ser Gly Thr Thr Cys Gln Lys Leu Asn Asp Tyr Tyr
            260                 265                 270

Ser Gln Cys Leu
        275
```

<210> SEQ ID NO 26
<211> LENGTH: 831

<212> TYPE: DNA
<213> ORGANISM: Artificial Sequence
<220> FEATURE:
<223> OTHER INFORMATION: Synthetic Sequence_N.A. encoding Ct.EG G2V2
      protein: Mature

<400> SEQUENCE: 26
gccgacggca agtccactag gtactgggac tgctgcaagc cttcttgctc gtggcccggc 60
aaggctgatg tgagccaacc cgtcttcgcc tgtgaccgca acttcaaccg cctgtccgac 120
ttcaatgtcc agtctggctg caacggcggt ccggcctata cttgcgccga ccagaccccg 180
tgggctgtca acgaccaatt ctcgtacggc ttcgctgcca ccaacattgc cggcggtaac 240
gaggcttcat ggtgctgcgc ttgctacaag ctcaccttca cctcgggacc cgtggccggc 300
aaggtcatgg ttgtccagtc gaccagcacg ggcggtgacc ttggcgacaa ccatttcgac 360
ctgaacatcc caggtggagg cgttggtatc ttcgatggtt gcacgcccca gttcggcggt 420
ctgcccggcg agcggtacgg cgggatctcg tcgcgcagcc agtgcgacag cttcccggat 480
gccctcaagc ctggctgcta ctggcgcttc gactggttcc tgaacgctga caacccgaac 540
ttcaccttcg agcgcgtcca gtgtccttcc gagcttgttg cccgcaccgg ctgcaagcgc 600
aatgacgacg gcaactaccc cgtcttcact cctccttcgg gaggcaacgg tggcaccggg 660
acgcccacgt cgactgcgcc tgggtcgggc cagacgtctc ccggcggcgg cagtggctgc 720
acctctcaaa agtgggctca gtgcggcggc attggcttca gcggctgcac tacctgcgtc 780
tcgggcacca cttgccagaa gctgaatgac tactactcgc agtgcctgta a 831

<210> SEQ ID NO 27
<211> LENGTH: 293
<212> TYPE: PRT
<213> ORGANISM: Artificial Sequence
<220> FEATURE:
<223> OTHER INFORMATION: Synthetic Sequence_Ct.EG G2V3 protein: Mature

<400> SEQUENCE: 27

Ala Asp Gly Lys Ser Thr Arg Tyr Trp Asp Cys Cys Lys Pro Ser Cys
1               5                   10                  15

Ser Trp Pro Gly Lys Ala Asp Val Asn Gln Pro Val Phe Ala Cys Asp
            20                  25                  30

Arg Asn Phe Asn Arg Leu Ser Asp Phe Asn Val Gln Ser Gly Cys Asn
        35                  40                  45

Gly Gly Pro Ala Tyr Ser Cys Ala Asp Gln Thr Pro Trp Ala Val Asn
    50                  55                  60

Asp Gln Phe Ser Tyr Gly Phe Ala Ala Thr Asn Ile Glu Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
            100                 105                 110

Asp Leu Gly Asn Asn His Phe Asp Leu Asn Ile Pro Gly Gly Gly Val
        115                 120                 125

Gly Ile Phe Asp Gly Cys Thr Pro Gln Phe Gly Gly Leu Pro Gly Glu
    130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

```
Asp Asn Pro Asn Phe Thr Phe Glu Arg Val Gln Cys Pro Ser Glu Leu
            180                 185                 190

Val Ala Arg Thr Gly Cys Lys Arg Asn Asp Asp Gly Asn Tyr Pro Val
        195                 200                 205

Phe Thr Pro Pro Ser Gly Asp Ser Pro Ser Ser Ser Ser Ala Ala Pro
    210                 215                 220

Thr Ser Thr Ser Thr Ser Gln Gln Pro Gln Gln Pro Thr Ser Ser Ser
225                 230                 235                 240

Ser Gln Ala Ser Val Pro Thr Ser Asn Pro Gly Gly Cys Thr Ser Gln
                245                 250                 255

Lys Trp Ala Gln Cys Gly Gly Ile Gly Phe Thr Gly Cys Thr Thr Cys
            260                 265                 270

Val Ser Gly Thr Thr Cys Thr Lys Leu Asn Asp Trp Tyr Ser Gln Cys
        275                 280                 285

Thr Met Ile Asn Leu
    290
```

<210> SEQ ID NO 28
<211> LENGTH: 882
<212> TYPE: DNA
<213> ORGANISM: Artificial Sequence
<220> FEATURE:
<223> OTHER INFORMATION: Synthetic Sequence_N.A. encoding Ct.EG G2V3 protein: Mature

<400> SEQUENCE: 28

```
gccgacggca agtccactag gtactgggac tgctgcaagc cttcttgctc gtggcccggc      60

aaggctgatg tgaaccaacc cgtcttcgcc tgtgaccgca acttcaaccg cctgtccgac     120

ttcaatgtcc agtctggctg caacggcggt ccggcctatt cttgcgccga ccagaccccg     180

tgggctgtca acgaccaatt ctcgtacggc ttcgctgcca ccaacattga aggcggtaac     240

gaggcttcat ggtgctgcgc ttgctacaag ctcaccttca cctcgggacc cgtggccggc     300

aaggtcatgg ttgtccagtc gaccagcacg ggcggtgacc ttggcaacaa ccatttcgac     360

ctgaacatcc caggtggagg cgttggtatc ttcgatggtt gcacgcccca gttcggcggt     420

ctgcccggcg agcggtacgg cgggatctcg tcgcgcagcc agtgcgacag cttcccggat     480

gccctcaagc ctggctgcta ctggcgcttc gactggttcc tgaacgctga caacccgaac     540

ttcaccttcg agcgcgtcca gtgtccttcc gagcttgttg cccgcaccgg ctgcaagcgc     600

aatgacgacg gcaactaccc cgtcttcact cctccttcgg gagacagccc cagcagcagc     660

agcgctgctc ctacctccac ctcgacttcg cagcagccgc agcagccgac ctccagcagc     720

tcgcaggctt ctgtgccgac tagcaaccct ggtggctgca cctctcaaaa gtgggctcag     780

tgcggcggca ttggcttcac tggctgcact acctgcgtct cgggcaccac ttgcaccaag     840

ctgaatgact ggtactcgca gtgcacaatg atcaacctgt aa                        882
```

<210> SEQ ID NO 29
<211> LENGTH: 297
<212> TYPE: PRT
<213> ORGANISM: Artificial Sequence
<220> FEATURE:
<223> OTHER INFORMATION: Synthetic Sequence_Ct.EG G2V1 protein: SP + Mature

<400> SEQUENCE: 29

```
Met Arg Ser Thr Pro Val Leu Arg Thr Ala Leu Ala Ala Ala Leu Pro
1               5                   10                  15
```

-continued

```
Phe Thr Val Leu Ala Ala Asp Gly Lys Ser Thr Arg Tyr Trp Asp Cys
            20                  25                  30

Cys Lys Pro Ser Cys Ser Trp Pro Gly Lys Ala Ala Val Ser Gln Pro
        35                  40                  45

Val Phe Ala Cys Asp Arg Asn Phe Asn Arg Leu Ser Asp Phe Asn Val
    50                  55                  60

Gln Ser Gly Cys Asn Gly Gly Pro Ala Tyr Ser Cys Ala Asp Gln Thr
65                  70                  75                  80

Pro Trp Ala Val Asn Asp Gln Phe Ser Tyr Gly Phe Ala Ala Thr Asn
                85                  90                  95

Ile Ala Gly Gly Asn Glu Ala Ser Trp Cys Cys Ala Cys Tyr Lys Leu
            100                 105                 110

Thr Phe Thr Ser Gly Pro Val Ala Gly Lys Val Met Val Val Gln Ser
        115                 120                 125

Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly Gly Asn Gly Gly Thr
225                 230                 235                 240

Gly Thr Pro Thr Ser Thr Ala Pro Gly Ser Gly Gln Thr Ser Pro Gly
                245                 250                 255

Gly Gly Ser Gly Cys Thr Ser Gln Lys Trp Ala Gln Cys Gly Gly Ile
            260                 265                 270

Gly Phe Ser Gly Cys Thr Thr Cys Val Ser Gly Thr Thr Cys Gln Lys
        275                 280                 285

Leu Asn Asp Tyr Tyr Ser Gln Cys Leu
    290                 295
```

<210> SEQ ID NO 30
<211> LENGTH: 894
<212> TYPE: DNA
<213> ORGANISM: Artificial Sequence
<220> FEATURE:
<223> OTHER INFORMATION: Synthetic Sequence_N.A. encoding Ct.EG G2V1
      protein: SP + Mature

<400> SEQUENCE: 30

```
atgcggtcga ctcctgttct ccgtaccgcc cttgcggctg ctctcccctt cactgtcctg      60

gctgccgacg gcaagtccac taggtactgg gactgctgca agccttcttg ctcgtggccc     120

ggcaaggctg ctgtgagcca acccgtcttc gcctgtgacc gcaacttcaa ccgcctgtcc     180

gacttcaatg tccagtctgg ctgcaacggc ggtccggcct attcttgcgc cgaccagacc     240

ccgtgggctg tcaacgacca attctcgtac ggcttcgctg ccaccaacat tgccggcggt     300

aacgaggctt catggtgctg cgcttgctac aagctcacct tcacctcggg acccgtggcc     360

ggcaaggtca tggttgtcca gtcgaccagc acgggcggtg accttggcaa caaccatttc     420
```

-continued

```
gacctgaaca tcccaggtgg aggcgttggt atcttcgatg gttgcacgcc ccagttcggc    480

ggtctgcccg gcgagcggta cggcgggatc tcgtcgcgca gccagtgcga cagcttcccg    540

gatgccctca agcctggctg ctactggcgc ttcgactggt tcctgaacgc tgacaacccg    600

aacttcacct tcgagcgcgt ccagtgtcct tccgagcttg ttgcccgcac cggctgcaag    660

cgcaatgacg acggcaacta ccccgtcttc actcctcctt cgggaggcaa cggtggcacc    720

gggacgccca cgtcgactgc gcctgggtcg ggccagacgt ctcccggcgg cggcagtggc    780

tgcacctctc aaaagtgggc tcagtgcggc ggcattggct tcagcggctg cactacctgc    840

gtctcgggca ccacttgcca gaagctgaat gactactact cgcagtgcct gtaa          894
```

```
<210> SEQ ID NO 31
<211> LENGTH: 297
<212> TYPE: PRT
<213> ORGANISM: Artificial Sequence
<220> FEATURE:
<223> OTHER INFORMATION: Synthetic Sequence_Ct.EG G2V2 variant protein:
      SP + Mature

<400> SEQUENCE: 31

Met Arg Ser Thr Pro Val Leu Arg Thr Ala Leu Ala Ala Ala Leu Pro
1               5                   10                  15

Phe Thr Val Leu Ala Ala Asp Gly Lys Ser Thr Arg Tyr Trp Asp Cys
            20                  25                  30

Cys Lys Pro Ser Cys Ser Trp Pro Gly Lys Ala Ala Val Ser Gln Pro
        35                  40                  45

Val Phe Ala Cys Asp Arg Asn Phe Asn Arg Leu Ser Asp Phe Asn Val
    50                  55                  60

Gln Ser Gly Cys Asn Gly Gly Pro Ala Tyr Ser Cys Ala Asp Gln Thr
65                  70                  75                  80

Pro Trp Ala Val Asn Asp Gln Phe Ser Tyr Gly Phe Ala Ala Thr Asn
                85                  90                  95

Ile Ala Gly Gly Asn Glu Ala Ser Trp Cys Cys Ala Cys Tyr Lys Leu
            100                 105                 110

Thr Phe Thr Ser Gly Pro Val Ala Gly Lys Val Met Val Val Gln Ser
        115                 120                 125

Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly Gly Asn Gly Gly Thr
225                 230                 235                 240

Gly Thr Pro Thr Ser Thr Ala Pro Gly Ser Gly Gln Thr Ser Pro Gly
                245                 250                 255

Gly Gly Ser Gly Cys Thr Ser Gln Lys Trp Ala Gln Cys Gly Gly Ile
            260                 265                 270

Gly Phe Ser Gly Cys Thr Thr Cys Val Ser Gly Thr Thr Cys Gln Lys
```

```
        275                 280                 285

Leu Asn Asp Tyr Tyr Ser Gln Cys Leu
    290                 295
```

<210> SEQ ID NO 32
<211> LENGTH: 894
<212> TYPE: DNA
<213> ORGANISM: Artificial Sequence
<220> FEATURE:
<223> OTHER INFORMATION: Synthetic Sequence_N.A. encoding Ct.EG G2V2 protein: SP + Mature

<400> SEQUENCE: 32

```
atgcggtcga ctcctgttct ccgtaccgcc cttgcggctg ctctcccctt cactgtcctg      60

gctgccgacg gcaagtccac taggtactgg gactgctgca agccttcttg ctcgtggccc     120

ggcaaggctg atgtgagcca acccgtcttc gcctgtgacc gcaacttcaa ccgcctgtcc     180

gacttcaatg tccagtctgg ctgcaacggc ggtccggcct atacttgcgc cgaccagacc     240

ccgtgggctg tcaacgacca attctcgtac ggcttcgctg ccaccaacat tgccggcggt     300

aacgaggctt catggtgctg cgcttgctac aagctcacct tcacctcggg acccgtggcc     360

ggcaaggtca tggttgtcca gtcgaccagc acgggcggtg accttggcga caaccatttc     420

gacctgaaca tcccaggtgg aggcgttggt atcttcgatg gttgcacgcc ccagttcggc     480

ggtctgcccg gcgagcggta cggcgggatc tcgtcgcgca gccagtgcga cagcttcccg     540

gatgccctca agcctggctg ctactggcgc ttcgactggt tcctgaacgc tgacaacccg     600

aacttcacct tcgagcgcgt ccagtgtcct tccgagcttg ttgcccgcac cggctgcaag     660

cgcaatgacg acggcaacta ccccgtcttc actcctcctt cgggaggcaa cggtggcacc     720

gggacgccca cgtcgactgc gcctgggtcg ggccagacgt ctcccggcgg cggcagtggc     780

tgcacctctc aaaagtgggc tcagtgcggc ggcattggct tcagcggctg cactacctgc     840

gtctcgggca ccacttgcca gaagctgaat gactactact cgcagtgcct gtaa           894
```

<210> SEQ ID NO 33
<211> LENGTH: 314
<212> TYPE: PRT
<213> ORGANISM: Artificial Sequence
<220> FEATURE:
<223> OTHER INFORMATION: Synthetic Sequence_Ct.EG G2V3 protein: SP + Mature

<400> SEQUENCE: 33

```
Met Arg Ser Thr Pro Val Leu Arg Thr Ala Leu Ala Ala Ala Leu Pro
1               5                   10                  15

Phe Thr Val Leu Ala Ala Asp Gly Lys Ser Thr Arg Tyr Trp Asp Cys
            20                  25                  30

Cys Lys Pro Ser Cys Ser Trp Pro Gly Lys Ala Asp Val Asn Gln Pro
        35                  40                  45

Val Phe Ala Cys Asp Arg Asn Phe Asn Arg Leu Ser Asp Phe Asn Val
    50                  55                  60

Gln Ser Gly Cys Asn Gly Gly Pro Ala Tyr Ser Cys Ala Asp Gln Thr
65                  70                  75                  80

Pro Trp Ala Val Asn Asp Gln Phe Ser Tyr Gly Phe Ala Ala Thr Asn
                85                  90                  95

Ile Glu Gly Gly Asn Glu Ala Ser Trp Cys Cys Ala Cys Tyr Lys Leu
            100                 105                 110

Thr Phe Thr Ser Gly Pro Val Ala Gly Lys Val Met Val Val Gln Ser
```

-continued

```
        115                 120                 125

Thr Ser Thr Gly Gly Asp Leu Gly Asn Asn His Phe Asp Leu Asn Ile
    130                 135                 140

Pro Gly Gly Gly Val Gly Ile Phe Asp Gly Cys Thr Pro Gln Phe Gly
145                 150                 155                 160

Gly Leu Pro Gly Glu Arg Tyr Gly Gly Ile Ser Ser Arg Ser Gln Cys
                165                 170                 175

Asp Ser Phe Pro Asp Ala Leu Lys Pro Gly Cys Tyr Trp Arg Phe Asp
            180                 185                 190

Trp Phe Leu Asn Ala Asp Asn Pro Asn Phe Thr Phe Glu Arg Val Gln
        195                 200                 205

Cys Pro Ser Glu Leu Val Ala Arg Thr Gly Cys Lys Arg Asn Asp Asp
    210                 215                 220

Gly Asn Tyr Pro Val Phe Thr Pro Pro Ser Gly Asp Ser Pro Ser Ser
225                 230                 235                 240

Ser Ser Ala Ala Pro Thr Ser Thr Ser Thr Ser Gln Gln Pro Gln Gln
                245                 250                 255

Pro Thr Ser Ser Ser Ser Gln Ala Ser Val Pro Thr Ser Asn Pro Gly
            260                 265                 270

Gly Cys Thr Ser Gln Lys Trp Ala Gln Cys Gly Gly Ile Gly Phe Thr
        275                 280                 285

Gly Cys Thr Thr Cys Val Ser Gly Thr Thr Cys Thr Lys Leu Asn Asp
    290                 295                 300

Trp Tyr Ser Gln Cys Thr Met Ile Asn Leu
305                 310


<210> SEQ ID NO 34
<211> LENGTH: 945
<212> TYPE: DNA
<213> ORGANISM: Artificial Sequence
<220> FEATURE:
<223> OTHER INFORMATION: Synthetic Sequence_N.A. encoding Ct.EG G2V3
      protein: SP + Mature

<400> SEQUENCE: 34

atgcggtcga ctcctgttct ccgtaccgcc cttgcggctg ctctcccctt cactgtcctg      60

gctgccgacg gcaagtccac taggtactgg gactgctgca agccttcttg ctcgtggccc     120

ggcaaggctg atgtgaacca acccgtcttc gcctgtgacc gcaacttcaa ccgcctgtcc     180

gacttcaatg tccagtctgg ctgcaacggc ggtccggcct attcttgcgc cgaccagacc     240

ccgtgggctg tcaacgacca attctcgtac ggcttcgctg ccaccaacat tgaaggcggt     300

aacgaggctt catggtgctg cgcttgctac aagctcacct tcacctcggg acccgtggcc     360

ggcaaggtca tggttgtcca gtcgaccagc acgggcggtg accttggcaa caaccatttc     420

gacctgaaca tcccaggtgg aggcgttggt atcttcgatg gttgcacgcc ccagttcggc     480

ggtctgcccg gcgagcggta cggcgggatc tcgtcgcgca gccagtgcga cagcttcccg     540

gatgccctca agcctggctg ctactggcgc ttcgactggt tcctgaacgc tgacaacccg     600

aacttcacct tcgagcgcgt ccagtgtcct tccgagcttg ttgcccgcac cggctgcaag     660

cgcaatgacg acggcaacta ccccgtcttc actcctcctt cgggagacag ccccagcagc     720

agcagcgctg ctcctacctc cacctcgact tcgcagcagc cgcagcagcc gacctccagc     780
```

-continued

```
agctcgcagg cttctgtgcc gactagcaac cctggtggct gcacctctca aaagtgggct    840

cagtgcggcg gcattggctt cactggctgc actacctgcg tctcgggcac cacttgcacc    900

aagctgaatg actggtactc gcagtgcaca atgatcaacc tgtaa                    945
```

ADDITIONAL ENDOGLUCANASE VARIANTS AND METHODS

SEQUENCE LISTING SUBMISSION VIA EFS-WEB

A computer readable text file, entitled "SequenceListing.txt" created on Dec. 14, 2021 with a file size of 63,312 bytes contains the sequence listing for this application and is hereby incorporated by reference in its entirety.

FIELD OF THE INVENTION

This invention relates to the (variant) endoglucanase enzymes, polynucleotides encoding the (variant) endoglucanase enzymes, methods of producing the (variant) endoglucanase enzymes, and methods of using the (variant) endoglucanase enzymes. Also described are the use of endoglucanases of the invention in the textile, detergent and pulp and paper industries. The invention also relates to compositions comprising one or more (variant) endoglucanases of the invention.

BACKGROUND OF THE INVENTION

Cellulose is the major structural component of higher plants and occurs naturally in almost pure form in cotton fiber. It provides plant cells with high tensile strength helping them to resist mechanical stress and osmotic pressure. Cellulose is a linear polysaccharide of glucose residues connected by β-1,4 linkages.

Cellulolytic enzymes hydrolyze cellulose and are produced by a wide variety of bacteria and fungi. Cellulases are industrially important enzymes. In the textile industry, cellulases are used in denim finishing to create a fashionable stone washed appearance in denim cloths in a biostoning process, and they are also used, for instance, to clean fuzz and prevent formation of pills on the surface of cotton garments. In detergent industry, cellulases are used to brighten colors and to prevent graying and pilling of garments. Cellulases are further used in food industry and animal feed manufacturing, and they have a great potential in the pulp and paper industry, for instance, in deinking to release ink from fiber surfaces and in improving pulp drainage.

Endoglucanases of the present invention mean enzymes classified as E.C. 3.2.1.4 and are one type of cellulases generally needed for the biological conversion of cellulose to glucose. Endoglucanases cut internal beta-1,4-glucosidic bonds, whereas cellobiohydrolases cut the disaccharide cellobiose from the end of the cellulose polymer chain, and beta-1,4-glucosidases hydrolyze the cellobiose and other short cello-oligosaccharides to glucose. Some naturally occurring endoglucanases have a cellulose-binding domain, while others do not. Endoglucanases are also widely used in textile, detergent, and pulp and paper industry. For instance, the endoglucanases as described in U.S. Pat. Nos. 7,256,032, 6,001,639, WO 2004/053039, U.S. Pat. Nos. 5,958,082, 5,948,672, which are all hereby incorporated by reference in their entireties.

However, there remains a need in the art for variant endoglucanases with increased total activity, specific activity, temperature activity, pH activity, total stability, temperature stability, and pH tolerance. The present invention meets this need and provides variant endoglucanases with improved properties compared to a parent endoglucanase.

It is an object of the present invention to provide (variant) endoglucanase enzymes having endoglucanase activity, polynucleotides encoding the (variant) endoglucanase enzymes and methods of using the (variant) endoglucanase enzymes in various processes.

BRIEF SUMMARY OF THE INVENTION

Accordingly, the present invention provides (variant) endoglucanases and methods of producing and using them. The amino acid sequence numbers and nucleic acid sequence numbers of the present invention are listed in Table 1.

TABLE 1

| Amino acid sequence numbers and nucleic acid sequence numbers. | |
|---|---|
| Ct.EG G1P (wild-type) mature protein | SEQ ID NO: 1 |
| Ct.EG G1V1 variant mature protein | SEQ ID NO: 3 |
| Ct.EG G1V2 variant mature protein | SEQ ID NO: 5 |
| Ct.EG G1V3 variant mature protein | SEQ ID NO: 7 |
| Ct.EG G1V4 variant mature protein | SEQ ID NO: 9 |
| Ct.EG G1P (wild-type) protein including a signal peptide and a mature region | SEQ ID NO: 11 |
| Ct.EG G1V1 variant protein including a signal peptide and a mature region | SEQ ID NO: 13 |
| Ct.EG G1V2 variant protein including a signal peptide and a mature region | SEQ ID NO: 15 |
| Ct.EG G1V3 variant protein including a signal peptide and a mature region | SEQ ID NO: 17 |
| Ct.EG G1V4 variant protein including a signal peptide and a mature region | SEQ ID NO: 19 |
| Nucleic acid encoding the Ct.EG G1P (wild-type) mature protein | SEQ ID NO: 2 |
| Nucleic acid encoding the Ct.EG G1V1 variant mature protein | SEQ ID NO: 4 |
| Nucleic acid encoding the Ct.EG G1V2 variant mature protein | SEQ ID NO: 6 |
| Nucleic acid encoding the Ct.EG G1V3 variant mature protein | SEQ ID NO: 8 |
| Nucleic acid encoding the Ct.EG G1V4 variant mature protein | SEQ ID NO: 10 |
| Nucleic acid encoding the Ct.EG G1P (wild-type) protein including a signal peptide and a mature region | SEQ ID NO: 12 |
| Nucleic acid encoding the Ct.EG G1V1 variant protein including a signal peptide and a mature region | SEQ ID NO: 14 |
| Nucleic acid encoding the Ct.EG G1V2 variant protein including a signal peptide and a mature region | SEQ ID NO: 16 |
| Nucleic acid encoding the Ct.EG G1V3 variant protein including a signal peptide and a mature region | SEQ ID NO: 18 |
| Nucleic acid encoding the Ct.EG G1V4 variant protein including a signal peptide and a mature region | SEQ ID NO: 20 |
| Signal peptide (wild-type) | SEQ ID NO: 21 |
| Variant signal peptide | SEQ ID NO: 22 |
| Ct.EG G2V1 variant mature protein | SEQ ID NO: 23 |
| Ct.EG G2V2 variant mature protein | SEQ ID NO: 25 |
| Ct.EG G2V3 variant mature protein | SEQ ID NO: 27 |
| Ct.EG G2V1 variant protein including a signal peptide and a mature region | SEQ ID NO: 29 |
| Ct.EG G2V2 variant protein including a signal peptide and a mature region | SEQ ID NO: 31 |
| Ct.EG G2V3 variant protein including a signal peptide and a mature region | SEQ ID NO: 33 |
| Nucleic acid encoding the Ct.EG G2V1 variant mature protein | SEQ ID NO: 24 |
| Nucleic acid encoding the Ct.EG G2V2 variant mature protein | SEQ ID NO: 26 |
| Nucleic acid encoding the Ct.EG G2V3 variant mature protein | SEQ ID NO: 28 |
| Nucleic acid encoding the Ct.EG G2V1 variant protein including a signal peptide and a mature region | SEQ ID NO: 30 |

TABLE 1-continued

| Amino acid sequence numbers and nucleic acid sequence numbers. | |
|---|---|
| Nucleic acid encoding the Ct.EG G2V2 variant protein including a signal peptide and a mature region | SEQ ID NO: 32 |
| Nucleic acid encoding the Ct.EG G2V3 variant protein including a signal peptide and a mature region | SEQ ID NO: 34 |

In one aspect, the invention provides a composition comprising a variant endoglucanase enzyme comprising one or more amino acid modifications as compared to SEQ ID NO:1, wherein said one or more amino acid modifications occur at positions corresponding to positions selected from the group consisting of positions 2, 17, 23, 25, 29, 33, 36, 38, 39, 42, 43, 44, 48, 51, 54, 66, 67, 68, 75, 77, 80, 82, 90, 102, 116, 121, 122, 123, 132, 135, 136, 141, 144, 145, 153, 160, 161, 164, 167, 174, 180, 184, 185, 190, 192, 194, 195, 196, 204, 205, 206, 215, 216, 217, 218, 219, 220, 221, 222, 223, 228, 229, 230, 231, 232, 233, 234, 235, 237, 238, 239, 241, 242, 243, 244, 245, 246, 247, 248, 249, 250, 251, 258, 259, 267, 268, 269, 270, 271, 273, 274, 275, 276, 277, 278, 279, 280, 281, 282, 283, 284, 285, 286, 287, 288, 289, 290, 291, 292, and 293, wherein said variant endoglucanase enzyme exhibits at least 80% sequence identity to SEQ ID NO:1; and wherein said variant endoglucanase enzyme has endoglucanase activity.

In a further aspect, the invention provides a composition comprising a variant endoglucanase enzyme comprising one or more amino acid modifications as compared to SEQ ID NO:1, wherein said one or more amino acid modifications are selected from the group consisting of modifications corresponding to D2E, D2F, D2N, D2Q, D2S, D2T, S17G, A23D, A23N, A23S, S25N, F29Y, R33A, N36Q, I38L, Y39S, G42N, A43E, A43L, A43S, A43T, A43V, K44E, K44Q, E48N, P51E, P51N, P51S, P51T, S54T, Q66N, Q66T, F67L, F67Y, S68A, N75S, A77E, A77Q, N80S, A82S, K90A, V102Q, V102R, V102T, N116D, N116E, N116S, L121I, N122A, N122S, I123M, D132N, T135S, P136S, L141S, E144A, R145Q, S153D, D160A, A161K, A161P, P164S, P164T, Y167Q, L174Q, N180T, E184A, E184K, E184N, E184Q, E184R, E184S, E184T, R185Q, S190A, L192I, A194T, R195S, T196S, G204S, N205S, Y206F, D215*, D215G, S216N, P217G, S218G, S219T, S220G, S221-, A222-, A223T, S228A, T229P, S230G, Q231S, Q232G, P233Q, Q234T, Q235S, T237G, S238G, S239G, S241-, Q242-, A243-, S244-, V245-, P246-, T247-, S248-, N249-, P250-, G251-, W258*, W258R, W258S, A259*, A259D, T267S, G268N, C269R, C269S, T270*, T271E, V273*, V273D, V273G, S274R, G275*, G275A, G275E, G275N, G275T, T276G, T276H, T276P, T276R, T277D, T277E, T277L, C278*, C278A, C278L, T279H, T279P, T279Q, K280Q, K280S, L281*, L281A, L281E, L281G, L281K, L281S, N282E, N282S, D283*, W284*, W284G, W284M, W284R, W284T, W284Y, Y285*, S286A, S286G, Q287H, Q287S, C288*, C288A, T289-, T289K, T289Q, M290-, M290*, I291-, I291A, I291Q, I291S, N292-, N292S, L293G, L293N, L293T, and L293V of SEQ ID NO:1.

In an additional aspect, the invention provides a composition comprising a variant endoglucanase enzyme comprising one or more amino acid modifications as compared to SEQ ID NO:1 as described herein, wherein said amino acid substitution(s) occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions, twenty of said positions, twenty-one of said positions, twenty-two of said positions, twenty-three of said positions, twenty-four of said positions, twenty-five of said positions, twenty-six of said positions, twenty-seven of said positions, twenty-eight of said positions, twenty-nine of said positions, thirty of said positions, thirty-one of said positions, thirty-two of said positions, thirty-three of said positions, thirty-four of said positions, thirty-five of said positions, thirty-six of said positions, thirty-seven of said positions, thirty-eight of said positions, thirty-nine of said positions, forty of said positions, forty-one of said positions, forty-two of said positions, forty-three of said positions, forty-four of said positions, forty-five of said position, forty-six of said positions, or forty-seven of said positions of SEQ ID NO:1.

In a further aspect, the invention provides a composition comprising a variant endoglucanase enzyme comprising one or more amino acid modifications as compared to SEQ ID NO:1 as described herein, wherein said variant endoglucanase enzyme exhibits at least 85%, 90% or 95% sequence identity to SEQ ID NO:1.

In an additional aspect, the invention provides a composition comprising a variant endoglucanase enzyme comprising one or more amino acid modifications as compared to SEQ ID NO:1 as described herein, wherein said variant endoglucanase enzyme comprises said amino acid modification(s) selected from the group consisting of D215*, A23D/I38L/Y39S/G42N/A43E/K44E/E48N/S54T/A77Q/N116D/N122S/L141S/L281G, A23D/I38L/Y39S/G42N/A43E/K44Q/E48N/S54T/N116E/W258S/A259D/G275E/T277D, A23D/I38L/Y39S/G42N/A43S/K44E/E48N/A77E/N116S/N122A/N180T/W258S/A259D/G275E/T277D/I291S/L293T, A23D/I38L/Y39S/G42N/A43S/K44E/E48N/S54T/A77E/N122S/P164T/N180T/A259D/S286A/L293T, A23D/I38L/Y39S/G42N/A43S/K44Q/E48N/A77Q/N116E/L141S/G257E/T277D/W284R, A23D/I38L/Y39S/G42N/A43S/K44Q/E48N/S54T/N116D/W258S/G275T/L281E/I291Q, A23D/I38L/Y39S/G42N/A43S/K44Q/E48N/V102Q/W258S/L281E/N282S/I291A, A23D/I38L/Y39S/G42N/A43S/K44Q/E48N/V102R/W258R/A259D/L281E/N282S, A23D/I38L/Y39S/G42N/A43T/K44E/E48N/P164T/N108T/A194T/W258S/A259D/G275T/L281G, A23D/I38L/Y39S/G42N/A43T/K44E/E48N/V102Q/N116D/L281G/N282S, A23D/I38L/Y39S/G42N/A43T/K44Q/E48N/V102Q/N116D/W258S/G278T/L281E/I291A, A23D/I38L/Y39S/G42N/A43T/K44Q/E48N/A77Q/N108T/W258S/G275E/I291Q, A23D/I38L/Y39S/G42N/A43V/K44E/E48A77E/N116D/G275T/L281E, A23D/I38L/Y39S/G42N/A43V/K44E/E48N/N122A/N180T/T277D/L281E/N282S, A23D/I38L/Y39S/G42N/A43V/K44Q/E48N, A23D/I38L/Y39S/G42N/A43V/K44Q/E48N/A161K/P164T/N180T, A23D/I38L/Y39S/G42N/A43V/K44Q/E48N/A77E/A161K/P164T/N180T, A23D/I38L/Y39S/G42N/A43V/K44Q/E48N/A77E/N116D/W258S/L281E, A23D/I38L/Y39S/G42N/A43V/K44Q/E48N/A77Q/N116S/N180T/G275E/T277E, A23D/I38L/Y39S/G42N/A43V/K44Q/E48N/A77Q/N180T, A23D/I38L/Y39S/G42N/A43V/K44Q/E48N/F67Y/A77Q/N116S/N180T/W258S/A259D/G275T/T277E/L281K/N282S/I291S/L293N, A23D/I38L/Y39S/G42N/A43V/K44Q/E48N/F67Y/A77Q/N122S/N180T/A194T/W258R/L281K, A23D/

I38L/Y39S/G42N/A43V/K44Q/E48N/F67Y/N180T, A23D/I38L/Y39S/G42N/A43V/K44Q/E48N/L141S, A23D/I38L/Y39S/G42N/A43V/K44Q/E48N/N116D/G275T/L281E/N282S/I291A, A23D/I38L/Y39S/G42N/A43V/K44Q/E48N/N116D/L281K/N282S/I291S/N292S/L293N, A23D/I38L/Y39S/G42N/A43V/K44Q/E48N/N116F/W258S/L281G, A23D/I38L/Y39S/G42N/A43V/K44Q/E48N/N180T, A23D/I38L/Y39S/G42N/A43V/K44Q/E48N/N180T/A259D/G275T/N282S, A23D/I38L/Y39S/G42N/A43V/K44Q/E48N/Q66T/A77Q/N122A/L141S/G275T/W284G/S286A, A23D/I38L/Y39S/G42N/A43V/K44Q/E48N/S54T/A77E/A161P/W258S/W284M/I291Q, A23D/I38L/Y39S/G42N/A43V/K44Q/E48N/S54T/A77E/T277E/L281E/S286A, A23D/I38L/Y39S/G42N/A43V/K44Q/E48N/S54T/A77E/V102Q/G275T/T277D/W284M/I291Q, A23D/I38L/Y39S/G42N/A43V/K44Q/E48N/S54T/A77E/W258S/T277D/W284M/I291A, A23D/I38L/Y39S/G42N/A43V/K44Q/E48N/S54T/I291A, A23D/I38L/Y39S/G42N/A43V/K44Q/E48N/S54T/L281E, A23D/I38L/Y39S/G42N/A43V/K44Q/E48N/S54T/N116D/A161P/L281E/N282S, A23D/I38L/Y39S/G42N/A43V/K44Q/E48N/S54T/N116D/A161P/W258S/G275T/L281E/I291A, A23D/I38L/Y39S/G42N/A43V/K44Q/E48N/S54T/N116D/A161P/W258S/W284M/I291A, A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, A23D/I38L/Y39S/G42N/A43V/K44Q/E48N/S54T/N116D/L141S/A161K/N180T/W258R/A259D/G275E/T277D/W284R/I291Q/N292S/L293G, A23D/I38L/Y39S/G42N/A43V/K44Q/E48N/S54T/N116D/L141S/N180T/G275T/W284R/I291Q/L293N, A23D/I38L/Y39S/G42N/A43V/K44Q/E48N/S54T/N116D/W258S/G275T/N282S/I291A, A23D/I38L/Y39S/G42N/A43V/K44Q/E48N/S54T/N116D/W284M/I291Q, A23D/I38L/Y39S/G42N/A43V/K44Q/E48N/S54T/N116E/L141S/N180T/L281G/N282S, A23D/I38L/Y39S/G42N/A43V/K44Q/E48N/S54T/N116S/G275E/Y285*, A23D/I38L/Y39S/G42N/A43V/K44Q/E48N/S54T/Q66T/F67Y/N122S/N180T/L281G/I291S/N292S/L293G, A23D/I38L/Y39S/G42N/A43V/K44Q/E48N/S54T/V102Q/N116D/A161P/T277D/W284M/I291Q, A23D/I38L/Y39S/G42N/A43V/K44Q/E48N/S54T/V102Q/N116D/W258S/G275T/I291Q, A23D/I38L/Y39S/G42N/A43V/K44Q/E48N/S54T/V102Q/N116D/W258S/G275T/T277E, A23D/I38L/Y39S/G42N/A43V/K44Q/E48N/S54T/V102Q/N116D/W258S/G275T/T277E/L281G, A23D/I38L/Y39S/G42N/A43V/K44Q/E48N/S54T/V102Q/N116D/W258S/L281G/I291A, A23D/I38L/Y39S/G42N/A43V/K44Q/E48N/S54T/V102Q/W258S/G275T/T277D/N282S, A23D/I38L/Y39S/G42N/A43V/K44Q/E48N/S54T/V102Q/W258S/W284M/S286A, A23D/I38L/Y39S/G42N/A43V/K44Q/E48N/S54T/W258S, A23D/I38L/Y39S/G42N/A43V/K44Q/E48N/V102Q/A161P/W258S, A23D/I38L/Y39S/G42N/A43V/K44Q/E48N/V102Q/W258S/I291Q, A23D/I38L/Y39S/G42N/A43V/K44Q/E48N/V102R/N180T, A23D/I38L/Y39S/G42N/A43V/K44Q/E48N/W258S/I291A, A23D/I38L/Y39S/G42N/K44Q/E48N/A77E/N116D/L281E/I291A, A23D/S25N/I38L/Y39S/G42N/A43E/K44E/E48N/V102R/N116S/N122A/L141S/A161K/P164T/A194T/W258R/A259D/L281E, A23D/S25N/I38L/Y39S/G42N/A43E/K44Q/E48N/Q66T/F67Y/L141S/N180T, A23D/S25N/I38L/Y39S/G42N/A43S/K44Q/E48N/S54T/Q66T/L141S/N180T/W258S/A259D/T277D/W284G/Y285*, A23D/S25N/I38L/Y39S/G42N/A43V/K44Q/E48N/A161K/N180T, A23D/S25N/I38L/Y39S/G42N/A43V/K44Q/E48N/A161P, A23D/S25N/I38L/Y39S/G42N/A43V/K44Q/E48N/A77E, A23D/S25N/I38L/Y39S/G42N/A43V/K44Q/E48N/A77E/N180T, A23D/S25N/I38L/Y39S/G42N/A43V/K44Q/E48N/A77E/N180T/A259D/L281K/L293T, A23D/S25N/I38L/Y39S/G42N/A43V/K44Q/E48N/A77E/V102Q/N180T, A23D/S25N/I38L/Y39S/G42N/A43V/K44Q/E48N/A77Q/N180T/A194T/W258S/W284G/S286G, A23D/S25N/I38L/Y39S/G42N/A43V/K44Q/E48N/A77Q/V102Q/N180T/A194T, A23D/S25N/I38L/Y39S/G42N/A43V/K44Q/E48N/A77Q/W258S/G275T/T277D/W284M/I291S/L293T, A23D/S25N/I38L/Y39S/G42N/A43V/K44Q/E48N/F67Y/A77E/A161P/P164T/N180T, A23D/S25N/I38L/Y39S/G42N/A43V/K44Q/E48N/F67Y/N180T, A23D/S25N/I38L/Y39S/G42N/A43V/K44Q/E48N/L281E/N282S/N292S/L293G, A23D/S25N/I38L/Y39S/G42N/A43V/K44Q/E48N/N116D/A194T/W258S/A259D/G275T/W284G/S286G/L293T, A23D/S25N/I38L/Y39S/G42N/A43V/K44Q/E48N/N116E/N122S/A194T/T277L/C278A/T279P/K280S/L281*, A23D/S25N/I38L/Y39S/G42N/A43V/K44Q/E48N/N180T, A23D/S25N/I38L/Y39S/G42N/A43V/K44Q/E48N/Q66T/F67Y/A77Q/N180T, A23D/S25N/I38L/Y39S/G42N/A43V/K44Q/E48N/Q66T/N122S/L141S/W284R/C288*, A23D/S25N/I38L/Y39S/G42N/A43V/K44Q/E48N/S54T/A77Q/N116D/L141S/W258S/A259D/G275 T/L281E/N292S/L293T, A23D/S25N/I38L/Y39S/G42N/A43V/K44Q/E48N/S54T/L281E/N282S/C288A/T289Q/M290*, A23D/S25N/I38L/Y39S/G42N/A43V/K44Q/E48N/S54T/N116D/A161P/N180T/W258R/G275E/T277E/I291S/L293G, A23D/S25N/I38L/Y39S/G42N/A43V/K44Q/E48N/S54T/N180T/L281E/N282S/C288A/T289Q/M290*, A23D/S25N/I38L/Y39S/G42N/A43V/K44Q/E48N/S54T/Q66T/F67Y/A77Q/N122S/L141S/W258R/N282S, A23D/S25N/I38L/Y39S/G42N/K44E/E48N/A161P/A194T/G275E/T277D, A23D/S25N/I38L/Y39S/G42N/K44Q/E48N/S54T/A77E/V102R/N122S/L141S/A259D/W284G/I291S/L293T, A23N/I38L/Y39S/G42N/A43E/K44E/E48N/S54T/A77EN102Q/N116D/W258S/W284M/I291Q, A23N/I38L/Y39S/G42N/A43E/K44Q/E48N/S54T/A77E/A161P/G275T/N282S/I291Q, A23N/I38L/Y39S/G42N/A43E/K44Q/E48N/S54T/A77E/N116D/W284M/S286A/I291Q, A23N/I38L/Y39S/G42N/A43E/K44Q/E48N/S54TN102Q/N116D/W258S/G275T/L281E/N282S/I291A, A23N/I38L/Y39S/G42N/A43L/K44Q/E48N/Q66T/F67Y/A77EN102Q/N116D/L141S/N180T/W258R/I291S, A23N/I38L/Y39S/G42N/A43S/K44E/E48N/S54T/A77E/L141S/W258S/G275T, A23N/I38L/Y39S/G42N/A43S/K44Q/E48N/S54T/A77E/I291Q, A23N/I38L/Y39S/G42N/A43S/K44Q/E48N/S54T/A77E/N116E/N180T/W258S/W284R/S286G, A23N/I38L/Y39S/G42N/A43S/K44Q/E48N/S54T/N116D/S286A/I291A, A23N/I38L/Y39S/G42N/A43S/K44Q/E48N/S54T/Q66T/F67Y/N116D/L141S, A23N/I38L/Y39S/G42N/A43V/K44E/E48N/A77Q/N122S/L141S/N180T/W284M/S286A, A23N/I38L/Y39S/G42N/A43V/K44Q/E48N, A23N/I38L/Y39S/G42N/A43V/K44Q/E48N/A161P/G275T/L281E/N282S/I291A, A23N/I38L/Y39S/G42N/A43V/K44Q/E48N/A161P/N180T, A23N/I38L/Y39S/G42N/A43V/K44Q/E48N/A77E/N116D/R195S/W258S/T277E/N282S/I291A, A23N/I38L/Y39S/G42N/A43V/K44Q/E48N/A77E/N180T, A23N/I38L/Y39S/G42N/A43V/K44Q/E48N/A77E/N180T/A194T, A23N/I38L/Y39S/G42N/A43V/K44Q/E48N/A77E/V102Q/W284M/S286A/I291A, A23N/I38L/Y39S/G42N/A43V/K44Q/E48N/F67Y/A77Q/N116D/N180T/G275E/T277D/W284R/I291S/L293N, A23N/I38L/Y39S/G42N/A43V/K44Q/E48N/N180T, A23N/I38L/Y39S/G42N/A43V/K44Q/

E48N/S54T/A161P/G275T/L281G/I291Q, A23N/I38L/Y39S/G42N/A43V/K44Q/E48N/S54T/A77E/V102Q/A161P/W258S/W284M, A23N/I38L/Y39S/G42N/A43V/K44Q/E48N/S54T/N116D/A161P/G275T/L281E, A23N/I38L/Y39S/G42N/A43V/K44Q/E48N/S54T/N116D/A161P/P164T/G275E/L281E, A23N/I38L/Y39S/G42N/A43V/K44Q/E48N/S54T/Q66T/F67Y/A161P/W284M/I291Q, A23N/I38L/Y39S/G42N/A43V/K44Q/E48N/S54T/Q66T/N116S/A259D/W284G/I291S/L293T, A23N/I38L/Y39S/G42N/A43V/K44Q/E48N/S54T/V102Q/W258S/G275T/N282S, A23N/I38L/Y39S/G42N/A43V/K44Q/E48N/S54T/V102Q/W258S/N282S/I291A, A23N/I38L/Y39S/G42N/A43V/K44Q/E48N/S54T/V102Q/W258S/T277D/L281E, A23N/I38L/Y39S/G42N/A43V/K44Q/E48N/S54T/W258R/A259D/I291S/L293T, A23N/I38L/Y39S/G42N/A43V/K44Q/E48N/S54T/W258S/A259D/L281K/N282S, A23N/I38L/Y39S/G42N/A43V/K44Q/E48N/T277E/W284M, A23N/I38L/Y39S/G42N/A43V/K44Q/E48N/V102Q/G275T/W284M, A23N/I38L/Y39S/G42N/A43V/K44Q/E48N/V102R/N180T, A23N/I38L/Y39S/G42N/K44E/E48N/S54T/N180T/A194T/G275T/I291S/N292S/L293N, A23N/S25N/I38L/Y39S/G42N/A43E/K44Q/E48N/S54T/Q66T/N116E/N122S/A161P/A259D/L281G, A23N/S25N/I38L/Y39S/G42N/A43S/K44Q/E48N/S54T/F67Y/A77E/N122S/N180T/A259D/W284R, A23N/S25N/I38L/Y39S/G42N/A43V/K44Q/E48N, A23N/S25N/I38L/Y39S/G42N/A43V/K44Q/E48N/A77E/N180T, A23N/S25N/I38L/Y39S/G42N/A43V/K44Q/E48N/F67Y/A77E/N180T/A194T/G275T/L281G, A23N/S25N/I38L/Y39S/G42N/A43V/K44Q/E48N/N180T/A194T, A23N/S25N/I38L/Y39S/G42N/A43V/K44Q/E48N/S54T/F67Y/N122S/L141S/A161P/P164T/A194T/G275T, A23N/S25N/I38L/Y39S/G42N/A43V/K44Q/E48N/S54T/N116D/L141S/A161K/N180T/A194T/W258S/A259D/W284R/I291Q/N292S, D215G/S216N/P217G/S218G/S219T/S220G/S221-/A222-/A233T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, D2E/I38L/Y39S/G42N/A43V/K244Q/E48N, D2F/I38L/Y39S/G42N/A43V/K44Q/E48N, D2N/I38L/Y39S/G42N/A43V/K44Q/E48N/S54T/V102Q/A161P/W258S/T277D/W284M/I291A, D2Q/I38L/Y39S/G42N/A43V/K44Q/E48N, D2S/I38L/Y39S/G42N/A43V/K44Q/E48N, D2T/I38L/Y39S/G42N/A43V/K44Q/E48N, I38L/Y39S/G42N/A43V/K44Q/E48N, I38L/Y39S/G42N/A43E/K44Q/E48N/G275E/L281G/N282S/S286A, I38L/Y39S/G42N/A43E/K44Q/E48N/S54T/N116E/L114S, I38L/Y39S/G42N/A43L/K44E/E48N, I38L/Y39S/G42N/A43L/K44Q/E48N, I38L/Y39S/G42N/A43L/K44Q/E48N/A116P/A194T, I38L/Y39S/G42N/A43S/K44Q/E48N/S54T/F67Y/A77Q/V102R/N116D/N122S/W258R/L281K/I291S/N292S/L293G, I38L/Y39S/G42N/A43S/K44E/E48N/S54T/Q66T/N116E/L141S/N180T/W258R/A259D, I38L/Y39S/G42N/A43S/K44Q/E48N, I38L/Y39S/G42N/A43S/K44Q/E48N/F67Y, I38L/Y39S/G42N/A43S/K44Q/E48N/S54T/A77E/N116E/N180T/A259D/W284G/I291Q/L293G, I38L/Y39S/G42N/A43S/K44Q/E48N/S54T/A77Q/L141S/W258S/W284G/I291Q/N292S/L293T, I38L/Y39S/G42N/A43T/K44E/E48N/F67Y/N116S/W284R/N292S, I38L/Y39S/G42N/A43T/K44E/E48N/Q66T/N116E/A161P/P164T/A194T/G275T/L281K/N282S, I38L/Y39S/G42N/A43T/K44Q/E48N, I38L/Y39S/G42N/A43V/K44E/E48N, I38L/Y39S/G42N/A43V/K44E/E48N/S286A/I291A, I38L/Y39S/G42N/A43V/K44E/E48N/S54T/N116S/L141S, I38L/Y39S/G42N/A43V/K44E/E48N/S54T/Q66T/V102Q/N116S/L141S/N180T/W258R, I38L/Y39S/G42N/A43V/K44Q/E48N, I38L/Y39S/G42N/A43V/K44Q/E48N/A161P, I38L/Y39S/G42N/A43V/K44Q/E48N/A194T, I38L/Y39S/G42N/A43V/K44Q/E48N/A259*, I38L/Y39S/G42N/A43V/K44Q/E48N/A259D, I38L/Y39S/G42N/A43V/K44Q/E48N/A77E, I38L/Y39S/G42N/A43V/K44Q/E48N/A77E/V102Q/W258S/G275T/T277E/W284M/S286A/I291A, I38L/Y39S/G42N/A43V/K44Q/E48N/A77Q, I38L/Y39S/G42N/A43V/K44Q/E48N/A77Q/N180T, I38L/Y39S/G42N/A43V/K44Q/E48N/C269R, I38L/Y39S/G42N/A43V/K44Q/E48N/C296S/W284*, I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, I38L/Y39S/G42N/A43V/K44Q/E48N/D283*, I38L/Y39S/G42N/A43V/K44Q/E48N/E184A, I38L/Y39S/G42N/A43V/K44Q/E48N/E184K, I38L/Y39S/G42N/A43V/K44Q/E48N/E184N, I38L/Y39S/G42N/A43V/K44Q/E48N/E184R, I38L/Y39S/G42N/A43V/K44Q/E48N/E184S, I38L/Y39S/G42N/A43V/K44Q/E48N/E184T, I38L/Y39S/G42N/A43V/K44Q/E48N/F67Y/A77Q/N116D/A161P, I38L/Y39S/G42N/A43V/K44Q/E48N/F67Y/G275E/T277E/W284M/Q287S/C288A/T289Q/M290*, I38L/Y39S/G42N/A43V/K44Q/E48N/F67Y/N116D/N122S, I38L/Y39S/G42N/A43V/K44Q/E48N/F67Y/N122A/L141S, I38L/Y39S/G42N/A43V/K44Q/E48N/G268N, I38L/Y39S/G42N/A43V/K44Q/E48N/G275*, I38L/Y39S/G42N/A43V/K44Q/E48N/G275N, I38L/Y39S/G42N/A43V/K44Q/E48N/G275T, I38L/Y39S/G42N/A43V/K44Q/E48N/G275T/T277E/N282S/I291A, I38L/Y39S/G42N/A43V/K44Q/E48N/I291Q, I38L/Y39S/G42N/A43V/K44Q/E48N/I291S, I38L/Y39S/G42N/A43V/K44Q/E48N/L141S/N180T/A259D/L281G/N282S/L293N, I38L/Y39S/G42N/A43V/K44Q/E48N/L141S/W258R, I38L/Y39S/G42N/A43V/K44Q/E48N/L281E, I38L/Y39S/G42N/A43V/K44Q/E48N/L281G, I38L/Y39S/G42N/A43V/K44Q/E48N/L281K, I38L/Y39S/G42N/A43V/K44Q/E48N/L281S/Q284H, I38L/Y39S/G42N/A43V/K44Q/E48N/L293N, I38L/Y39S/G42N/A43V/K44Q/E48N/L293T, I38L/Y39S/G42N/A43V/K44Q/E48N/L293V, I38L/Y39S/G42N/A43V/K44Q/E48N/N116D, I38L/Y39S/G42N/A43V/K44Q/E48N/N116D/L141S/N180T/A259D/N282S, I38L/Y39S/G42N/A43V/K44Q/E48N/N116S, I38L/Y39S/G42N/A43V/K44Q/E48N/N116S/L141S/P164T/W258S/L281G/N282S/S286A, I38L/Y39S/G42N/A43V/K44Q/E48N/N122A, I38L/Y39S/G42N/A43V/K44Q/E48N/N180T, I38L/Y39S/G42N/A43V/K44Q/E48N/N282S, I38L/Y39S/G42N/A43V/K44Q/E48N/P51N, I38L/Y39S/G42N/A43V/K44Q/E48N/P51T, I38L/Y39S/G42N/A43V/K44Q/E48N/Q66T/F67Y/A77Q/N116E/N122A/A161K/N180T/W258S/L293G, I38L/Y39S/G42N/A43V/K44Q/E48N/S286A, I38L/Y39S/G42N/A43V/K44Q/E48N/S286G, I38L/Y39S/G42N/A43V/K44Q/E48N/S54T, I38L/Y39S/G42N/A43V/K44Q/E48N/S54T/A277E/S286A/I291A, I38L/Y39S/G42N/A43V/K44Q/E48N/S54T/G275T/T277D/L281G/N282S/I291A, I38L/Y39S/G42N/A43V/K44Q/E48N/S54T/L141S, I38L/Y39S/G42N/A43V/K44Q/E48N/S54T/N116D, I38L/Y39S/G42N/A43V/K44Q/E48N/S54T/N116S/N122S/L141S, I38L/Y39S/G42N/A43V/K44Q/E48N/S54T/N122A, I38L/Y39S/G42N/A43V/K44Q/E48N/S54T/P164T/N180T/W258R/A259D/L281G/N282S/I291S/N292S/L293N, I38L/Y39S/G42N/A43V/K44Q/E48N/T270*, I38L/Y39S/G42N/A43V/K44Q/E48N/T271E, I38L/Y39S/G42N/A43V/K44Q/E48N/T276G/K280S/L281*, I38L/Y39S/G42N/

A43V/K44Q/E48N/T276H/C278*, I38L/Y39S/G42N/A43V/K44Q/E48N/T276R/K280Q/L281A/N282E/D283*, I38L/Y39S/G42N/A43V/K44Q/E48N/T277D, I38L/Y39S/G42N/A43V/K44Q/E48N/V102Q/N116D, I38L/Y39S/G42N/A43V/K44Q/E48N/V102Q/T277D/L281G, I38L/Y39S/G42N/A43V/K44Q/E48N/V273*, I38L/Y39S/G42N/A43V/K44Q/E48N/V273D/S274R/G275A/T276P/T277L/C278A/T279P/K280S/L281*, I38L/Y39S/G42N/A43V/K44Q/E48N/W258*, I38L/Y39S/G42N/A43V/K44Q/E48N/W258R, I38L/Y39S/G42N/A43V/K44Q/E48N/W258S, I38L/Y39S/G42N/A43V/K44Q/E48N/W284G, I38L/Y39S/G42N/A43V/K44Q/E48N/W284M, I38L/Y39S/G42N/A43V/K44Q/E48N/W258S, I38L/Y39S/G42N/A43V/K44Q/E48N/W284G, I38L/Y39S/G42N/A43V/K44Q/E48N/W284M, I38L/Y39S/G42N/A43V/K44Q/E48N/W284M/I291Q, I38L/Y39S/G42N/A43V/K44Q/E48N/W284R, I38L/Y39S/G42N/A43V/K44Q/E48N/W284T, I38L/Y39S/G42N/A43V/K44Q/E48N/N116D/L141S, I38L/Y39S/G42N/K44E/E48N/Q66T/F67Y/A77Q/N122A/A161K/S286G/T289K/M290*, I38L/Y39S/G42N/K44E/E48N/S54T/N116D/W258S/G275T/W284M/I291Q, I38L/Y39S/G42N/K44E/E48N/S54T/N116E/N122S/L141S, I38L/Y39S/G42N/K44E/E48N/S54T/N116S/N122A, I38L/Y39S/G42N/K44Q/E48N, I38L/Y39S/G42N/K44Q/E48N/S54T/N116D/L141S, S17G/A23D/I38L/Y39S/G42N/A43T/K44E/E48N/A77E/V102Q/A161P/G275T/N282S/I291A, S17G/A23D/I38L/Y39S/G42N/A43V/K44Q/E48N/A77E/V102Q/A161P/W258S/L281E/I291Q, S17G/A23D/I38L/Y39S/G42N/A43V/K44Q/E48N/F67Y/G275T/W284M/I291S, S17G/A23D/I38L/Y39S/G42N/A43V/K44Q/E48N/F67Y/V102Q/N116S/N122A/L141S/N180T/A194T/W284R/N292S/L293T, S17G/A23D/I38L/Y39S/G42N/A43V/K44Q/E48N/S54T/A77E/V102Q/N116D/A161P/L281G, S17G/A23D/I38L/Y39S/G42N/A43V/K44Q/E48N/S54T/A77E/V102Q/S286A/I291Q, S17G/A23D/I38L/Y39S/G42N/A43V/K44Q/E48N/S54T/V102Q/W258S/L281E, S17G/A23D/I38L/Y39S/G42N/A43V/K44Q/E48N/S54T/W258S/L281G/N282S/I291A, S17G/A23D/I38L/Y39S/G42N/A43V/K44Q/E48N/V102Q/A161P/T277D/W284M, S17G/A23D/I38L/Y39S/G42N/A43V/K44Q/E48N/V102Q/N116D/L141S/N180T/L281G/I291Q/N292S/L293N, S17G/A23D/I38L/Y39S/G42N/A43V/K44Q/E48N/Q66T/A77E/A194T, S17G/A23D/S25N/I38L/Y39S/G42N/A43V/K44Q/E48N/S54T/Q66T/F67Y/A77Q/N116E/L141S/N180T/A194T/W258S/A259D/G275E/L281G/N282S/I291S/N292S/L293T, S17G/A23D/I38L/Y39S/G42N/A43E/K44E/E48N/N116D/W258S/G275T/W284M/S286A, S17G/A23D/I38L/Y39S/G42N/A43L/K44E/E48N/N116S/A161K/A194T, S17G/A23D/I38L/Y39S/G42N/A43S/K44E/E48N/A77E/V102Q/G275T, S17G/A23D/I38L/Y39S/G42N/A43S/K44Q/E48N/S54T/V102Q/N116E, S17G/A23D/I38L/Y39S/G42N/A43V/K44Q/E48N/A77E/V102Q/A161P/W284M/I291Q, S17G/A23D/I38L/Y39S/G42N/A43V/K44Q/E48N/N116S/N122S/G275T/L281E, S17G/A23D/I38L/Y39S/G42N/A43V/K44Q/E48N/S54T/N116D/L141S/N180T/G275T/T277E/W284G, S17G/A23D/I38L/Y39S/G42N/A43V/L44Q/E48N/S54T/V102Q/W258S/W284M/I291Q, S17G/A23D/I38L/Y39S/G42N/A43V/K44Q/E48N/S54T/W258S/G275T/T277E, S17G/A23D/I38L/Y39S/G42N/A43V/K44Q/E48N/V102Q/N116D/A161P/W258S, S17G/A23D/I38L/Y39S/G42N/A43S/K44Q/E48N/Q66T/V102Q/N122S/A161P/P164T/L281K/N282S, S17G/A23D/I38L/Y39S/G42N/A43V/K44Q/E48N/S54T/Q66T/N116E/A259D/W284G, S17G/A23D/I38L/Y39S/G42N/A43V/K44Q/E48N/Q66T/F67Y/N116E/L114S/N180T/A194T/G275E/W284G/I291S/N292S, S17G/A23D/I38L/Y39S/G42N/A43V/K44Q/E48N/L141S, S17G/I38L/Y39S/G42N/A43E/K44Q/E48N/S54T/N122S, S17G/I38L/Y39S/G42N/A43S/K44E/E48N/Q66T/A77Q/V102Q/N116S/N122S/L141S/W258R/A259D/W284R, S17G/I38L/Y39S/G42N/A43S/K44E/E48N/S54T/A77Q/N116E/N122A/L141S/A161K/P164T/N180T/A194T/T277E/W284G, S17G/I38L/Y39S/G42N/A43S/K44E/E48N/S54T/N180T/W258S/A259D, S17G/I38L/Y39S/G42N/A43S/K44Q/E48N/Q66T/N116D/N122S/N180T, S17G/I38L/Y39S/G42N/A43S/K44Q/E48N/S54T/L141S, S17G/I38L/Y39S/G42N/A43S/K44Q/E48N/S54T/N116D/L141S, S17G/I38L/Y39S/G42N/A43S/K44Q/E48N/S54T/V102Q/N116D/A161P/W258S/N282S/W284M/I291A, S17G/I38L/Y39S/G42N/A43T/K44Q/E48N/S54T/V102Q/N116D/A161P/L281E/N282S, S17G/I38L/Y39S/G42N/A43V/K44E/E48N/S54T/N116S/N122S, S17G/I38L/Y39S/G42N/A43V/K44Q/E48N, S17G/I38L/Y39S/G42N/A43V/K44Q/E48N/I291S/N292S/L293N, S17G/I38L/Y39S/G42N/A43V/K44Q/E48N/N116S/N180T/T277E/W284R/L293T, S17G/I38L/Y39S/G42N/A43V/K44Q/E48N/N122A/A194T/A259D/G275T/T277D/L281K/L293N, S17G/I38L/Y39S/G42N/A43V/K44Q/E48N/N122S, S17G/I38L/Y39S/G42N/A43V/K44Q/E48N/Q66T/A77E/N116S/G275T/W284M, S17G/I38L/Y39S/G42N/A43V/K44Q/E48N/S54T, S17G/I38L/Y39S/G42N/A43V/K44Q/E48N/S54T/A77E/N116D/L141S/L281E, S17G/I38L/Y39S/G42N/A43V/K44Q/E48N/S54T/A77E/V102Q/G275T, S17G/I38L/Y39S/G42N/A43V/K44Q/E48N/S54T/A77Q/N116E/L141S/N180T/A194T/W258S/A259D/W284G/S286G/I291Q/L293G, S17G/I38L/Y39S/G42N/A43V/K44Q/E48N/S54T/A77Q/N116S/L141S/A194T/W258R/L281G, S17G/I38L/Y39S/G42N/A43V/K44Q/E48N/S54T/N116D, S17G/I38L/Y39S/G42N/A43V/K44Q/E48N/S54T/N116E, S17G/I38L/Y39S/G42N/A43V/K44Q/E48N/S54T/N116E/L141S, S17G/I38L/Y39S/G42N/A43V/K44Q/E48N/S54T/V102Q/N116D/A161P/W258S/W284M/I291A, S17G/I38L/Y39S/G42N/K44Q/E48N/N122S/L141S, S17G/I38L/Y39S/G42N/K44Q/E48N/Q66T/F67Y/T277D/L281G, S17G/I38L/Y39S/G42N/K44Q/E48N/S54T/N116E/N122S/L141S, S25G/I38L/Y39S/G42N/A43E/K44Q/E48N/S54T/N180T/W258S/G275E, S25G/I38L/Y39S/G42N/A43S/K44E/E48N/S54T/A77Q/V102Q/N116D/L141S/A194T/W258S/W284M, S25G/I38L/Y39S/G42N/A43S/K44E/E48N/S54T/N116D/N122S/L141S/N180T/W258R/G275T/T277E/W284M/I291Q/N292S/L293T, S25G/I38L/Y39S/G42N/A43S/K44Q/E48N/S54T/Q66T/A77E/N116E/N180T/A259D/G275T/T277D/S286A/I291Q/N292S/L293T, S25G/I38L/Y39S/G42N/A43S/K44Q/E48N/Q66T/N116E/L141S/N180T/W258S, S25G/I38L/Y39S/G42N/A43T/K44E/E48N/A77E/N116S/L141S, S25G/I38L/Y39S/G42N/A43V/K44Q/E48N, S25G/I38L/Y39S/G42N/A43V/K44Q/E48N/A161P/N180T/A194T, S25G/I38L/Y39S/G42N/A43V/K44Q/E48N/A77E, S25G/I38L/Y39S/G42N/A43V/K44Q/E48N/A77Q/N116D/L141S/N180T/W258R/G275E/T277E, S25G/I38L/Y39S/G42N/A43V/K44Q/E48N/F67Y/A161K, S25G/I38L/Y39S/G42N/A43V/K44Q/E48N/L141S/N180T/A194T/W258S/A259D/L281K/N282S, S25G/I38L/Y39S/G42N/A43V/K44Q/E48N/N180T/A194T, S25G/I38L/Y39S/G42N/A43V/K44Q/E48N/Q66T/A77Q/N116D/A161K/P164T/W284G/N292S/L293G, S25G/I38L/Y39S/G42N/A43VK44Q/E48N/S54T/A77Q/L141S/N180T/G275E/W284G/I291Q/N292S/L293G, S25G/I38L/Y39S/G42N/A43V/K44Q/E48N/S54T/A77Q/N116D/W258S/A259D/L281G, S25G/I38L/Y39S/G42N/A43V/K44Q/E48N/S54T/A77Q/N116S/N180T/A194T/A295D/T277D/W284G/I291Q, S25N/I38L/

Y39S/G42N/A43V/K44Q/E48N/S54T/L141S/N180T/G275T/W284M/I291S/L293T, S25N/I38L/Y39S/G42N/A43V/K44Q/E48N/S54T/L141S/N180T/W258R/A259D, and A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S143D/D160A/A161P/Y167Q/L174Q/N180T/E184Q/R185Q/S190A/L196S/G204S/N205S/Y206F.

In a further aspect, the invention provides a composition comprising a variant endoglucanase enzyme comprising one or more amino acid modifications as compared to SEQ ID NO:1 as described herein, wherein said variant endoglucanase enzyme comprises said amino acid modification(s) selected from the group consisting of D215*, I38L/Y39S/G42N/A43V/K44Q/E48N, D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, and T-18S/F-5L/T-4A/V-3A/A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N 180T/E184Q/R185Q/S190A/L192I/T196S/G204S/N205S/Y206F.

In an additional aspect, the invention provides a composition comprising a variant endoglucanase enzyme comprising one or more amino acid modifications as compared to SEQ ID NO:1 as described herein, wherein said variant endoglucanase enzyme comprises said amino acid modification(s) selected from the group consisting of I38L/Y39S/G42N/A43V/K44Q/E48N, D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, A23D/S25N/I38L/Y39S/G42N/A43V/K44Q/E48N/A77E, A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, D215* and A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F.

In a further aspect, the invention provides a composition comprising a variant endoglucanase enzyme comprising one or more amino acid modifications as compared to SEQ ID NO:1 as described herein, wherein said variant endoglucanase enzyme comprises said amino acid modifications I38L/Y39S/G42N/A43V/K44Q/E48N.

In an additional aspect, the invention provides a composition comprising a variant endoglucanase enzyme comprising one or more amino acid modifications as compared to SEQ ID NO:1 as described herein, wherein said variant endoglucanase enzyme comprises said amino acid modifications D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-.

In a further aspect, the invention provides a composition comprising a variant endoglucanase enzyme comprising one or more amino acid modifications as compared to SEQ ID NO:1 as described herein, wherein said variant endoglucanase enzyme comprises said amino acid modifications I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-.

In an additional aspect, the invention provides a composition comprising a variant endoglucanase enzyme comprising one or more amino acid modifications as compared to SEQ ID NO:1 as described herein, wherein said variant endoglucanase enzyme comprises said amino acid modifications A23D/S25N/I38L/Y39S/G42N/A43V/K44Q/E48N/A77E.

In a further aspect, the invention provides a composition comprising a variant endoglucanase enzyme comprising one or more amino acid modifications as compared to SEQ ID NO:1 as described herein, wherein said variant endoglucanase enzyme comprises said amino acid modifications A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-.

In an additional aspect, the invention provides a composition comprising a variant endoglucanase enzyme comprising one or more amino acid modifications as compared to SEQ ID NO:1 as described herein, wherein said variant endoglucanase enzyme comprises said amino acid modification D215*.

In a further aspect, the invention provides a composition comprising a variant endoglucanase enzyme comprising one or more amino acid modifications as compared to SEQ ID NO:1 as described herein, wherein said variant endoglucanase enzyme comprises said amino acid modifications A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153 D/D160A/A161P/Y167Q/L174Q/N180T/E184Q/R185Q/S190A/L192I/T196S/G204S/N205S/Y206F.

In a further aspect, the invention provides a composition comprising a variant endoglucanase enzyme as described herein, wherein said variant endoglucanase enzyme exhibits at least 90% sequence identity to the amino acid sequence selected from the group consisting of SEQ ID NO:3, SEQ ID NO:5, SEQ ID NO:7, SEQ ID NO:9, SEQ ID NO:23, SEQ ID NO:25, and SEQ ID NO:27.

In an additional aspect, the invention provides a composition comprising a variant endoglucanase enzyme as described herein, wherein said variant endoglucanase enzyme exhibits at least 90% sequence identity to SEQ ID NO:5.

In a further aspect, the invention provides a composition comprising a variant endoglucanase enzyme as described herein, wherein said variant endoglucanase enzyme exhibits at least 90% sequence identity to SEQ ID NO:7.

In an additional aspect, the invention provides a composition comprising a variant endoglucanase enzyme as described herein, wherein said variant endoglucanase enzyme exhibits at least 90% sequence identity to SEQ ID NO:23.

In a further aspect, the invention provides a composition comprising a variant endoglucanase enzyme as described herein, wherein said variant endoglucanase enzyme exhibits at least 90% sequence identity to SEQ ID NO:27.

In an additional aspect, the invention provides a composition comprising a variant endoglucanase enzyme as described herein, wherein said variant endoglucanase enzyme has SEQ ID NO:3.

In a further aspect, the invention provides a composition comprising a variant endoglucanase enzyme as described herein, wherein said variant endoglucanase enzyme has SEQ ID NO:5.

In an additional aspect, the invention provides a composition comprising a variant endoglucanase enzyme as described herein, wherein said variant endoglucanase enzyme has SEQ ID NO:7.

In a further aspect, the invention provides a composition comprising a variant endoglucanase enzyme as described herein, wherein said variant endoglucanase enzyme has SEQ ID NO:9.

In an additional aspect, the invention provides a composition comprising a variant endoglucanase enzyme as described herein, wherein said variant endoglucanase enzyme has SEQ ID NO:23.

In a further aspect, the invention provides a composition comprising a variant endoglucanase enzyme as described herein, wherein said variant endoglucanase enzyme has SEQ ID NO:25.

In an additional aspect, the invention provides a composition comprising a variant endoglucanase enzyme as described herein, wherein said variant endoglucanase enzyme has SEQ ID NO:27.

In a further aspect, the invention provides a nucleic acid encoding the variant endoglucanase enzymes as described herein.

In an additional aspect, the invention provides the nucleic acid as described herein, wherein said nucleic acid is codon optimized for a host organism for expression of the variant endoglucanase enzyme in said organism.

In a further aspect, the invention provides the nucleic acid as described herein, wherein the nucleic acid comprises a nucleic acid sequence selected from the group consisting of SEQ ID NO:4, SEQ ID NO:6, SEQ ID NO:8, SEQ ID NO:10, SEQ ID NO:24, SEQ ID NO:26, and SEQ ID NO:28.

In an additional aspect, the invention provides an expression vector comprising the nucleic acid as described herein.

In a further aspect, the invention provides a host cell comprising the nucleic acid of any variant enzymes as described herein.

In an additional aspect, the invention provides a host cell comprising the expression vector as described herein.

In a further aspect, the invention provides the host cell as described herein, wherein said host cell is selected from the group consisting of a bacterial cell, a fungal cell, and a yeast cell.

In an additional aspect, the invention provides a method of making a variant endoglucanase enzyme comprising: a) culturing the host cell under conditions as described herein, wherein said variant endoglucanase enzyme is expressed; and b) recovering said variant endoglucanase enzyme.

In a further aspect, the invention provides a nucleic acid encoding a preprotein comprising a signal peptide and a mature protein, wherein said signal peptide is a wild-type signal peptide or a variant signal peptide comprising one or more amino acid modifications as compared to a wild-type signal peptide; and wherein said mature protein comprises said one or more amino acid modifications as compared to SEQ ID NO:1 as described herein.

In an additional aspect, the invention provides the nucleic acid as described herein, wherein said signal peptide is a wild-type signal peptide.

In a further aspect, the invention provides the nucleic acid as described herein, wherein said wild-type signal peptide comprises the amino acid sequence of SEQ ID NO:21.

In an additional aspect, the invention provides the nucleic acid as described herein, wherein said signal peptide is a variant signal peptide comprising one or more amino acid modifications as compared to SEQ ID NO:21, wherein said one or more amino acid modifications in the variant signal peptide occur at positions corresponding to positions selected from the group consisting of positions-18, -5, -4, and -3.

In a further aspect, the invention provides the nucleic acid as described herein, wherein said variant signal peptide comprises said one or more amino acid modification(s) selected from the group consisting of T-18S, F-5L, T-4A, and V-3A.

In an additional aspect, the invention provides the nucleic acid as described herein, wherein said variant signal peptide comprises the amino acid sequence of SEQ ID NO:22.

In a further aspect, the invention provides the nucleic acid as described herein, wherein the preprotein comprises the amino acid sequence selected from the group consisting of SEQ ID NO:13, SEQ ID NO:15, SEQ ID NO:17, SEQ ID NO:19, SEQ ID NO:29, SEQ ID NO:31 and SEQ ID NO:33.

In an additional aspect, the invention provides the nucleic acids as described herein, comprising the nucleic acid sequence selected from the group consisting of SEQ ID NO: 14, SEQ ID NO:16, SEQ ID NO:18, SEQ ID NO:20, SEQ ID NO:30, SEQ ID NO:32 and SEQ ID NO:34.

In a further aspect, the invention provides the nucleic acid as described herein, wherein the preprotein is operably linked to an exogenous construct sequence.

In an additional aspect, the invention provides the nucleic acid as described herein, wherein the exogenous construct sequence is an exogenous promoter.

In a further aspect, the invention provides an expression vector comprising the nucleic acid as described herein.

In an additional aspect, the invention provides a host cell comprising the nucleic acid as described herein.

In a further aspect, the invention provides a host cell comprising the expression vector as described herein.

In an additional aspect, the invention provides the host cell described herein, wherein said host cell is selected from the group consisting of a bacterial cell, a fungal cell, and a yeast cell.

In a further aspect, the invention provides a method of making a variant endoglucanase enzyme comprising: a) culturing the host cell as described herein under conditions wherein said variant endoglucanase enzyme is expressed; and b) recovering said variant endoglucanase enzyme.

In an additional aspect, the invention provides a method of biostoning comprising the step of contacting the variant endoglucanase enzyme as described herein with cotton-containing fabrics or garments.

In a further aspect, the invention provides the method of biostoning as described herein, wherein the cotton-containing fabrics or garments are denim.

In an additional aspect, the invention provides a method of biofinishing comprising the step of contacting the variant endoglucanase enzyme as described herein with a textile material.

In a further aspect, the invention provides the method of biofinishing as described herein, wherein the textile material is selected from the group consisting of fabrics, garments, and yarn.

In an additional aspect, the invention provides a detergent composition comprising the variant endoglucanase enzyme as described herein.

In a further aspect, the invention provides the detergent composition as described herein further comprising at least one surface active agent and optionally at least one auxiliary ingredient.

In an additional aspect, the invention provides a method of treating cellulosic fiber containing textile material(s) comprising contacting said textile material(s) with the detergent composition as described herein.

In a further aspect, the invention provides a method for treating wood-derived pulp or fiber, comprising the step of contacting the variant endoglucanase enzyme as described herein with wood-derived mechanical or chemical pulp or secondary fiber.

BRIEF DESCRIPTION OF THE DRAWINGS

FIG. 2 shows activity improvement results for Ct.EG wild-type (G1P) and top Ct.EG variants produced by *Aspergillus niger*. PF: Performance Factor. D215* means D215 was mutated to a STOP codon to truncate the C-termius of the protein. "+" means PF=1.1-1.5 fold increase, "++" means PF=1.6-2.0 fold increase.

FIG. 3 shows Bio-stoning performance for Ct.EG wild-type (G1P) and several Ct.EG variants produced by *Aspergillus niger*. D215* means D215 was mutated to a STOP codon to truncate the C-terminus of the protein. Bio-stoning performance was evaluated by visual inspection described in Example 8; more "+" means better bio stoning performance assessed by qualitative visual inspection and ranking of fabric by multiple researchers.

FIGS. 4A-4N display the Ct.EG G2P variants' activities as described in Example 11 as a comparison to Ct.EG G2P performance. The markers denote the following activity: + indicates PF >1.1-1.5 fold improvement (a positive effect), ++ indicates PF >1.5-2.0 fold improvement, +++ indicates PF >2.0-2.5 fold improvement, and ++++ indicates PF >2.5-fold improvement compared to G2P. Sequences are displayed with respect to the G1P (Wild-type) sequence. * Indicates a mutation to a stop codon to truncate the C-termius of the protein, while – indicates a deletion of the corresponding amino acid.

FIGS. 5A-5C display particular variants of Ct.EG G2P by position that demonstrate beneficial performance in their pH 6.5 activity compared to G2P as described in Example 11. Mutations are displayed with respect to the G1P (wild-type) sequence. An * indicates a mutation to a stop codon at the referenced position to truncate the C-termius of the protein, while a – indicates a deletion of the corresponding amino acid. Negative amino acids positions refer the signal peptide positions prior to the start codon of the mature protein.

FIG. 6 shows Bio-stoning performance for Ct.EG wild-type (G2P) and variants produced by *A. niger*. Bio-stoning performance was evaluated by visual inspection described in Example 13; more "+"'s means better bio stoning performance assessed by qualitative visual inspection and ranking of fabric by multiple researchers.

FIG. 7 contains results of alkaline depilling experiments performed as indicated in Example 14. Ct.EG G2P and variants produced by *A. niger* were visually inspected after depilling and ranked according to the procedure in Example 14. The number of +'s indicates the relative performance of the enzymes with more +'s indicating superior performance assessed by qualitative visual inspection and ranking of fabric by multiple researchers.

FIG. 8 displays the performance of Ct.EG G2P and variants produced by *A. niger* in decontamination ability under alkaline conditions as outlined in Example 15. The performance of the various enzymes was measured by whiteness difference after the experiment and – indicates a whiteness difference of $<1.05$ compared to the control, while + indicates a 1.05-1.1-fold improvement and ++ indicates $>1.1$ fold improvement compared to the no enzyme control.

FIG. 9A-B shows Sequence Alignment of Ct.EG wild-type and several Ct.EG variants. Signal Peptide: amino acids at position numbers 1-21; Catalytic Domain (CD): amino acids at position numbers 22 to 235; Linker domain: amino acids at position numbers 236-277; Carbohydrate-binding Modules (CBM): amino acids at position numbers 278-314.

FIGS. 10A-10M. FIG. 10A shows the amino acid sequence of the mature region of Ct.EG G1P (wild-type) protein (SEQ ID NO:1), the sequence of a nucleic acid (SEQ ID NO:2) encoding the mature region of Ct.EG G1P (wild-type) protein, the amino acid sequence of the mature region of Ct.EG G1V1 variant protein (SEQ ID NO:3), as well as the sequence of a nucleic acid (SEQ ID NO:4) encoding the mature region of Ct.EG G1V1 variant protein. FIG. 10B shows the amino acid sequence of the mature region of Ct.EG G1V2 variant protein (SEQ ID NO:5), the sequence of a nucleic acid (SEQ ID NO:6) encoding the mature region of Ct.EG G1V2 variant protein, as well as the amino acid sequence of the mature region of Ct.EG G1V3 variant protein (SEQ ID NO:7). FIG. 10C shows the sequence of a nucleic acid (SEQ ID NO:8) encoding the mature region of Ct.EG G1V3 variant protein, the amino acid sequence of the mature region of Ct.EG G1V4 variant protein (SEQ ID NO:9), as well as the sequence of a nucleic acid (SEQ ID NO:10) encoding the mature region of Ct.EG G1V4 variant protein. FIG. 10D shows the amino acid sequence of Ct.EG G1P (wild-type) protein including a signal peptide and mature region (SEQ ID NO:11), the sequence of a nucleic acid (SEQ ID NO:12) encoding Ct.EG G1P (wilde-type) protein including the signal peptide and mature region, as well as the amino acid sequence of Ct.EG G1V1 variant protein including a signal peptide and mature region (SEQ ID NO:13). FIG. 10E shows the sequence of a nucleic acid (SEQ ID NO:14) encoding Ct.EG G1V1 variant protein including the signal peptide and mature region, as well as the amino acid sequence of Ct.EG G1V2 variant protein including a signal peptide and mature region (SEQ ID NO:15). FIG. 10F shows the sequence of a nucleic acid (SEQ ID NO:16) encoding Ct.EG G1V2 variant protein including the signal peptide and mature region, as well as the amino acid sequence of Ct.EG G1V3 variant protein including a signal peptide and mature region (SEQ ID NO:17). FIG. 10G shows the sequence of a nucleic acid (SEQ ID NO:18) encoding Ct.EG G1V3 variant protein including the signal peptide and mature region, as well as the amino acid sequence of Ct.EG G1V4 variant protein including a signal peptide and mature region (SEQ ID NO:19). FIG. 10H shows the sequence of a nucleic acid (SEQ ID NO:20) encoding Ct.EG G1V4 variant protein including the signal peptide and mature region, the amino acid sequence of a wild-type signal peptide (SEQ ID NO:21), as well as the amino acid sequence of a variant signal peptide (SEQ ID NO:22). FIG. 10I shows the amino acid sequence of the mature region of the Ct.EG G2V1 variant protein (SEQ ID NO:23), the sequence of a nucleic acid (SEQ ID NO:24) encoding the mature region of Ct.EG G2V1, the amino acid sequence of the mature region of the Ct.EG G2V2 variant protein (SEQ ID NO:25), as well as the sequence of a nucleic acid (SEQ ID NO:26) encoding the mature region of Ct.EG G2V2. FIG. 10J shows the amino acid sequence of the mature region of the Ct.EG G2V3 variant protein (SEQ ID NO:27), as well as the sequence of a nucleic acid (SEQ ID NO:28) encoding the mature region of Ct.EG G2V3. FIG. 10K shows the amino acid sequence of the Ct.EG G2V1 variant protein including a signal peptide and mature region (SEQ ID NO:29), as well as the sequence of a nucleic acid (SEQ ID NO:30) encoding Ct.EG G2V1 including the signal peptide and mature region. FIG. 10L shows the amino acid sequence of the Ct.EG G2V2 variant protein including a signal peptide and mature region (SEQ ID NO:31), as well as the sequence of a nucleic acid (SEQ ID NO:32) encoding Ct.EG G2V2 including the signal peptide and mature region. FIG. 10M shows the amino acid sequence of the Ct.EG G2V3 variant protein including a signal peptide and mature region (SEQ ID NO:33), as well as the sequence of a nucleic acid (SEQ ID NO:34) encoding Ct.EG G2V3 including the signal peptide and mature region.

DETAILED DESCRIPTION OF THE INVENTION

I. Introduction

Figure 1:
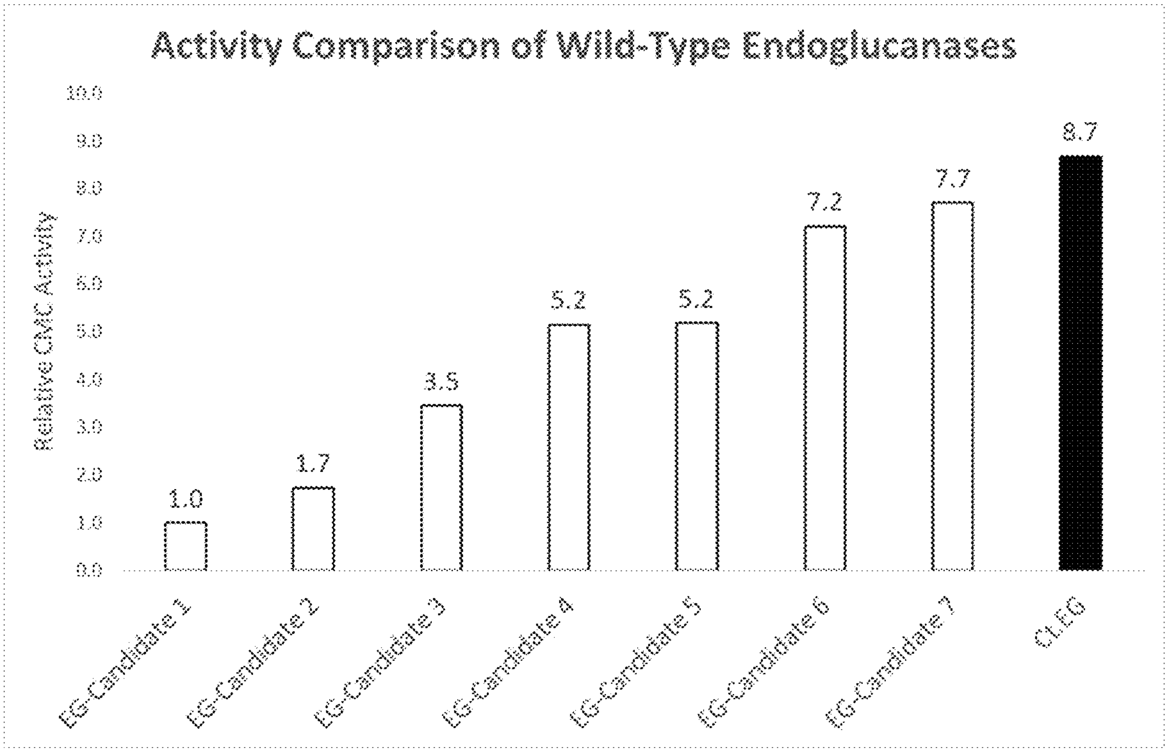
FIG. 1 provides relative activity of wild-type endoglucanases produced by *Aspergillus niger.*

In the textile industry, a "stonewashed look" or an abraded look has been an interest of denim producers in recent years. Stone washing has been traditionally achieved by locally removing the indigo dye using a process in which pumice stones are added to the washing drum to abrade the garment. This traditional 'stone-washed' finish on denim fabric reduces the strength of fabric, burdens the laundering machinery and causes pollution in waste water. The trend has been towards an environmental-friendly process, termed "biostoning", which uses enzymes, such as cellulases, to wash/bio-stone denim, producing its desired abraded look without harming the machinery or the environment. Controlled enzyme treatments result in cost saving and improved quality without the need for disposal of stones.

Additionally, textile industry uses cellulases in biofinishing, i.e. to create permanent improvement of depilling and improved pilling resistance, cleared surface structure by reduced fuzz, improved textile handle, such as softness, smoothness and a silkier feel, improved drapability and brighter colors of the textile and improved moisture absorbability.

Endoglucanases, as one type of cellulases are generally needed for the biological conversion of cellulose to glucose, and have a wide range of applications in textile, detergent, and pulp and paper industries.

However, many of the industrial processes that utilize endoglucanases are run under a wide temperature range, e.g. 20-60° C. and a wide pH range, e.g. pH 4-12; accordingly, active, temperature and pH stable endoglucanases are desired and provided herein.

II. Definitions

By "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "amino acid" and "amino acid identity" as used herein is meant one of the 20 naturally occurring amino acids that are coded for by DNA and RNA.

By "position" as used herein is meant a location in the sequence of a protein. In general, the positive position number is relative to the first amino acid of the mature endoglucanase sequence, e.g. excluding the signal peptide. For example, A23 of the sequence of the wild-type endoglucanase (SEQ ID NO:1) represents that the twenty-third amino acid of the wild-type endoglucanase counting forward from the mature region is Alanine. In the context of a preprotein that includes a signal peptide, the numbering counts backwards from the first amino acid of the mature protein at position "1", with the last amino acid at the C-terminal of the signal peptide being "−1". That is, a 10 amino acid signal peptide using "X" as an amino acid is "X−9/X−8/X−7/X−6/X−5/X−4/X−3/X−2/X−1/X+1 (start of the mature protein)". For example, F-5 of the wild-type endoclucanase protein including the signal peptide and mature region (SEQ ID NO:11) represents that the fifth amino acid counting backwards from the last amino acid of the signal peptide (or the sixth amino acid counting backwards from the first amino acid of the mature region) is phenylalanine. In some cases, the position number is relative to the first amino acid of the endoglucanase sequence which includes the signal peptide and mature region, e.g. FIG. 4.

The term "mature polypeptide" means a polypeptide in its final form following translation and any post-translational modifications, such as N-terminal processing, C-terminal truncation, glycosylation, phosphorylation, etc.

The phrase "mature polypeptide coding sequence" refers to a polynucleotide that encodes a mature polypeptide having endoglucanase activity.

By "residue" as used herein is meant a position in a protein and its associated amino acid identity. For example, Glycine 3 (also referred to as Gly3 or G3) is a residue at position 3 in the wild-type endoglucanase enzyme (SEQ ID NO:1).

The term "wild-type" endoglucanase refers to the sequence of the typical form of an endoglucanase as it occurs in a naturally occurring microorganism, such as a bacterium, yeast, or filamentous fungus found in nature. Example 1 shows multiple wild-type endoglucanases from different sources.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize wild-type endoglucanase mature protein (SEQ ID NO:1) as the parent polypeptide. Some embodiments utilize wild-type endoglucanase protein including the signal peptide and mature protein (SEQ ID NO:11) as the parent polypeptide.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about fifty amino acid modifications. As described below, in some embodiments, the parent polypeptide is the wild-type sequence (not including the signal peptide) of SEQ ID NO:1. In some embodiments, the parent polypeptide is the wild-type sequence (including the signal peptide) of SEQ ID NO:11. As further discussed below, the protein variant sequence herein will preferably possess at least about 80% identity with a parent protein sequence, and more preferably at least about 85% identity. Variant protein can refer to the variant protein itself, compositions comprising the protein variant, or the DNA sequence that encodes it. Thus, by "variant endoglucanase" herein is meant a novel endoglucanase that has at least one amino acid modification in the amino acid sequence as compared to a parent endoglucanase enzyme. As discussed herein, in some cases the parent endoglucanase is a second or higher generation of a variant endoglucanase. Unless otherwise noted or as will be obvious from the context, the variant endoglucanases of the invention generally are compared to the wild-type sequence (SEQ ID NO:1 or SEQ ID NO:11). Additionally, unless otherwise noted, the variant endoglucanases of the invention are enzymatically active, that is, there is detectable endoglucanase activity using the endoglucanase assay described in Examples below.

A substitution means replacement of the amino acid occupying a position with a different amino acid; a deletion means removal of the amino acid occupying a position; and an insertion means adding an amino acid adjacent to and immediately following the amino acid occupying a position.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification always refers to a modification in an amino acid coded by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution A23S refers to a variant polypeptide, in this case an endoglucanase, in which the alanine at position 23 is replaced with serine. Multiple mutations are separated by forward slash marks ("/"), e.g., "I38L/Y39S/G42N" represents substitutions at positions 38, 39 and 42, respectively (in some cases a "+" can be used). For clarity, a protein which has been engineered to change the nucleic acid coding sequence but not change the starting amino acid (for example, exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence.

By "amino acid deletion" or "deletion" as used herein is meant the removal of an amino acid sequence at a particular position in a parent polypeptide sequence. For example, S221- or S221#, S221( ) or S221del designates a deletion of serine at position 221. Additionally, SAA221- or SAA221# designates a deletion of the sequence SerAlaAla that begins at position 221. "*" represents mutation to a STOP codon to truncate the C-termius of the protein. For example, D215* means D215 was mutated to a STOP codon to truncate the C-termius of the protein.

By "non-naturally occurring modification" as used herein is meant an amino acid modification that is not found in the wild-type enzyme.

The term "endoglucanases" or called "1,4-β-D-glucan glucanohydrolase" are enzymes classified as E.C. 3.2.1.4 and are one type of cellulases generally needed for the biological conversion of cellulose to glucose. Endoglucanases cut internal beta-1,4-glucosidic bonds, whereas cellobiohydrolases cut the disaccharide cellobiose from the end of the cellulose polymer chain, and beta-1,4-glucosidases hydrolyze the cellobiose and other short cello-oligosaccharides to glucose. Some naturally occurring endoglucanases have a cellulose-binding domain, while others do not. For purposes of the present invention, endoglucanase activity is determined according to the procedures described in the Examples herein, for example, the CMC (carboxymethyl cellulose) Assay to determine endoglucanase activity in Example 3.

The term "biostoning" of fabric or garment means the use of enzymes in place of or in addition to, pumice stones for the treatment of fabric or garment, especially denim, to provide a "stonewash look" or an abraded look. By "stonewash look" or called an "abraded look" or "worn look" is meant, the appearance of fabric or garment, especially denim after it has been treated by cellulase enzymes or stones, or both, which results in contrasts between dyed areas and areas from which dye has been removed due to the treatment for un-even dye removal. In enzymatic stone washing, or biostoning, abrasion with pumice stones is completely or partially eliminated and enzyme is added to facilitate the abrasion of Indigo dye from the fiber surface. The endoglucanases of this invention are especially useful to provide an abraded look and to minimize backstaining in biostoning. The term "backstaining" refers to the tendency of released dye to redeposit on the surface of the fabric fibers. Treatment with endoglucanases of the present invention can completely replace the traditional treatment with pumice stones. However, endoglucanase treatment can be combined with pumice stone treatment when it is desired to produce a heavily abraded finish. By "denim" is meant, in connection of this invention, denim fabric, usually denim garments, particularly jeans. Advantageously, the denim is Indigo dyed denim. Denim can also be treated with Indigo, with derivatives of Indigo or denim dyed with Indigo together with some other dye(s), for example, Indigo-dyed denim with Sulphur bottom.

Biostoning is typically performed at about pH 3.0-8.0, and preferably at pH 4.0-6.5. The temperature of the reaction can range from about 20° C. to 70° C. and is preferably between 45-55° C. or 20-30° C. The liquor ratio (the ratio of the volume of liquid per weight of fabric) may range from about 3:1 to 20:1, preferably 10:1 to 20:1. The treatment time can range between 15 min-90 min and preferably 30 min-60 min. It should be emphasized that the enzyme dosage depends greatly on the type of the fabrics, machinery, process conditions (pH, temperature, liquor ratio, treatment time, denim load, process scale) and type of enzyme preparation and like.

The term "biofinishing" (also called depilling, defuzzing or biopolishing) refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability, which may improve the dyeability too.

Biofinishing is typically performed at about pH 4.0-12. The temperature of the reaction can range from about 20° C. to 70° C., and is preferably 45-60° C. or 20-40° C. The liquor ratio (the ratio of the Volume of liquid per weight of fabric) may range from about 3:1 to 200:1, preferably 10:1 to 15:1, 150:1 to 250:1. The incubation time is generally 15 to 90 minutes, preferably 30 to 60 min. The enzyme dosage depends greatly on the type of the fabrics, machinery, process conditions (pH, temperature, liquor ratio, treatment time, denim load, laundry load, detergent, process scale) and type of enzyme preparation and like.

The term "destaining" (also called "decontamination" or "anti-soiling") refers to the use of enzymes in concert with detergent and washing processes to remove any type of soiling agent deposited in fabric fibers with the resulting fabric after the destaining process being less-soiled, and/or brighter in color or whiteness.

Destaining is typically performed at pH 4.0-12, and is preferably performed at pH 9-12. The temperature of the reaction can range from 20° C.-60° C., and is preferably performed at 20-40° C. The liquor ratio (the ratio of the Volume of liquid per weight of fabric) may range from about 3:1 to 200:1, preferably 10:1 to 15:1, 150:1 to 250:1. The incubation time is generally 10 to 90 minutes, preferably 20 to 40 min. The enzyme dosage depends greatly on the type of the fabrics, machinery, process conditions (pH, temperature, liquor ratio, treatment time, laundry load, detergent, process scale) and type of enzyme preparation and like.

The term "coding sequence" refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "detergent" refers to a cleansing agent that can contain surface active agent(s) (anionic, non-ionic, cationic and ampholytic surfactants), and optionally other auxiliary ingredient(s) such as anti-redeposition and soil suspension agents, optical brighteners, bleaching agents, dyes and pigments and hydrolases. A suitable listing of the contents of detergents is given in U.S. Pat. No. 5,433,750, hereby incorporated by reference in its entirety. A suitable list of surfactants is given in U.S. Pat. No. 3,664,961, hereby incorporated by reference in its entirety.

By "exogeneous" in the context of nucleic acid sequences herein is meant that the exogeneous element is not normally associated with the second element in nature and is thus an artificial or synthetic construct. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the endoglucanase. In many embodiments, the invention provides nucleic acid constructs that comprise the coding sequence of an endoglucanase linked to exogeneous construct sequences such as an exogeneous promoter. For clarity, in general the reference to "exogeneous" is in reference to the endoglucanase and not the host cell. For example, if the host cell is an *A. niger* cell, the promoter that is operably linked to the endoglucanase gene may be endogeneous to *A. niger* but exogeneous to the endoglucanase (for example, the promoter from *A. niger* α-amylase can be linked to the endoglucanase of the invention). Accordingly, in some embodiments, the invention provides nucleic acid constructs that encode both an endoglucanase enzyme (whether wild-type or variant) operably linked to exogeneous construct nucleic acid sequences. By "exogeneous construct sequence" herein is meant a construct sequence (whether amino acid or nucleic acid sequences, although as will be appreciated by the context in which the term is used, usually refers to the nucleic acid sequence) that is not normally associated with the nucleic acid encoding the endoglucanase.

Suitable construct sequences that can be included in extrachromosomal or integrating expression vectors include, but are not limited to, selectable markers, purificaiton tags, origin(s) of replication and regulatory sequences including but not limited to promoters (inducible and constituative), enhancers, ribosomal binding sites, start codons, termination codons, Shine-Dalgarno sequences, etc.

By "selection marker" or "selectable marker" or "selection protein" herein is meant a protein that is introduced into a host cell that confers a trait suitable for artificial selection during the growth of the host cells, such that only those cells that contain the selectable marker grow. Thus, a selectable marker is a gene the product of which provides for biocide or viral resistance, resistance to heavy metals, prototrophy to auxotrophs, and the like. Examples of selection markers are outlined below. Accordingly, a "selection gene" is a nucleic acid that encodes a selection protein.

By "extrachromosomal expression vector" (also generally referred to as a "plasmid") herein is meant a self-replicating expression vector (generally a plasmid) that carries genes of interest, which remains within the cell and does not integrate into the genome of the host cell.

By "integrating expression vector" herein is meant a vector that is designed to be inserted into the genome of the host cell, sometimes referred to as "episomes".

The term "control sequences" means nucleic acid sequences necessary for expression of a polynucleotide encoding an endoglucanase of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of a polypeptide, protein or preprotein described herein, including, but not limited to, transcription, post-transcriptional modification, translation, post-translational modification, and secretion.

The term "preprotein" refers to a protein precursor that is an inactive protein or peptide and contains a signal peptode sequence. The preprotein can be turned into a protein in an active form by post-translational modification, such as cleaving off the signal peptide.

The term "expression vector" refers to a linear or circular DNA molecule that comprises a polynucleotide encoding a polypeptide, protein or preprotein as described herein, and is operably linked to control sequences that provide for its expression.

The term "fragment" means a polypeptide having one or more (e.g., several) amino acids absent from the amino and/or carboxyl terminus of a mature polypeptide. A "endoglucanase fragment" herein means a portion of an amino acid sequence depicted herein that maintains endoglucanase activity. In one aspect, an endoglucanase fragment contains at least 50, at least 100, at least 150, at least 200, at least 220, at least 240, at least 260, at least 280 amino acid residues of a mature endoglucanase polypeptide having zero, one or more of the substitutions according to the invention. In some aspects, an endoglucanase fragment comprises the amino acid sequence of SEQ ID NO:7.

The term "host cell" refers to any cell type that is susceptible to transformation, transfection, transduction, or the like with a nucleic acid construct or expression vector comprising a polynucleotide of the present invention, and that allows for expression of the enzyme. The term "host cell" encompasses any progeny of a parent cell that is not identical to the parent cell due to mutations that occur during replication. In many embodiments, the endoglucanases of the invention (including both the endoglucanase and variant enzymes described herein) are not produced in the endogeneous host.

The term "improved property" refers to a characteristic associated with a variant endoglucanase enzyme described herein that is improved compared to the parent endoglucanase enzyme. Such improved properties of endoglucanases include, but are not limited to, increased total activity, increased specific activity (e.g. the catalytic activity, its ability to bind to cellulosic materials, and/or its cellulolytic/hydrolytic activity), increased temperature activity (e.g., increased activity at a broad range of temperature), increased pH activity (e.g., increased activity at a broad range of pH), increased total stability, increased temperature stability (e.g., increased stability against a broad range of temperature), and increased pH tolerance (e.g., increased stability against a broad range of pH). Further improved property includes but not limited to improvements in efficiency or effects in fabric treatment and in other fields, where cellulases traditionally are used, for example, increased efficiency or improved effects in biostoning and/or biofinishing process.

The term "isolated" refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance, etc.). With specific reference to isolated endoglucanases of the present invention, the isolated endoglucanase is generally either: a) purified away from other proteins with which it is normally associated; b) when the enzyme is in a concentration not found in nature, or c) when the enzyme is produced in a host cell that is not endogenous.

The term "nucleic acid construct" refers to a nucleic acid molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a construct sequence is placed at an appropriate position relative to the coding sequence of a polynucleotide such that the control sequence directs, allows or facilitates expression of the coding sequence.

The terms "parent" or "parent endoglucanase" refer to an endoglucanase to which an alteration is made to produce the variant endoglucanases of the present invention. The parent may be a naturally occurring (wild-type) polypeptide or a variant or fragment thereof. In some embodiments, the parent polypeptide of the present invention is SEQ ID NO:1. In some embodiments, the parent polypeptide of the present invention is SEQ ID NO:11.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, *Rice* et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

The term "subsequence" refers to a polynucleotide having one or more (e.g., several) nucleotides absent from the 5'- and/or 3'-end of a mature polypeptide coding sequence; wherein the subsequence encodes a fragment having endoglucanase activity. In some embodiments, a subsequence of the present invention comprises the nucleic acid sequence of SEQ ID NO:4. In some embodiments, a subsequence of the present invention comprises the nucleic acid sequence of SEQ ID NO:8. In some embodiments, a subsequence of the present invention comprises the nucleic acid sequence of SEQ ID NO:23. In some embodiments, a subsequence of the present invention comprises the nucleic acid sequence of SEQ ID NO:25.

III. Endoglucanases of the Invention

The invention provides thermoactive, thermostable and/or pH stable and active endoglucanases for use in a variety of applications, including in the textile, detergent and pulp and paper industries. The invention provides compositions and methods using an endoglucanase comprising SEQ ID NO:1, as well as variants thereof, as more fully described below.

IV. Variant Endoglucanases of the Invention

Accordingly, the present invention provides variant endoglucanases with improved properties that can be used in a variety of applications, including in the textile, detergent and pulp and paper industries.

In general, the variant endoglucanases of the invention can have an improvement in one or more of a number of biochemical properties as compared to the parental endoglucanase as set forth in SEQ ID NO:1. The biochemical properties of the variant endoglucanases that can be improved herein include, but are not limited to, total activity, specific activity, temperature activity, pH activity, total stability, temperature stability, pH tolerance, formulation stability (including liquid, solid and pellets), protease stability, performance in the processes of biostoning, biofinishing, etc. In general, improvements are measured as compared to the Ct.EG wild-type (G1P) endoglucanase enzyme (as set forth in SEQ ID NO:1) using an endoglucanase activity assay and/or Biostoning efficacy assay, as outlined below.

The variant endoglucanases of the invention have one or more improved properties as compared to the wild-type englucanase as set forth in SEQ ID NO:1. By "improved" herein is meant a desirable change of at least one biochemical property. "Improved function" can be measured as a percentage increase or decrease of a particular activity, or as a "fold" change, with increases of desirable properties (e.g. total activity and pH tolerance) or decreases of undesirable properties (e.g. protease sensitivity). That is, a variant endoglucanase may have a 10% increase in total activity or a 10% decrease in protease sensitivity, as compared to wild-type endoglucanase. Alternatively, a variant endoglucanase may have a 2-fold increase in pH tolerance or a 3-fold decrease in protease sensitivity. In general, percentage changes are used to describe changes in biochemical activity of less than 100%, and fold-changes are used to describe changes in biochemical activity of greater than 100% as compared to the parental enzyme. In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the FIG. 2, G1V1 has a 1.6-2.0 fold increase in total activity as compared to Ct.EG wild-type (SEQ ID NO:1): this is calculated by [(activity of variant)/(activity of parent)]. In many embodiments, the improvement is at least one and a tenth fold (1.1), one and a half fold (1.5 fold), 2 fold, 2.5 fold or higher.

A. CMC Assay to Determine Total Activity

In some embodiments, a CMC assay is employed to determine endoglucanase total activity, such as the one described in the Examples 3 and 6. Specifically, 1.8 mL of 1.5% low viscosity CMC dissolved in 100 mM sodium phosphate, pH 6.5 buffer (Catalog #C5678) is added into a glass test tube. 500 μL of diluted enzyme supernatant from Example 2 is added into a 1.5 mL Eppendorf tube. Both Eppendorf tube and glass test tube containing CMC are pre-heated in 50° C. water bath for 5 minutes. Once 5 mintues is reached, 200 μL of diluted enzyme is transferred from Eppendorf tube to glass test tube with CMC and mixed for 2-3 seconds. The glass test tube is quickly placed in 50° C. water bath and the timer is started for 15 minutes. Once 15 minutes is up, 3 mL of DNS solution is transferred into the glass test tube and the glass test tube is placed in boiling water bath for 5 minutes. After 5 minutes, the glass test tube is transferred to room temperature water bath and 5 mL of MilliQ water is added to the glass test tube. After mixing, 1 mL of reaction solution is transferred from the glass test tube to a cuvette and absorbance at 540 nm is read for activity. Relative CMC activity in FIG. 1 is calculated as the CMC activity of a EG candidate divided by the CMC activity of EG-Candidate 1 which showed the lowest CMC activity.

Accordingly, as shown in the FIG. 2, a number of variant endoglucanases of the invention exhibited increased activity as compared to G1P (as set forth in SEQ ID NO:1).

B. Biostoning Efficacy Assay

In some embodiments, an assay such as the one described in the Example 8 is employed to determine the biostoning efficacy of the (variant) endoglucanase enzymes. Specifically, Jean legs in size of 9 inches by 7.5 inches are de-sized by placing in industrial size washing machine manufactured by Foshan Yanuo Precision Machinery Manufacturing Co., Ltd, China (model number GX-350Z). Along with Jean legs, 20 L of water, 15 g of high-concentration anti-dyeing oil and 15 g of anti-dyeing powder are added. Temperature is set to 60° C. and rotation is set at 50 rpm for 15 minutes. Once 15 minutes of rotation is completed, the water is drained, 18 L of water is added, rotation is continued for 2 minutes, and this step is repeated for 2 times. Once finished, Jean legs are rinsed over running water and dried in oven at 60° C. For subsequent bio stoning, 2 desized jean legs are added to washing machine with 18 L of water and pH is adjust to pH 6.5. Once temperature reached to 50° C., normalized enzyme amount is added. Bio stoning is performed for 50 minutes with 50 rpm of rotation. Once finished, water is drained, and 18 L of water is added, rotation is continued for 2 minutes, and this step is repeated for 2 times. Next, jean legs are rinsed over running water and dried in oven at 60° C. Once dried, biostoning efficacy was compared by visually inspecting blue and white contrast on biostoned jean materials.

Accordingly, as shown in the FIG. 3, a number of variant endoglucanases of the invention exhibited increased biostoning efficacy or improved biostoning performance as compared to G1P (as set forth in SEQ ID NO:1).

C. pH Tolerance

In many embodiments, the variant endoglucanases of the invention have altered pH toelrance as compared to the parent endoglucanase. "Increased pH tolerance" in this context means that the variant enzymes are more stable than the parent endoglucanase (e.g. G1P) under the same pH challenge conditions, that is, the activity of the variant is higher than that of the G1P under identical conditions. For example, biostoning or biofinishing processing can be done at a variety of pHs, depending on the raw substrates and reaction conditions.

Taken together, the variant endoglucanases of the invention can exhibit increased tolerance to pH 6.5 as compared to SEQ ID NO:1 at 50° C. for a period, generally ranging from about 10 minutes to 3 hours. The variant endoglucanases of the invention can also exhibit increased tolerance to pH 10.0, pH 10.5, and/or pH 11.0 as compared to parent endoglucanases at 30° C., and or 40° C. for a period ranging from 20 minutes to 30 minutes.

D. Thermostability

In many embodiments, the variant endoglucanases of the invention have increased thermostability, particularly under the high temperature conditions used in the biostoning or biofinishing process. "Thermostability" in this context means that the variant enzymes are more stable than the parent endoglucanase (e.g. G1P) under the same thermal challenge conditions, that is, the activity of the variant is higher than that of the G1P under identical conditions (generally using the endoglucanase assay as outlined herein).

A suitable thermostability assay is as follows. 50 µl of the enzymes from the lysate plates are added to 96 well Biorad PCR plates and are challenged from 30-70° C. for 10 minutes. The control reaction was placed at room temperature for the same amount of time. Following the thermal challenge, the residual activity was determined using the control reaction. Activity of endoglucanase variant is compared to the parent under the same conditions to determine thermostability improvement.

Taken together, the variant endoglucanases of the invention can exhibit increased thermostability as compared to SEQ ID NO:1 at 30° C., 40° C., 45° C., 50° C., 55° C., 58° C., 60° C., 65° C., 66° C., 70° C., 75° C., 80° C. and/or 85° C. for a period of time, generally ranging from about 10 minutes to 3 hours.

E. Specific Activity Assays

In some embodiments, the variant endoglucanases of the invention have increased specific activity as compared to a parent endoglucanase, particularly G1P. By "specific activity" herein is meant the activity per amount (weight) of enzyme, generally determined by dividing the enzymatic activity of a sample (sometimes measured in "endoglucanase units") by the amount of endoglucanase enzyme, generally determined as is known in the art.

F. Protease Susceptibility

In some embodiments, the variant endoglucanases of the invention are less susceptible to protease degradation than the parent enzyme under identical conditions. In some cases, protease degradation during the production of variant endoglucanases in a production host organism by protease enzymes produced by the host organism can be a problem, thus resulting in lower yield of active enzyme. Similarly, depending on the use of the variant enzymes, there may be other proteases present in the raw substrates or other enzymes for use in combination that can degrade the endoglucanases.

This is generally determined as is known in the art, for example by allowing proteolytic degradation and then doing N-terminal sequencing on the resulting fragments to determine the cleavage site(s). In some cases, depending on the variant and the host production organism, there may not be significant proteolytic degradation.

As needed, as will be appreciated by those in the art, the specific mutations that can be made will depend on the endogenous proteases that the host organism produces, and also generally occurs in surface exposed loop structures or turns that are therefore accessible to proteases.

V. Specific Variant Endoglucanases

The present invention provides variant endoglucanase enzymes comprising one or more amino acid modifications as compared to SEQ ID NO:1, wherein said one or more amino acid modifications occur at positions corresponding to positions selected from the group consisting of positions 2, 17, 23, 25, 29, 33, 36, 38, 39, 42, 43, 44, 48, 51, 54, 66, 67, 68, 75, 77, 80, 82, 90, 102, 116, 121, 122, 123, 132, 135, 136, 141, 144, 145, 153, 160, 161, 164, 167, 174, 180, 184, 185, 190, 192, 194, 195, 196, 204, 205, 206, 215, 216, 217, 218, 219, 220, 221, 222, 223, 228, 229, 230, 231, 232, 233, 234, 235, 237, 238, 239, 241, 242, 243, 244, 245, 246, 247, 248, 249, 250, 251, 258, 259, 267, 268, 269, 270, 271, 273, 274, 275, 276, 277, 278, 279, 280, 281, 282, 283, 284, 285, 286, 287, 288, 289, 290, 291, 292, and 293, wherein said variant endoglucanase enzyme has endoglucanase activity. In some embodiments, said variant endoglucanase enzyme exhibits at least 80% sequence identity to SEQ ID NO:1. In some embodiments, said variant endoglucanase enzyme exhibits at least 81% sequence identity to SEQ ID NO:1. In some embodiments, said variant endoglucanase enzyme exhibits at least 82% sequence identity to SEQ ID NO:1. In some embodiments, said variant endoglucanase enzyme exhibits at least 83% sequence identity to SEQ ID NO:1. In some embodiments, said variant endoglucanase enzyme exhibits at least 84% sequence identity to SEQ ID NO:1. In some embodiments, said variant endoglucanase enzyme exhibits at least 85% sequence identity to SEQ ID NO:1.

The present invention provides variant endoglucanase enzymes comprising one or more amino acid modifications as compared to SEQ ID NO:1, wherein said one or more amino acid modifications occur at positions corresponding to positions selected from the group consisting of positions 2, 17, 23, 25, 29, 33, 36, 38, 39, 42, 43, 44, 48, 51, 54, 66, 67, 68, 75, 77, 80, 82, 90, 102, 116, 121, 122, 123, 132, 135, 136, 141, 144, 145, 153, 160, 161, 164, 167, 174, 180, 184, 185, 190, 192, 194, 195, 196, 204, 205, 206, 215, 216, 217, 218, 219, 220, 221, 222, 223, 228, 229, 230, 231, 232, 233, 234, 235, 237, 238, 239, 241, 242, 243, 244, 245, 246, 247, 248, 249, 250, 251, 258, 259, 267, 268, 269, 270, 271, 273, 274, 275, 276, 277, 278, 279, 280, 281, 282, 283, 284, 285, 286, 287, 288, 289, 290, 291, 292, and 293, wherein said variant endoglucanase enzyme exhibits at least 80% sequence identity to SEQ ID NO:1; and wherein said variant endoglucanase enzyme has endoglucanase activity.

In some embodiments, the variant endoglucanase has an amino acid substitution of the aspartic acid at position 2 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from D2E, D2F, D2N, D2Q, D2S, and D2T.

In some embodiments, the variant endoglucanase has an amino acid substitution of the serine at position 17 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S17G.

In some embodiments, the variant endoglucanase has an amino acid substitution of the alanine at position 23 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from A23D, A23N, and A23S.

In some embodiments, the variant endoglucanase has an amino acid substitution of the serine at position 25 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S25N.

In some embodiments, the variant endoglucanase has an amino acid substitution of the phenylalanine at position 29 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is F29Y.

In some embodiments, the variant endoglucanase has an amino acid substitution of the arginine at position 33 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is R33A.

In some embodiments, the variant endoglucanase has an amino acid substitution of the asparagine at position 36 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N36Q.

In some embodiments, the variant endoglucanase has an amino acid substitution of the isoleucine at position 38 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is I38L.

In some embodiments, the variant endoglucanase has an amino acid substitution of the tyrosine at position 39 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Y39S.

In some embodiments, the variant endoglucanase has an amino acid substitution of the glycine at position 42 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is G42N.

In some embodiments, the variant endoglucanase has an amino acid substitution of the alanine at position 43 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from A43E, A43L, A43S, A43T, and A43V.

In some embodiments, the variant endoglucanase has an amino acid substitution of the lysine at position 44 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is K44E or K44Q.

In some embodiments, the variant endoglucanase has an amino acid substitution of the glutamic acid at position 48 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is E48N.

In some embodiments, the variant endoglucanase has an amino acid substitution of the proline at position 51 of SEQ ID NO:1. In some embodiments, the substitution is with any other of the 19 naturally occurring amino acids, with some embodiments not utilizing cysteine (due to possible disulfide formation). In some embodiments, the amino acid substitution is selected from P51E, P51N, P51S, and P51T.

In some embodiments, the variant endoglucanase has an amino acid substitution of the serine at position 54 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S54T.

In some embodiments, the variant endoglucanase has an amino acid substitution of the glutamine at position 66 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Q66N or Q66T.

In some embodiments, the variant endoglucanase has an amino acid substitution of the phenylalanine at position 67 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is F67L or F67Y.

In some embodiments, the variant endoglucanase has an amino acid substitution of the serine at position 68 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S68A.

In some embodiments, the variant endoglucanase has an amino acid substitution of the asparagine at position 75 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N75S.

In some embodiments, the variant endoglucanase has an amino acid substitution of the alanine at position 77 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is A77E or A77Q.

In some embodiments, the variant endoglucanase has an amino acid substitution of the asparagine at position 80 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N80S.

In some embodiments, the variant endoglucanase has an amino acid substitution of the alanine at position 82 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is A82S.

In some embodiments, the variant endoglucanase has an amino acid substitution of the lysine at position 90 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is K90A.

In some embodiments, the variant endoglucanase has an amino acid substitution of the valine at position 102 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from V102Q, V102R, and V102T.

In some embodiments, the variant endoglucanase has an amino acid substitution of the asparagine at position 116 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from N116D, N116E, and N116S.

In some embodiments, the variant endoglucanase has an amino acid substitution of the leucine at position 121 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is L121I.

In some embodiments, the variant endoglucanase has an amino acid substitution of the asparagine at position 122 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N122A or N122S.

In some embodiments, the variant endoglucanase has an amino acid substitution of the isoleucine at position 123 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is I123M.

In some embodiments, the variant endoglucanase has an amino acid substitution of the aspartic acid at position 132 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is D132N.

In some embodiments, the variant endoglucanase has an amino acid substitution of the threonine at position 135 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is T135S.

In some embodiments, the variant endoglucanase has an amino acid substitution of the proline at position 136 of SEQ ID NO:1. In some embodiments, the substitution is with any other of the 19 naturally occurring amino acids, with some embodiments not utilizing cysteine (due to possible disulfide formation). In some embodiments, the amino acid substitution is P136S.

In some embodiments, the variant endoglucanase has an amino acid substitution of the leucine at position 141 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is L141S.

In some embodiments, the variant endoglucanase has an amino acid substitution of the glutamic acid at position 144 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is E144A.

In some embodiments, the variant endoglucanase has an amino acid substitution of the arginine at position 145 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is R145Q.

In some embodiments, the variant endoglucanase has an amino acid substitution of the serine at position 153 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S153D.

In some embodiments, the variant endoglucanase has an amino acid substitution of the aspartic acid at position 160 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is D160A.

In some embodiments, the variant endoglucanase has an amino acid substitution of the alanine at position 161 of SEQ ID NO:1. In some embodiments, the substitution is with any other of the 19 naturally occurring amino acids, with some embodiments not utilizing cysteine (due to possible disulfide formation). In some embodiments, the amino acid substitution is A161K or A161P.

In some embodiments, the variant endoglucanase has an amino acid substitution of the proline at position 164 of SEQ ID NO:1. In some embodiments, the substitution is with any other of the 19 naturally occurring amino acids, with some embodiments not utilizing cysteine (due to possible disulfide formation). In some embodiments, the amino acid substitution is P164S or P164T.

In some embodiments, the variant endoglucanase has an amino acid substitution of the tyrosine at position 167 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Y167Q.

In some embodiments, the variant endoglucanase has an amino acid substitution of the leucine at position 174 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is L174Q.

In some embodiments, the variant endoglucanase has an amino acid substitution of the asparagine at position 180 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N180T.

In some embodiments, the variant endoglucanase has an amino acid substitution of the glutamic acid at position 184 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from E184A, E184K, E184N, E184Q, E184R, E184S, and E184T.

In some embodiments, the variant endoglucanase has an amino acid substitution of the arginine at position 185 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is R185Q.

In some embodiments, the variant endoglucanase has an amino acid substitution of the serine at position 190 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S190A.

In some embodiments, the variant endoglucanase has an amino acid substitution of the leucine at position 192 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is L192I.

In some embodiments, the variant endoglucanase has an amino acid substitution of the alanine at position 194 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is A194T.

In some embodiments, the variant endoglucanase has an amino acid substitution of the arginine at position 195 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is R195S.

In some embodiments, the variant endoglucanase has an amino acid substitution of the threonine at position 196 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is T196S.

In some embodiments, the variant endoglucanase has an amino acid substitution of the glycine at position 204 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is G204S.

In some embodiments, the variant endoglucanase has an amino acid substitution of the asparagine at position 205 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N205S.

In some embodiments, the variant endoglucanase has an amino acid substitution of the tyrosine at position 206 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Y206F.

In some embodiments, the variant endoglucanase has an amino acid substitution of the aspartic acid at position 215 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is D215G.

In some embodiments, the variant endoglucanase has an amino acid substitution of the serine at position 216 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S216N.

In some embodiments, the variant endoglucanase has an amino acid substitution of the proline at position 217 of SEQ ID NO:1. In some embodiments, the substitution is with any other of the 19 naturally occurring amino acids, with some embodiments not utilizing cysteine (due to possible disulfide formation). In some embodiments, the amino acid substitution is P217G.

In some embodiments, the variant endoglucanase has an amino acid substitution of the serine at position 218 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S218G.

In some embodiments, the variant endoglucanase has an amino acid substitution of the serine at position 219 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S219T.

In some embodiments, the variant endoglucanase has an amino acid substitution of the serine at position 220 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S220G.

In some embodiments, the variant endoglucanase has an amino acid substitution of the alanine at position 223 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is A223T.

In some embodiments, the variant endoglucanase has an amino acid substitution of the serine at position 228 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S228A.

In some embodiments, the variant endoglucanase has an amino acid substitution of the threonine at position 229 of SEQ ID NO:1. In some embodiments, the substitution is with any other of the 19 naturally occurring amino acids, with some embodiments not utilizing cysteine (due to possible disulfide formation). In some embodiments, the amino acid substitution is T229P.

In some embodiments, the variant endoglucanase has an amino acid substitution of the serine at position 230 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S230G.

In some embodiments, the variant endoglucanase has an amino acid substitution of the glutamine at position 231 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Q231S.

In some embodiments, the variant endoglucanase has an amino acid substitution of the glutamine at position 232 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Q232G.

In some embodiments, the variant endoglucanase has an amino acid substitution of the proline at position 233 of SEQ ID NO:1. In some embodiments, the substitution is with any other of the 19 naturally occurring amino acids, with some embodiments not utilizing cysteine (due to possible disulfide formation). In some embodiments, the amino acid substitution is P233Q.

In some embodiments, the variant endoglucanase has an amino acid substitution of the glutamine at position 234 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Q234T.

In some embodiments, the variant endoglucanase has an amino acid substitution of the glutamine at position 235 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Q235S.

In some embodiments, the variant endoglucanase has an amino acid substitution of the threonine at position 237 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is T237G.

In some embodiments, the variant endoglucanase has an amino acid substitution of the serine at position 238 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S238G.

In some embodiments, the variant endoglucanase has an amino acid substitution of the serine at position 239 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S239G.

In some embodiments, the variant endoglucanase has an amino acid substitution of the tryptophan at position 258 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is W258R or W258S.

In some embodiments, the variant endoglucanase has an amino acid substitution of the alanine at position 259 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is A259D.

In some embodiments, the variant endoglucanase has an amino acid substitution of the threonine at position 267 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is T267S.

In some embodiments, the variant endoglucanase has an amino acid substitution of the glycine at position 268 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is G268N.

In some embodiments, the variant endoglucanase has an amino acid substitution of the cysteine at position 269 of SEQ ID NO:1. In some embodiments, the substitution is with any other of the 19 naturally occurring amino acids, with some embodiments not utilizing proline (due to steric effects). In some embodiments, the amino acid substitution is C269R or C269S.

In some embodiments, the variant endoglucanase has an amino acid substitution of the threonine at position 271 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is T271E.

In some embodiments, the variant endoglucanase has an amino acid substitution of the valine at position 273 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is V273D or V273G.

In some embodiments, the variant endoglucanase has an amino acid substitution of the serine at position 274 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S274R.

In some embodiments, the variant endoglucanase has an amino acid substitution of the glycine at position 275 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from G275A, G275E, G275N, and G275T.

In some embodiments, the variant endoglucanase has an amino acid substitution of the threonine at position 276 of SEQ ID NO:1. In some embodiments, the substitution is with any other of the 19 naturally occurring amino acids, with some embodiments not utilizing cysteine (due to possible disulfide formation). In some embodiments, the amino acid substitution is selected from T276G, T276H, T276P, and T276R.

In some embodiments, the variant endoglucanase has an amino acid substitution of the threonine at position 277 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from T277D, T277E, and T277L.

In some embodiments, the variant endoglucanase has an amino acid substitution of the cysteine at position 278 of SEQ ID NO:1. In some embodiments, the substitution is with any other of the 19 naturally occurring amino acids, with some embodiments not utilizing proline (due to steric effects). In some embodiments, the amino acid substitution is C278A or C278L.

In some embodiments, the variant endoglucanase has an amino acid substitution of the threonine at position 279 of SEQ ID NO:1. In some embodiments, the substitution is with any other of the 19 naturally occurring amino acids, with some embodiments not utilizing cysteine (due to possible disulfide formation). In some embodiments, the amino acid substitution is selected from T279H, T279P, and T279Q.

In some embodiments, the variant endoglucanase has an amino acid substitution of the lysine at position 280 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is K280Q or K280S.

In some embodiments, the variant endoglucanase has an amino acid substitution of the leucine at position 281 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from L281A, L281E, L281G, L281K, and L281S.

In some embodiments, the variant endoglucanase has an amino acid substitution of the aspargine at position 282 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N282E or N282S.

In some embodiments, the variant endoglucanase has an amino acid substitution of the tryptophan at position 284 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from W284G, W284M, W284R, W284T, and W284Y.

In some embodiments, the variant endoglucanase has an amino acid substitution of the serine at position 286 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is S286A or S286G.

In some embodiments, the variant endoglucanase has an amino acid substitution of the glutamine at position 287 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is Q287H or Q287S.

In some embodiments, the variant endoglucanase has an amino acid substitution of the cysteine at position 288 of SEQ ID NO:1. In some embodiments, the substitution is with any other of the 19 naturally occurring amino acids, with some embodiments not utilizing proline (due to steric effects). In some embodiments, the amino acid substitution is C288A.

In some embodiments, the variant endoglucanase has an amino acid substitution of the threonine at position 289 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is T289K or T289Q.

In some embodiments, the variant endoglucanase has an amino acid substitution of the isoleucine at position 291 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from I291A, I291Q, and I291S.

In some embodiments, the variant endoglucanase has an amino acid substitution of the asparagine at position 292 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is N292S.

In some embodiments, the variant endoglucanase has an amino acid substitution of the leucine at position 293 of SEQ ID NO:1. In some embodiments, the substitution is with any other of the 19 naturally occurring amino acids, with some embodiments not utilizing cysteine (due to possible disulfide formation) or proline (due to steric effects). In some embodiments, the amino acid substitution is selected from L293G, L293N, L293T, and L293V.

In some embodiments, the variant endoglucanase comprises one or more amino acid deletion(s) as compared to SEQ ID NO:1, wherein said one or more amino acid deletion(s) occur at positions selected from the group consisting of positions 221, 222, 241, 242, 243, 244, 245, 246, 247, 248, 249, 250, 251, 289, 290, 291, and 292 of SEQ ID NO:1. In some embodiments, a variant endoglucanase comprises one or more amino acid substitution(s) as disclosed herein and one or more amino acid deletion(s) as compared to SEQ ID NO:1, wherein the amino acid deletion(s) is selected from the group consisting of S221-, A222-, S241-, Q242-, A243-, S244-, V245-, P246-, T247-, S248-, N249-, P250-, G251-, T289-, M290-, I291-, and N292- of SEQ ID NO:1.

In some embodiments, the variant endoglucanase comprises a C-terminal truncation as compared to SEQ ID NO:1, wherein said C-terminal truncation occurs at a position selected from the group consisting of positions 215, 258, 259, 270, 273, 275, 278, 281, 283, 284, 285, 288, and 290 of SEQ ID NO:1. In some embodiments,a variant endoglucanase comprises one or more amino acid substitution(s) as disclosed herein and a C-terminal truncation, wherein the C-terminal truncation is selected from the group consisting of D215*, W258*, A259*, T270*, V273*, G275*, C278*, L281*, D283*, W284*, Y285*, C288*, and M290* of SEQ ID NO:1.

The present invention provides variant endoglucanase enzymes comprising one or more amino acid modifications as compared to SEQ ID NO:1, wherein said one or more amino acid modifications are selected from the group consisting of modifications corresponding to D2E, D2F, D2N, D2Q, D2S, D2T, 517G, A23D, A23N, A23S, S25N, F29Y, R33A, N36Q, I38L, Y39S, G42N, A43E, A43L, A43S, A43T, A43V, K44E, K44Q, E48N, P51E, P51N, P51S, P51T, S54T, Q66N, Q66T, F67L, F67Y, S68A, N75S, A77E, A77Q, N80S, A82S, K90A, V102Q, V102R, V102T, N116D, N116E, N116S, L121I, N122A, N122S, I123M, D132N, T135S, P136S, L141S, E144A, R145Q, S153D, D160A, A161K, A161P, P164S, P164T, Y167Q, L174Q, N180T, E184A, E184K, E184N, E184Q, E184R, E184S, E184T, R185Q, S190A, L192I, A194T, R195S, T196S, G204S, N205S, Y206F, D215*, D215G, S216N, P217G, S218G, S219T, S220G, S221-, A222-, A223T, S228A, T229P, S230G, Q231S, Q232G, P233Q, Q234T, Q235S, T237G, S238G, S239G, S241-, Q242-, A243-, S244-, V245-, P246-, T247-, S248-, N249-, P250-, G251-, W258*, W258R, W258S, A259*, A259D, T267S, G268N, C269R, C269S, T270*, T271E, V273*, V273D, V273G, S274R, G275*, G275A, G275E, G275N, G275T, T276G, T276H, T276P, T276R, T277D, T277E, T277L, C278*, C278A, C278L, T279H, T279P, T279Q, K280Q, K280S, L281*, L281A, L281E, L281G, L281K, L281S, N282E, N282S, D283*, W284*, W284G, W284M, W284R, W284T, W284Y, Y285*, S286A, S286G, Q287H, Q287S, C288*, C288A, T289-, T289K, T289Q, M290-, M290*, I291-, I291A, I291Q, I291S, N292-, N292S, L293G, L293N, L293T, and L293V of SEQ ID NO:1.

The present invention provides the variant endoglucanase enzymes as disclosed herein, wherein said one or more amino acid modifications as compared to SEQ ID NO:1 occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions, twenty of said positions, twenty-one of said positions, twenty-two of said positions, twenty-three of said positions, twenty-four of said positions, twenty-five of said positions, twenty-six of said positions, twenty-seven of said positions, twenty-eight of said positions, twenty-nine of said positions, thirty of said positions, thirty-one of said positions, thirty-two of said positions, thirty-three of said positions, thirty-four of said positions, thirty-five of said positions, thirty-six of said positions, thirty-seven of said positions, thirty-eight of said positions, thirty-nine of said positions, forty of said positions, forty-one of said positions, forty-two of said positions, forty-three of said positions, forty-four of said positions, forty-five of said position, forty-six of said positions, or forty-seven of said positions of SEQ ID NO:1.

The present invention provides the variant endoglucanase enzymes as disclosed herein, wherein said variant endoglucanase enzyme exhibits at least 85%, 90% or 95% sequence identity to SEQ ID NO:1. In some embodiments, said variant endoglucanase enzyme exhibits at least 85% sequence identity to SEQ ID NO:1. In some embodiments, said variant endoglucanase enzyme exhibits at least 86% sequence identity to SEQ ID NO:1. In some embodiments, said variant endoglucanase enzyme exhibits at least 87% sequence identity to SEQ ID NO:1. In some embodiments, said variant endoglucanase enzyme exhibits at least 88% sequence identity to SEQ ID NO:1. In some embodiments, said variant endoglucanase enzyme exhibits at least 89% sequence identity to SEQ ID NO:1. In some embodiments, said variant endoglucanase enzyme exhibits at least 90% sequence identity to SEQ ID NO:1. In some embodiments, said variant endoglucanase enzyme exhibits at least 91% sequence identity to SEQ ID NO:1. In some embodiments, said variant endoglucanase enzyme exhibits at least 92% sequence identity to SEQ ID NO:1. In some embodiments, said variant endoglucanase enzyme exhibits at least 93% sequence identity to SEQ ID NO:1. In some embodiments, said variant endoglucanase enzyme exhibits at least 94% sequence identity to SEQ ID NO:1. In some embodiments, said variant endoglucanase enzyme exhibits at least 95% sequence identity to SEQ ID NO:1. In some embodiments, said variant endoglucanase enzyme exhibits at least 96% sequence identity to SEQ ID NO:1. In some embodiments, said variant endoglucanase enzyme exhibits at least 97% sequence identity to SEQ ID NO:1. In some embodiments, said variant endoglucanase enzyme exhibits at least 98% sequence identity to SEQ ID NO:1. In some embodiments, said variant endoglucanase enzyme exhibits at least 99% sequence identity to SEQ ID NO:1.

The present invention provides the variant endoglucanase enzymes as disclosed herein, wherein said variant endoglucanase enzyme comprises said amino acid modification(s) selected from the group consisting of D215*, A23D/I38L/Y39S/G42N/A43E/K44E/E48N/S54T/A77Q/N116D/N122S/L141S/L281G, A23D/I38L/Y39S/G42N/A43E/K44Q/E48N/S54T/N116E/W258S/A259D/G275E/T277D, A23D/I38L/Y39S/G42N/A43S/K44E/E48N/A77E/N116S/N122A/N180T/W258S/A259D/G275E/T277D/I291S/L293T, A23D/I38L/Y39S/G42N/A43S/K44E/E48N/S54T/A77E/N122S/P164T/N180T/A259D/S286A/L293T, A23D/I38L/Y39S/G42N/A43S/K44Q/E48N/A77Q/N116E/L141S/G257E/T277D/W284R, A23D/I38L/Y39S/G42N/A43S/K44Q/E48N/S54T/N116D/W258S/G275T/L281E/I291Q, A23D/I38L/Y39S/G42N/A43S/K44Q/E48N/V102Q/W258S/L281E/N282S/I291A, A23D/I38L/Y39S/G42N/A43S/K44Q/E48N/V102R/W258R/A259D/L281E/N282S, A23D/I38L/Y39S/G42N/A43T/K44E/E48N/P164T/N108T/A194T/W258S/A259D/G275T/L281G, A23D/I38L/Y39S/G42N/A43T/K44E/E48N/V102Q/N116D/L281G/N282S, A23D/I38L/Y39S/G42N/A43T/K44Q/E48N/V102Q/N116D/W258S/G278T/L281E/I291A, A23D/I38L/Y39S/G42N/A43T/K44Q/E48N/A77Q/N108T/W258S/G275E/I291Q, A23D/I38L/Y39S/G42N/A43V/K44E/E48A77E/N116D/G275T/L281E, A23D/I38L/Y39S/G42N/A43V/K44E/E48N/N122A/N180T/T277D/L281E/N282S, A23D/I38L/Y39S/G42N/A43V/K44Q/E48N, A23D/I38L/Y39S/G42N/A43V/K44Q/E48N/A161K/P164T/N180T, A23D/I38L/Y39S/G42N/A43V/K44Q/E48N/A77E/A161K/P164T/N180T, A23D/I38L/Y39S/G42N/A43V/K44Q/E48N/A77E/N116D/W258S/L281E, A23D/I38L/Y39S/G42N/A43V/K44Q/E48N/A77Q/N116S/N180T/G275E/T277E, A23D/I38L/Y39S/G42N/A43V/K44Q/E48N/A77Q/N180T, A23D/I38L/Y39S/G42N/A43V/K44Q/E48N/F67Y/A77Q/N116S/N180T/W258S/A259D/G275T/T277E/L281K/N282S/I291S/L293N, A23D/I38L/Y39S/G42N/A43V/K44Q/E48N/F67Y/A77Q/N122S/N180T/A194T/W258R/L281K, A23D/I38L/Y39S/G42N/A43V/K44Q/E48N/F67Y/N180T, A23D/I38L/Y39S/G42N/A43V/K44Q/E48N/L141S, A23D/I38L/Y39S/G42N/A43V/K44Q/E48N/N116D/G275T/L281E/N282S/I291A, A23D/I38L/Y39S/G42N/A43V/K44Q/E48N/N116D/L281K/N282S/I291S/N292S/L293N, A23D/I38L/Y39S/G42N/A43V/K44Q/E48N/N116F/W258S/L281G, A23D/I38L/Y39S/G42N/A43V/K44Q/E48N/N180T, A23D/I38L/Y39S/G42N/A43V/K44Q/E48N/N180T/A259D/G275T/N282S, A23D/I38L/Y39S/G42N/

A43V/K44Q/E48N/Q66T/A77Q/N122A/L141S/G275T/W284G/S286A, A23D/I38L/Y39S/G42N/A43V/K44Q/E48N/S54T/A77E/A161P/W258S/W284M/I291Q, A23D/I38L/Y39S/G42N/A43V/K44Q/E48N/S54T/A77E/T277E/L281E/S286A, A23D/I38L/Y39S/G42N/A43V/K44Q/E48N/S54T/A77E/V102Q/G275T/T277D/W284M/I291Q, A23D/I38L/Y39S/G42N/A43V/K44Q/E48N/S54T/A77E/W258S/T277D/W284M/I291A, A23D/I38L/Y39S/G42N/A43V/K44Q/E48N/S54T/I291A, A23D/I38L/Y39S/G42N/A43V/K44Q/E48N/S54T/L281E, A23D/I38L/Y39S/G42N/A43V/K44Q/E48N/S54T/N116D/A161P/L281E/N282S, A23D/I38L/Y39S/G42N/A43V/K44Q/E48N/S54T/N116D/A161P/W258S/G275T/L281E/I291A, A23D/I38L/Y39S/G42N/A43V/K44Q/E48N/S54T/N116D/A161P/W258S/W284M/I291A, A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, A23D/I38L/Y39S/G42N/A43V/K44Q/E48N/S54T/N116D/L141S/A161K/N180T/W258R/A259D/G275E/T277D/W284R/I291Q/N292S/L293G, A23D/I38L/Y39S/G42N/A43V/K44Q/E48N/S54T/N116D/L141S/N180T/G275T/W284R/I291Q/L293N, A23D/I38L/Y39S/G42N/A43V/K44Q/E48N/S54T/N116D/W258S/G275T/N282S/I291A, A23D/I38L/Y39S/G42N/A43V/K44Q/E48N/S54T/N116D/W284M/I291Q, A23D/I38L/Y39S/G42N/A43V/K44Q/E48N/S54T/N116E/L141S/N180T/L281G/N282S, A23D/I38L/Y39S/G42N/A43V/K44Q/E48N/S54T/N116S/G275E/Y285*, A23D/I38L/Y39S/G42N/A43V/K44Q/E48N/S54T/Q66T/F67Y/N122S/N180T/L281G/I291S/N292S/L293G, A23D/I38L/Y39S/G42N/A43V/K44Q/E48N/S54T/V102Q/N116D/A161P/T277D/W284M/I291Q, A23D/I38L/Y39S/G42N/A43V/K44Q/E48N/S54T/V102Q/N116D/W258S/G275T/I291Q, A23D/I38L/Y39S/G42N/A43V/K44Q/E48N/S54T/V102Q/N116D/W258S/G275T/T277E, A23D/I38L/Y39S/G42N/A43V/K44Q/E48N/S54T/V102Q/N116D/W258S/G275T/T277E/L281G, A23D/I38L/Y39S/G42N/A43V/K44Q/E48N/S54T/V102Q/N116D/W258S/L281G/I291A, A23D/I38L/Y39S/G42N/A43V/K44Q/E48N/S54T/V102Q/W258S/G275T/T277D/N282S, A23D/I38L/Y39S/G42N/A43V/K44Q/E48N/S54T/V102Q/W258S/W284M/S286A, A23D/I38L/Y39S/G42N/A43V/K44Q/E48N/S54T/W258S, A23D/I38L/Y39S/G42N/A43V/K44Q/E48N/V102Q/A161P/W258S, A23D/I38L/Y39S/G42N/A43V/K44Q/E48N/V102Q/W258S/I291Q, A23D/I38L/Y39S/G42N/A43V/K44Q/E48N/V102R/N180T, A23D/I38L/Y39S/G42N/A43V/K44Q/E48N/W258S/I291A, A23D/I38L/Y39S/G42N/K44Q/E48N/A77E/N116D/L281E/I291A, A23D/S25N/I38L/Y39S/G42N/A43E/K44E/E48N/V102R/N116S/N122A/L141S/A161K/P164T/A194T/W258R/A259D/L281E, A23D/S25N/I38L/Y39S/G42N/A43E/K44Q/E48N/Q66T/F67Y/L141S/N180T, A23D/S25N/I38L/Y39S/G42N/A43S/K44Q/E48N/S54T/Q66T/L141S/N180T/W258S/A259D/T277D/W284G/Y285*, A23D/S25N/I38L/Y39S/G42N/A43V/K44Q/E48N/A161K/N180T, A23D/S25N/I38L/Y39S/G42N/A43V/K44Q/E48N/A161P, A23D/S25N/I38L/Y39S/G42N/A43V/K44Q/E48N/A77E, A23D/S25N/I38L/Y39S/G42N/A43V/K44Q/E48N/A77E/N180T, A23D/S25N/I38L/Y39S/G42N/A43V/K44Q/E48N/A77E/N180T/A259D/L281K/L293T, A23D/S25N/I38L/Y39S/G42N/A43V/K44Q/E48N/A77E/V102Q/N180T, A23D/S25N/I38L/Y39S/G42N/A43V/K44Q/E48N/A77Q/N180T/A194T/W258S/W284G/S286G, A23D/S25N/I38L/Y39S/G42N/A43V/K44Q/E48N/A77Q/V102Q/N180T/A194T, A23D/S25N/I38L/Y39S/G42N/A43V/K44Q/E48N/A77Q/W258S/G275T/T277D/W284M/I291S/L293T, A23D/S25N/I38L/Y39S/G42N/A43V/K44Q/E48N/F67Y/A77E/A161P/P164T/N180T, A23D/S25N/I38L/Y39S/G42N/A43V/K44Q/E48N/F67Y/N180T, A23D/S25N/I38L/Y39S/G42N/A43V/K44Q/E48N/L281E/N282S/N292S/L293G, A23D/S25N/I38L/Y39S/G42N/A43V/K44Q/E48N/N116D/A194T/W258S/A259D/G275T/W284G/S 286G/L293T, A23D/S25N/I38L/Y39S/G42N/A43V/K44Q/E48N/N116E/N122S/A194T/T277L/C278A/T279P/K280S/L281*, A23D/S25N/I38L/Y39S/G42N/A43V/K44Q/E48N/N180T, A23D/S25N/I38L/Y39S/G42N/A43V/K44Q/E48N/Q66T/F67Y/A77Q/N180T, A23D/S25N/I38L/Y39S/G42N/A43V/K44Q/E48N/Q66T/N122S/L141S/W284R/C288*, A23D/S25N/I38L/Y39S/G42N/A43V/K44Q/E48N/S54T/A77Q/N116D/L141S/W258S/A259D/G275 T/L281E/N292S/L293T, A23D/S25N/I38L/Y39S/G42N/A43V/K44Q/E48N/S54T/L281E/N282S/C288A/T289Q/M290*, A23D/S25N/I38L/Y39S/G42N/A43V/K44Q/E48N/S54T/N116D/A161P/N180T/W258R/G275E/T277E/I291S/L293G, A23D/S25N/I38L/Y39S/G42N/A43V/K44Q/E48N/S54T/N180T/L281E/N282S/C288A/T289Q/M290*, A23D/S25N/I38L/Y39S/G42N/A43V/K44Q/E48N/S54T/Q66T/F67Y/A77Q/N122S/L141S/W258R/N282S, A23D/S25N/I38L/Y39S/G42N/K44E/E48N/A161P/A194T/G275E/T277D, A23D/S25N/I38L/Y39S/G42N/K44Q/E48N/S54T/A77E/V102R/N122S/L141S/A259D/W284G/I291S/L293T, A23N/I38L/Y39S/G42N/A43E/K44E/E48N/S54T/A77EN102Q/N116D/W258S/W284M/I291Q, A23N/I38L/Y39S/G42N/A43E/K44Q/E48N/S54T/A77E/A161P/G275T/N282S/I291Q, A23N/I38L/Y39S/G42N/A43E/K44Q/E48N/S54T/A77E/N116D/W284M/S286A/I291Q, A23N/I38L/Y39S/G42N/A43E/K44Q/E48N/S54TN102Q/N116D/W258S/G275T/L281E/N282S/I291A, A23N/I38L/Y39S/G42N/A43L/K44Q/E48N/Q66T/F67Y/A77EN102Q/N116D/L141S/N180T/W258 R/I291S, A23N/I38L/Y39S/G42N/A43S/K44E/E48N/S54T/A77E/L141S/W258S/G275T, A23N/I38L/Y39S/G42N/A43S/K44Q/E48N/S54T/A77E/I291Q, A23N/I38L/Y39S/G42N/A43S/K44Q/E48N/S54T/A77E/N116E/N180T/W258S/W284R/S286G, A23N/I38L/Y39S/G42N/A43S/K44Q/E48N/S54T/N116D/S286A/I291A, A23N/I38L/Y39S/G42N/A43S/K44Q/E48N/S54T/Q66T/F67Y/N116D/L141S, A23N/I38L/Y39S/G42N/A43V/K44E/E48N/A77Q/N122S/L141S/N180T/W284M/S286A, A23N/I38L/Y39S/G42N/A43V/K44Q/E48N, A23N/I38L/Y39S/G42N/A43V/K44Q/E48N/A161P/G275T/L281E/N282S/I291A, A23N/I38L/Y39S/G42N/A43V/K44Q/E48N/A161P/N180T, A23N/I38L/Y39S/G42N/A43V/K44Q/E48N/A77E/N116D/R195S/W258S/T277E/N282S/I291A, A23N/I38L/Y39S/G42N/A43V/K44Q/E48N/A77E/N180T, A23N/I38L/Y39S/G42N/A43V/K44Q/E48N/A77E/N180T/A194T, A23N/I38L/Y39S/G42N/A43V/K44Q/E48N/A77E/V102Q/W284M/S286A/I291A, A23N/I38L/Y39S/G42N/A43V/K44Q/E48N/F67Y/A77Q/N116D/N180T/G275E/T277D/W284R/I291S/L293N, A23N/I38L/Y39S/G42N/A43V/K44Q/E48N/N180T, A23N/I38L/Y39S/G42N/A43V/K44Q/E48N/S54T/A161P/G275T/L281G/I291Q, A23N/I38L/Y39S/G42N/A43V/K44Q/E48N/S54T/A77E/V102Q/A161P/W258S/W284M, A23N/I38L/Y39S/G42N/A43V/K44Q/E48N/S54T/N116D/A161P/G275T/L281E, A23N/I38L/Y39S/G42N/A43V/K44Q/E48N/S54T/N116D/A161P/P164T/G275E/L281E, A23N/I38L/Y39S/G42N/A43V/K44Q/E48N/S54T/Q66T/F67Y/A161P/W284M/I291Q, A23N/I38L/Y39S/G42N/A43V/K44Q/E48N/S54T/Q66T/N116S/A259D/W284G/I291S/L293T, A23N/I38L/

Y39S/G42N/A43V/K44Q/E48N/S54T/V102Q/W258S/G275T/N282S, A23N/I38L/Y39S/G42N/A43V/K44Q/E48N/S54T/V102Q/W258S/N282S/I291A, A23N/I38L/Y39S/G42N/A43V/K44Q/E48N/S54T/V102Q/W258S/T277D/L281E, A23N/I38L/Y39S/G42N/A43V/K44Q/E48N/S54T/W258R/A259D/I291S/L293T, A23N/I38L/Y39S/G42N/A43V/K44Q/E48N/S54T/W258S/A259D/L281K/N282S, A23N/I38L/Y39S/G42N/A43V/K44Q/E48N/T277E/W284M, A23N/I38L/Y39S/G42N/A43V/K44Q/E48N/V102Q/G275T/W284M, A23N/I38L/Y39S/G42N/A43V/K44Q/E48N/V102R/N180T, A23N/I38L/Y39S/G42N/K44E/E48N/S54T/N180T/A194T/G275T/I291S/N292S/L293N, A23N/S25N/I38L/Y39S/G42N/A43E/K44Q/E48N/S54T/Q66T/N116E/N122S/A161P/A259D/L281G, A23N/S25N/I38L/Y39S/G42N/A43S/K44Q/E48N/S54T/F67Y/A77E/N122S/N180T/A259D/W284R, A23N/S25N/I38L/Y39S/G42N/A43V/K44Q/E48N, A23N/S25N/I38L/Y39S/G42N/A43V/K44Q/E48N/A77E/N180T, A23N/S25N/I38L/Y39S/G42N/A43V/K44Q/E48N/F67Y/A77E/N180T/A194T/G275T/L281G, A23N/S25N/I38L/Y39S/G42N/A43V/K44Q/E48N/N180T/A194T, A23N/S25N/I38L/Y39S/G42N/A43V/K44Q/E48N/S54T/F67Y/N122S/L141S/A161P/P164T/A194T/G275T, A23N/S25N/I38L/Y39S/G42N/A43V/K44Q/E48N/S54T/N116D/L141S/A161K/N180T/A194T/W258S/A259D/W284R/I291Q/N292S, D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, D2E/I38L/Y39S/G42N/A43V/K244Q/E48N, D2F/I38L/Y39S/G42N/A43V/K44Q/E48N, D2N/I38L/Y39S/G42N/A43V/K44Q/E48N/S54T/V102Q/A161P/W258S/T277D/W284M/I291A, D2Q/I38L/Y39S/G42N/A43V/K44Q/E48N, D2S/I38L/Y39S/G42N/A43V/K44Q/E48N, D2T/I38L/Y39S/G42N/A43V/K44Q/E48N, I38L/Y39S/G42N/A43V/K44Q/E48N, I38L/Y39S/G42N/A43E/K44Q/E48N/G275E/L281G/N282S/S286A, I38L/Y39S/G42N/A43E/K44Q/E48N/S54T/N116E/L114S, I38L/Y39S/G42N/A43L/K44E/E48N, I38L/Y39S/G42N/A43L/K44Q/E48N, I38L/Y39S/G42N/A43L/K44Q/E48N/A116P/A194T, I38L/Y39S/G42N/A43S/K44Q/E48N/S54T/F67Y/A77Q/V102R/N116D/N122S/W258R/L281K/I291S/N292S/L293G, I38L/Y39S/G42N/A43S/K44E/E48N/S54T/Q66T/N116E/L141S/N180T/W258R/A259D, I38L/Y39S/G42N/A43S/K44Q/E48N, I38L/Y39S/G42N/A43S/K44Q/E48N/F67Y, I38L/Y39S/G42N/A43S/K44Q/E48N/S54T/A77E/N116E/N180T/A259D/W284G/I291Q/L293G, I38L/Y39S/G42N/A43S/K44Q/E48N/S54T/A77Q/L141S/W258S/W284G/I291Q/N292S/L293T, I38L/Y39S/G42N/A43T/K44E/E48N/F67Y/N116S/W284R/N292S, I38L/Y39S/G42N/A43T/K44E/E48N/Q66T/N116E/A161P/P164T/A194T/G275T/L281K/N282S, I38L/Y39S/G42N/A43T/K44Q/E48N, I38L/Y39S/G42N/A43V/K44E/E48N, I38L/Y39S/G42N/A43V/K44E/E48N/S286A/I291A, I38L/Y39S/G42N/A43V/K44E/E48N/S54T/N116S/L141S, I38L/Y39S/G42N/A43V/K44E/E48N/S54T/Q66T/V102Q/N116S/L141S/N180T/W258R, I38L/Y39S/G42N/A43V/K44Q/E48N, I38L/Y39S/G42N/A43V/K44Q/E48N/A161P, I38L/Y39S/G42N/A43V/K44Q/E48N/A194T, I38L/Y39S/G42N/A43V/K44Q/E48N/A259*, I38L/Y39S/G42N/A43V/K44Q/E48N/A259D, I38L/Y39S/G42N/A43V/K44Q/E48N/A77E, I38L/Y39S/G42N/A43V/K44Q/E48N/A77E/V102Q/W258S/G275T/T277E/W284M/S286A/I291A, I38L/Y39S/G42N/A43V/K44Q/E48N/A77Q, I38L/Y39S/G42N/A43V/K44Q/E48N/A77Q/N180T, I38L/Y39S/G42N/A43V/K44Q/E48N/C269R, I38L/Y39S/G42N/A43V/K44Q/E48N/C296S/W284*, I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, I38L/Y39S/G42N/A43V/K44Q/E48N/D283*, I38L/Y39S/G42N/A43V/K44Q/E48N/E184A, I38L/Y39S/G42N/A43V/K44Q/E48N/E184K, I38L/Y39S/G42N/A43V/K44Q/E48N/E184N, I38L/Y39S/G42N/A43V/K44Q/E48N/E184R, I38L/Y39S/G42N/A43V/K44Q/E48N/E184S, I38L/Y39S/G42N/A43V/K44Q/E48N/E184T, I38L/Y39S/G42N/A43V/K44Q/E48N/F67Y/A77Q/N116D/A161P, I38L/Y39S/G42N/A43V/K44Q/E48N/F67Y/G275E/T277E/W284M/Q287S/C288A/T289Q/M290*, I38L/Y39S/G42N/A43V/K44Q/E48N/F67Y/N116D/N122S, I38L/Y39S/G42N/A43V/K44Q/E48N/F67Y/N122A/L141S, I38L/Y39S/G42N/A43V/K44Q/E48N/G268N, I38L/Y39S/G42N/A43V/K44Q/E48N/G275*, I38L/Y39S/G42N/A43V/K44Q/E48N/G275N, I38L/Y39S/G42N/A43V/K44Q/E48N/G275T, I38L/Y39S/G42N/A43V/K44Q/E48N/G275T/T277E/N282S/I291A, I38L/Y39S/G42N/A43V/K44Q/E48N/I291Q, I38L/Y39S/G42N/A43V/K44Q/E48N/I291S, I38L/Y39S/G42N/A43V/K44Q/E48N/L141S/N180T/A259D/L281G/N282S/L293N, I38L/Y39S/G42N/A43V/K44Q/E48N/L141S/W258R, I38L/Y39S/G42N/A43V/K44Q/E48N/L281E, I38L/Y39S/G42N/A43V/K44Q/E48N/L281G, I38L/Y39S/G42N/A43V/K44Q/E48N/L281K, I38L/Y39S/G42N/A43V/K44Q/E48N/L281S/Q284H, I38L/Y39S/G42N/A43V/K44Q/E48N/L293N, I38L/Y39S/G42N/A43V/K44Q/E48N/L293T, I38L/Y39S/G42N/A43V/K44Q/E48N/L293V, I38L/Y39S/G42N/A43V/K44Q/E48N/N116D, I38L/Y39S/G42N/A43V/K44Q/E48N/N116D/L141S/N180T/A259D/N282S, I38L/Y39S/G42N/A43V/K44Q/E48N/N116S, I38L/Y39S/G42N/A43V/K44Q/E48N/N116S/L141S/P164T/W258S/L281G/N282S/S286A, I38L/Y39S/G42N/A43V/K44Q/E48N/N122A, I38L/Y39S/G42N/A43V/K44Q/E48N/N180T, I38L/Y39S/G42N/A43V/K44Q/E48N/N282S, I38L/Y39S/G42N/A43V/K44Q/E48N/P51N, I38L/Y39S/G42N/A43V/K44Q/E48N/P51T, I38L/Y39S/G42N/A43V/K44Q/E48N/Q66T/F67Y/A77Q/N116E/N122A/A161K/N180T/W258S/L293G, I38L/Y39S/G42N/A43V/K44Q/E48N/S286A, I38L/Y39S/G42N/A43V/K44Q/E48N/S286G, I38L/Y39S/G42N/A43V/K44Q/E48N/S54T, I38L/Y39S/G42N/A43V/K44Q/E48N/S54T/A277E/S286A/I291A, I38L/Y39S/G42N/A43V/K44Q/E48N/S54T/G275T/T277D/L281G/N282S/I291A, I38L/Y39S/G42N/A43V/K44Q/E48N/S54T/L141S, I38L/Y39S/G42N/A43V/K44Q/E48N/S54T/N116D, I38L/Y39S/G42N/A43V/K44Q/E48N/S54T/N116S/N122S/L141S, I38L/Y39S/G42N/A43V/K44Q/E48N/S54T/N122A, I38L/Y39S/G42N/A43V/K44Q/E48N/S54T/P164T/N180T/W258R/A259D/L281G/N282S/I291S/N292S/L293N, I38L/Y39S/G42N/A43V/K44Q/E48N/T270*, I38L/Y39S/G42N/A43V/K44Q/E48N/T271E, I38L/Y39S/G42N/A43V/K44Q/E48N/T276G/K280S/L281*, I38L/Y39S/G42N/A43V/K44Q/E48N/T276H/C278*, I38L/Y39S/G42N/A43V/K44Q/E48N/T276R/K280Q/L281A/N282E/D283*, I38L/Y39S/G42N/A43V/K44Q/E48N/T277D, I38L/Y39S/G42N/A43V/K44Q/E48N/V102Q/N116D, I38L/Y39S/G42N/A43V/K44Q/E48N/V102Q/T277D/L281G, I38L/Y39S/G42N/A43V/K44Q/E48N/V273*, I38L/Y39S/G42N/A43V/K44Q/E48N/V273D/S274R/G275A/T276P/T277L/C278A/T279P/K280S/L281*, I38L/Y39S/G42N/A43V/K44Q/E48N/W258*, I38L/Y39S/G42N/A43V/

K44Q/E48N/W258R, I38L/Y39S/G42N/A43V/K44Q/E48N/W258S, I38L/Y39S/G42N/A43V/K44Q/E48N/W284G, I38L/Y39S/G42N/A43V/K44Q/E48N/W284M, I38L/Y39S/G42N/A43V/K44Q/E48N/W258S, I38L/Y39S/G42N/A43V/K44Q/E48N/W284G, I38L/Y39S/G42N/A43V/K44Q/E48N/W284M, I38L/Y39S/G42N/A43V/K44Q/E48N/W284M/I291Q, I38L/Y39S/G42N/A43V/K44Q/E48N/W284R, I38L/Y39S/G42N/A43V/K44Q/E48N/W284T, I38L/Y39S/G42N/A43V/K44Q/E48N/N116D/L141S, I38L/Y39S/G42N/K44E/E48N/Q66T/F67Y/A77Q/N122A/A161K/S286G/T289K/M290*, I38L/Y39S/G42N/K44E/E48N/S54T/N116D/W258S/G275T/W284M/I291Q, I38L/Y39S/G42N/K44E/E48N/S54T/N116E/N122S/L141S, I38L/Y39S/G42N/K44E/E48N/S54T/N116S/N122A, I38L/Y39S/G42N/K44Q/E48N, I38L/Y39S/G42N/K44Q/E48N/S54T/N116D/L141S, S17G/A23D/I38L/Y39S/G42N/A43T/K44E/E48N/A77E/V102Q/A161P/G275T/N282S/I291A, S17G/A23D/I38L/Y39S/G42N/A43V/K44Q/E48N/A77E/V102Q/A161P/W258S/L281E/I291Q, S17G/A23D/I38L/Y39S/G42N/A43V/K44Q/E48N/F67Y/G275T/W284M/I291S, S17G/A23D/I38L/Y39S/G42N/A43V/K44Q/E48N/F67Y/V102Q/N116S/N122A/L141S/N180T/A194T/W284R/N292S/L293T, S17G/A23D/I38L/Y39S/G42N/A43V/K44Q/E48N/S54T/A77E/V102Q/N116D/A161P/L281G, S17G/A23D/I38L/Y39S/G42N/A43V/K44Q/E48N/S54T/A77E/V102Q/S286A/I291Q, S17G/A23D/I38L/Y39S/G42N/A43V/K44Q/E48N/S54T/V102Q/W258S/L281E, S17G/A23D/I38L/Y39S/G42N/A43V/K44Q/E48N/S54T/W258S/L281G/N282S/I291A, S17G/A23D/I38L/Y39S/G42N/A43V/K44Q/E48N/V102Q/A161P/T277D/W284M, S17G/A23D/I38L/Y39S/G42N/A43V/K44Q/E48N/V102Q/N116D/L141S/N180T/L281G/I291Q/N292S/L293N, S17G/A23D/I38L/Y39S/G42N/A43V/K44Q/E48N/Q66T/A77E/A194T, S17G/A23D/S25N/I38L/Y39S/G42N/A43V/K44Q/E48N/S54T/Q66T/F67Y/A77Q/N116E/L141S/N180T/A194T/W258S/A259D/G275E/L281G/N282S/I291S/N292S/L293T, S17G/A23D/I38L/Y39S/G42N/A43E/K44E/E48N/N116D/W258S/G275T/W284M/S286A, S17G/A23D/I38L/Y39S/G42N/A43L/K44E/E48N/N116S/A161K/A194T, S17G/A23D/I38L/Y39S/G42N/A43S/K44E/E48N/A77E/V102Q/G275T, S17G/A23D/I38L/Y39S/G42N/A43S/K44Q/E48N/S54T/V102Q/N116E, S17G/A23D/I38L/Y39S/G42N/A43V/K44Q/E48N/A77E/V102Q/A161P/W284M/I291Q, S17G/A23D/I38L/Y39S/G42N/A43V/K44Q/E48N/N116S/N122S/G275T/L281E, S17G/A23D/I38L/Y39S/G42N/A43V/K44Q/E48N/S54T/N116D/L141S/N180T/G275T/T277E/W284G, S17G/A23D/I38L/Y39S/G42N/A43V/L44Q/E48N/S54T/V102Q/W258S/W284M/I291Q, S17G/A23D/I38L/Y39S/G42N/A43V/K44Q/E48N/S54T/W258S/G275T/T277E, S17G/A23D/I38L/Y39S/G42N/A43V/K44Q/E48N/V102Q/N116D/A161P/W258S, S17G/A23D/I38L/Y39S/G42N/A43S/K44Q/E48N/Q66T/V102Q/N122S/A161P/P164T/L281K/N282S, S17G/A23D/I38L/Y39S/G42N/A43V/K44Q/E48N/S54T/Q66T/N116E/A259D/W284G, S17G/A23D/I38L/Y39S/G42N/A43V/K44Q/E48N/Q66T/F67Y/N116E/L114S/N180T/A194T/G275E/W284G/I291S/N292S, S17G/A23D/I38L/Y39S/G42N/A43V/K44Q/E48N/L141S, S17G/I38L/Y39S/G42N/A43E/K44Q/E48N/S54T/N122S, S17G/I38L/Y39S/G42N/A43S/K44E/E48N/Q66T/A77Q/V102Q/N116S/N122S/L141S/W258R/A259D/W284R, S17G/I38L/Y39S/G42N/A43S/K44E/E48N/S54T/A77Q/N116E/N122A/L141S/A161K/P164T/N180T/A194T/T277E/W284G, S17G/I38L/Y39S/G42N/A43S/K44E/E48N/S54T/N180T/W258S/A259D, S17G/I38L/Y39S/G42N/A43S/K44Q/E48N/Q66T/N116D/N122S/N180T, S17G/I38L/Y39S/G42N/A43S/K44Q/E48N/S54T/L141S, S17G/I38L/Y39S/G42N/A43S/K44Q/E48N/S54T/N116D/L141S, S17G/I38L/Y39S/G42N/A43S/K44Q/E48N/S54T/V102Q/N116D/A161P/W258S/N282S/W284M/I291A, S17G/I38L/Y39S/G42N/A43T/K44Q/E48N/S54T/V102Q/N116D/A161P/L281E/N282S, S17G/I38L/Y39S/G42N/A43V/K44E/E48N/S54T/N116S/N122S, S17G/I38L/Y39S/G42N/A43V/K44Q/E48N, S17G/I38L/Y39S/G42N/A43V/K44Q/E48N/I291S/N292S/L293N, S17G/I38L/Y39S/G42N/A43V/K44Q/E48N/N116S/N180T/T277E/W284R/L293T, S17G/I38L/Y39S/G42N/A43V/K44Q/E48N/N122A/A194T/A259D/G275T/T277D/L281K/L293N, S17G/I38L/Y39S/G42N/A43V/K44Q/E48N/N122S, S17G/I38L/Y39S/G42N/A43V/K44Q/E48N/Q66T/A77E/N116S/G275T/W284M, S17G/I38L/Y39S/G42N/A43V/K44Q/E48N/S54T, S17G/I38L/Y39S/G42N/A43V/K44Q/E48N/S54T/A77E/N116D/L141S/L281E, S17G/I38L/Y39S/G42N/A43V/K44Q/E48N/S54T/A77E/V102Q/G275T, S17G/I38L/Y39S/G42N/A43V/K44Q/E48N/S54T/A77Q/N116E/L141S/N180T/A194T/W258S/A259D/W284G/S286G/I291Q/L293G, S17G/I38L/Y39S/G42N/A43V/K44Q/E48N/S54T/A77Q/N116S/L141S/A194T/W258R/L281G, S17G/I38L/Y39S/G42N/A43V/K44Q/E48N/S54T/N116D, S17G/I38L/Y39S/G42N/A43V/K44Q/E48N/S54T/N116E, S17G/I38L/Y39S/G42N/A43V/K44Q/E48N/S54T/N116E/L141S, S17G/I38L/Y39S/G42N/A43V/K44Q/E48N/S54T/V102Q/N116D/A161P/W258S/W284M/I291A, S17G/I38L/Y39S/G42N/K44Q/E48N/N122S/L141S, S17G/I38L/Y39S/G42N/K44Q/E48N/Q66T/F67Y/T277D/L281G, S17G/I38L/Y39S/G42N/K44Q/E48N/S54T/N116E/N122S/L141S, S25G/I38L/Y39S/G42N/A43E/K44Q/E48N/S54T/N180T/W258S/G275E, S25G/I38L/Y39S/G42N/A43S/K44E/E48N/S54T/A77Q/V102Q/N116D/L141S/A194T/W258S/W284M, S25G/I38L/Y39S/G42N/A43S/K44E/E48N/S54T/N116D/N122S/L141S/N180T/W258R/G275T/T277E/W284M/I291Q/N292S/L293T, S25G/I38L/Y39S/G42N/A43S/K44Q/E48N/S54T/Q66T/A77E/N116E/N180T/A259D/G275T/T277D/S286A/I291Q/N292S/L293T, S25G/I38L/Y39S/G42N/A43S/K44Q/E48N/Q66T/N116E/L141S/N180T/W258S, S25G/I38L/Y39S/G42N/A43T/K44E/E48N/A77E/N116S/L141S, S25G/I38L/Y39S/G42N/A43V/K44Q/E48N, S25G/I38L/Y39S/G42N/A43V/K44Q/E48N/A161P/N180T/A194T, S25G/I38L/Y39S/G42N/A43V/K44Q/E48N/A77E, S25G/I38L/Y39S/G42N/A43V/K44Q/E48N/A77Q/N116D/L141S/N180T/W258R/G275E/T277E, S25G/I38L/Y39S/G42N/A43V/K44Q/E48N/F67Y/A161K, S25G/I38L/Y39S/G42N/A43V/K44Q/E48N/L141S/N180T/A194T/W258S/A259D/L281K/N282S, S25G/I38L/Y39S/G42N/A43V/K44Q/E48N/N180T/A194T, S25G/I38L/Y39S/G42N/A43V/K44Q/E48N/Q66T/A77Q/N116D/A161K/P164T/W284G/N292S/L293G, S25G/I38L/Y39S/G42N/A43VK44Q/E48N/S54T/A77Q/L141S/N180T/G275E/W284G/I291Q/N292S/L293G, S25G/I38L/Y39S/G42N/A43V/K44Q/E48N/S54T/A77Q/N116D/W258S/A259D/L281G, S25G/I38L/Y39S/G42N/A43V/K44Q/E48N/S54T/A77Q/N116S/N180T/A194T/A295D/T277D/W284G/I291Q, S25N/I38L/Y39S/G42N/A43V/K44Q/E48N/S54T/L141S/N180T/G275T/W284M/I291S/L293T, S25N/I38L/Y39S/G42N/A43V/K44Q/E48N/S54T/L141S/N180T/W258R/A259D, and A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S143D/D160A/A161P/Y167Q/L174Q/N180T/E184Q/R185Q/S190A/L196S/G204S/N205S/Y206F.

The present invention provides the variant endoglucanase enzymes as disclosed herein, wherein said amino acid modification(s) is selected from group consisting of D215*, I38L/Y39S/G42N/A43V/K44Q/E48N, D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, and T-18S/F-5L/T-4A/V-3A/A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F.

The present invention provides the variant endoglucanase enzymes as disclosed herein, wherein said variant endoglucanase enzyme comprises said amino acid modification(s) selected from the group consisting of I38L/Y39S/G42N/A43V/K44Q/E48N, D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, A23D/S25N/I38L/Y39S/G42N/A43V/K44Q/E48N/A77E, A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-, D215* and A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F.

The present invention provides the variant endoglucanase enzymes as disclosed herein, wherein said variant endoglucanase enzyme comprises said amino acid modifications I38L/Y39S/G42N/A43V/K44Q/E48N.

The present invention provides the variant endoglucanase enzymes as disclosed herein, wherein said variant endoglucanase enzyme comprises said amino acid modifications D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-.

The present invention provides the variant endoglucanase enzymes as disclosed herein, wherein said variant endoglucanase enzyme comprises said amino acid modifications I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-.

The present invention provides the variant endoglucanase enzymes as disclosed herein, wherein said variant endoglucanase enzyme comprises said amino acid modifications A23D/S25N/I38L/Y39S/G42N/A43V/K44Q/E48N/A77E.

The present invention provides the variant endoglucanase enzymes as disclosed herein, wherein said variant endoglucanase enzyme comprises said amino acid modifications A23D/I38L/Y39S/G42N/A43V/K44Q/E48N/S54T/N116D/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/I291-/N292-.

The present invention provides the variant endoglucanase enzymes as disclosed herein, wherein said variant endoglucanase enzyme comprises said amino acid modification D215*.

The present invention provides the variant endoglucanase enzymes as disclosed herein, wherein said variant endoglucanase enzyme comprises said amino acid modifications A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F.

The present invention provides the variant endoglucanase enzymes as disclosed herein, wherein said variant endoglucanase enzyme exhibits at least 90% sequence identity to the amino acid sequence selected from the group consisting of SEQ ID NO:3, SEQ ID NO:5, SEQ ID NO:7, SEQ ID NO:9, SEQ ID NO:23, SEQ ID NO:25, and SEQ ID NO:27.

The present invention provides the variant endoglucanase enzymes as disclosed herein, wherein said variant endoglucanase enzyme exhibits at least 90% sequence identity to SEQ ID NO:5.

The present invention provides the variant endoglucanase enzymes as disclosed herein, wherein said variant endoglucanase enzyme exhibits at least 90% sequence identity to SEQ ID NO:7.

The present invention provides the variant endoglucanase enzymes as disclosed herein, wherein said variant endoglucanase enzyme exhibits at least 90% sequence identity to SEQ ID NO:23.

The present invention provides the variant endoglucanase enzymes as disclosed herein, wherein said variant endoglucanase enzyme exhibits at least 90% sequence identity to SEQ ID NO:27.

In some embodiments, the variant endoglucanase enzyme comprises the amino acid sequence of SEQ ID NO:3.

In some embodiments, the variant endoglucanase enzyme comprises the amino acid sequence of SEQ ID NO:5.

In some embodiments, the variant endoglucanase enzyme comprises the amino acid sequence of SEQ ID NO:7.

In some embodiments, the variant endoglucanase enzyme comprises the amino acid sequence of SEQ ID NO:9.

In some embodiments, the variant endoglucanase enzyme comprises the amino acid sequence of SEQ ID NO:23.

In some embodiments, the variant endoglucanase enzyme comprises the amino acid sequence of SEQ ID NO:25.

In some embodiments, the variant endoglucanase enzyme comprises the amino acid sequence of SEQ ID NO:27.

In some embodiments, the variant enzymes comprise one or more variants selected from those endoglucanase variants shown in FIG. 2, FIG. 3, FIG. 4 or FIG. 6.

In some embodiments, the variant endoglucanase enzyme is an isolated variant endoglucanase enzyme.

In some embodiments, the variant endoglucanase enzymes have improved activities as compared to the parental endoglucanase enzyme. In some embodiments, the variant endoglucanase enzyme has at least 1.1 fold increase in activity as compared to the wild-type G1P endoglucanase enzyme (SEQ ID NO:1). In some embodiments, the variant endoglucanase enzyme has at least 1.5 fold increase in activity as compared to the wild-type G1P endoglucanase enzyme (SEQ ID NO:1). In some embodiments, the variant endoglucanase enzyme has at least 2.0 fold increase in activity as compared to the wild-type G1P endoglucanase enzyme (SEQ ID NO:1). In some embodiments, the variant endoglucanase enzyme has at least 2.5 fold increase in activity as compared to the wild-type G1P endoglucanase enzyme (SEQ ID NO:1). Examples 6 and 11, FIG. 2 and FIG. 4 show that multiple variant endoglucanase enzymes exhibit increased activities as compared to the wild-type G1P endoglucanase enzyme (SEQ ID NO:1) and/or as compared to G2P (i.e. variant G1V2 as set forth in SEQ ID NO: 5).

In some embodiments, the variant endoglucanase enzymes have improved biostoning efficacy or performance as compared to the parental endoglucanase enzyme. In some embodiments, the variant endoglucanase enzyme has at least 1.1 fold increase in biostoning efficacy as compared to the wild-type G1P endoglucanase enzyme (SEQ ID NO:1). In some embodiments, the variant endoglucanase enzyme has at least 1.5 fold increase in biostoning efficacy as compared to the wild-type G1P endoglucanase enzyme (SEQ ID NO:1). In some embodiments, the variant endoglucanase enzyme has at least 2.0 fold increase in biostoning efficacy as compared to the wild-type G1P endoglucanase enzyme (SEQ ID NO:1). In some embodiments, the variant endoglucanase enzyme has at least 2.5 fold increase in biostoning efficacy as compared to the wild-type G1P endoglucanase enzyme (SEQ ID NO:1). Examples 8 and 13, as well as FIGS. 3 and 6 show that multiple variant endoglucanase enzymes exhibit improved biostoning performance as compared to the wild-type G1P endoglucanase enzyme (SEQ ID NO:1) and/or as compared to G2P (i.e. variant G1V2 as set forth in SEQ ID NO: 5).

In some embodiments, the variant endoglucanase enzymes have improved alkaline (detergent) depilling efficacy or performance as compared to the parental endoglucanase enzyme. In some embodiments, the variant endoglucanase enzyme has at least 1.1 fold increase in alkaline (detergent) depilling efficacy as compared to the wild-type G1P endoglucanase enzyme (SEQ ID NO:1). In some embodiments, the variant endoglucanase enzyme has at least 1.5 fold increase in alkaline (detergent) depilling efficacy as compared to the wild-type G1P endoglucanase enzyme (SEQ ID NO:1). In some embodiments, the variant endoglucanase enzyme has at least 2.0 fold increase in alkaline (detergent) depilling efficacy as compared to the wild-type G1P endoglucanase enzyme (SEQ ID NO:1). In some embodiments, the variant endoglucanase enzyme has at least 2.5 fold increase in alkaline (detergent) depilling efficacy as compared to the wild-type G1P endoglucanase enzyme (SEQ ID NO:1). Example 14 and FIG. 7 show that multiple variant endoglucanase enzymes exhibit improved alkaline (detergent) depilling performance as compared to G2P (i.e. variant G1V2 as set forth in SEQ ID NO: 5).

In some embodiments, the variant endoglucanase enzymes have improved alkaline (detergent) destaining activity/alkaline (detergent) decontamination performance as compared to the parental endoglucanase enzyme. In some embodiments, the variant endoglucanase enzyme has at least 1.1 fold increase in alkaline (detergent) decontamination ability as compared to the wild-type G1P endoglucanase enzyme (SEQ ID NO:1). In some embodiments, the variant endoglucanase enzyme has at least 1.5 fold increase in alkaline (detergent) decontamination ability as compared to the wild-type G1P endoglucanase enzyme (SEQ ID NO:1). In some embodiments, the variant endoglucanase enzyme has at least 2.0 fold increase in alkaline (detergent) decontamination ability as compared to the wild-type G1P endoglucanase enzyme (SEQ ID NO:1). In some embodiments, the variant endoglucanase enzyme has at least 2.5 fold increase in alkaline (detergent) decontamination ability as compared to the wild-type G1P endoglucanase enzyme (SEQ ID NO:1).

In one embodiment, the variant endoglucanase enzymes are more stable than the parent endoglucanase enzyme when exposed to temperatures of 20° C., 25° C., 30° C., 40° C., 45° C., 50° C., 52° C., 55° C., 56° C., 58° C., 60° C., 65° C., 66° C., 70° C., 75° C., 80° C. and/or 85° C. for a period of time, generally ranging from about 1, 2, 3, 4, 5, 6, 7, 8, 9 or 10 minutes or longer, depending on the ultimate conditions for the use of the variant endoglucanase enzyme, with some embodiments utilizing thermal challenge times of 5 minutes to 10 minutes, 5 minutes to 15 minutes, 5 minutes to 60 minutes, 10 minutes to 180 minutes all finding use in the present invention. In some embodiments, the variant endoglucanase enzymes have increased total activity as compared to a parent endoglucanase enzyme, particularly G1P, for at least 180 minutes at 50° C. In other emodiments, the variant endoglucanase enzymes have increased activity compared to a parent endoglucanase enzyme for at least 30 minutes at 30° C. and/or 40° C.

In addition, tolerance to pH 6.5, pH 7.0, pH 7.5, pH 8.0, pH 8.5, pH 9.0, pH 9.5, pH 10.0, pH 10.5, pH 11.0, and/or pH 11.5 can be a consideration for improvement as well. Accordingly, in some embodiments the variant endoglucanase enzymes have increased tolerance to pH 6.5 as compared to a parent endoglucanase enzyme. In some embodiments, the variant endoglucanase enzymes have increased tolerance to pH 6.5 as compared to a parent endoglucanase enzyme for at least 3 hours at 50° C. In other emodiments, the variant endoglucanase enzymes have increased activity and/or tolerance compared to a parent endoglucanase enzyme for at least 30 minutes at pH 10.0, pH 10.5, and pH 11.0.

The amino acid changes that may be present in addition to the specific substitutions described herein may be of a minor nature, that is conservative amino acid substitutions or insertions that do not significantly affect the folding and/or activity of the protein; small deletions, typically of 1 to about 30 amino acids; small amino- or carboxyl-terminal extensions, such as an amino-terminal methionine residue; a small linker peptide of up to about 20 to about 25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R.L. Hill, 1979, In, *The Proteins*, Academic Press, New York. Common substitutions are Ala/Ser, Val/Ile, Asp/Glu, Thr/Ser, Ala/Gly, Ala/Thr, Ser/

Asn, Ala/Val, Ser/Gly, Tyr/Phe, Ala/Pro, Lys/Arg, Asp/Asn, Leu/Ile, LeuA al, Ala/Glu, and Asp/Gly.

A. Parent Endoglucanase

In most embodiments of the present invention, the parent endoglucanase enzyme is the *Chaetomium thermophilum* (Ct.EG) wild-type endoglucanase (G1P) having the amino acid sequence of SEQ ID NO:1. In some embodiments, the parent endoglucanase enzyme has a sequence identity to the polypeptide of SEQ ID NO:1 of at least 90%, at least 91%, at least 92%, at least 93%, at least 94%, at least 95%, at least 96%, at least 97%, at least 98%, at least 99%, or 100%, and have endoglucanase activity. In some embodiments, the parent endoglucanase enzyme is G2P having the amino acid sequence of SEQ ID NO:5. In some embodiments, the parent endoglucanase enzyme has a sequence identity to the polypeptide of SEQ ID NO:5 of at least 90%, at least 91%, at least 92%, at least 93%, at least 94%, at least 95%, at least 96%, at least 97%, at least 98%, at least 99%, or 100%, and have endoglucanase activity.

B. Nucleic Acid Compositions

The present invention also provides compositions comprising a variant endoglucanase enzyme encoding nucleic acid of the present invention. Such variant endoglucanase polypeptide encoding nucleic acids can encode any of the variant endoglucanase enzymes recited in the present application, including under section "Variant Endoglucanases of the Invention" above. In some embodiments, the composition comprises a nucleic acid selected from the group consisting of the even numbered sequence of SEQ ID NOs: 2 to 20.

In some embodiments, the composition comprises a nucleic acid of SEQ ID NO:2. In some embodiments, the composition comprises a nucleic acid of SEQ ID NO:4. In some embodiments, the composition comprises a nucleic acid of SEQ ID NO:6. In some embodiments, the composition comprises a nucleic acid of SEQ ID NO:8. In some embodiments, the composition comprises a nucleic acid of SEQ ID NO:10. In some embodiments, the composition comprises a nucleic acid of SEQ ID NO:12. In some embodiments, the composition comprises a nucleic acid of SEQ ID NO:14. In some embodiments, the composition comprises a nucleic acid of SEQ ID NO:16. In some embodiments, the composition comprises a nucleic acid of SEQ ID NO:18. In some embodiments, the composition comprises a nucleic acid of SEQ ID NO:20. In some embodiments, the composition comprises a nucleic acid of SEQ ID NO:24. In some embodiments, the composition comprises a nucleic acid of SEQ ID NO:26. In some embodiments, the composition comprises a nucleic acid of SEQ ID NO:28. In some embodiments, the composition comprises a nucleic acid of SEQ ID NO:30. In some embodiments, the composition comprises a nucleic acid of SEQ ID NO:32. In some embodiments, the composition comprises a nucleic acid of SEQ ID NO:34.

In some embodiments, the variant endoglucanase enzyme encoding nucleic acid comprises a codon optimized version or variant of any of the even numbered sequences of SEQ ID NOs: 2 to 20 and SEQ ID NOs: 24 to 34.

In some embodiments, the invention provides the nucleic acid encoding the variant endoglucanase enzyme as described herein, wherein said nucleic acid is codon optimized for a host organism for expression of the variant endoglucanase enzyme in said organism.

In some embodiments, the invention provides a nucleic acid comprising a nucleic acid sequence selected from the group consisting of SEQ ID NO:4, SEQ ID NO:6, SEQ ID NO:8, SEQ ID NO:10, SEQ ID NO:14, SEQ ID NO:16, SEQ ID NO:18, SEQ ID NO:20, SEQ ID NO:24, SEQ ID NO:26, SEQ ID NO:28, SEQ ID NO:30, SEQ ID NO:32 and SEQ ID NO:34.

In some embodiments, the invention provides a nucleic acid comprising a nucleic acid sequence selected from the group consisting of SEQ ID NO:4, SEQ ID NO:6, SEQ ID NO:8, SEQ ID NO:10, SEQ ID NO:24, SEQ ID NO:26, and SEQ ID NO:28.

In some embodiments, the invention provides a nucleic acid comprising a nucleic acid sequence selected from the group consisting of SEQ ID NO: 14, SEQ ID NO:16, SEQ ID NO:18, SEQ ID NO:20, SEQ ID NO:30, SEQ ID NO:32 and SEQ ID NO:34.

In some embodiments, the invention provides a nucleic acid construct comprising a nucleic acid encoding SEQ ID NO:1 operably linked to an exogenous construct sequence.

In some embodiments, the invention provides the nucleic acid construct as described herein, wherein the exogenous construct sequence is an exogenous promoter.

"Codon optimized" in this context is done in relation to a particular host organism and its generally preferred amino acid codons; that is, the host production organism, e.g. an *Aspergillus* species, may yield higher translation and/or secretion using *Aspergillus* preferred codons as compared to a yeast production organism.

In some embodiments, the compositions are enriched in such a variant endoglucanase enzyme encoding nucleic acid of the present invention. The term "enriched" indicates that the endoglucanase activity capable of being obtained from the composition has been increased, e.g., with an enrichment factor of at least 1. In some embodiments, the compositions are formulated to provide desirable characteristics such as low color, low odor and acceptable storage stability.

1. Preparation of Variants

The variants can be prepared generally by construction genes encoding the protein sequence using well known techniques, including site-directed mutagenesis of a parental gene and synthetic gene construction.

i. Regulatory Sequences

The present invention also relates to nucleic acid constructs comprising a polynucleotide encoding a variant of the present invention operably linked to one or more control sequences that direct the expression of the coding sequence in a suitable host cell under conditions compatible with the control sequences. The control sequence may include a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from *Aspergillus* species genes, as is known in the art, including *A. nidulans, A. niger* and *A. oryzae*, as well as *Rhizomucor* species genes such as *R. miehei, Trichoderma* species genes including *T. reesei, Fusarium* species genes including *F. venenaturn*. Yeast control sequences including promoters are also well known from *Saccharomyces cerevisiae.*

Suitable promoter sequences (as well as other control sequences) from these species include the promoters from amylases (α-amylase in particular), glucoamylases, proteases, phosphatases, endoglucanases, cellulases, etc. as are known in the art. In addition, as for codon-optimization, it may be desirable to use promoters (and other control sequences) that are endogeneous to the host production strain, operably linked to the nucleic acids encoding the variant endoglucanases. In many embodiments, the promoter that is operably attached to the coding sequence is not the native promoter sequence.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators (and other control sequences such as promoters) for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triosephosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant endoglucanase being expressed into the cell's secretory pathway. In some instances, the signal sequence is that depicted in FIG. 4 or FIG. 5F, i.e. the wild-type signal peptide (SEQ ID NO:21) or the variant signal peptide (SEQ ID NO:22).

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the Gpd (Glyceraldehyde-3-phosphate dehydrogenase) from *Ascomycota* such as *Aspergillus, Aspergillus niger* glucoamylase promoter, *Aspergillus oryzae* TAKA alpha-amylase promoter, and *Aspergillus oryzae* glucoamylase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

In some embodiments, the present invention provides a nucleic acid encoding a preprotein comprising a signal peptide and a mature protein, wherein the mature protein can be any of the variant endoglucanase enzymes as described herein, and wherein the signal peptide can be endogenous or exogenous. In some embodiments, the invention provides a nucleic acid encoding a preprotein comprising a signal peptide and a mature protein, wherein the mature protein is the variant endoglucanase enzyme as described herein and is operably linked to an endogenous or exogeneous construct sequence.

In some embodiments, the present invention provides a nucleic acid encoding a preprotein comprising a signal peptide and a mature protein, wherein said signal peptide is a wild-type signal peptide or a variant signal peptide comprising one or more amino acid modifications as compared to a wild-type signal peptide; and wherein said mature protein comprises one or more amino acid modifications as compared to SEQ ID NO:1 as disclosed herein. In some embodiments, the signal peptide is a wild-type signal peptide. In some embodiments, said wild-type signal peptide comprises the amino acid sequence of SEQ ID NO:21. In some embodiments, the signal peptide is a variant signal peptide comprising one or more amino acid modifications as compared to SEQ ID NO:21, and said one or more amino acid modifications in the variant signal peptide occur at positions corresponding to positions selected from the group consisting of positions-18, -5, -4, and -3. In some embodiments, the variant signal peptide comprises said one or more amino acid modification(s) selected from the group consisting of T-18S, F-5L, T-4A, and V-3A. In some embodiments, the variant signal peptide comprises amino acid modifications T-18S/F-5L/T-4A/V-3A. In some embodiments, the variant signal peptide comprises the amino acid sequence of SEQ ID NO:22. In some embodiments, the variant signal peptide consists of the amino acid sequence of SEQ ID NO:22.

In some embodiments, the invention provides a nucleic acid encoding a preprotein comprising a signal peptide and a mature protein, wherein said signal peptide comprises the amino acid sequence of SEQ ID NO:21 and wherein said mature protein comprises the amino acid sequence selected from the group consisting of SEQ ID NO:3, SEQ ID NO:5, SEQ ID NO:7, SEQ ID NO:9, SEQ ID NO:23, SEQ ID NO:25, and SEQ ID NO:27. In some embodiments, said signal peptide comprises the amino acid sequence of SEQ ID NO:21 and said mature protein comprises the amino acid sequence of SEQ ID NO:3. In some embodiments, said signal peptide comprises the amino acid sequence of SEQ ID NO:21 and said mature protein comprises the amino acid sequence of SEQ ID NO:5. In some embodiments, said signal peptide comprises the amino acid sequence of SEQ ID NO:21 and said mature protein comprises the amino acid sequence of SEQ ID NO:7. In some embodiments, said signal peptide comprises the amino acid sequence of SEQ ID NO:21 and said mature protein comprises the amino acid sequence of SEQ ID NO:9. In some embodiments, said signal peptide comprises the amino acid sequence of SEQ ID NO:21 and said mature protein comprises the amino acid sequence of SEQ ID NO:23. In some embodiments, said signal peptide comprises the amino acid sequence of SEQ ID NO:21 and said mature protein comprises the amino acid sequence of SEQ ID NO:25. In some embodiments, said signal peptide comprises the amino acid sequence of SEQ ID NO:21 and said mature protein comprises the amino acid sequence of SEQ ID NO:27.

In some embodiments, the invention provides a nucleic acid encoding a preprotein comprising a signal peptide and a mature protein, wherein said signal peptide comprises the amino acid sequence of SEQ ID NO:22 and wherein said mature protein comprises the amino acid sequence selected from the group consisting of SEQ ID NO:3, SEQ ID NO:5, SEQ ID NO:7, SEQ ID NO:9, SEQ ID NO:23, SEQ ID NO:25, and SEQ ID NO:27. In some embodiments, said signal peptide comprises the amino acid sequence of SEQ ID NO:22 and said mature protein comprises the amino acid sequence of SEQ ID NO:3. In some embodiments, said signal peptide comprises the amino acid sequence of SEQ ID NO:22 and said mature protein comprises the amino acid sequence of SEQ ID NO:5. In some embodiments, said signal peptide comprises the amino acid sequence of SEQ ID NO:22 and said mature protein comprises the amino acid sequence of SEQ ID NO:7. In some embodiments, said signal peptide comprises the amino acid sequence of SEQ ID NO:22 and said mature protein comprises the amino acid sequence of SEQ ID NO:9. In some embodiments, said signal peptide comprises the amino acid sequence of SEQ ID NO:22 and said mature protein comprises the amino acid sequence of SEQ ID NO:23. In some embodiments, said signal peptide comprises the amino acid sequence of SEQ ID NO:22 and said mature protein comprises the amino acid sequence of SEQ ID NO:25. In some embodiments, said signal peptide comprises the amino acid sequence of SEQ ID NO:22 and said mature protein comprises the amino acid sequence of SEQ ID NO:27.

In some embodiments, the invention provides the nucleic acid as described herein, wherein said mature protein comprises the amino acid sequence of SEQ ID NO:3.

In some embodiments, the invention provides the nucleic acid as described herein, wherein said mature protein comprises the amino acid sequence of SEQ ID NO:5.

In some embodiments, the invention provides the nucleic acid as described herein, wherein said mature protein comprises the amino acid sequence of SEQ ID NO:7.

In some embodiments, the invention provides the nucleic acid as described herein, wherein said mature protein comprises the amino acid sequence of SEQ ID NO:9.

In some embodiments, the invention provides the nucleic acid as described herein, wherein said mature protein comprises the amino acid sequence of SEQ ID NO:23.

In some embodiments, the invention provides the nucleic acid as described herein, wherein said mature protein comprises the amino acid sequence of SEQ ID NO:25.

In some embodiments, the invention provides the nucleic acid as described herein, wherein said mature protein comprises the amino acid sequence of SEQ ID NO:27.

In some embodiments, the invention provides a nucleic acid comprising the nucleic acid sequence of SEQ ID NO:14.

In some embodiments, the invention provides a nucleic acid comprising the nucleic acid sequence of SEQ ID NO:16.

In some embodiments, the invention provides a nucleic acid comprising the nucleic acid sequence of SEQ ID NO:18.

In some embodiments, the invention provides a nucleic acid comprising the nucleic acid sequence of SEQ ID NO:20.

In some embodiments, the invention provides a nucleic acid comprising the nucleic acid sequence of SEQ ID NO:30.

In some embodiments, the invention provides a nucleic acid comprising the nucleic acid sequence of SEQ ID NO:32.

In some embodiments, the invention provides a nucleic acid comprising the nucleic acid sequence of SEQ ID NO:34.

In some embodiments, the invention provides a nucleic acid encoding a preprotein comprising a signal peptide and a mature protein, wherein the preprotein comprises the amino acid sequence selected from the group consisting of SEQ ID NO:13, SEQ ID NO:15, SEQ ID NO:17, SEQ ID NO:19, SEQ ID NO:29, SEQ ID NO:31 and SEQ ID NO:33.

In some embodiments, the invention provides a nucleic acid encoding a preprotein comprising a signal peptide and a mature protein, wherein the preprotein comprises amino acid modifications corresponding to T-18S/F-5L/T-4A/V-3A/A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/I123M/D132N/T135S/P136S/E144A/R145Q/S153D/D160A/A161P/Y167Q/L174Q/N180T/E184Q/R185Q/S190A/L192I/T196S/G204S/N205S/Y206F of SEQ ID NO:11.

In some embodiments, the invention provides a nucleic acid encoding a preprotein comprising a signal peptide and a mature protein, wherein the preprotein is operably linked to an exogenous promoter. In some embodiments, the mature protein comprises SEQ ID NO:1. In some embodiments, the mature protein has the amino acid sequence of any of the variant endoglucanases as disclosed herein. In some embodiments, the exogenous construct sequence is an exogenous promoter.

In some embodiments, the invention provides the nucleic acid as described herein, wherein the signal peptide comprises the amino acid sequence of SEQ ID NO:21 or any of the variant signal peptides as disclosed herein. In some embodiments, the invention provides the nucleic acid as described herein, wherein the signal peptide comprises the amino acid sequence of SEQ ID NO:22.

In some embodiments, the invention provides the nucleic acid as described herein, wherein the signal peptide is exogenous.

2. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention can be inserted into a host cell to increase production of a variant, including the use of multiple genes encoding the variant endoglucanase in a vector, multiple vectors transformed into a cell, or multiple integrations of a vector into the genome. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

In some embodiments, the invention provides an expression vector comprising the nucleic acid as described herein.

In some embodiments, the invention provides an expression vector comprising the nucleic acid construct as described herein.

C. Particular Constructs

For expression in fungus, one embodiment utilizes *Aspergillus niger* strain as disclosed in Example 1.

1. Codon Optimization

Codon optimization can be employed with any of the variant endoglucanase enzymes of the present invention, in order to optimize expression in the host cell employed. Such methods are well known in the art and described in, for example, WO 2007/142954. In heterologous expression systems, optimization steps can improve the ability of the host to produce the desired variant endoglucanase enzymes. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can affect heterologous protein expression. By modifying restriction sites that could interfere with subsequent sub-cloning of transcription units into host expression vectors a polynucleotide sequence can be optimized.

In some embodiments, the optimized nucleic acid sequence can express the variant endoglucanase enzyme of the invention, at a level which is at least 110%, 150%, 200%, 500%, 1,000%, 5,000% or even 10,000% of that expressed by nucleic acid sequence that has not been optimized.

D. Host Cells and Production Strains

As will be appreciated by those in the art, there are a wide variety of production host organisms for the recombinant production of the variant endoglucanase enzymes of the invention, including, but not limited to bacterial cells and fungal cells including yeast.

The present invention also relates to recombinant host cells, comprising a polynucleotide encoding a variant endoglucanase of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The choice of a host cell will to a large extent depend upon the gene encoding the variant and the ability of the host production organism to yield high protein titers of expressed and/or secreted proteins. In some embodiments, the host cell exhibits transitory expression of the variant endoglucanase. In some embodiments, the host cell is a stably transfected host or a host cell that stably (i.e., permanently) expresses the variant endoglucanase. In some embodiments, the host cell is a production host cell. The transformation and/or transfection of the host cells with the expression vectors comprising the coding region for the variant endoglucanases of the invention is done as is well known in the art (See Sambrook, id.).

The host cell can be any cell useful in the recombinant production of a variant, e.g., a prokaryote or a eukaryote. Such host cells include but are not limited to bacterial, fungal, and yeast cells. The host cell can also be a eukaryote, such as a mammalian, insect, plant, or fungal cell.

The host cell can be a fungal cell. "Fungi" as used herein includes the phyla *Ascomycota, Basidiomycota, Chytridiomycota*, and *Zygomycota* as well as the *Oomycota* and all mitosporic fungi (as defined by Hawksworth et al., In, Ainsworth and Bisby's Dictionary of The Fungi, 8th edition, 1995, CAB International, University Press, Cambridge, UK). In many cases, host cells include *Aspergillus* species including *A. nidulans, A. niger* and *A. oryzae*, as well as *Rhizomucor* species such as *R. miehei, Trichoderma* species including *T. reesei* and *Fusarium* species genes including *F. venenatum*. The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In some embodiments, the fungal host cell can be a yeast cell. "Yeast" as used herein includes ascosporogenous yeast (*Endomycetales*), basidiosporogenous yeast, and yeast belonging to the *Fungi Imperfecti* (*Blastomycetes*). The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

In some embodiments, the invention provides a host cell comprising the nucleic acid as described herein.

In some embodiments, the invention provides a host cell comprising the nucleic acid construct as described herein.

In some embodiments, the invention provides a host cell comprising the expression vector as described herein.

In some embodiments, the invention provides the host cell as described herein, wherein said host cell is selected from the group consisting of a bacterial cell, a fungal cell, and a yeast cell.

E. Protein Compositions

The present invention also provides compositions comprising a variant endoglucanase enzyme of the present invention. In some embodiments, the composition comprises a carrier and/or an excipient. In some embodiments, the compositions are enriched in such a variant endoglucanase enzyme of the present invention. The term "enriched" indicates that the endoglucanase activity of the composition has been increased, e.g., with an enrichment factor of at least 1. In some embodiments, the compositions are formulated to provide desirable characteristics such as low color, low odor and acceptable storage stability.

In some embodiments, the composition comprises a variant endoglucanase enzyme of the present invention as the major enzymatic component, e.g., a mono-component composition.

In some embodiments, the composition may comprise one or more additional enzymes, depending on the end use, including, but not limited to, aminopeptidase, alpha-amylase, beta-amylase, isoamylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, polyphenoloxidase, pullulanase, proteolytic enzyme, ribonuclease, transglutaminase, and/or xylanase.

In some embodiments, the composition comprises the (variant) endoglucanase enzyme of the invention, and further comprises other cellulases such as acid and/or neutral cellulases. In some embodiments, the composition comprises the (variant) endoglucanase enzyme of the invention, and further comprises acid, neutral and/or alkaline proteases. In another embodiment, the composition comprises the variant endoglucanase according to the invention and a cocktail of enzymes including alpha-amylase, proteases, peptidase, lipase, cellulose, pancreatin, and others.

In some embodiments, the composition comprises the (variant) endoglucanase enzyme of the invention, and further comprises other macromolecules that are not necessarily all produced from the same host (for example, other enzymes such as endoglucanases, amylases, lipases, proteases, pectinases and/or oxidases, such as laccases and peroxidases) or chemicals that may enhance the performance, stability, or buffering of the desired enzyme composition.

In some embodiments, the composition comprising the (variant) endoglucanase enzyme of the invention further comprises a surfactant which can be anionic, non-ionic, cationic, amphoteric or a mixture of these types, especially when used as a detergent composition. Useful detergent compositions are described e.g. in WO94/07998, U.S. Pat. Nos. 5,443,750 and 3,664,961, which are all incorporated by reference in their entireties.

In some embodiments, a desired enzyme may be further purified in accordance with conventional conditions, such as extraction, precipitation, chromatography, affinity chromatography, electrophoresis, or the like.

F. Formulations of Variant Endoglucanases

In some embodiments, the compositions can be prepared in accordance with methods known in the art and can be in the form of a liquid or a dry composition. For instance, the composition may be in the form of granulate or microgranulate. In some embodiments, the non-dusting granules may be coated. The (variant) endoglucanases of the invention can be stabilized in accordance with methods known in the art, for example, liquid enzyme compositions can be stabilized by adding a polyol such as propylene glycol, a sugar or sugar alcohol, lactic acid or boric acid, or sodium chloride, according to established methods. (see U.S. Pat. No. 7,256,032 incorporated by reference in its entirety). Protected forms of the enzyme composition may be prepared as described in EP 238,216, incorporated by reference in its entirety.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

G. Methods of Production

The present invention also relates to methods of making a variant endoglucanase enzyme comprising: a) culturing the host cell as described herein under conditions wherein said variant endoglucanase enzyme is expressed; and b) optionally recovering said variant endoglucanase enzyme.

The host cells are cultivated in a nutrient medium suitable for production of the variant endoglucanase polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant endoglucanase polypeptide is secreted into the nutrient medium, the variant endoglucanase polypeptide can be recovered directly from the medium. If the variant is not secreted, it can be recovered from cell lysates.

The variant endoglucanase polypeptide can be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant endoglucanase polypeptide.

The variant endoglucanase polypeptide can be recovered using methods known in the art. For example, the variant endoglucanase polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

H. Methods of Using Variant Endoglucanases

The endoglucanases of the present invention possess valuable properties allowing for a variety of industrial applications, such as, in textile, detergent, and pulp and paper industries. The novel (variant) endoglucanase enzymes of the invention have the advantage of being active at acid and neutral pH values, they have highly improved performance in textile biostoning and biofinishing applications and in detergent and other applications.

With the improved efficiency of the endoglucanases of the invention, the use of the enzymes is significantly more economical. Additional advantages are achieved also in terms of logistics and the storage of the enzyme products, when smaller amounts of the enzyme product are needed. Furthermore, the novel endoglucanases of the present invention, act more rapidly, affording time- and cost-effective treatment procedures and savings in equipment as well as treatment facilities.

In some embodiments, the dosage of the polypeptide composition of the invention and other conditions under which the composition is used may be determined on the basis of methods known in the art.

1. In Textile Industry

The (variant) endoglucanases of the invention have a wide range of textile applications. For example, fabrics or garments manufactured from denim, such as jeans, are one of the world's most popular clothing items. The "stonewash look" has been traditionally achieved by locally removing the indigo dye using a process in which pumice stone is added to the washing drum to abrade the garment. This traditional 'stone-washed' finish on denim fabric virtually damaged the machinery and caused pollution in waste water. The new environmental-friendly process, termed as biostoning, uses enzymes to wash/bio-stone denim, producing distressed appearance, without harming the machinery or the environment. The bio-stoning of denims has resulted in cost saving and improved quality and is used by many denim manufacturers (see Agrawal et al., Current Trends in Biomedical Engineering & Biosciences. 2017. 3(3):1-3, hereby incorporated by reference in its entirety).

The (variant) endoglucanases of the invention exhibit high efficiency in producing a "stonewash look" or an "abraded look" and to minimize backstaining in biostoning treatment of cellulose-containing textile materials, especially denim. In some embodiments, the present invention provides a method of biostoning comprising the step of contacting the (variant) endoglucanase enzyme(s) as described herein with cotton-containing fabrics or garments. In some embodiments, the cotton-containing fabrics as described herein are denim.

In cotton fabric, fuzz (microfibers) emerges from the surface, which may entangle during processing, thus forming pills. Enzymes weaken the microfibers raising up from the surface and shear forces of the treatment then remove them (U.S. Pat. No. 7,256,032, hereby incorporated by reference in its entirety). The (variant) endoglucanases of the invention are especially useful in the textile industry for biofinishing of fabrics or garments, e.g., depilling, defuzzing, color clarification, harshness reduction, creation of different finishes (for example, a peach skin, worn out, sand washed, or antique look effect) and for biofinishing of yarn, for example, reduction of hairiness and improvement of smoothness and/or softness.

In some embodiments, the (variant) endoglucanases of the invention exhibit high efficiency in a biofinishing process to depill, defuzz or reduce harshness in a textile material. In some embodiments, the present invention provides a method of biofinishing comprising the step of contacting the (variant) endoglucanase enzyme (s) as described herein with a textile material. In some embodiments, the textile material as described herein is selected from the group consisting of fabrics, garments, and yarn.

2. In Detergent Industry

Additional uses of the (variant) endoglucanases of the invention include their use in detergent compositions to improve fabric care properties by antipilling, antigraying, color clarification and softening, and to improve textile-cleaning effect, for instance soil removal. In some embodiments, the (variant) endoglucanases of the invention can be used to brighten colors and to prevent graying and pilling in detergent industry.

In some embodiments, the present invention provides a detergent composition comprising the (variant) endoglucanase enzymes as described herein. In additional embodiments, the present invention provides a detergent composition comprising the (variant) endoglucanase enzymes as described herein, and further comprising at least one surface active agent and optionally at least one auxiliary ingredient. Surface active agents include but not limited to anionic, non-ionic, cationic and ampholytic surfactants. Other auxiliary ingredients include but not limited to builders, antiredeposition and soil suspension agents, optical brighteners, bleaching agents, dyes and pigments and hydrolases. A suitable listing of the contents of detergents is given in U.S. Pat. No. 5,433,750, hereby incorporated by reference in its entirety. A suitable list of surfactants is given in U.S. Pat. No. 3,664,961, hereby incorporated by reference in its entirety. Useful detergent compositions are described e.g. in WO94/07998, U.S. Pat. Nos. 5,443,750 and 3,664,961, which are all incorporated by reference in their entireties.

In some embodiments, the present invention provides a method of treating cellulosic fiber containing textile material(s) comprising contacting said textile material(s) with the detergent composition comprising the variant endoglucanase enzymes as described herein or the wild-type endoglucanase enzyme as set forth in SEQ ID NO:1.

3. In Pulp and Paper Industries

In the pulp and paper industry, the (variant) endoglucanases of the invention can be used, for example, in deinking or modifying fiber of different recycled papers and paperboards having neutral or alkaline pH, in improving the fiber quality, or increasing the drainage in paper manufacture. Other examples of uses of the (variant) endoglucanases as described herein include the removal of printing paste thickener and excess dye after textile printing, and as a treatment for animal feed. For example, if the intended application is improvement of the strength of the mechanical pulp, then the (variant) endoglucanase enzymes of the invention may provide one or more of these proteins so as to enhance or facilitate the ability of cellulose fibers to bind together. In a similar manner, in the application of pulp refining, the (variant) endoglucanases of the invention may provide one or more of these proteins at a level that enhance or facilitate such swelling.

In some embodiments, the (variant) endoglucanase enzymes of the invention are used in deinking to release ink from fiber surfaces and in improving pulp drainage in the pulp and paper industry.

In some embodiments, the present invention provides a method for treating wood-derived pulp or fiber, comprising the step of contacting the (variant) endoglucanase enzymes as described herein with wood-derived mechanical or chemical pulp or secondary fiber.

VI. EXAMPLES

Example 1

Wild-Type Gene Selection, Synthesis, Cloning and Integration

Multiple wild-type endoglucanases from different sources were selected from UniProt knowledgebase (see, the World Wide Web at uniprot.org) based on sequence and structure analysis.

All the genes encoding wild-type endoglucanases were synthesized by GeneWiz (see, the World Wide Web at genewiz.com). The synthesized genes were integrated into a proprietary fungus expression plasmid. Part of the expression plasmid was amplified by PCR and then integrated into a proprietary *Aspergillus niger* strain.

Example 2

Preparation of Wild-Type Endoglucanases Produced by *Aspergillus Niger* in 2 L Fermentor The *Aspergillus niger* strains from Example 1 containing recombinant endogluconase-encoding genes were evaluated in 2 L fermentors. To prepare flask seed culture, ~20 colonies of each strain from agar plates were inoculated into 1000 mL baffled flasks containing 200 mL of proprietary flask medium as primary flask seed culture. After shaking at 32° C., 200 rpm for 4 days, 20% (v/v) of primary seed culture was inoculated into 1000 mL baffled flasks containing 200 mL of proprietary flask medium and shaked at 32° C., 200 rpm for 2 days as secondary flask seed culture for 2 L fermentor inoculation.

For 2 L fermentor evaluation, 150 mL of secondary flask seed culture was inoculated into 850 mL of proprietary fermentation medium. The following fermentation conditions were used: the agitation, aeration rate and temperature were set at 1200 rpm, 2 vvm and 33° C., respectively; The pH was controlled at 4.7 by automatically adding 14% Ammonium hydride; The residual sugar concentration during fermentation was maintained between 5 and 25 g/L by continuously feeding proprietary ingredients. The fermentation broth supernatant was collected at ~200 hr's fermentation time and stored at −20° C. for activity assay.

Example 3

CMC Assay to Evaluate the Activity of *Aspergillus Niger* Produced Wild-Type Endoglucanases 1.8 mL of 1.5% low viscosity CMC dissolved in 100 mM sodium phosphate, pH 6.5 buffer (Catalog #C5678) was added into a glass test tube. 500 µL of diluted enzyme supernatant from Example 2 was added into a 1.5 mL Eppendorf tube. Both Eppendorf tube and glass test tube containing CMC were pre-heated in 50° C. water bath for 5 minutes. Once 5 mintues was reached, 200 µL of diluted enzyme was transferred from Eppendorf tube to glass test tube with CMC and mixed for 2-3 seconds. The glass test tube was quickly placed in 50° C. water bath and the timer was started for 15 minutes. Once 15 minutes was up, 3 mL of DNS solution was transferred into the glass test tube and the glass test tube was placed in boiling water bath for 5 minutes. After 5 minutes, the glass test tube was transferred to room temperature water bath and 5 mL of MilliQ water was added to the glass test tube. After mixing, 1 mL of reaction solution was transferred from the glass test tube to a cuvette and absorbance at 540 nm was read for activity.

The activity comparison for 8 wild-type endoglucanases (EG) is shown in FIG. 1. Relative CMC activity is calculated as the CMC activity of an EG candidate divided by the CMC activity of EG-Candidate 1 which showed the lowest CMC activity. Endoglucanases from *Chaetomium thermophilum* (Ct.EG) with UniProt knowledgebase accession number G0S9D9 showed the highest activity and potential. Wild-type Ct.EG was therefore chosen as G1P for further activity improvement.

Example 4

Ct.EG Variant Design, Synthesis, Cloning and Integration

To improve the activity of Ct.EG, multiple Ct.EG variants were designed based on sequence and structure analysis. All the genes encoding Ct.EG variants were synthesized, cloned and integrated into a proprietary *Aspergillus niger* strain following the same procedure as shown in Example 1.

Example 5

Preparation of Ct.EG Variants Produced by *Aspergillus Niger* in Microtiter Plates The *Aspergillus niger* strains from Example 4 containing recombinant endogluconase-encoding genes from single colonies were inoculated into individual wells of 24 well plates containing 2000 µl of Potato Dextrose Broth with 1.5% Yeast Extract and additional 20 g/L of glucose. The cultures were grown at 30° C., 200 rpm and 85% humidity for 72 hr. Supernatant were collected at 72 hr and stored at −20° C.

Example 6

CMC Assay to Evaluate the Activity of *Aspergillus Niger* Produced Ct.EG Variants CMC activity of Ct.EG wild-type (G1P) and variants from Example 5 were evaluated using the same procedure as shown in Example 3. The activity improvement results for the best variants are shown in FIG. 2. PF (Performance Factor) is calculated as the CMC activity of a variant divided by the CMC activity of G1P.

Example 7

Preparation of Ct.EG Variants Produced by *Aspergillus Niger* in 2 L Fermentor The *Aspergillus niger* strains from Example 4 containing recombinant endogluconase-encoding genes were fermented in 2 L fermentors. The preparation of flask seed culture and fermentation conditions followed the same procedure as shown in Example 2. The fermentation broth supernatant was collected at ~200 hr's fermentation time and stored at 4° C. for biostoning test.

Example 8

Bio-Stoning of Ct.EG Wild-Type and Variants Produced by *Aspergillus Niger* in 2 L Fermentor The *Aspergillus niger* strains from Example 2 and Example 7 were evaluated for bio stoning efficiency as follows. Jean legs in size of 9 inches by 7.5 inches were de-sized by placing in industrial size washing machine manufactured by Foshan Yanuo Precision Machinery Manufacturing Co., Ltd, China (model number GX-350Z). Along with Jean legs, 20 L of water, 15 g of high-concentration anti-dyeing oil and 15 g of anti-dyeing powder were added. Temperature was set to 60° C. and rotation was set at 50 rpm for 15 minutes. Once 15 minutes of rotation was completed, the water was drained, 18 L of water was added, rotation was continued for 2 minutes, and this step was repeated for 2 times. Once finished, Jean legs were rinsed over running water and dried in oven at 60° C. For subsequent bio stoning, 2 desized jean legs were added to washing machine with 18 L of water and pH was adjust to pH 6.5. Once temperature reached to 50° C., normalized enzyme amount was added. Bio stoning was performed for 50 minutes with 50 rpm of rotation. Once finished, water was drained, and 18 L of water was added, rotation was continued for 2 minutes, and this step was repeated for 2 times. Next, jean legs were rinsed over running water and dried in oven at 60° C. Once dried, bio stoning efficiency was compared by visually inspecting blue and white contrast on bio stoned jean materials. The enzymes samples produced better bio stoning effect has more +, as shown in FIG. 3. One of the best variants, G1V2, was selected as G2P and targeted for further improvement by directed evolution in *Saccharomyces cerevisiae.*

Example 9

Design and Construction of Ct.EG G2 Collections in *Saccharomyces Cerevisiae*

To further improve the activity of G2P (G1V2), multiple variant collections were designed based on sequence and structure analysis. The design includes one to multiple specific mutations per variant. The variant collections were subsequently constructed using standard site-directed mutagenesis methods and subsequently cloned into the pESC-URA vector (Agilent Technologies: catalogue #217454).

Example 10

Preparation of Ct.EG G2P and G2 Variants Produced by *Saccharomyces Cerevisiae* in HTP The Recombinant Ct.EG-encoding genes from single colonies of the *Saccharomyces cerevisiae* INVSc1 strain (ThermoFisher Scientific, USA: Catalogue #V8251-20) were inoculated into 350 μL Synthetic Minimal Medium with 2% Glucose and no uracil supplementation in 96-well plates. Following inoculation, the plates were incubated overnight at 30° C., in 85% humidity while shaking at 200 rpm. The $OD_{600}$ of the overnight cultures was determined and all cultures were diluted to a final $OD_{600}$ of 0.4 into fresh 96-well plates containing SC selective medium supplemented with 2% galactose and 1% raffinose in a total volume of 300 μL. The induction plates were incubated at 30° C., in 85% humidity while shaking at 200 rpm for 72 h upon which the plates cells were pelleted by centrifugation at 4000 rpm for 15 minutes while chilled to 4° C. The supernatant was transferred to fresh 96-well plates, covered, and stored at −20° C. until further use.

Example 11

Enzymatic Assay to Determine the pH 6.5 Activity at 50° C. of *Saccharomyces Cerevisiae* Produced Ct.EG G2P and G2 Variants in HTP Plates containing G2P and/or G2 variants of Ct.EG produced according to Example 10 were thawed. The supernatant was diluted two-fold into 0.1 M Sodium phosphate buffer (pH 6.5). A 1.6% CMC solution was prepared by dissolving 1.60 g of CMC (Sodium salt, Sigma) in 80 mL of pH 6.5, 0.1 M sodium phosphate buffer, followed by stirring until the CMC was fully dissolved. The volume was adjusted to 100 mL with pH 6.5, 0.1 M sodium phosphate buffer.

The 1.6% CMC solution was added to 96-well round-bottom plates (100 μL/well). The reaction was initiated by addition of 20 μL of the diluted enzyme. The plates were then sealed, incubated at 50° C. shaking at 650 rpm for 3 hours. Following incubation, the reaction solution was transferred (60 μL) to a 96-well PCR plate and quenched by addition of 90 μL DNS (dinitrosalicylic acid) reagent.

The plates after DNS reagent addition were sealed, centrifuged for 30 s at 1000 rpm, heated to 95° C. for 5 min using a thermocycler, cooled to 4° C. for 2 min, mixed by inverting 5-6 times, and then centrifuged for 30 s at 1000 rpm. The assay plates were unsealed and 100 μL from each well was transferred to new clear-bottom plates containing 100 μL water and thoroughly mixed. The absorbance of each well was measured at 540 nm and absorbance values indicated enzyme activity in each well. G2 variants with improved enzyme activity compared to G2P were identified as shown in FIGS. 4 and 5. PF (Performance Factor) is calculated as the CMC activity of a variant divided by the CMC activity of G2P.

Example 12

Ct.EG G2 Variant Cloning and Integration into an *Aspergillus Niger* Strain and Production of Variants in 2 L Fermentor To test the Gt.EG G2 variant (G2V3) identified from Examples 9-11 and rationally designed variants G2V1, and G2V2 identified from Examples 4-11, the genes encoding these variants were cloned and integrated into a proprietary fungus expression plasmid. Part of the expression plasmid was amplified by PCR and then integrated into a proprietary *Aspergillus niger* strain.

These *Aspergillus niger* strains from containing recombinant endogluconase-encoding (Ct.EG G2P and G2 variants) genes were fermented in 2 L fermentors. The preparation of flask seed culture and fermentation conditions followed the same procedure as shown in Example 2. The fermentation broth supernatant was collected at ~200 hr's fermentation time and stored at 4° C. for further testing.

Example 13

Bio-Stoning of Ct.EG G2P and G2 Variants Produced by *Aspergillus Niger* in 2 L Fermentor The *Aspergillus niger* strains from Example 12 were evaluated for bio stoning efficiency as outlined in Example 8. The results of each sample's biostoning effect was visually inspected and the outcome is displayed in FIG. 6. The results suggest G2P and G2V3 have the best bio-stoning activity, followed by G2V1 and G2V2.

Example 14

Alkaline Detergent Depilling Activity of Ct.EG G2P and G2 Variants Produced by *Aspergillus Niger* in 2 L Fermentor The *Aspergillus niger* strains producing Ct.EG G2P or enzyme variants were tested for their effectiveness in depilling pre-pilled test fabric under alkaline detergent conditions. A laundry testing instrument (RHLQ-III Vertical Decontimination Machine, China Daily Use Chemical Industry Academy) with six sample compartments was used to test the depilling activity of the strains. For each condition, 1 g of deactivated detergent (Libai Group, deactivated at 150° C. for 4 h), and 1 mg of commercial protease was added to 500 mL of hard water (1.5 mmol calcium chloride, 1 mmol magnesium sulfate) in a container of the laundry machine resulting in a solution with a pH of between pH 10 to pH 11. This solution was heated to 40° C. with stirring. Once the desired temperature was reached either a high dose or low dose of of EG enzyme (normalized by CMC activity, U calculated by CMC activity at pH 6.5, 50° C.), and a 2.5 g strip of pre-pilled test fabric (Swissatest, item #253) was added to the container and stirred using the laundry instrument for 30 min. After completion the fabric pieces were collected and rinsed with tap water three times. The fabric pieces were then dried overnight at 55° C. After the fabric dried, all pieces were compared to each other visually based on the amount of pilling present and the overall brightness of colors. The results are summarized in FIG. 7. The results suggest G2V3 maintains comparable alkaline depilling activity as G2P at a low dose, while G2V1 and G2V2 outperform G2P at the higher dosing, while maintaining similar performance at lower dosing.

Example 15

Alkaline Detergent Destaining Activity of Ct.EG G2P and G2 Variants Produced by *Aspergillus Niger* in 2 L Fermentor Four 6×6 cm fabric sheets that are pre-stained from three stain types: (National Standardization Center for Surfactant Detergents) carbon black, sebum, and protein stains (12 sheets total/condition), are prepared. The sheets are numbered with an oil-based marker, cut into the desired size and each sheet's whiteness is measured with a whiteness meter (YQ-Z-48A, CNBM Intelligent Automation Research Institute Co, Ltd.). To measure each sheet 4 total readings per sheet were recorded, 2 from the each side of the fabric.

For each condition, 2 g of deactivated detergent (Libai Group, deactivated at 150° C. for 4 h), and 2 mg of commercial protease was added to 1 L of hard water (1.5 mmol calcium chloride, 1 mmol magnesium sulfate) in a container of the laundry machine, resulting in a solution with a pH of between pH 10 to pH 11 (RHLQ-III Vertical Decontimination Machine, China Daily Use Chemical Industry Academy). This solution was heated to 30° C. with stirring. Once the desired temperature was reached 1 μL of the fermentation supernatant being tested, and the 12 the sheets of fabric (4 from each stain type) were added to the container and stirred at 30° C. for 20 min. Once complete the fabric pieces were removed and rinsed twice with tap water. The fabric was then hung and dried overnight at room temperature.

Once dry, the fabric pieces were measured for whiteness as described above for the pre-washing measurement. The whiteness differences from before and after were calculated for each sheet and averaged over each stain type and further compared to the control where no EG was added. See FIG. 8 for relative performance of Ct.EG G2P and G2 variants. The results suggest G2V1 maintains comparable alkaline decontamination activity as G2P with sebum and carbon black stains. G2V2 maintains similar decontamination activity as G2P with the carbon black stain, and G2V3 maintains similar activity as G2P when tested with the protein stain.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

What is claimed:

1. A composition comprising a variant endoglucanase enzyme comprising one or more amino acid modifications as compared to SEQ ID NO:1, wherein said one or more amino acid modifications occur at positions corresponding to positions selected from the group consisting of positions 2, 17, 23, 25, 29, 33, 36, 38, 39, 42, 43, 44, 48, 51, 54, 66, 67, 68, 75, 77, 80, 82, 90, 102, 116, 121, 122, 123, 132, 135, 136, 141, 144, 145, 153, 160, 161, 164, 167, 174, 180, 184, 185, 190, 192, 194, 195, 196, 204, 205, 206, 215, 216, 217, 218, 219, 220, 221, 222, 223, 228, 229, 230, 231, 232, 233, 234, 235, 237, 238, 239, 241, 242, 243, 244, 245, 246, 247, 248, 249, 250, 251, 258, 259, 267, 268, 269, 270, 271, 273, 274, 275, 276, 277, 278, 279, 280, 281, 282, 283, 284, 285, 286, 287, 288, 289, 290, 291, 292, and 293, wherein said variant endoglucanase enzyme exhibits at least 80% sequence identity to SEQ ID NO:1; wherein said variant endoglucanase enzyme has endoglucanase activity; and wherein said variant endoglucanase enzyme comprises said amino acid modification(s) selected from the group consisting of D215*, A23D/I38L/Y39S/G42N/A43E/K44E/E48N/S54T/A77Q/N116D/N122S/L141S/L281G, A23D/I38L/Y39S/G42N/A43E/K44Q/E48N/S54T/N116E/W258S/A259D/G275E/T277D, A23D/I38L/Y39S/G42N/A43S/K44E/E48N/A77E/N116S/N122A/N180T/W258S/A259D/G275E/T277D/I29 1S/L293T, A23D/I38L/Y39S/G42N/A43S/K44E/E48N/S54T/A77E/N122S/P164T/N180T/A259D/S286A/L293T, A23D/I38L/Y39S/G42N/A43S/K44Q/E48N/A77Q/N116E/L141S/G275E/T277D/W284R, A23D/I38L/Y39S/G42N/A43S/K44Q/E48N/S54T/N116D/W258S/G275T/L281E/1291Q, A23D/I38L/Y39S/G42N/A43S/K44Q/E48N/V102Q/W258S/L281E/N282S/I291A, A23D/I38L/Y39S/G42N/A43S/K44Q/E48N/V102R/W258R/A259D/L281E/N282S, A23D/I38L/Y39S/G42N/A43T/K44E/E48N/P164T/N180T/A194T/W258S/A259D/G275T/L281G, A23D/I38L/Y39S/G42N/A43T/K44E/E48N/V102Q/N116D/L281G/N282S, A23D/I38L/Y39S/G42N/A43T/K44Q/E48N/A77E/V102Q/N116D/W258S/G275T/L281E/1291A, A23D/I38L/Y39S/G42N/A43T/K44Q/E48N/A77Q/N180T/W258S/G275E/1291Q, A23D/I38L/Y39S/G42N/A43V/K44E/E48N/A77E/N116D/G275T/L281E, A23D/I38L/Y39S/G42N/A43V/K44E/E48N/N122A/N180T/T277D/L281E/N282S, A23D/I38L/Y39S/G42N/A43V/K44Q/E48N, A23D/I38L/Y39S/G42N/A43V/K44Q/E48N/A161K/P164T/N180T, A23D/ILK/Y39S/G42N/A43V/K44Q/E48N/A77E/A161K/P164T/N180T, A23D/I38L/Y39S/G42N/A43V/K44Q/E48N/A77E/N116D/W258S/L281E, A23D/I38L/Y39S/G42N/A43V/K44Q/E48N/A77Q/N116S/N180T/G275E/T277E, A23D/I38L/Y39S/G42N/A43V/K44Q/E48N/A77Q/N180T, A23D/I38L/Y39S/G42N/A43V/K44Q/E48N/F67Y/A77Q/N116S/N180T/W258S/A259D/G275T/T277E/L28 1K/N282S/1291S/L293N, A23D/I38L/Y39S/G42N/A43V/K44Q/E48N/F67Y/A77Q/N122S/L141S/N180T/A194T/W258R/L281K, A23D/I38L/Y39S/G42N/A43V/K44Q/E48N/F67Y/N180T, A23D/I38L/Y39S/G42N/A43V/K44Q/E48N/L141S, A23D/I38L/Y39S/G42N/A43V/K44Q/E48N/N116D/G275T/L281E/N282S/1291A, A23D/I38L/Y39S/G42N/A43V/K44Q/E48N/N116D/L281K/N282S/1291S/N292S/L293N, A23D/I38L/Y39S/G42N/A43V/K44Q/E48N/N116D/W258S/L281G, A23D/I38L/Y39S/G42N/A43V/K44Q/E48N/N180T, A23D/I38L/Y39S/G42N/A43V/K44Q/E48N/N180T/A259D/G275T/N282S, A23D/I38L/Y39S/G42N/A43V/K44Q/E48N/Q66T/A77Q/N122A/L141S/G275T/W284G/S286A, A23D/I38L/Y39S/G42N/A43V/K44Q/E48N/S54T/A77E/A161P/W258S/W284M/1291Q, A23D/I38L/Y39S/G42N/A43V/K44Q/E48N/S54T/A77E/T277E/L281E/S286A, A23D/I38L/Y39S/G42N/A43V/K44Q/E48N/S54T/A77E/V102Q/G275T/T277D/W284M/1291Q, A23D/I38L/Y39S/G42N/A43V/K44Q/E48N/S54T/A77E/W258S/T277D/W284M/1291A, A23D/I38L/Y39S/G42N/A43V/K44Q/E48N/S54T/1291A, A23D/I38L/Y39S/G42N/A43V/K44Q/E48N/S54T/L281E, A23D/I38L/Y39S/G42N/A43V/K44Q/E48N/S54T/N116D/A161P/L281E/N282S, A23D/I38L/Y39S/G42N/A43V/K44Q/E48N/S54T/N116D/A161P/W258S/G275T/L281E/1291A, A23D/I38L/Y39S/G42N/A43V/K44Q/E48N/S54T/N116D/A161P/W258S/W284M/1291A, A23D/I38L/Y39S/G42N/A43V/K44Q/E48N/S54T/N116D/D215G/S216N/P217G/S218G/S219T/S220G/S22 1-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/1291-/N292-, A23D/I38L/Y39S/G42N/A43V/K44Q/E48N/S54T/N116D/L141S/A161K/N180T/W258R/A259D/G275E/T2 77D/W284R/1291Q/N292S/L293G, A23D/I38L/Y39S/G42N/A43V/K44Q/E48N/S54T/N116D/L141S/N180T/G275T/W284R/1291Q/L293N, A23D/I38L/Y39S/G42N/A43V/K44Q/E48N/S54T/N116D/W258S/G275T/N282S/1291A, A23D/I38L/Y39S/G42N/A43V/K44Q/E48N/S54T/N116D/W284M/1291Q, A23D/I38L/Y39S/G42N/A43V/K44Q/E48N/S54T/N116E/L141S/N180T/L281G/N282S, A23D/I38L/Y39S/G42N/A43V/K44Q/E48N/S54T/N116S/G275E/Y285*, A23D/I38L/Y39S/G42N/A43V/K44Q/E48N/S54T/Q66T/F67Y/N122S/N180T/L281G/1291S/N292S/L293G, A23D/I38L/Y39S/G42N/A43V/K44Q/E48N/S54T/V102Q/N116D/A161P/T277D/W284M/1291Q, A23D/I38L/Y39S/G42N/A43V/K44Q/E48N/S54T/V102Q/N116D/W258S/G275T/1291Q, A23D/I38L/Y39S/G42N/A43V/K44Q/E48N/S54T/V102Q/N116D/W258S/G275T/T277E, A23D/I38L/Y39S/G42N/A43V/K44Q/E48N/S54T/V102Q/N116D/W258S/G275T/T277E/L281G, A23D/I38L/Y39S/G42N/A43V/K44Q/E48N/S54T/V102Q/N116D/W258S/L281G/1291A, A23D/I38L/Y39S/

G42N/A43V/K44Q/E48N/S54T/V102Q/W258S/G275T/T277D/N282S, A23D/I38L/Y39S/G42N/A43V/K44Q/E48N/S54T/V102Q/W258S/W284M/S286A, A23D/I38L/Y39S/G42N/A43V/K44Q/E48N/S54T/W258S, A23D/I38L/Y39S/G42N/A43V/K44Q/E48N/V102Q/A161P/W258S, A23D/I38L/Y39S/G42N/A43V/K44Q/E48N/V102Q/W258S/1291Q, A23D/I38L/Y39S/G42N/A43V/K44Q/E48N/V102R/N180T, A23D/I38L/Y39S/G42N/A43V/K44Q/E48N/W258S/1291A, A23D/I38L/Y39S/G42N/K44Q/E48N/A77E/N116D/L281E/1291A, A23D/S25N/I38L/Y39S/G42N/A43E/K44E/E48N/V102R/N116S/N122A/L141S/A161K/P164T/A194T/W25 8R/A259D/L281E, A23D/S25N/I38L/Y39S/G42N/A43E/K44Q/E48N/Q66T/F67Y/L141S/N180T, A23D/S25N/I38L/Y39S/G42N/A43S/K44Q/E48N/S54T/Q66T/L141S/N180T/W258S/A259D/T277D/W284 G/Y285*, A23D/S25N/I38L/Y39S/G42N/A43V/K44Q/E48N/A161K/N180T, A23D/S25N/I38L/Y39S/G42N/A43V/K44Q/E48N/A161P, A23D/S25N/I38L/Y39S/G42N/A43V/K44Q/E48N/A77E, A23D/S25N/I38L/Y39S/G42N/A43V/K44Q/E48N/A77E/N180T, A23D/S25N/I38L/Y39S/G42N/A43V/K44Q/E48N/A77E/N180T/A259D/L281K/L293T, A23D/S25N/I38L/Y39S/G42N/A43V/K44Q/E48N/A77E/V102Q/N180T, A23D/S25N/I38L/Y39S/G42N/A43V/K44Q/E48N/A77Q/N180T/A194T/W258S/W284G/S286G, A23D/S25N/I38L/Y39S/G42N/A43V/K44Q/E48N/A77Q/V102Q/N180T/A194T, A23D/S25N/I38L/Y39S/G42N/A43V/K44Q/E48N/A77Q/W258S/G275T/T277D/W284M/1291S/L293T, A23D/S25N/I38L/Y39S/G42N/A43V/K44Q/E48N/F67Y/A77E/A161P/P164T/N180T, A23D/S25N/I38L/Y39S/G42N/A43V/K44Q/E48N/F67Y/N180T, A23D/S25N/I38L/Y39S/G42N/A43V/K44Q/E48N/L281E/N282S/N292S/L293G, A23D/S25N/I38L/Y39S/G42N/A43V/K44Q/E48N/N116D/A194T/W258S/A259D/G275T/W284G/S286G/L 293T, A23D/S25N/I38L/Y39S/G42N/A43V/K44Q/E48N/N116E/N122S/A194T/T277L/C278A/T279P/K280S/L281*, A23D/S25N/I38L/Y39S/G42N/A43V/K44Q/E48N/N180T, A23D/S25N/I38L/Y39S/G42N/A43V/K44Q/E48N/Q66T/F67Y/A77Q/N180T, A23D/S25N/I38L/Y39S/G42N/A43V/K44Q/E48N/Q66T/N122S/L141S/W284R/C288*, A23D/S25N/I38L/Y39S/G42N/A43V/K44Q/E48N/S54T/A77Q/N116D/L141S/W258S/A259D/G275T/L281E/N292S/L293T, A23D/S25N/I38L/Y39S/G42N/A43V/K44Q/E48N/S54T/L281E/N282S/C288A/T289Q/M290*, A23D/S25N/I38L/Y39S/G42N/A43V/K44Q/E48N/S54T/N116D/A161P/N180T/W258R/G275E/T277E/1291 S/L293G, A23D/S25N/I38L/Y39S/G42N/A43V/K44Q/E48N/S54T/N180T/L281E/N282S/C288A/T289Q/M290*, A23D/S25N/I38L/Y39S/G42N/A43V/K44Q/E48N/S54T/Q66T/F67Y/A77Q/N122S/L141S/W258R/N282S, A23D/S25N/I38L/Y39S/G42N/K44E/E48N/A161P/A194T/G275E/T277D, A23D/S25N/I38L/Y39S/G42N/K44Q/E48N/S54T/A77E/V102R/N122S/L141S/A259D/W284G/1291S/L293T, A23N/I38L/Y39S/G42N/A43E/K44E/E48N/S54T/A77E/V102Q/N116D/W258S/W284M/1291Q, A23N/I38L/Y39S/G42N/A43E/K44Q/E48N/S54T/A77E/A161P/G275T/N282S/1291Q, A23N/I38L/Y39S/G42N/A43E/K44Q/E48N/S54T/A77E/N116D/W284M/S286A/1291Q, A23N/I38L/Y39S/G42N/A43E/K44Q/E48N/S54T/V102Q/N116D/W258S/G275T/L281E/N282S/1291A, A23N/I38L/Y39S/G42N/A43L/K44Q/E48N/Q66T/F67Y/A77E/V102Q/N116D/L141S/N180T/W258R/1291S, A23N/I38L/Y39S/G42N/A43S/K44E/E48N/S54T/A77E/L141S/W258S/G275T, A23N/I38L/Y39S/G42N/A43S/K44Q/E48N/S54T/A77E/1291Q, A23N/I38L/Y39S/G42N/A43S/K44Q/E48N/S54T/A77E/N116E/N180T/W258S/W284R/S286G, A23N/I38L/Y39S/G42N/A43S/K44Q/E48N/S54T/N116D/S286A/1291A, A23N/I38L/Y39S/G42N/A43S/K44Q/E48N/S54T/Q66T/F67Y/N116D/L141S, A23N/I38L/Y39S/G42N/A43V/K44E/E48N/A77Q/N122S/L141S/N180T/W284M/S286A, A23N/I38L/Y39S/G42N/A43V/K44Q/E48N, A23N/I38L/Y39S/G42N/A43V/K44Q/E48N/A161P/G275T/L281E/N282S/1291A, A23N/I38L/Y39S/G42N/A43V/K44Q/E48N/A161P/N180T, A23N/I38L/Y39S/G42N/A43V/K44Q/E48N/A77E/N116D/R195S/W258S/T277E/N282S/1291A, A23N/I38L/Y39S/G42N/A43V/K44Q/E48N/A77E/N180T, A23N/I38L/Y39S/G42N/A43V/K44Q/E48N/A77E/N180T/A194T, A23N/I38L/Y39S/G42N/A43V/K44Q/E48N/A77E/V102Q/W284M/S286A/1291A, A23N/I38L/Y39S/G42N/A43V/K44Q/E48N/F67Y/A77Q/N116D/N180T/G275E/T277D/W284R/1291S/L293 N, A23N/I38L/Y39S/G42N/A43V/K44Q/E48N/N180T, A23N/I38L/Y39S/G42N/A43V/K44Q/E48N/S54T/A161P/G275T/L281G/1291Q, A23N/I38L/Y39S/G42N/A43V/K44Q/E48N/S54T/A77E/V102Q/A161P/W258S/W284M, A23N/I38L/Y39S/G42N/A43V/K44Q/E48N/S54T/N116D/A161P/G275T/L281E, A23N/I38L/Y39S/G42N/A43V/K44Q/E48N/S54T/N116D/A161P/P164T/G275E/L281E, A23N/I38L/Y39S/G42N/A43V/K44Q/E48N/S54T/Q66T/F67Y/A161P/W284M/1291Q, A23N/I38L/Y39S/G42N/A43V/K44Q/E48N/S54T/Q66T/N116S/A259D/W284G/1291S/L293T, A23N/I38L/Y39S/G42N/A43V/K44Q/E48N/S54T/V102Q/W258S/G275T/N282S, A23N/I38L/Y39S/G42N/A43V/K44Q/E48N/S54T/V102Q/W258S/N282S/1291A, A23N/I38L/Y39S/G42N/A43V/K44Q/E48N/S54T/V102Q/W258S/T277D/L281E, A23N/I38L/Y39S/G42N/A43V/K44Q/E48N/S54T/W258R/A259D/I291S/L293T, A23N/I38L/Y39S/G42N/A43V/K44Q/E48N/S54T/W258S/A259D/L281K/N282S, A23N/I38L/Y39S/G42N/A43V/K44Q/E48N/T277E/W284M, A23N/I38L/Y39S/G42N/A43V/K44Q/E48N/V102Q/G275T/W284M, A23N/I38L/Y39S/G42N/A43V/K44Q/E48N/V102R/N180T, A23N/I38L/Y39S/G42N/K44E/E48N/S54T/N180T/A194T/G275T/1291S/N292S/L293N, A23N/S25N/I38L/Y39S/G42N/A43E/K44Q/E48N/S54T/Q66T/N116E/N122S/A161P/A259D/L281G, A23N/S25N/I38L/Y39S/G42N/A43S/K44Q/E48N/S54T/F67Y/A77E/N122S/N180T/A259D/W284R, A23N/S25N/I38L/Y39S/G42N/A43V/K44Q/E48N, A23N/S25N/I38L/Y39S/G42N/A43V/K44Q/E48N/A77E/N180T, A23N/S25N/I38L/Y39S/G42N/A43V/K44Q/E48N/F67Y/A77E/N180T/A194T/G275T/L281G, A23N/S25N/I38L/Y39S/G42N/A43V/K44Q/E48N/N180T/A194T, A23N/S25N/I38L/Y39S/G42N/A43V/K44Q/E48N/S54T/F67Y/N122S/L141S/A161P/P164T/A194T/G275T, A23N/S25N/I38L/Y39S/G42N/A43V/K44Q/E48N/S54T/N116D/L141S/A161K/N180T/A194T/W258S/A25 9D/W284R/1291Q/N292S, D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/1291-/N292-,

D2E/I38L/Y39S/G42N/A43V/K44Q/E48N, D2F/I38L/Y39S/G42N/A43V/K44Q/E48N, D2N/A23D/I38L/Y39S/G42N/A43V/K44Q/E48N/S54T/V102Q/A161P/W258S/T277D/W284M/1291A, D2Q/I38L/Y39S/G42N/A43V/K44Q/E48N, D2S/I38L/Y39S/G42N/A43V/K44Q/E48N, D2T/I38L/Y39S/G42N/A43V/K44Q/E48N, I38L/Y39S/G42N/A43E/K44Q/E48N, I38L/Y39S/G42N/A43E/K44Q/E48N/G275E/L281G/N282S/S286A, I38L/Y39S/G42N/A43E/K44Q/E48N/S54T/N116E/L141S, I38L/Y39S/G42N/A43L/K44E/E48N, I38L/Y39S/G42N/A43L/K44Q/E48N, I38L/Y39S/G42N/A43L/K44Q/E48N/A161P/A194T, I38L/Y39S/G42N/A43S/K44E/E48N/S54T/F67Y/A77Q/V102R/N116D/N122S/W258R/L281K/1291S/N292S/L293G, I38L/Y39S/G42N/A43S/K44E/E48N/S54T/Q66T/N116E/L141S/N180T/W258R/A259D, I38L/Y39S/G42N/A43S/K44Q/E48N, I38L/Y39S/G42N/A43S/K44Q/E48N/F67Y, I38L/Y39S/G42N/A43S/K44Q/E48N/S54T/A77E/N116E/N180T/A259D/W284G/1291Q/L293G, I38L/Y39S/G42N/A43S/K44Q/E48N/S54T/A77Q/L141S/W258S/W284G/1291Q/N292S/L293T, I38L/Y39S/G42N/A43T/K44E/E48N/F67Y/N116S/W284R/N292S, I38L/Y39S/G42N/A43T/K44E/E48N/Q66T/N116E/A161P/P164T/A194T/G275T/L281K/N282S, I38L/Y39S/G42N/A43T/K44Q/E48N, I38L/Y39S/G42N/A43V/K44E/E48N, I38L/Y39S/G42N/A43V/K44E/E48N/S286A/1291A, I38L/Y39S/G42N/A43V/K44E/E48N/S54T/N116S/L141S, I38L/Y39S/G42N/A43V/K44E/E48N/S54T/Q66T/V102Q/N116S/L141S/N180T/W258R, I38L/Y39S/G42N/A43V/K44Q/E48N, I38L/Y39S/G42N/A43V/K44Q/E48N/A161P, I38L/Y39S/G42N/A43V/K44Q/E48N/A194T, I38L/Y39S/G42N/A43V/K44Q/E48N/A259*, 138L/Y39S/G42N/A43V/K44Q/E48N/A259D, I38L/Y39S/G42N/A43V/K44Q/E48N/A77E, I38L/Y39S/G42N/A43V/K44Q/E48N/A77E/V102Q/W258S/G275T/T277E/W284M/S286A/1291A, I38L/Y39S/G42N/A43V/K44Q/E48N/A77Q, I38L/Y39S/G42N/A43V/K44Q/E48N/A77Q/N180T, I38L/Y39S/G42N/A43V/K44Q/E48N/C269R, I38L/Y39S/G42N/A43V/K44Q/E48N/C269S/W284*, I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/1291-/N292-, I38L/Y39S/G42N/A43V/K44Q/E48N/D283*, 138L/Y39S/G42N/A43V/K44Q/E48N/E184A, I38L/Y39S/G42N/A43V/K44Q/E48N/E184K, I38L/Y39S/G42N/A43V/K44Q/E48N/E184N, I38L/Y39S/G42N/A43V/K44Q/E48N/E184R, I38L/Y39S/G42N/A43V/K44Q/E48N/E184S, I38L/Y39S/G42N/A43V/K44Q/E48N/E184T, I38L/Y39S/G42N/A43V/K44Q/E48N/F67Y/A77Q/N116D/A161P, I38L/Y39S/G42N/A43V/K44Q/E48N/F67Y/G275E/T277E/W284M/Q287S/C288A/T289Q/M290*, 138L/Y39S/G42N/A43V/K44Q/E48N/F67Y/N116D/N122S, I38L/Y39S/G42N/A43V/K44Q/E48N/F67Y/N122A/L141S, I38L/Y39S/G42N/A43V/K44Q/E48N/G268N, I38L/Y39S/G42N/A43V/K44Q/E48N/G275*, I38L/Y39S/G42N/A43V/K44Q/E48N/G275N, I38L/Y39S/G42N/A43V/K44Q/E48N/G275T, I38L/Y39S/G42N/A43V/K44Q/E48N/G275T/T277E/L281E/N282S/1291A, I38L/Y39S/G42N/A43V/K44Q/E48N/1291Q, I38L/Y39S/G42N/A43V/K44Q/E48N/1291S, I38L/Y39S/G42N/A43V/K44Q/E48N/L141S/N180T/A259D/L281G/N282S/L293N, I38L/Y39S/G42N/A43V/K44Q/E48N/L141S/W258R, I38L/Y39S/G42N/A43V/K44Q/E48N/L281E, I38L/Y39S/G42N/A43V/K44Q/E48N/L281G, I38L/Y39S/G42N/A43V/K44Q/E48N/L281K, I38L/Y39S/G42N/A43V/K44Q/E48N/L281S/Q287H, I38L/Y39S/G42N/A43V/K44Q/E48N/L293N, I38L/Y39S/G42N/A43V/K44Q/E48N/L293T, I38L/Y39S/G42N/A43V/K44Q/E48N/L293V, I38L/Y39S/G42N/A43V/K44Q/E48N/N116D, I38L/Y39S/G42N/A43V/K44Q/E48N/N116D/L141S/N180T/A259D/N282S, I38L/Y39S/G42N/A43V/K44Q/E48N/N116S, I38L/Y39S/G42N/A43V/K44Q/E48N/N116S/L141S/P164T/W258S/L281G/N282S/S286A, I38L/Y39S/G42N/A43V/K44Q/E48N/N122A, I38L/Y39S/G42N/A43V/K44Q/E48N/N180T, I38L/Y39S/G42N/A43V/K44Q/E48N/N282S, I38L/Y39S/G42N/A43V/K44Q/E48N/P164S, I38L/Y39S/G42N/A43V/K44Q/E48N/P51E, I38L/Y39S/G42N/A43V/K44Q/E48N/P51N, I38L/Y39S/G42N/A43V/K44Q/E48N/P51T, I38L/Y39S/G42N/A43V/K44Q/E48N/Q66T/F67Y/A77Q/N116E/N122A/A161K/N180T/W258S/L293G, I38L/Y39S/G42N/A43V/K44Q/E48N/S286A, I38L/Y39S/G42N/A43V/K44Q/E48N/S286G, I38L/Y39S/G42N/A43V/K44Q/E48N/S54T, I38L/Y39S/G42N/A43V/K44Q/E48N/S54T/A77E/S286A/1291A, I38L/Y39S/G42N/A43V/K44Q/E48N/S54T/G275T/T277D/L281G/N282S/1291A, I38L/Y39S/G42N/A43V/K44Q/E48N/S54T/L141S, I38L/Y39S/G42N/A43V/K44Q/E48N/S54T/N116D, I38L/Y39S/G42N/A43V/K44Q/E48N/S54T/N116S/N122S/L141S, I38L/Y39S/G42N/A43V/K44Q/E48N/S54T/N122A, I38L/Y39S/G42N/A43V/K44Q/E48N/S54T/P164T/N180T/W258R/A259D/L281G/N282S/1291S/N292S/L29 3N, I38L/Y39S/G42N/A43V/K44Q/E48N/T270*, 138L/Y39S/G42N/A43V/K44Q/E48N/T271E, I38L/Y39S/G42N/A43V/K44Q/E48N/T276G/K280S/L281*, 138L/Y39S/G42N/A43V/K44Q/E48N/T276H/C278*, 138L/Y39S/G42N/A43V/K44Q/E48N/T276R/K280Q/L281A/N282E/D283*, 138L/Y39S/G42N/A43V/K44Q/E48N/T277D, I38L/Y39S/G42N/A43V/K44Q/E48N/T277E, I38L/Y39S/G42N/A43V/K44Q/E48N/V102Q, I38L/Y39S/G42N/A43V/K44Q/E48N/V102Q/N116D, I38L/Y39S/G42N/A43V/K44Q/E48N/V102Q/T277D/L281G, I38L/Y39S/G42N/A43V/K44Q/E48N/V273*, I38L/Y39S/G42N/A43V/K44Q/E48N/V273D/S274R/G275A/T276P/T277L/C278A/T279P/K280S/L281*, 138L/Y39S/G42N/A43V/K44Q/E48N/V273G/C278L/T279H/K280Q/L281A/N282E/D283*, 138L/Y39S/G42N/A43V/K44Q/E48N/W258*, 138L/Y39S/G42N/A43V/K44Q/E48N/W258R, I38L/Y39S/G42N/A43V/K44Q/E48N/W258S, I38L/Y39S/G42N/A43V/K44Q/E48N/W284G, I38L/Y39S/G42N/A43V/K44Q/E48N/W284M, I38L/Y39S/G42N/A43V/K44Q/E48N/W284M/1291Q, I38L/Y39S/G42N/A43V/K44Q/E48N/W284R, I38L/Y39S/G42N/A43V/K44Q/E48N/W284T, I38L/Y39S/G42N/K44E/E48N/N116D/L141S, I38L/Y39S/G42N/K44E/E48N/Q66T/F67Y/A77Q/N122A/A161K/S286G/T289K/M290*, 138L/Y39S/G42N/K44E/E48N/S54T/N116D/W258S/G275T/W284M/1291Q, I38L/Y39S/G42N/K44E/E48N/S54T/N116E/N122S/L141S, I38L/Y39S/G42N/K44E/E48N/S54T/N116S/N122A, I38L/Y39S/G42N/K44Q/E48N, I38L/Y39S/G42N/K44Q/E48N/S54T/N116D/L141S, S17G/A23D/I38L/Y39S/G42N/A43T/K44E/E48N/A77E/V102Q/A161P/G275T/N282S/1291A, S17G/A23D/I38L/Y39S/G42N/A43V/K44Q/

E48N/A77E/V102Q/A161P/W258S/L281E/1291Q, S17G/A23D/I38L/Y39S/G42N/A43V/K44Q/E48N/F67Y/G275T/W284M/1291S, S17G/A23D/I38L/Y39S/G42N/A43V/K44Q/E48N/F67Y/V102Q/N116S/N122A/L141S/N180T/A194T/W28 4R/N292S/L293T, S17G/A23D/I38L/Y39S/G42N/A43V/K44Q/E48N/S54T/A77E/V102Q/N116D/A161P/L281G, S17G/A23D/I38L/Y39S/G42N/A43V/K44Q/E48N/S54T/A77E/V102Q/S286A/1291Q, S17G/A23D/I38L/Y39S/G42N/A43V/K44Q/E48N/S54T/V102Q/W258S/L281E, S17G/A23D/I38L/Y39S/G42N/A43V/K44Q/E48N/S54T/W258S/L281G/N282S/1291A, S17G/A23D/I38L/Y39S/G42N/A43V/K44Q/E48N/V102Q/A161P/T277D/W284M, S17G/A23D/S25N/I38L/Y39S/G42N/A43S/K44E/E48N/V102Q/N116D/L141S/N180T/L281G/1291Q/N292 S/L293N, S17G/A23D/S25N/I38L/Y39S/G42N/A43V/K44Q/E48N/Q66T/A77E/A194T, S17G/A23D/S25N/I38L/Y39S/G42N/A43V/K44Q/E48N/S54T/Q66T/F67Y/A77Q/N116E/L141S/N180T/A1 94T/W258S/A259D/G275E/L281G/N282S/1291S/N292S/L293T, S17G/A23N/I38L/Y39S/G42N/A43E/K44E/E48N/N116D/W258S/G275T/W284M/S286A, S17G/A23N/I38L/Y39S/G42N/A43L/K44E/E48N/N116S/A161K/A194T, S17G/A23N/I38L/Y39S/G42N/A43S/K44E/E48N/A77E/V102Q/G275T, S17G/A23N/I38L/Y39S/G42N/A43S/K44Q/E48N/S54T/V102Q/N116E, S17G/A23N/I38L/Y39S/G42N/A43V/K44Q/E48N/A77E/V102Q/A161P/W284M/1291Q, S17G/A23N/I38L/Y39S/G42N/A43V/K44Q/E48N/N116S/N122S/G275T/L281E, S17G/A23N/I38L/Y39S/G42N/A43V/K44Q/E48N/S54T/N116D/L141S/N180T/G275T/T277E/W284G, S17G/A23N/I38L/Y39S/G42N/A43V/K44Q/E48N/S54T/V102Q/W258S/W284M/1291Q, S17G/A23N/I38L/Y39S/G42N/A43V/K44Q/E48N/S54T/W258S/G275T/T277E, S17G/A23N/I38L/Y39S/G42N/A43V/K44Q/E48N/V102Q/N116D/A161P/W258S, S17G/A23N/S25N/I38L/Y39S/G42N/A43S/K44Q/E48N/Q66T/V102Q/N122S/A161P/P164T/L281K/N282S, S17G/A23N/S25N/I38L/Y39S/G42N/A43T/K44Q/E48N/S54T/Q66T/N116E/A259D/W284G, S17G/A23N/S25N/I38L/Y39S/G42N/A43V/K44Q/E48N/Q66T/F67Y/N116E/L141S/N180T/A194T/G275E/W284G/1291S/N292S, S17G/I38L/Y39S/G42N/A43E/K44Q/E48N/L141S, S17G/I38L/Y39S/G42N/A43E/K44Q/E48N/S54T/N122S, S17G/I38L/Y39S/G42N/A43S/K44E/E48N/Q66T/A77Q/V102Q/N116S/N122S/L141S/W258R/A259D/W28 4R, S17G/I38L/Y39S/G42N/A43S/K44E/E48N/S54T/A77Q/N116E/N122A/L141S/A161K/P164T/N180T/A194T/T277E/W284G, S17G/I38L/Y39S/G42N/A43S/K44E/E48N/S54T/N180T/W258S/A259D, S17G/I38L/Y39S/G42N/A43S/K44Q/E48N/Q66T/N116D/N122S/N180T, S17G/I38L/Y39S/G42N/A43S/K44Q/E48N/S54T/L141S, S17G/I38L/Y39S/G42N/A43S/K44Q/E48N/S54T/N116D/L141S, S17G/I38L/Y39S/G42N/A43S/K44Q/E48N/S54T/V102Q/N116D/A161P/W258S/N282S/W284M/1291A, S17G/I38L/Y39S/G42N/A43T/K44Q/E48N/S54T/V102Q/N116D/A161P/L281E/N282S, S17G/I38L/Y39S/G42N/A43V/K44E/E48N/S54T/N116S/N122S, S17G/I38L/Y39S/G42N/A43V/K44Q/E48N, S17G/I38L/Y39S/G42N/A43V/K44Q/E48N/1291S/N292S/L293N, S17G/I38L/Y39S/G42N/A43V/K44Q/E48N/N116S/N180T/T277E/W284R/L293T, S17G/I38L/Y39S/G42N/A43V/K44Q/E48N/N122A/A194T/A259D/G275T/T277D/L281K/L293N, S17G/I38L/Y39S/G42N/A43V/K44Q/E48N/N122S, S17G/I38L/Y39S/G42N/A43V/K44Q/E48N/Q66T/A77E/N116S/G275T/W284M, S17G/I38L/Y39S/G42N/A43V/K44Q/E48N/S54T, S17G/I38L/Y39S/G42N/A43V/K44Q/E48N/S54T/A77E/N116D/L141S/L281E, S17G/I38L/Y39S/G42N/A43V/K44Q/E48N/S54T/A77E/V102Q/G275T, S17G/I38L/Y39S/G42N/A43V/K44Q/E48N/S54T/A77Q/N116E/L141S/N180T/A194T/W258S/A259D/W28 4G/S286G/1291Q/L293G, S17G/I38L/Y39S/G42N/A43V/K44Q/E48N/S54T/A77Q/N116S/L141S/A194T/W258R/L281G, S17G/I38L/Y39S/G42N/A43V/K44Q/E48N/S54T/N116D, S17G/I38L/Y39S/G42N/A43V/K44Q/E48N/S54T/N116E, S17G/I38L/Y39S/G42N/A43V/K44Q/E48N/S54T/N116E/L141S, S17G/I38L/Y39S/G42N/A43V/K44Q/E48N/S54T/V102Q/N116D/A161P/W258S/W284M/1291A, S17G/I38L/Y39S/G42N/K44Q/E48N/N122S/L141S, S17G/I38L/Y39S/G42N/K44Q/E48N/Q66T/F67Y/T277D/L281G, S17G/I38L/Y39S/G42N/K44Q/E48N/S54T/N116E/N122S/L141S, S25N/I38L/Y39S/G42N/A43E/K44Q/E48N/S54T/N180T/W258S/G275E, S25N/I38L/Y39S/G42N/A43S/K44E/E48N/S54T/A77Q/V102Q/N116D/L141S/A194T/W258S/W284M, S25N/I38L/Y39S/G42N/A43S/K44E/E48N/S54T/N116D/N122S/L141S/N180T/W258R/G275T/T277E/W28 4M/1291Q/N292S/L293T, S25N/I38L/Y39S/G42N/A43S/K44E/E48N/S54T/Q66T/A77E/N116E/N180T/A259D/G275T/T277D/S286A/1291Q/N292S/L293T, S25N/I38L/Y39S/G42N/A43S/K44Q/E48N/Q66T/N116E/L141S/N180T/W258S, S25N/I38L/Y39S/G42N/A43T/K44E/E48N/A77E/N116S/L141S, S25N/I38L/Y39S/G42N/A43V/K44Q/E48N, S25N/I38L/Y39S/G42N/A43V/K44Q/E48N/A161P/N180T/A194T, S25N/I38L/Y39S/G42N/A43V/K44Q/E48N/A77E, S25N/I38L/Y39S/G42N/A43V/K44Q/E48N/A77Q/N116D/L141S/N180T/W258R/G275E/T277E, S25N/I38L/Y39S/G42N/A43V/K44Q/E48N/F67Y/A161K, S25N/I38L/Y39S/G42N/A43V/K44Q/E48N/L141S/N180T/A194T/W258S/A259D/L281K/N282S, S25N/I38L/Y39S/G42N/A43V/K44Q/E48N/N180T/A194T, S25N/I38L/Y39S/G42N/A43V/K44Q/E48N/Q66T/A77Q/N116D/A161K/P164T/W284G/N292S/L293G, S25N/I38L/Y39S/G42N/A43V/K44Q/E48N/S54T/A77Q/L141S/N180T/G275E/W284G/1291Q/N292S/L293 G, S25N/I38L/Y39S/G42N/A43V/K44Q/E48N/S54T/A77Q/N116D/W258S/A259D/L281G, S25N/I38L/Y39S/G42N/A43V/K44Q/E48N/S54T/A77Q/N116S/N180T/A194T/A259D/T277D/W284G/129 1Q, S25N/I38L/Y39S/G42N/A43V/K44Q/E48N/S54T/L141S/N180T/G275T/W284M/1291S/L293T, S25N/I38L/Y39S/G42N/A43V/K44Q/E48N/S54T/L141S/N180T/W258R/A259D, and A23S/S25N/F29Y/R33A/N36Q/I38L/Y39S/G42N/A43V/K44Q/E48N/P51S/Q66N/F67L/S68A/N75S/N80S/A82S/K90A/V102T/N116S/L121I/N122A/1123M/D132N/T135S/P136S/E144A/R145Q/S153D/D160A/A16 1P/Y167Q/L174Q/N180T/E184Q/R185Q/S190A/L192I/T196S/G204S/N205S/Y206F.

2. The composition of claim 1, wherein said one or more amino acid modifications are selected from the group consisting of modifications corresponding to D2E, D2F, D2N, D2Q, D2S, D2T, S17G, A23D, A23N, A23S, S25N, F29Y, R33A, N36Q, 138L, Y39S, G42N, A43E, A43L, A43S, A43T, A43V, K44E, K44Q, E48N, P51E, P51N, P51S, P51T, S54T, Q66N, Q66T, F67L, F67Y, S68A, N75S, A77E, A77Q, N80S, A82S, K90A, V102Q, V102R, V102T, N116D, N116E, N116S, L121I, N122A, N122S, 1123M, D132N, T135S, P136S, L141S, E144A, R145Q, S153D, D160A, A161K, A161P, P164S, P164T, Y167Q, L174Q, N180T, E184A, E184K, E184N, E184Q, E184R, E184S, E184T, R185Q, S190A, L192I, A194T, R195S, T196S, G204S, N205S, Y206F, D215*, D215G, S216N, P217G, S218G, S219T, S220G, S221-, A222-, A223T, S228A, T229P, S230G, Q231S, Q232G, P233Q, Q234T, Q235S, T237G, S238G, S239G, S241-, Q242-, A243-, S244-, V245-, P246-, T247-, S248-, N249-, P250-, G251-, W258*, W258R, W258S, A259*, A259D, T267S, G268N, C269R, C269S, T270*, T271E, V273*, V273D, V273G, S274R, G275*, G275A, G275E, G275N, G275T, T276G, T276H, T276P, T276R, T277D, T277E, T277L, C278*, C278A, C278L, T279H, T279P, T279Q, K280Q, K280S, L281*, L281A, L281E, L281G, L281K, L281S, N282E, N282S, D283*, W284*, W284G, W284M, W284R, W284T, W284Y, Y285*, S286A, S286G, Q287H, Q287S, C288*, C288A, T289-, T289K, T289Q, M290-, M290*, 1291-, 1291A, 1291Q, 1291S, N292-, N292S, L293G, L293N, L293T, and L293V of SEQ ID NO:1.

3. The composition of claim 1, wherein said one or more amino acid modifications of SEQ ID NO:1 occur at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions, twenty of said positions, twenty-one of said positions, twenty-two of said positions, twenty-three of said positions, twenty-four of said positions, twenty-five of said positions, twenty-six of said positions, twenty-seven of said positions, twenty-eight of said positions, twenty-nine of said positions, thirty of said positions, thirty-one of said positions, thirty-two of said positions, thirty-three of said positions, thirty-four of said positions, thirty-five of said positions, thirty-six of said positions, thirty-seven of said positions, thirty-eight of said positions, thirty-nine of said positions, forty of said positions, forty-one of said positions, forty-two of said positions, forty-three of said positions, forty-four of said positions, forty-five of said position, forty-six of said positions, or forty-seven of said positions of SEQ ID NO:1.

4. The composition of claim 1, wherein said variant endoglucanase enzyme exhibits at least 85%, 90% or 95% sequence identity to SEQ ID NO:1.

5. The composition of claim 1, wherein said variant endoglucanase enzyme comprises said amino acid modifications I38L/Y39S/G42N/A43V/K44Q/E48N and has at least 90% sequence identity to SEQ ID NO:5.

6. A composition comprising a variant endoglucanase enzyme comprising one or more amino acid modifications as compared to SEQ ID NO:7, wherein said variant endoglucanase enzyme comprises said amino acid modifications D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/1291-/N292- and has at least 90% sequence identity to SEQ ID NO:7.

7. A composition comprising a variant endoglucanase enzyme comprising one or more amino acid modifications as compared to SEQ ID NO:23, wherein said variant endoglucanase enzyme comprises said amino acid modifications I38L/Y39S/G42N/A43V/K44Q/E48N/D215G/S216N/P217G/S218G/S219T/S220G/S221-/A222-/A223T/S228A/T229P/S230G/Q231S/Q232G/P233Q/Q234T/Q235S/T237G/S238G/S239G/S241-/Q242-/A243-/S244-/V245-/P246-/T247-/S248-/N249-/P250-/G251-/T267S/T279Q/W284Y/T289-/M290-/1291-/N292- and has at least 90% sequence identity to SEQ ID NO:23.

8. A method of biostoning comprising the step of contacting the composition of claim 1 with cotton-containing fabrics or garments that are denim.

9. A method of biofinishing comprising the step of contacting the composition of claim 1 with a textile material that is selected from the group consisting of fabrics, garments, and yarn.

10. A detergent composition comprising the composition of claim 1.

11. A method for treating wood-derived pulp or fiber, comprising the step of contacting the composition of claim 1 with wood-derived mechanical or chemical pulp or secondary fiber.

12. A method of biostoning comprising the step of contacting the composition of claim 6 with cotton-containing fabrics or garments that are denim.

13. A method of biofinishing comprising the step of contacting the composition of claim 6 with a textile material that is selected from the group consisting of fabrics, garments, and yarn.

14. A detergent composition comprising the composition of claim 6.

15. A method for treating wood-derived pulp or fiber, comprising the step of contacting the composition of claim 6 wood-derived mechanical or chemical pulp or secondary fiber.

16. A method of biostoning comprising the step of contacting the composition of claim 7 with cotton-containing fabrics or garments that are denim.

17. A method of biofinishing comprising the step of contacting the composition of claim 7 with a textile material that is selected from the group consisting of fabrics, garments, and yarn.

18. A detergent composition comprising the composition of claim 7.

19. A method for treating wood-derived pulp or fiber, comprising the step of contacting the composition of claim 7 wood-derived mechanical or chemical pulp or secondary fiber.

* * * * *